United States Patent
Chang et al.

(10) Patent No.: US 7,276,476 B2
(45) Date of Patent: *Oct. 2, 2007

(54) CYCLOSPORIN COMPOSITIONS

(75) Inventors: James N. Chang, Newport Beach, CA (US); Orest Olejnik, Coto De Caza, CA (US); Bruce A. Firestone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/181,187

(22) Filed: Jul. 13, 2005

(65) Prior Publication Data

US 2007/0015710 A1    Jan. 18, 2007

(51) Int. Cl.
    A61K 38/12     (2006.01)

(52) U.S. Cl. .................... 514/9; 530/317; 514/912; 514/975; 435/112

(58) Field of Classification Search ............... None
    See application file for complete search history.

(56) References Cited

U.S. PATENT DOCUMENTS

| | | | |
|---|---|---|---|
| 4,388,307 A | 6/1983 | Cavanak | |
| 4,649,047 A | 3/1987 | Kaswan | |
| 4,814,323 A | 3/1989 | Andrieu et al. | |
| 4,839,342 A | 6/1989 | Kaswan | |
| 4,996,193 A | 2/1991 | Hewitt et al. | |
| 5,047,396 A | 9/1991 | Orban et al. | |
| 5,051,402 A | 9/1991 | Kurihara et al. | |
| 5,342,625 A | 8/1994 | Hauer et al. | |
| 5,474,979 A | 12/1995 | Ding et al. | |
| 5,543,393 A | 8/1996 | Kim et al. | |
| 5,614,491 A | 3/1997 | Walch et al. | |
| 5,639,724 A | 6/1997 | Cavanak | |
| 5,652,212 A | 7/1997 | Cavanak et al. | |
| 5,759,997 A | 6/1998 | Cavanak | |
| 5,766,629 A | 6/1998 | Cho et al. | |
| 5,798,333 A | 8/1998 | Sherman | |
| 5,827,822 A | 10/1998 | Floc'h et al. | |
| 5,834,017 A | 11/1998 | Cho et al. | |
| 5,891,846 A * | 4/1999 | Ishida et al. ................ | 514/11 |
| 5,916,589 A | 6/1999 | Hauer et al. | |
| 5,951,971 A | 9/1999 | Kawashima et al. | |
| 5,962,014 A | 10/1999 | Hauer et al. | |
| 5,962,017 A | 10/1999 | Hauer et al. | |
| 5,962,019 A | 10/1999 | Cho et al. | |
| 5,977,066 A | 11/1999 | Cavanak | |
| 6,007,840 A | 12/1999 | Hauer et al. | |
| 6,024,978 A | 2/2000 | Hauer et al. | |
| 6,057,289 A | 5/2000 | Mulye | |
| 6,190,691 B1 * | 2/2001 | Mak ........................... | 424/449 |
| 6,197,335 B1 | 3/2001 | Sherman | |
| 6,254,860 B1 | 7/2001 | Garst | |
| 6,254,885 B1 | 7/2001 | Cho et al. | |
| 6,267,985 B1 | 7/2001 | Chen et al. | |
| 6,284,268 B1 | 9/2001 | Mishra et al. | |
| 6,294,192 B1 | 9/2001 | Patel et al. | |
| 6,306,825 B1 | 10/2001 | Cavanak | |
| 6,350,442 B2 | 2/2002 | Garst | |
| 6,468,968 B2 | 10/2002 | Cavanak et al. | |
| 6,475,519 B1 | 11/2002 | Meinzer et al. | |
| 6,486,124 B2 | 11/2002 | Olbrich et al. | |
| 6,569,463 B2 | 5/2003 | Patel et al. | |
| 6,582,718 B2 | 6/2003 | Kawashima et al. | |
| 6,638,522 B1 | 10/2003 | Mulye | |
| 6,656,504 B1 | 12/2003 | Bosch et al. | |
| 6,723,339 B2 | 4/2004 | Meinzer et al. | |
| 6,916,785 B2 | 7/2005 | Patel | |
| 2001/0003589 A1 | 6/2001 | Neuer et al. | |
| 2001/0036449 A1 | 11/2001 | Garst | |
| 2002/0012680 A1 | 1/2002 | Patel et al. | |
| 2002/0013272 A1 | 1/2002 | Cavanak et al. | |
| 2002/0016290 A1 | 2/2002 | Floc'h et al. | |
| 2002/0016292 A1 | 2/2002 | Richter et al. | |
| 2002/0025927 A1 | 2/2002 | Olbrich et al. | |
| 2002/0045601 A1 | 4/2002 | Kawashima et al. | |
| 2002/0107183 A1 | 8/2002 | Petswzulat et al. | |
| 2002/0119190 A1 | 8/2002 | Meinzer et al. | |
| 2002/0165134 A1 | 11/2002 | Richter et al. | |
| 2003/0060402 A1 | 3/2003 | Cavanak et al. | |
| 2003/0133984 A1 | 7/2003 | Ambuhl et al. | |
| 2003/0143250 A1 | 7/2003 | Hauer et al. | |
| 2003/0147954 A1 | 8/2003 | Yang et al. | |
| 2003/0166517 A1 | 9/2003 | Fricker et al. | |
| 2003/0211983 A1 | 11/2003 | Petszulat et al. | |
| 2003/0215496 A1 | 11/2003 | Patel et al. | |
| 2004/0048789 A1 | 3/2004 | Patel | |
| 2004/0101552 A1 | 5/2004 | Patel | |
| 2004/0102366 A1 | 5/2004 | Patel | |
| 2004/0161458 A1 | 8/2004 | Meinzer et al. | |
| 2004/0167063 A1 | 8/2004 | Cavanak et al. | |
| 2004/0198645 A1 | 10/2004 | Ambuhl et al. | |
| 2005/0048087 A1 | 3/2005 | Posanski | |
| 2005/0059583 A1 | 3/2005 | Acheampong et al. | |
| 2005/0118254 A1 | 6/2005 | Choi et al. | |
| 2005/0129718 A1 | 6/2005 | Sherman | |
| 2005/0147659 A1 | 7/2005 | Carli et al. | |

FOREIGN PATENT DOCUMENTS

| | | |
|---|---|---|
| EP | 0471293 | 2/1992 |
| WO | WO 00/00179 | 1/2000 |
| WO | WO 2004/091578 | * 10/2004 |

OTHER PUBLICATIONS

Restasis®(cyclosporine ophthalmic emulsion)0.05% Sterile, Preservative-Free, (Prescribing Information), 2 pages.

Kuwano et al, "Cyclosporine A Formulation Affects Its Ocular Distribution in Rabbits", Pharmaceutical Research, vol. 19, No. 1, Jan. 2002, 108-111.

* cited by examiner

Primary Examiner—Anish Gupta
Assistant Examiner—Satyanarayana R. Gudibande
(74) Attorney, Agent, or Firm—Brent A. Johnson; Martin A. Voet

(57) ABSTRACT

A composition comprising from 0.001% to about 0.4% cyclosporin A, a surfactant, and an oil selected from the group consisting of anise oil, clove oil, cassia oil, cinnamon oil, and combinations thereof, wherein said composition is an ophthalmically acceptable emulsion is disclosed herein.

10 Claims, No Drawings

CYCLOSPORIN COMPOSITIONS

BACKGROUND

Description of the Relevant Art

Cyclosporins are a group of nonpolar cyclic oligopeptides with known immunosuppressant activity. In addition, as set forth in U.S. Pat. No. 4,839,342, cyclosporin (sometimes referred to in the literature as "cyclosporine") has been found as effective in treating immune medicated keratoconjunctivitis sicca (KCS or dry eye disease) in a patient suffering therefrom.

As hereinabove noted, cyclosporin comprises a group of cyclic oligopeptides and the major component thereof is cyclosporin A ($C_{62}H_{111}N_{11}O_{12}$) which has been identified along with several other minor metabolites, cyclosporin B through I. In addition, a number of synthetic analogs have been prepared.

In general, commercially available cyclosporins may contain a mixture of several individual cyclosporins which all share a cyclic peptide structure consisting of eleven amino acid residues with a total molecular weight of about 1,200, but with different substituents or configurations of some of the amino acids.

The activity of cyclosporins, as hereinabove noted, is as an immunosuppressant and in the enhancement or restoring of lacrimal gland tearing.

Unfortunately, the solubility of cyclosporin in water is extremely low and as elaborated in U.S. Pat. No. 5,051,402, it has been considered not merely difficult but practically impossible to prepare a pharmaceutical composition containing cyclosporin dissolved in an aqueous medium.

As reported, the solubility of cyclosporin in water is between about 20 µg/ml to 30 µg/ml for cyclosporin A. Hence, heretofore prepared formulations incorporating cyclosporin have been prepared as oily solutions containing ethanol. However, these preparations limit the bioavailability to oral preparations and this is believed to be due to the separation of cyclosporin as a solid immediately after it comes into contact with water, such as in the mouth or eye of a patient.

Surface active agents such as polyoxyethylated castor oil have been utilized as solubilizers to inject preparations in order to prevent cyclosporin from separating. However, this also may give rise to safety problems (see U.S. Pat. No. 5,051,402).

U.S. Pat. No. 5,474,979 discloses a pharmaceutical composition in the form of a nonirritating emulsion which includes at least one cyclosporin in admixture with a higher fatty acid glyceride and polysorbate 80. More particularly, the cyclosporin may be cyclosporin A and the higher fatty acid glyceride may be castor oil.

U.S. Pat. No. 6,582,718 discloses an ophthalmic composition particularly in the form of eye-drops suitable for the treatment of diseases of the eye and surrounding areas. The composition contains a cyclosporin and a surfactant selected from polyoxyethylene fatty acid esters, polyoxyethylene alkylphenyl ethers and polyoxyethylene alkyl ethers, or mixtures thereof.

Copending U.S. Patent Application No. 60/503,137, filed Sep. 15, 2003, and U.S. patent application Ser. No. 10/865,638, filed Jun. 9, 2004 also disclose compositions of interest.

DESCRIPTION OF THE INVENTION

A composition is disclosed herein comprising from 0.001% to about 0.4% cyclosporin A, a surfactant, and an oil selected from the group consisting of anise oil, clove oil, cassia oil, cinnamon oil, and combinations thereof, wherein said composition is an ophthalmically acceptable emulsion.

Combinations of oils are specifically contemplated.

One embodiment comprises a combination of clove oil and anise oil.

Another embodiment comprises cassia oil and anise oil.

Another embodiment comprises cinnamon oil and anise oil.

Another embodiment comprises cassia oil and clove oil.

Another embodiment comprises cinnamon oil and clove oil.

Another embodiment comprises cinnamon oil and cassia oil.

Combinations with other oils are possible, in particular, combinations with castor oil area also contemplated.

Another embodiment comprises anise and castor oil.

Another embodiment comprises clove oil and castor oil.

Another embodiment comprises cassia oil and castor oil.

Another embodiment comprises cinnamon oil and castor oil.

One embodiment comprises from 0.001% to 0.1% cyclosporin A.

Another embodiment comprises from 0.005% to about 0.05% cyclosporin A.

Another embodiment comprises about 0.05% cyclosporine A.

While not intending to limit the scope of the invention in any way, one type of useful surfactant is a sorbitan ester. Examples include, but are not limited to, Polysorbate 20, Polysorbate 40, Polysorbate 60, and Polysorbate 80.

While not intending to limit the scope of the invention in any way, another type of useful surfactant is a stearate. Examples include, but are not limited to, glyceryl stearate, isopropyl stearate, polyoxyl stearate, propylene glycol stearate, and sucrose stearate.

While not intending to limit the scope of the invention in any way, another useful surfactant is polyethylene glycol.

While not intending to limit the scope of the invention in any way. Other useful surfactants comprise polyethylene oxide or polypropylene oxide. Examples, include, but are not limited to, polyethylene oxides, polypropylene oxides, polyethylene oxide, polypropylene oxide copolymers, alcohol ethoxylates, and alkylphenol ethoxylates.

While not intending to limit the scope of the invention in any way, another useful type of surfactant is an alkyl glycoside.

While not intending to limit the scope of the invention in any way, another useful type of surfactant is an alkyl polyglycoside.

While not intending to limit the scope of the invention in any way, another useful type of surfactant is a fatty alcohol.

While not intending to limit the scope of the invention in any way, another useful type of surfactant is a cellulose derivative, including, but not limited to, hydroxypropylmethyl cellulose (HPMC) and carboxymethyl cellulose (CMC).

While not intending to limit the scope of the invention in any way, another useful type of surfactant is a polyacrylic acid, including, but not limited to, a Carbomer.

While not intending to limit the scope of the invention in any way, another useful type of surfactant is a phosphalipid, including, but not limited to, phosphatidyl chloline and phosphatidyl serine.

Other useful surfactants include, but are not limited to:

Alcohols, including but not limited to,
Diglycerol®, which is available from Solvay Chemicals, Inc.;
Hetoxide GT-80®, which is available from Global-Seven, Inc.;
Lexemul BEO®, which is available from Inolex Chemical Co.;
Polyglycerol-3®, which is available from Solvay Chemicals, Inc.;
Redicote E Series®, which is available from Akzo Nobel Surface Chemistry LLC;
Simulsol OX 1005L®, which is available from Seppic Inc.;
Stanfax 567®, which is available from Para-Chem Standard Div.;
TA-1618®, which is available from Procter & Gamble; and
Witconol H-31A®, which is available from Akzo Nobel Surface Chemistry LLC;

Amine Oxides, including but not limited to,
AO-405®, which is available from Tomah Products®, Inc.;
AO-455®, which is available from Tomah Products®, Inc.;
AO 728 Special®, which is available from Tomah Products®, Inc.;
Barlox 12®, which is available from Lonza Inc.;
Barlox 14®, which is available from Lonza Inc.;
Burcoxide Lo®, which is available from Burlington Chemical Co.®, Inc.;
Caloxamine LO®, which is available from Pilot Chemical Co.;
Chemoxide CAW®, which is available from Chemron Corp.;
Chemoxide LM-30®, which is available from Chemron Corp.;
Chemoxide LO®, which is available from Chemron Corp.;
Chemoxide MO®, which is available from Chemron Corp.;
Colalux CAO-35®, which is available from Colonial Chemical Co.;
Colalux LO®, which is available from Colonial Chemical Co.;
DeMox CAPO®, which is available from DeForest Enterprises, Inc.;
DeMox CSG-30®, which is available from DeForest Enterprises, Inc.;
DeMox LAO®, which is available from DeForest Enterprises, Inc.;
Emcol L®, which is available from Crompton Corp.;
Empigen OB®, which is available from Huntsman LLC;
Empigen OS/A®, which is available from Huntsman LLC;
Foamox CDO®, which is available from Alzo International, Inc.;
Foamox DMM®, which is available from Alzo International, Inc.;
Foamox DMS®, which is available from Alzo International, Inc.;
Genaminox KC®, which is available from Clariant Corporation;
Genaminox LA®, which is available from Clariant Corporation;
Hartofoam SAO®, which is available from Hart Chemical Corp.;
Hartox DMCD®, which is available from Hart Chemical Corp.;
Lipowax DAT®, which is available from Lipo Chemicals, Inc.;
Lipowax PB Pastilles®, which is available from Lipo Chemicals, Inc.;
Mackamine C8®, which is available from The McIntyre Group;
Mackamine C10®, which is available from The McIntyre Group;
Mackamine C14®, which is available from The McIntyre Group;
Mackamine CAO®, which is available from The McIntyre Group;
Mackamine CO®, which is available from The McIntyre Group;
Mackamine LO®, which is available from The McIntyre Group;
Mackamine O2®, which is available from The McIntyre Group;
Mackamine SAO®, which is available from The McIntyre Group;
Mackamine SO®, which is available from The McIntyre Group;
Mazox KCAO®, which is available from BASF Corp.;
Monalac MO®, which is available from Uniqema;
Norfox LDA®, which is available from Norman, Fox & Co.;
Rhodamox LO®, which is available from Rhodia, Inc.;
Schercamox C-AA®, which is available from Noveon®, Inc.;
Schercamox DMA®, which is available from Noveon®, Inc.;
Schercamox DML®, which is available from Noveon®, Inc.;
Schercamox DMM®, which is available from Noveon®, Inc.;
Schercamox DMS®, which is available from Noveon®, Inc.;
Tegotens DO®, which is available from Goldschmidt Chemical Corp.;
Tomah AO-14-2®, which is available from Tomah Products®, Inc.; and
Triaminox CDO®, which is available from Tri-Tex Co.®, Inc.;

Block Polymers, including but not limited to,
AL 2070®, which is available from Uniqema;
Antarox 17-R-2®, which is available from Rhodia, Inc.;
Antarox 25-R-2®, which is available from Rhodia, Inc.;
Antarox 31-R-1®, which is available from Rhodia, Inc.;
Antarox P-84®, which is available from Rhodia, Inc.;
Antarox P-104/H®, which is available from Rhodia, Inc.;
Arnox BP-Series®, which is available from Crompton Corp.;
Chemonic 435®, which is available from Chemron Corp.;
Chemonic D-25®, which is available from Chemron Corp.;
Chemonic PL Series®, which is available from Chemron Corp.;
Ethox L-121®, which is available from Ethox Chemicals, LLC;
Ethox L-122®, which is available from Ethox Chemicals, LLC;
Genapol PF-10®, which is available from Clariant Corporation;
Genapol PF-20®, which is available from Clariant Corporation;
Genapol PF-40A®, which is available from Clariant Corporation;
Norfox 2-LF®, which is available from Norman, Fox & Co.;

Pluronic, which is available from BASF;
Simulsol NW 342®, which is available from Seppic Inc.;
T-Det BP-1®, which is available from Harcros Chemicals Inc.;
T-Det XD®, which is available from Harcros Chemicals Inc.;
T-Det XH®, which is available from Harcros Chemicals Inc.;
Triton CF-32®, which is available from Dow Chemical Company;
Witconol 171®, which is available from Akzo Nobel Surface Chemistry LLC;
Witconol 324®, which is available from Akzo Nobel Surface Chemistry LLC;
Witconol 324D®, which is available from Akzo Nobel Surface Chemistry LLC; and
Witconol PD-2000®, which is available from Akzo Nobel Surface Chemistry LLC;

Carboxylated Alcohol or Alkylphenol Ethoxylates, including but not limited to,
Emcol CN-6®, which is available from Crompton Corp.;
Ethcarb®, which is available from Ethox Chemicals, LLC;
Gemtex WNT-Conc®, which is available from Finetex Inc.;
Incrodet TD7-C®, which is available from Croda Inc.;
Marlinat CM 105/80®, which is available from Sasol North America Inc.;
Marlowet 1072®, which is available from Sasol North America Inc.;
Marlowet 4530®, which is available from Sasol North America Inc.;
Marlowet 4530 LF®, which is available from Sasol North America Inc.;
Marlowet 4534®, which is available from Sasol North America Inc.;
Marlowet 4538®, which is available from Sasol North America Inc.;
Marlowet 4539®, which is available from Sasol North America Inc.;
Marlowet 4539 LF®, which is available from Sasol North America Inc.;
Marlowet 4541®, which is available from Sasol North America Inc.;
Miranate LEC-80®, which is available from Rhodia, Inc.;
Sandopan B®, which is available from Clariant Corporation;
Sandopan B Modified®, which is available from Clariant Corporation;
Sandopan LS-24 Gel®, which is available from Clariant Corporation; and
Surfine T-A®, which is available from Finetex Inc.;

Carboxylic Acids/Fatty Acids, including but not limited to,
Colaterge RAM®, which is available from Colonial Chemical Co.;
Colatrope INC®, which is available from Colonial Chemical Co.;
Crodacid B®, which is available from Croda Inc.;
DeTrope CA-100®, which is available from DeForest Enterprises, Inc.;
Latol MTO®, which is available from Georgia-Pacific Corp.;
Lumulse CC-33 K®, which is available from Lambent Technologies Corp.;
Mulls 2218®, which is available from Bernel Chemical Co.®, Inc.;
OL-600®, which is available from Procter & Gamble;
OL-800®, which is available from Procter & Gamble;
R-910®, which is available from Procter & Gamble;
S-210®, which is available from Procter & Gamble;
Sandopan DTC Acid®, which is available from Clariant Corporation;
Sandopan LS 24 N®, which is available from Clariant Corporation; and
Sandopan MA-18®, which is available from Clariant Corporation;

Ethoxylated Alcohols, including but not limited to,
Adsee 799®, which is available from Akzo Nobel Surface Chemistry LLC;
Adsee 799®, which is available from Crompton Corp.;
Alfonic 610-3.5®, which is available from Sasol North America Inc.;
Alfonic 810-2®, which is available from Sasol North America Inc.;
Alfonic 810-6®, which is available from Sasol North America Inc.;
Alfonic 1012-3®, which is available from Sasol North America Inc.;
Alfonic 1012-5®, which is available from Sasol North America Inc.;
Alfonic 1216CO-1.5®, which is available from Sasol North America Inc.;
Alfonic 1216CO-7®, which is available from Sasol North America Inc.;
Alfonic 1412-3®, which is available from Sasol North America Inc.;
Alfonic 1412-7®, which is available from Sasol North America Inc.;
Arlasolve 200®, which is available from Uniqema;
Arlasolve 200 Liquid®, which is available from Uniqema;
Armix 180-C®, which is available from Crompton Corp.;
Armix 183®, which is available from Crompton Corp.;
Armul 2404®, which is available from Akzo Nobel Surface Chemistry LLC;
Armul 2404®, which is available from Crompton Corp.;
Atlas EMJ-C®, which is available from Atlas Refinery Inc.;
Atlas G-2109®, which is available from Uniqema;
Atlas G-3886®, which is available from Uniqema;
Atlas G-3890®, which is available from Uniqema;
Bio Soft E-200®, which is available from Stepan Canada Inc.;
Bio Soft E-300®, which is available from Stepan Canada Inc.;
Bio Soft E-400®, which is available from Stepan Canada Inc.;
Bio Soft EN 600®, which is available from Stepan Canada Inc.;
Bio Soft TD-400®, which is available from Stepan Canada Inc.;
Bio Soft TD-630®, which is available from Stepan Canada Inc.;
Brij 30®, which is available from Uniqema;
Brij 52®, which is available from Uniqema;
Brij 56®, which is available from Uniqema;
Brij 58®, which is available from Uniqema;
Brij 72®, which is available from Uniqema;
Brij 76®, which is available from Uniqema;
Brij 78®, which is available from Uniqema;
Brij 93®, which is available from Uniqema;
Brij 97®, which is available from Uniqema;
Brij 98®, which is available from Uniqema;
Brij 700®, which is available from Uniqema;
Brij 700 S®, which is available from Uniqema;
Brij 721®, which is available from Uniqema;

Brij 721 S®, which is available from Uniqema;
Burcoterge CDG®, which is available from Burlington Chemical Co.®, Inc.;
Canasol AT 600®, which is available from Canamex Quimicos S.A de C.v;
Canasol AT 800®, which is available from Canamex Quimicos S.A de C.v;
Canasol AT 1200®, which is available from Canamex Quimicos S.A de C.v;
Canasol BJ 35®, which is available from Canamex Quimicos S.A de C.v;
Canasol BJ 36®, which is available from Canamex Quimicos S.A de C.v;
Canasol BJ 52®, which is available from Canamex Quimicos S.A de C.v;
Canasol BJ 58®, which is available from Canamex Quimicos S.A de C.v;
Canasol BJ 72®, which is available from Canamex Quimicos S.A de C.v;
Canasol BJ 78®, which is available from Canamex Quimicos S.A de C.v;
Canasol BJ 98®, which is available from Canamex Quimicos S.A de C.v;
Canasol BJ 307®, which is available from Canamex Quimicos S.A de C.v;
Cerfak 1400®, which is available from Houghton International Inc.;
Cetomacrogol 1000 BP®, which is available from Croda Inc.;
Chemonic C-2®, which is available from Chemron Corp.;
Chemonic C-10®, which is available from Chemron Corp.;
Chemonic C-20®, which is available from Chemron Corp.;
Chemonic CT-12®, which is available from Chemron Corp.;
Chemonic CT-20®, which is available from Chemron Corp.;
Chemonic CT-30®, which is available from Chemron Corp.;
Chemonic CT-55®, which is available from Chemron Corp.;
Chemonic G-7®, which is available from Chemron Corp.;
Chemonic G-26®, which is available from Chemron Corp.;
Chemonic L-4®, which is available from Chemron Corp.;
Chemonic L-7®, which is available from Chemron Corp.;
Chemonic L-12®, which is available from Chemron Corp.;
Chemonic L-23®, which is available from Chemron Corp.;
Chemonic O-2®, which is available from Chemron Corp.;
Chemonic O-5®, which is available from Chemron Corp.;
Chemonic O-10®, which is available from Chemron Corp.;
Chemonic O-20®, which is available from Chemron Corp.;
Chemonic S-2®, which is available from Chemron Corp.;
Chemonic S-10®, which is available from Chemron Corp.;
Chemonic S-20®, which is available from Chemron Corp.;
Colamulse FE®, which is available from Colonial Chemical Co.;
Cremophor A 20®, which is available from BASF Corp.;
Cremophor SA 2®, which is available from BASF Corp.;
Dehydol 100®, which is available from Cognis Canada Corp.;
Dehydol O-4®, which is available from Cognis Canada Corp.;
Delonic C-18®, which is available from DeForest Enterprises, Inc.;
DeSonic 6T®, which is available from Crompton Corp.;
DeSonic 9D®, which is available from Crompton Corp.;
DeSonic 9T®, which is available from Crompton Corp.;
DeSonic 12D®, which is available from Crompton Corp.;
DeSonic 12T®, which is available from Crompton Corp.;
DeSonic 15T®, which is available from Crompton Corp.;
DeSonic TDA-9®, which is available from Crompton Corp.;
DeThox GLG-7®, which is available from DeForest Enterprises, Inc.;
DeThox GLG-26®, which is available from DeForest Enterprises, Inc.;
DeThox LA-4®, which is available from DeForest Enterprises, Inc.;
DeThox LA-23®, which is available from DeForest Enterprises, Inc.;
DeThox SA-80®, which is available from DeForest Enterprises, Inc.;
Disponil O5®, which is available from Cognis Corporation;
Eccoterge EO-41B®, which is available from Eastern Color & Chemical Co.;
Empilan KA2.5/90®, which is available from Huntsman LLC;
Empilan KA5/90®, which is available from Huntsman LLC;
Empilan KM-20®, which is available from Huntsman LLC;
Empilan KM-50®, which is available from Huntsman LLC;
Empilan L-23®, which is available from Huntsman LLC;
Ethylan 25-3®, which is available from Akzo Nobel Surface Chemistry LLC;
Ethylan 1204®, which is available from Akzo Nobel Surface Chemistry LLC;
Ethylan DA-4®, which is available from Akzo Nobel Surface Chemistry LLC;
Ethylan LA-230®, which is available from Akzo Nobel Surface Chemistry LLC;
Ethylan SN®, which is available from Akzo Nobel Surface Chemistry LLC;
Ethylan TD-60®, which is available from Akzo Nobel Surface Chemistry LLC;
Ethylan TD-100®, which is available from Akzo Nobel Surface Chemistry LLC;
Ethylan TD-1407®, which is available from Akzo Nobel Surface Chemistry LLC;
Eumulgin B1®, which is available from Cognis Canada Corp.;
Eumulgin B2®, which is available from Cognis Canada Corp.;
Eumulgin B3®, which is available from Cognis Canada Corp.;
Eumulgin O-10®, which is available from Cognis Canada Corp.;
Flo Mo 80/20®, which is available from Crompton Corp.;
Flo Mo Low Foam®, which is available from Crompton Corp.;
Forlan C-24®, which is available from RITA Corp.;
Genapol 1454®, which is available from Clariant Corporation;
Genapol BA-020®, which is available from Clariant Corporation;
Genapol BA-040®, which is available from Clariant Corporation;
Genapol C-100®, which is available from Clariant Corporation;
Genapol DA 060®, which is available from Clariant Corporation;
Genapol HS 020®, which is available from Clariant Corporation;
Genapol HS 200®, which is available from Clariant Corporation;
Genapol ID-040®, which is available from Clariant Corporation;
Genapol ID-060®, which is available from Clariant Corporation;
Genapol ID-090®, which is available from Clariant Corporation;

Genapol LA 010®, which is available from Clariant Corporation;
Genapol LA 020®, which is available from Clariant Corporation;
Genapol LA 030®, which is available from Clariant Corporation;
Genapol LA 040®, which is available from Clariant Corporation;
Genapol LA 050®, which is available from Clariant Corporation;
Genapol LA 060®, which is available from Clariant Corporation;
Genapol LA 070®, which is available from Clariant Corporation;
Genapol LA 070S®, which is available from Clariant Corporation;
Genapol LA 230®, which is available from Clariant Corporation;
Genapol O 020®, which is available from Clariant Corporation;
Genapol O 050®, which is available from Clariant Corporation;
Genapol O 100®, which is available from Clariant Corporation;
Genapol O 200®, which is available from Clariant Corporation;
Genapol SA 030®, which is available from Clariant Corporation;
Genapol SA 120®, which is available from Clariant Corporation;
Genapol T-020®, which is available from Clariant Corporation;
Genapol UD-030®, which is available from Clariant Corporation;
Genapol UD-050®, which is available from Clariant Corporation;
Genapol UD-070®, which is available from Clariant Corporation;
Genapol UD-079®, which is available from Clariant Corporation;
Genapol UD-080®, which is available from Clariant Corporation;
Genapol UD-110®, which is available from Clariant Corporation;
Genapol X 030®, which is available from Clariant Corporation;
Genapol X 050®, which is available from Clariant Corporation;
Genapol X 060®, which is available from Clariant Corporation;
Genapol X 070®, which is available from Clariant Corporation;
Genapol X 080®, which is available from Clariant Corporation;
Genapol X 100®, which is available from Clariant Corporation;
Genapol X159®, which is available from Clariant Corporation;
Generol 122 E5®, which is available from Cognis Canada Corp.;
Generol 122 E25®, which is available from Cognis Canada Corp.;
Hostacerin T-3®, which is available from Clariant Corporation;
Iconol LF 110®, which is available from BASF Corp.;
Incropol CS-20®, which is available from Croda Inc.;
Lexemul CS-20®, which is available from Inolex Chemical Co.;
Liponic EG-1®, which is available from Lipo Chemicals, Inc.;
Lipowax D®, which is available from Lipo Chemicals, Inc.;
Lipowax G®, which is available from Lipo Chemicals, Inc.;
Lipowax NI®, which is available from Lipo Chemicals, Inc.;
Lipowax P®, which is available from Lipo Chemicals, Inc.;
Lipowax P-31®, which is available from Lipo Chemicals, Inc.;
Lipowax PR®, which is available from Lipo Chemicals, Inc.;
Lumulse CS-20®, which is available from Lambent Technologies Corp.;
Macol CSA-20®, which is available from BASF Corp.;
Marlox B 24/50®, which is available from Sasol North America Inc.;
Mazawet 77®, which is available from BASF Corp.;
Norfox 1713®, which is available from Norman, Fox & Co.;
Norfox 2579®, which is available from Norman, Fox & Co.;
Norfox Lo Foam®, which is available from Norman, Fox & Co.;
Promulgen D®, which is available from Amerchol Corp.;
Promulgen G®, which is available from Amerchol Corp.;
Renex 30®, which is available from Uniqema;
Renex 36®, which is available from Uniqema;
Rhodasurf A 24®, which is available from Rhodia, Inc.;
Rhodasurf AAE-10®, which is available from Rhodia, Inc.;
Rhodasurf BEH-25®, which is available from Rhodia, Inc.;
Rhodasurf BEH-40®, which is available from Rhodia, Inc.;
Rhodasurf DA 530®, which is available from Rhodia, Inc.;
Rhodasurf DA 630®, which is available from Rhodia, Inc.;
Rhodasurf DA 639®, which is available from Rhodia, Inc.;
Rhodasurf LAN-23®, which is available from Rhodia, Inc.;
Rhodasurf ON-870®, which is available from Rhodia, Inc.;
Rhodasurf ON-877®, which is available from Rhodia, Inc.;
Rhodasurf TB-970 FLK®, which is available from Rhodia, Inc.;
Ritacet-20®, which is available from RITA Corp.;
Ritachol 1000®, which is available from RITA Corp.;
Ritachol 2000®, which is available from RITA Corp.;
Ritachol 5000®, which is available from RITA Corp.;
Ritox 35®, which is available from RITA Corp.;
Surfonic DA-4®, which is available from Huntsman LLC;
Surfonic DA-6®, which is available from Huntsman LLC;
Surfonic L46-7®, which is available from Huntsman LLC;
Surfonic POA®, which is available from Huntsman LLC;
Synthrapol KB®, which is available from Uniqema;
Teginacid®, which is available from Goldschmidt Chemical Corp.;
Teginacid C®, which is available from Goldschmidt Chemical Corp.;
Tegotens EC 11®, which is available from Goldschmidt Chemical Corp.;
Tinegal NA®, which is available from Ciba Specialty Chemicals Corp.;
Tomadol 400®, which is available from Tomah Products®, Inc.;
Tomadol 600®, which is available from Tomah Products®, Inc.;
Tomadol 900®, which is available from Tomah Products®, Inc.;
Uniperol O®, which is available from BASF Corp.;
Witconol SN Series®, which is available from Crompton Corp.;

Ethoxylated Alkylphenols, including but not limited to,
Antarox LF-222®, which is available from Rhodia, Inc.;
Atlox 775®, which is available from Uniqema;
Caloxylate N-9®, which is available from Pilot Chemical Co.;
Canasol NF-1000®, which is available from Canamex Quimicos S.A de C.v;
Canasol NF-3000®, which is available from Canamex Quimicos S.A de C.v;
Canasol NF-3070®, which is available from Canamex Quimicos S.A de C.v;
Canasol OF 1670®, which is available from Canamex Quimicos S.A de C.v;
Canasol OF 2570®, which is available from Canamex Quimicos S.A de C.v;
Canasol OF 4070®, which is available from Canamex Quimicos S.A de C.v;
Chemax DNP-8®, which is available from Chemax Performance Solutions;
Chemax DNP-18®, which is available from Chemax Performance Solutions;
Chemax DNP-150/50®, which is available from Chemax Performance Solutions;
DeSonic 1.5N®, which is available from Crompton Corp.;
DeSonic 4N®, which is available from Crompton Corp.;
DeSonic 5N®, which is available from Crompton Corp.;
DeSonic 6D®, which is available from Crompton Corp.;
DeSonic 6N®, which is available from Crompton Corp.;
DeSonic 7N®, which is available from Crompton Corp.;
DeSonic 9N®, which is available from Crompton Corp.;
DeSonic 10D®, which is available from Crompton Corp.;
DeSonic 11N®, which is available from Crompton Corp.;
DeSonic 12N®, which is available from Crompton Corp.;
DeSonic 15N®, which is available from Crompton Corp.;
DeSonic 20N®, which is available from Crompton Corp.;
Eccoscour RC®, which is available from Eastern Color & Chemical Co.;
Eccoterge EO-100®, which is available from Eastern Color & Chemical Co.;
Emulsifier 632/90%®, which is available from Ethox Chemicals, LLC;
Geronol AG-821®, which is available from Rhodia, Inc.;
Gradonic N-95®, which is available from Graden Chemical Co. Inc.;
Hetoxide NP-4®, which is available from Global-Seven, Inc.;
Hetoxide NP-30®, which is available from Global-Seven, Inc.;
Hostapal N-100®, which is available from Clariant Corporation;
Hostapal N-110®, which is available from Clariant Corporation;
Igepal CTA-639W®, which is available from Rhodia, Inc.;
Igepal DAP-9®, which is available from Rhodia, Inc.;
Igepal OD-410®, which is available from Rhodia, Inc.;
Igepal SS-837®, which is available from Rhodia, Inc.;
Lipocol NP-9 USP®, which is available from Lipo Chemicals, Inc.;
Macol DNP-10®, which is available from BASF Corp.;
Marlophen NP 5®, which is available from Sasol North America Inc.;
Marlophen P 1®, which is available from Sasol North America Inc.;
Surfonic NB®, which is available from Huntsman LLC;
Surfonic OPB-307®, which is available from Huntsman LLC;
Surfonic OPB-407®, which is available from Huntsman LLC;
Syn Fac 334®, which is available from Milliken Chemical;
Syn Fac 8216®, which is available from Milliken Chemical;
Triton N-57®, which is available from Dow Chemical Company;
Trycol 6956®, which is available from Cognis Corporation;
Trycol 6961®, which is available from Cognis Corporation;
Trycol 6964®, which is available from Cognis Corporation;
Trycol 6969®, which is available from Cognis Corporation;
Trycol 6974®, which is available from Cognis Corporation;
Witbreak DRB-127®, which is available from Akzo Nobel Surface Chemistry LLC;
Witbreak DRB-127®, which is available from Crompton Corp.; and
Witconol NP Series®, which is available from Akzo Nobel Surface Chemistry LLC;

Ethoxylated Aryl Phenols, including but not limited to,
Soprophor BSU®, which is available from Rhodia, Inc.;
Soprophor CY/8®, which is available from Rhodia, Inc.;
Soprophor S/25®, which is available from Rhodia, Inc.;
Witconol NIO®, which is available from Akzo Nobel Surface Chemistry LLC;
Witconol NIW®, which is available from Akzo Nobel Surface Chemistry LLC; and
Witconol S-100®, which is available from Akzo Nobel Surface Chemistry LLC;

Ethoxylated Fatty Acids, including but not limited to,
Aldo PGHMS®, which is available from Lonza Inc.;
Alkamuls TO-15/HR®, which is available from Rhodia, Inc.;
Armotan AL-69-66®, which is available from Akzo Nobel Surface Chemistry LLC;
Cerasynt 840®, which is available from International Specialty Products/IS;
Cerasynt 945®, which is available from International Specialty Products/IS;
Crystal Inhibitor No. 5®, which is available from Harcros Chemicals Inc.;
DeThox Acid L-9®, which is available from DeForest Enterprises, Inc.;
DeThox Acid S-8®, which is available from DeForest Enterprises, Inc.;
Ethofat 242/25®, which is available from Akzo Nobel Surface Chemistry LLC;
Hydropalat 65®, which is available from Cognis Corporation;
Lipo EGMS®, which is available from Lipo Chemicals, Inc.;
Lipopeg 2 DL®, which is available from Lipo Chemicals, Inc.;
Lipopeg 4 DL®, which is available from Lipo Chemicals, Inc.;
Lipopeg 4-L®, which is available from Lipo Chemicals, Inc.;
Lipopeg 39-S®, which is available from Lipo Chemicals, Inc.;
Lipopeg 4-S®, which is available from Lipo Chemicals, Inc.;
Lipopeg 10-S®, which is available from Lipo Chemicals, Inc.;
Lipopeg 100-S®, which is available from Lipo Chemicals, Inc.;
Lipopeg 6000 DS®, which is available from Lipo Chemicals, Inc.;

Lumulse 40-L®, which is available from Lambent Technologies Corp.;
Lumulse 40-S®, which is available from Lambent Technologies Corp.;
Lumulse 42-L®, which is available from Lambent Technologies Corp.;
Lumulse 42-S®, which is available from Lambent Technologies Corp.;
Lumulse 100-S®, which is available from Lambent Technologies Corp.;
Lumulse 602-S®, which is available from Lambent Technologies Corp.;
Magrabar PGE-20-0®, which is available from Magrabar Chemical Corp.;
Magrabar PGE-20L®, which is available from Magrabar Chemical Corp.;
Magrabar PGE-20T®, which is available from Magrabar Chemical Corp.;
Magrabar PGE-22-0®, which is available from Magrabar Chemical Corp.;
Magrabar PGE-22L®, which is available from Magrabar Chemical Corp.;
Magrabar PGE-22T®, which is available from Magrabar Chemical Corp.;
Magrabar PGE-40-0®, which is available from Magrabar Chemical Corp.;
Magrabar PGE-40L®, which is available from Magrabar Chemical Corp.;
Magrabar PGE-40T®, which is available from Magrabar Chemical Corp.;
Magrabar PGE-42-0®, which is available from Magrabar Chemical Corp.;
Magrabar PGE-42L®, which is available from Magrabar Chemical Corp.;
Magrabar PGE-42T®, which is available from Magrabar Chemical Corp.;
Magrabar PGE-60-0®, which is available from Magrabar Chemical Corp.;
Magrabar PGE-60L®, which is available from Magrabar Chemical Corp.;
Magrabar PGE-60T®, which is available from Magrabar Chemical Corp.;
Magrabar PGE-62-0®, which is available from Magrabar Chemical Corp.;
Magrabar PGE-62L®, which is available from Magrabar Chemical Corp.;
Magrabar PGE-62T®, which is available from Magrabar Chemical Corp.;
Mapeg S-40K®, which is available from BASF Corp.;
Marlowet OTS®, which is available from Sasol North America Inc.;
Naturechem PGR®, which is available from CasChem®, Inc.;
PG No. 4®, which is available from Hart Chemical Corp.;
Renex 20®, which is available from Uniqema;
Ritox 52®, which is available from RITA Corp.;
Ritox 53®, which is available from RITA Corp.;
Ritox 59®, which is available from RITA Corp.;
Surfax 8916/A®, which is available from Houghton International Inc.;
Tego Acid S 40 P®, which is available from Goldschmidt Chemical Corp.;
Tego Acid S 100 P®, which is available from Goldschmidt Chemical Corp.;
Tween 20®, which is available from Uniqema; and
Volpo 131®, which is available from Croda Inc.;

Ethoxylated Fatty Esters or Oils (Animal & Veg.), including but not limited to,
Acconon 6-C10®, which is available from Abitec Corporation;
Acconon CC-6®, which is available from Abitec Corporation;
Acconon CO-7®, which is available from Abitec Corporation;
Aldosperse 40/60 FG®, which is available from Lonza Inc.;
Aldosperse ML-23®, which is available from Lonza Inc.;
Aldosperse MS-20 FG®, which is available from Lonza Inc.;
Alkamuls EL-620®, which is available from Rhodia, Inc.;
Alkamuls EL-719®, which is available from Rhodia, Inc.;
Alkamuls EL-985®, which is available from Rhodia, Inc.;
Arlatone G®, which is available from Uniqema;
Arlatone T®, which is available from Uniqema;
Atlas G-1045A®, which is available from Uniqema;
Atlas G-1086®, which is available from Uniqema;
Atlas G-1087®, which is available from Uniqema;
Atlas G-1089®, which is available from Uniqema;
Atlas G-1096®, which is available from Uniqema;
Atlas G-1292®, which is available from Uniqema;
Atlas G-1293®, which is available from Uniqema;
Atlas G-1300®, which is available from Uniqema;
Atlas G-7076®, which is available from Uniqema;
Capmul EMG®, which is available from Abitec Corporation;
Chemonic CO-40®, which is available from Chemron Corp.;
Chemonic LI-3®, which is available from Chemron Corp.;
Chemonic LI-7®, which is available from Chemron Corp.;
Cirrasol GM®, which is available from Uniqema;
Cremophor CO 40®, which is available from BASF Corp.;
Cremophor CO 410®, which is available from BASF Corp.;
Cremophor EL®, which is available from BASF Corp.;
Cremophor GC7®, which is available from BASF Corp.;
Cremophor RH-40®, which is available from BASF Corp.;
Crovol A-40®, which is available from Croda Inc.;
Crovol A-70®, which is available from Croda Inc.;
Crovol M-70®, which is available from Croda Inc.;
Crovol PK-70®, which is available from Croda Inc.;
Cutina E-24®, which is available from Cognis Canada Corp.;
Dacospin 12-R®, which is available from Cognis Corporation;
Dehymuls HRE-7®, which is available from Cognis Corporation;
DeSonic 30C®, which is available from Crompton Corp.;
DeSonic 36C®, which is available from Crompton Corp.;
DeSonic 40C®, which is available from Crompton Corp.;
Durfax 60®, which is available from Loders Croklaan U.S.A.;
Durfax 65®, which is available from Loders Croklaan U.S.A.;
Durfax 80®, which is available from Loders Croklaan U.S.A.;
Durfax EOM®, which is available from Loders Croklaan U.S.A.;
Eccoterge NF-2®, which is available from Eastern Color & Chemical Co.;
Emulpon CO-360®, which is available from Akzo Nobel Surface Chemistry LLC;
Emulpon CO-550®, which is available from Akzo Nobel Surface Chemistry LLC;
Emulsogen EL®, which is available from Clariant Corporation;

Emulsogen HCO 040®, which is available from Clariant Corporation;
Emulsogen HCO 060®, which is available from Clariant Corporation;
Emulsynt 1055®, which is available from International Specialty Products/IS;
Ethox 3095®, which is available from Ethox Chemicals, LLC;
Eumulgin RO-40®, which is available from Cognis Canada Corp.;
Genapol G-260®, which is available from Clariant Corporation;
Glycosperse L-20®, which is available from Lonza Inc.;
Glycosperse O-5®, which is available from Lonza Inc.;
Glycosperse O-20®, which is available from Lonza Inc.;
Glycosperse O-20 FG®, which is available from Lonza Inc.;
Glycosperse S-20®, which is available from Lonza Inc.;
Glycosperse S-20 FG®, which is available from Lonza Inc.;
Glycosperse TS-20®, which is available from Lonza Inc.;
Glycosperse TS-20 FG®, which is available from Lonza Inc.;
Hetan SL®, which is available from Global-Seven, Inc.;
Hetan SO®, which is available from Global-Seven, Inc.;
Hetan SS®, which is available from Global-Seven, Inc.;
Hetoxide C-2®, which is available from Global-Seven, Inc.;
Hetoxide C-9®, which is available from Global-Seven, Inc.;
Hetoxide C-15®, which is available from Global-Seven, Inc.;
Hetoxide C-25®, which is available from Global-Seven, Inc.;
Hetoxide C-40®, which is available from Global-Seven, Inc.;
Hetoxide C-200®, which is available from Global-Seven, Inc.;
Hetoxide C-200-50%®, which is available from Global-Seven, Inc.;
Hetoxide GC-30®, which is available from Global-Seven, Inc.;
Hetoxide HC-60®, which is available from Global-Seven, Inc.;
Ice No. 2®, which is available from Loders Croklaan U.S.A.;
Incrocas 30/40®, which is available from Croda Inc.;
Lexol EC®, which is available from Inolex Chemical Co.;
Lexol EO®, which is available from Inolex Chemical Co.;
Lipocol HCO-40®, which is available from Lipo Chemicals, Inc.;
Lipocol HCO-60®, which is available from Lipo Chemicals, Inc.;
Lipocol O-3 Special®, which is available from Lipo Chemicals, Inc.;
Lipopeg 2-L®, which is available from Lipo Chemicals, Inc.;
Lipopeg 4-DO®, which is available from Lipo Chemicals, Inc.;
Lipopeg 4-DS®, which is available from Lipo Chemicals, Inc.;
Lipovol GTB®, which is available from Lipo Chemicals, Inc.;
Lonzest SML-20®, which is available from Lonza Inc.;
Lonzest SMO-20®, which is available from Lonza Inc.;
Lonzest SMS-20®, which is available from Lonza Inc.;
Lonzest STO-20®, which is available from Lonza Inc.;
Lonzest STS-20®, which is available from Lonza Inc.;
Lumulse GR-40®, which is available from Lambent Technologies Corp.;
Lumulse GRH-40®, which is available from Lambent Technologies Corp.;
Lumulse POE (7) GML®, which is available from Lambent Technologies Corp.;
Lumulse POE (12) Glyc®, which is available from Lambent Technologies Corp.;
Lumulse POE (40) MS KP®, which is available from Lambent Technologies Corp.;
Marlowet 4750®, which is available from Sasol North America Inc.;
Marlowet LVS®, which is available from Sasol North America Inc.;
Marlowet R 11®, which is available from Sasol North America Inc.;
Marlowet R 40®, which is available from Sasol North America Inc.;
Mazol 80 MGK®, which is available from BASF Corp.;
Nonionic Emulsifier T-9®, which is available from Werner G. Smith Inc.;
Oronal LCG®, which is available from Seppic Inc.;
Polyderm PPI-CO-200®, which is available from Alzo International, Inc.;
Polyderm PPI-CO-40®, which is available from Alzo International, Inc.;
Rewoderm LI 520-70®, which is available from Goldschmidt Chemical Corp.;
Ritapeg 150 DS®, which is available from RITA Corp.;
Softigen 767®, which is available from Sasol North America Inc.;
Surfactol 318®, which is available from CasChem®, Inc.;
Surfactol 365®, which is available from CasChems, Inc.;
Syn Lube 107®, which is available from Milliken Chemical;
Syn Lube 728®, which is available from Milliken Chemical;
Syn Lube 1632H®, which is available from Milliken Chemical;
Syn Lube 6277-A®, which is available from Milliken Chemical;
T-Det C-20®, which is available from Harcros Chemicals Inc.;
T-Det C-40®, which is available from Harcros Chemicals Inc.;
Tally 100 Plus®, which is available from Loders Croklaan U.S.A.; and
Uniperol EL®, which is available from BASF Corp.;

Fatty Esters, including but not limited to,
Actralube-Syn 147®, which is available from Georgia-Pacific Corp.;
Atlas G-1556®, which is available from Uniqema;
Atlas G-1564®, which is available from Uniqema;
Atlasol Base Oil S®, which is available from Atlas Refinery Inc.;
Base ML®, which is available from Keil Chemical;
Base MT®, which is available from Keil Chemical;
Cerasynt 303®, which is available from International Specialty Products/IS;
Dermol 1012®, which is available from Alzo International, Inc.;
Kemester 4000®, which is available from Crompton Corp.;
Lactipol S®, which is available from Canamex Quimicos S.A de C.v;
Magrabar PGO®, which is available from Magrabar Chemical Corp.;
Mayco Base BFO®, which is available from Dover Chemical Corp.;
Methyl Linoleate®, which is available from Hart Chemical Corp.;

Pationic 122A®, which is available from RITA Corp.;
Pationic 138C®, which is available from RITA Corp.;
Pationic CSL®, which is available from RITA Corp.;
Pationic ISL®, which is available from RITA Corp.;
Pationic SBL®, which is available from RITA Corp.;
Pationic SSL®, which is available from RITA Corp.;
Ritasol®, which is available from RITA Corp.;
Tego Alkanol CS 20®, which is available from Goldschmidt Chemical Corp.;
Tego Alkanol L23 P®, which is available from Goldschmidt Chemical Corp.;
Tego Alkanol S2®, which is available from Goldschmidt Chemical Corp.;
Tego Alkanol S20 P®, which is available from Goldschmidt Chemical Corp.; and
Triemulsifier 600 MS®, which is available from Tri-Tex Co.®, Inc.;

Glycerol Esters, including but not limited to,
Agro #9 Wint SBO®, which is available from Lambent Technologies Corp.;
Ahcovel Base 700®, which is available from Uniqema;
Ado HMS FG®, which is available from Lonza Inc.;
Aldo MLD®, which is available from Lonza Inc.;
Aldo MLD FG®, which is available from Lonza Inc.;
Aldo MO FG®, which is available from Lonza Inc.;
Aldo MS®, which is available from Lonza Inc.;
Aldo MS FG®, which is available from Lonza Inc.;
Aldo MS LG FG®, which is available from Lonza Inc.;
Aldo MSD®, which is available from Lonza Inc.;
Aldo MSD FG®, which is available from Lonza Inc.;
Aldosperse O-20 FG®, which is available from Lonza Inc.;
Aldosperse TS-20 FG®, which is available from Lonza Inc.;
Aldosperse TS-40 FG®, which is available from Lonza Inc.;
Arlacel 165®, which is available from Uniqema;
Arlacel 186®, which is available from Uniqema;
Capmul GMO®, which is available from Abitec Corporation;
Capmul GMS®, which is available from Abitec Corporation;
Caprol 3GO®, which is available from Abitec Corporation;
Caprol 3GVS®, which is available from Abitec Corporation;
Caprol 6G2S®, which is available from Abitec Corporation;
Caprol 10G40®, which is available from Abitec Corporation;
Caprol 10G100®, which is available from Abitec Corporation;
Caprol ET®, which is available from Abitec Corporation;
Caprol PGE860®, which is available from Abitec Corporation;
Cerasynt 945®, which is available from International Specialty Products/IS;
Cerasynt GMS®, which is available from International Specialty Products/IS;
Cerasynt Q®, which is available from International Specialty Products/IS;
Cerasynt SD®, which is available from International Specialty Products/IS;
Cerasynt WM®, which is available from International Specialty Products/IS;
Chemsperse 14®, which is available from Chemron Corp.;
Cremophor GO-32®, which is available from BASF Corp.;
Cremophor GS11®, which is available from BASF Corp.;
Cremophor GS-32®, which is available from BASF Corp.;
Cutina KD-16®, which is available from Cognis Canada Corp.;
Dehymuls PGPH®, which is available from Cognis Corporation;
Dermol DGDIS®, which is available from Alzo International, Inc.;
Dermol DGMIS®, which is available from Alzo International, Inc.;
Dermol G-76®, which is available from Alzo International, Inc.;
Dermol G-7DI®, which is available from Alzo International, Inc.;
Dermol NGDI®, which is available from Alzo International, Inc.;
Dermolan GLH®, which is available from Alzo International, Inc.;
Drewmulse GMO®, which is available from Stepan Company;
Drewpol 3-5-M®, which is available from Stepan Company;
Durlac 100 W®, which is available from Loders Croklaan U.S.A.;
Dur-Lo®, which is available from Loders Croklaan U.S.A.;
Dynasan 118®, which is available from Sasol North America Inc.;
EC-25®, which is available from Loders Croklaan U.S.A.;
EM 40®, which is available from Keil Chemical;
Emerest 2400®, which is available from Cognis Corporation;
Emerest 2452®, which is available from Cognis Corporation;
Empilan G-26®, which is available from Huntsman LLC;
Genapol TSM®, which is available from Clariant Corporation;
Hostacerin DGI®, which is available from Clariant Corporation;
Hostacerin DGL®, which is available from Clariant Corporation;
Hostacerin DGMS®, which is available from Clariant Corporation;
Hostacerin DGSB®, which is available from Clariant Corporation;
Ice No. 2®, which is available from Loders Croklaan U.S.A.;
Imwitor 742®, which is available from Sasol North America Inc.;
Imwitor 780 K®, which is available from Sasol North America Inc.;
Imwitor 960 Flakes®, which is available from Sasol North America Inc.;
Isolan GI 34®, which is available from Goldschmidt Chemical Corp.;
Isolan GO 33®, which is available from Goldschmidt Chemical Corp.;
Kemester 1000®, which is available from Crompton Corp.;
Kemester 2000®, which is available from Crompton;
Kemester 2000®, which is available from Crompton Corp.;
Kemester 6000SE®, which is available from Crompton Corp.;
Lamecreme DGE 18®, which is available from Cognis Corporation;
Lexemul 515®, which is available from Inolex Chemical Co.;
Lexemul 561®, which is available from Inolex Chemical Co.;
Lexemul AR®, which is available from Inolex Chemical Co.;
Lexemul AS®, which is available from Inolex Chemical Co.;

Lexemul GDL®, which is available from Inolex Chemical Co.;
Lexemul T®, which is available from Inolex Chemical Co.;
Lipomulse 165®, which is available from Lipo Chemicals, Inc.;
Lumulse GML K®, which is available from Lambent Technologies Corp.;
Lumulse GMO K®, which is available from Lambent Technologies Corp.;
Lumulse GMR K®, which is available from Lambent Technologies Corp.;
Lumulse GMT K®, which is available from Lambent Technologies Corp.;
Magrabar GMC®, which is available from Magrabar Chemical Corp.;
Magrabar GMO-CK®, which is available from Magrabar Chemical Corp.;
Magrabar MDG-5050®, which is available from Magrabar Chemical Corp.;
Magrabar PGO-315®, which is available from Magrabar Chemical Corp.;
Magrabar PGO-1010®, which is available from Magrabar Chemical Corp.;
Mazol 300K®, which is available from BASF Corp.;
Mazol GMO-K®, which is available from BASF Corp.;
Mazol GMS-K®, which is available from BASF Corp.;
Mazol PG031-K®, which is available from BASF Corp.;
Miglyol 812®, which is available from Sasol North America Inc.;
Norfox 165C®, which is available from Norman, Fox & Co.;
Schercemol GMIS®, which is available from Noveon®, Inc.;
Tegin®, which is available from Goldschmidt Chemical Corp.;
Tegin 4100 Pellets®, which is available from Goldschmidt Chemical Corp.;
Tegin M Pellets®, which is available from Goldschmidt Chemical Corp.;
Tegin OV®, which is available from Goldschmidt Chemical Corp.;
Teginacid H®, which is available from Goldschmidt Chemical Corp.;
Tego Cosmo P813®, which is available from Goldschmidt Chemical Corp.;
Wickenol 535®, which is available from Alzo International, Inc.;
Witconol 14®, which is available from Akzo Nobel Surface Chemistry LLC;
Witconol 14®, which is available from Crompton Corp.;
Witconol 14F®, which is available from Crompton Corp.;
Witconol 18L®, which is available from Crompton Corp.;
Witconol GOT®, which is available from Crompton Corp.;
Witconol MST®, which is available from Crompton Corp.; and
Witconol RHT®, which is available from Crompton Corp.;

Glycol Esters, including but not limited to,
Alkamuls 600 DO®, which is available from Rhodia, Inc.;
Alkamuls SEG®, which is available from Rhodia, Inc.;
Atlas EM-2®, which is available from Atlas Refinery Inc.;
Cerasynt IP®, which is available from International Specialty Products/IS;
Cerasynt M®, which is available from International Specialty Products/IS;
Cerasynt MN®, which is available from International Specialty Products/IS;
Cerasynt PA®, which is available from International Specialty Products/IS;
Chemsperse EGDS®, which is available from Chemron Corp.;
Chemsperse EGMS®, which is available from Chemron Corp.;
Colonial Monolaurin®, which is available from Colonial Chemical Co.;
DeMuls SGE-95®, which is available from DeForest Enterprises, Inc.;
Eccoterge 200®, which is available from Eastern Color & Chemical Co.;
Emerest 2380®, which is available from Cognis Corporation;
Ethox 2610®, which is available from Ethox Chemicals, LLC;
Ethox DO-9®, which is available from Ethox Chemicals, LLC;
Ethox DO-14®, which is available from Ethox Chemicals, LLC;
Ethox SO-9®, which is available from Ethox Chemicals, LLC;
Fizul MD-318®, which is available from Finetex Inc.;
Genapol EGDS-VHP®, which is available from Clariant Corporation;
Genapol TS Powder®, which is available from Clariant Corporation;
Hostacerin WO®, which is available from Clariant Corporation;
Inversol 140®, which is available from Keil Chemical;
Kemester 104®, which is available from Crompton Corp.;
Kemester 205®, which is available from Crompton Corp.;
Kemester 226®, which is available from Crompton Corp.;
Kemester 5221SE®, which is available from Crompton Corp.;
Kemester EGDS®, which is available from Crompton Corp.;
Lexemul EGDS®, which is available from Inolex Chemical Co.;
Lexemul EGMS®, which is available from Inolex Chemical Co.;
Lexemul P®, which is available from Inolex Chemical Co.;
Lipo DGLS®, Self-Emulsifying®, which is available from Lipo Chemicals, Inc.;
Lipo EGDS®, which is available from Lipo Chemicals, Inc.;
Lipo PGMS®, which is available from Lipo Chemicals, Inc.;
Liposorb S-4®, which is available from Lipo Chemicals, Inc.;
Liposorb TO-20®, which is available from Lipo Chemicals, Inc.;
Lumulse PGO®, which is available from Lambent Technologies Corp.;
Mackester EGDS®, which is available from The McIntyre Group;
Mackester EGMS®, which is available from The Mcintyre Group;
Mackester GSTP®, which is available from The McIntyre Group;
Mackester Series®, which is available from The McIntyre Group;
Magrabar PDG-50®, which is available from Magrabar Chemical Corp.;
Mapeg 6000 DS®, which is available from BASF Corp.;
Marlowet 4702®, which is available from Sasol North America Inc.;
Monalube 305®, which is available from Uniqema;

Monalube 310®, which is available from Uniqema;
Monalube 315®, which is available from Uniqema;
Monalube 320®, which is available from Uniqema;
Monalube 325®, which is available from Uniqema;
Monalube 330®, which is available from Uniqema;
Naturechem PGHS®, which is available from CasChem®, Inc.;
Polycastorol PLO-840®, which is available from Magrabar Chemical Corp.;
Polytex 10M®, which is available from Lipo Chemicals, Inc.;
Ritasynt IP®, which is available from RITA Corp.;
Ross Chem PEG 600 DT®, which is available from Lubrizol Foam Control Additives;
Schercemol PGMS®, which is available from Noveon®, Inc.;
Sponto H-44C®, which is available from Crompton Corp.;
Tegin G®, which is available from Goldschmidt Chemical Corp.;
Witbreak DGE-182®, which is available from Akzo Nobel Surface Chemistry LLC;
Witbreak DGE-182®, which is available from Crompton Corp.;
Witbreak DRA-21®, which is available from Akzo Nobel Surface Chemistry LLC;
Witbreak DRA-21®, which is available from Crompton Corp.;
Witbreak DRA-50®, which is available from Akzo Nobel Surface Chemistry LLC;
Witbreak DRA-50®, which is available from Crompton Corp.;
Witconol F26-46®, which is available from Crompton Corp.;
Witconol H-32®, which is available from Akzo Nobel Surface Chemistry LLC;
Witconol H-33®, which is available from Akzo Nobel Surface Chemistry LLC;
Witconol H-35A®, which is available from Crompton Corp.; and
Witconol RHP®, which is available from Crompton Corp.;

Lanolin-based Derivatives, including but not limited to,
Amerchol CAB®, which is available from Amerchol Corp.;
Amerchol L-101®, which is available from Amerchol Corp.;
Amerlate LFA-LO®, which is available from Amerchol Corp.;
Amerlate P®, which is available from Amerchol Corp.;
Barre Common Degras®, which is available from RITA Corp.;
Cholesterol NF®, which is available from Croda Inc.;
Crodalan AWS®, which is available from Croda Inc.;
Crodalan LA®, which is available from Croda Inc.;
Emery 1650®, which is available from Cognis Canada Corp.;
Emery 1650®, which is available from Cognis Corporation;
Emery 1740®, which is available from Cognis Canada Corp.;
Emery 1740®, which is available from Cognis Corporation;
Forlan 500®, which is available from RITA Corp.;
Forlan L®, which is available from RITA Corp.;
Laneto 50®, which is available from RITA Corp.;
Laneto 100®, which is available from RITA Corp.;
Laneto AWS®, which is available from RITA Corp.;
Lanfrax 1776®, which is available from Cognis Canada Corp.;
Lanfrax 1776®, which is available from Cognis Corporation;
Lanogel 21®, which is available from Amerchol Corp.;
Lipolan®, which is available from Lipo Chemicals, Inc.;
Lipolan 31®, which is available from Lipo Chemicals, Inc.;
OHlan®, which is available from Amerchol Corp.;
Polychol 5®, which is available from Croda Inc.;
Polychol 15®, which is available from Croda Inc.;
Ritacetyl®, which is available from RITA Corp.;
Ritachol®, which is available from RITA Corp.;
Ritahydrox®, which is available from RITA Corp.;
Ritalafa®, which is available from RITA Corp.;
Ritalan®, which is available from RITA Corp.;
Ritalan AWS®, which is available from RITA Corp.;
Ritalan C®, which is available from RITA Corp.;
Ritawax®, which is available from RITA Corp.;
Ritawax AEO®, which is available from RITA Corp.;
Ritawax ALA®, which is available from RITA Corp.;
Solan/Solan 50/Super Solan®, which is available from Croda Inc.;
Super Hartolan/Hartolan®, which is available from Croda Inc.;
Supersat AWS-4®, which is available from RITA Corp.; and
Supersat AWS-24®, which is available from RITA Corp.;

Lecithin and Lecithin Derivatives, including but not limited to,
Alcolec®, which is available from American Lecithin Co.;
Lecithin®, which is available from Archer Daniels Midland Company;
Lexin K®, which is available from American Lecithin Co.; and
Natipide®, which is available from American Lecithin Co.;

Lignin and Lignin Derivatives, including but not limited to,
Diwatex XP 9®, which is available from Borregaard Lignotech USA Inc.;
Dynasperse LCD®, which is available from Borregaard Lignotech USA Inc.;
Indulin SAL®, which is available from MeadWestvaco Corp.;
Indulin W-1®, which is available from MeadWestvaco Corp.;
Indulin W-5®, which is available from MeadWestvaco Corp.;
Lignosol FTA®, which is available from Borregaard Lignotech USA Inc.;
Lignosol SFX-65®, which is available from Borregaard Lignotech USA Inc.;
Marasperse 52 CP®, which is available from Borregaard Lignotech USA Inc.;
Marasperse AG®, which is available from Borregaard Lignotech USA Inc.;
Marasperse CBOS-4®, which is available from Borregaard Lignotech USA Inc.; and
Ufoxane 2®, which is available from Borregaard Lignotech USA Inc.;

Methyl Esters, including but not limited to,
E.B. Cleaner AK®, which is available from Eastern Color & Chemical Co.;
Oleocal ME-70®, which is available from Lambent Technologies Corp.;
Oleocal ME-92®, which is available from Lambent Technologies Corp.;
Oleocal ME-112®, which is available from Lambent Technologies Corp.; and
Oleocal ME-130®, which is available from Lambent Technologies Corp.;

Monoglycerides and Derivatives, including but not limited to,

Dynacet 211®, which is available from Sasol North America Inc.;
Hetsorb S-20®, which is available from Global-Seven, Inc.;
Imwitor 191®, which is available from Sasol North America Inc.;
Imwitor 370®, which is available from Sasol North America Inc.;
Imwitor 375®, which is available from Sasol North America Inc.;
Imwitor 900®, which is available from Sasol North America Inc.;
Imwitor 945®, which is available from Sasol North America Inc.;
Imwitor 2020®, which is available from Sasol North America Inc.;
Kemester 5500®, which is available from Crompton Corp.;
Kemester 6000®, which is available from Crompton Corp.;
Magrabar GMC®, which is available from Magrabar Chemical Corp.;
Magrabar GMO-CK®, which is available from Magrabar Chemical Corp.;
Magrabar GPC-10®, which is available from Magrabar Chemical Corp.;
Magrabar MDG-5050®, which is available from Magrabar Chemical Corp.;
Monalube 335®, which is available from Uniqema;
Monoglycerides Glyceryl Monestearate Archer Daniels Midland Company;
Rita GMS®, which is available from RITA Corp.;
Ritamulse SCG®, which is available from RITA Corp.;
Softigen 701®, which is available from Sasol North America Inc.; and
Tally 100 Plus®, which is available from Loders Croklaan U.S.A.;

Polyethylene Glycols, including but not limited to,
Emulgade PL 68/50®, which is available from Cognis Corporation;
Lumulse PEG®, which is available from Lambent Technologies Corp.;
Rhodasurf PEG-400®, which is available from Rhodia, Inc.;
Rhodasurf PEG-600®, which is available from Rhodia, Inc.; and
Witconol PEG-400®, which is available from Akzo Nobel Surface Chemistry LLC;

Polymeric Surfactants, including but not limited to,
Acritamer PNC-EG®, which is available from RITA Corp.;
Ag-Rho DEP-775®, which is available from Rhodia, Inc.;
APG 325N Glycoside®, which is available from Cognis Corporation;
Aristoflex AVC®, which is available from Clariant Corporation;
Aristoflex HMB®, which is available from Clariant Corporation;
Burco NPS-225®, which is available from Burlington Chemical Co.®, Inc.;
Burco NPS-816®, which is available from Burlington Chemical Co.®, Inc.;
Chemccinate 5603®, which is available from Chemron Corp.;
Cosmedia Guar C-261N®, which is available from Cognis Corporation;
Gantrez S-95®, which is available from International Specialty Products/IS;
Glucopon 220 UP®, which is available from Cognis Corporation;
Glucopon 225 DK®, which is available from Cognis Corporation;
Glucopon 425 N®, which is available from Cognis Corporation;
Glucopon 600 UP®, which is available from Cognis Corporation;
Glucopon 625 UP®, which is available from Cognis Corporation;
Pemulen 1621®, which is available from Noveon®, Inc.;
Pemulen 1622®, which is available from Noveon®, Inc.;
Pemulen TR-1®, which is available from Noveon®, Inc.;
Pemulen TR-2®, which is available from Noveon®, Inc.;
Plantacare 818®, which is available from Cognis Corporation;
Plantapon LGC Sorb®, which is available from Cognis Corporation;
Plantaren 1200N®, which is available from Cognis Corporation;
Plantaren 2000N®, which is available from Cognis Corporation;
Viscolam AT 64®, which is available from RITA Corp.;
Viscolam AT 64P®, which is available from RITA Corp.;
Viscolam AT 100®, which is available from RITA Corp.;
Viscolam MAC 7®, which is available from RITA Corp.;
Viscolam SMC 20®, which is available from RITA Corp.;
Witbreak RTC-323®, which is available from Crompton Corp.; and
WSI 3700®, which is available from Jacam Chemicals, L.L.C.;

Propoxylated & Ethoxylated Fatty Acids, Alcohols, or Alkyl Phenols, including but not limited to,
Antarox AA-60®, which is available from Rhodia, Inc.;
Antarox LF-224®, which is available from Rhodia, Inc.;
Burcomul DFE-45®, which is available from Burlington Chemical Co.®, Inc.;
Burcoterge LFE-1000®, which is available from Burlington Chemical Co.®, Inc.;
Chemal LF-25B®, which is available from Chemax Performance Solutions;
Chemal LF-40B®, which is available from Chemax Performance Solutions;
Dehypon LS-36®, which is available from Cognis Canada Corp.;
Dehypon LS-36®, which is available from Cognis Corporation;
Dehypon LS-54®, which is available from Cognis Canada Corp.;
Dehypon LS-54®, which is available from Cognis Corporation;
Delonic 100 VLF®, which is available from DeForest Enterprises, Inc.;
Delonic LF-60 MOD®, which is available from DeForest Enterprises, Inc.;
Empiderm B®, which is available from Huntsman LLC;
Ethylan 1206®, which is available from Akzo Nobel Surface Chemistry LLC;
Ethylan NS-500K®, which is available from Akzo Nobel Surface Chemistry LLC;
Ethylan NS-500LQ®, which is available from Akzo Nobel Surface Chemistry LLC;
Genapol 1392®, which is available from Clariant Corporation;
Genapol 2317®, which is available from Clariant Corporation;

Genapol 26EP710®, which is available from Clariant Corporation;
Genapol EP 1022®, which is available from Clariant Corporation;
Genapol EP 1024®, which is available from Clariant Corporation;
Genapol EP 6068®, which is available from Clariant Corporation;
Genapol NP915®, which is available from Clariant Corporation;
Kieralon MFB®, which is available from BASF Corp.;
Lumisolve CSA-80 V®, which is available from Lambent Technologies Corp.;
Marlowet 5001®, which is available from Sasol North America Inc.;
Marlox FK 64®, which is available from Sasol North America Inc.;
Marlox MO 124®, which is available from Sasol North America Inc.;
Marlox S 58®, which is available from Sasol North America Inc.;
Nonatell 1003®, which is available from Tomah Products®, Inc.;
Nonatell 1038®, which is available from Tomah Products®, Inc.;
Nonatell 1052®, which is available from Tomah Products®, Inc.;
Nonatell 1061®, which is available from Tomah Products®, Inc.;
Nonatell 1075®, which is available from Tomah Products®, Inc.;
Nonatell 1088®, which is available from Tomah Products®, Inc.;
Nonatell 1123®, which is available from Tomah Products®, Inc.;
Nonatell 1153®, which is available from Tomah Products®, Inc.;
Nonatell 1161®, which is available from Tomah Products®, Inc.;
Nonatell 1172®, which is available from Tomah Products®, Inc.;
Nonatell 1181®, which is available from Tomah Products®, Inc.;
Norfox 36®, which is available from Norman, Fox & Co.;
Procetyl AWS®, which is available from Croda Inc.;
Sandoxylate SX 412® Liquid, which is available from Clariant Corporation;
Sandoxylate SX 418®, which is available from Clariant Corporation;
Surfonic JL-80X®, which is available from Huntsman LLC;
Surfonic JL-80X-B1®, which is available from Huntsman LLC;
Surfonic L4-29X®, which is available from Huntsman LLC;
Surfonic LF®, which is available from Huntsman LLC;
T-Det A826®, which is available from Harcros Chemicals Inc.;
T-Det LF-416®, which is available from Harcros Chemicals Inc.;
Tergitol Min-Foam 1X®, which is available from Dow Chemical Company;
Tergitol Min-Foam 2X®, which is available from Dow Chemical Company;
Triton CF-21®, which is available from Dow Chemical Company;
Triton CF-76®, which is available from Dow Chemical Company;
Triton XL-80N®, which is available from Dow Chemical Company;
Witconol NS-98®, which is available from Akzo Nobel Surface Chemistry LLC;
Witconol NS-108LQ®, which is available from Akzo Nobel Surface Chemistry LLC;
Witconol NS-145®, which is available from Akzo Nobel Surface Chemistry LLC; and
Witconol NS-179®, which is available from Akzo Nobel Surface Chemistry LLC;

Protein-based Surfactants, including but not limited to,
AminoFoam W®, which is available from Croda Inc.;
Amiter LGOD-2®, which is available from Ajinomoto USA, Inc.;
Amiter LGS-2®, which is available from Ajinomoto USA, Inc.;
Amiter LGS-5®, which is available from Ajinomoto USA, Inc.;
Lamepon S®, which is available from Cognis Canada Corp.;
Lamepon S®, which is available from Cognis Corporation;
Maypon 4C®, which is available from Inolex Chemical Co.;
May-Tein C®, which is available from Maybrook, Inc.;
May-Tein CT®, which is available from Maybrook, Inc.;
May-Tein KTS®, which is available from Maybrook, Inc.;
May-Tein SY®, which is available from Maybrook, Inc.;
Plantapon S®, which is available from Cognis Corporation;
Proteol APL®, which is available from Seppic Inc.;
Proteol OAT®, which is available from Seppic Inc.;
Pyroter CPI-40®, which is available from Ajinomoto USA, Inc.;
Pyroter GPI-25®, which is available from Ajinomoto USA, Inc.;
Supro-Tein S®, which is available from Maybrook, Inc.; and
Supro-Tein V®, which is available from Maybrook, Inc.;

Sarcosine Derivatives, including but not limited to,
Crodasinic LS-30®, which is available from Croda Inc.;
Vanseal CS®, which is available from R. T. Vanderbilt Co. Inc.;
Vanseal LS®, which is available from R. T. Vanderbilt Co. Inc.;
Vanseal MS®, which is available from R. T. Vanderbilt Co. Inc.;
Vanseal NACS-30®, which is available from R. T. Vanderbilt Co. Inc.;
Vanseal NALS-95®, which is available from R. T. Vanderbilt Co. Inc.; and
Vanseal OS®, which is available from R. T. Vanderbilt Co. Inc.;

Silicone-based Surfactants, including but not limited to,
Abil-B-9950®, which is available from Goldschmidt Chemical Corp.;
Abil Care 85®, which is available from Goldschmidt Chemical Corp.;
Abil EM 90®, which is available from Goldschmidt Chemical Corp.;
Abil EM 97®, which is available from Goldschmidt Chemical Corp.;
Abil WE-09®, which is available from Goldschmidt Chemical Corp.;
Dow Corning 1248 Fluid®, which is available from Dow Corning Corp.;
Dow Corning 3225C® Formulation Aid, which is available from Dow Corning Corp.;
Dow Corning 5200® Formulation Aid, which is available from Dow Corning Corp.;

Dow Corning Q4-3667® Fluid, which is available from Dow Corning Corp.;
Monasil PCA®, which is available from Uniqema;
Monasil PDM®, which is available from Uniqema;
Monasil PLN®, which is available from Uniqema;
Polyderm PPI-SI-WS®, which is available from Alzo International, Inc.;
Troysol 380W®, which is available from Troy Corporation; and
Troysol S366®, which is available from Troy Corporation;

Sorbitan Derivatives, including but not limited to,
Alkamuls SML®, which is available from Rhodia, Inc.;
Alkamuls SMO®, which is available from Rhodia, Inc.;
Alkamuls STO®, which is available from Rhodia, Inc.;
Arlacel 20®, which is available from Uniqema;
Arlacel 40®, which is available from Uniqema;
Arlacel 60®, which is available from Uniqema;
Arlacel 80®, which is available from Uniqema;
Arlacel C®, which is available from Uniqema;
Armul 21®, which is available from Crompton Corp.;
Atlox 80®, which is available from Uniqema;
Atlox 847®, which is available from Uniqema;
Atlox 1045A®, which is available from Uniqema;
Canarcel 20®, which is available from Canamex Quimicos S.A de C.v;
Canarcel 60®, which is available from Canamex Quimicos S.A de C.v;
Canarcel 80®, which is available from Canamex Quimicos S.A de C.v;
Canarcel TW 20®, which is available from Canamex Quimicos S.A de C.v;
Canarcel TW 60®, which is available from Canamex Quimicos S.A de C.v;
Canarcel TW 80®, which is available from Canamex Quimicos S.A de C.v;
Coladet BSB-P®, which is available from Colonial Chemical Co.;
Customulse O-20®, which is available from Custom Ingredients, Inc.;
Dehymuls E®, which is available from Cognis Canada Corp.;
DeSotan SMO®, which is available from Crompton Corp.;
DeSotan SMO-20®, which is available from Crompton Corp.;
DeSotan SMT®, which is available from Crompton Corp.;
DeSotan SMT-20®, which is available from Crompton Corp.;
Durfax 60®, which is available from Loders Croklaan U.S.A.;
Durfax 65®, which is available from Loders Croklaan U.S.A.;
Durfax 80®, which is available from Loders Croklaan U.S.A.;
Durtan 60®, which is available from Loders Croklaan U.S.A.;
Durtan 65®, which is available from Loders Croklaan U.S.A.;
Liposorb L®, which is available from Lipo Chemicals, Inc.;
Liposorb L-10®, which is available from Lipo Chemicals, Inc.;
Liposorb L-20®, which is available from Lipo Chemicals, Inc.;
Liposorb O®, which is available from Lipo Chemicals, Inc.;
Liposorb O-20®, which is available from Lipo Chemicals, Inc.;
Liposorb P®, which is available from Lipo Chemicals, Inc.;
Liposorb P-20®, which is available from Lipo Chemicals, Inc.;
Liposorb S®, which is available from Lipo Chemicals, Inc.;
Liposorb S-20®, which is available from Lipo Chemicals, Inc.;
Liposorb SQO®, which is available from Lipo Chemicals, Inc.;
Liposorb TO®, which is available from Lipo Chemicals, Inc.;
Liposorb TS®, which is available from Lipo Chemicals, Inc.;
Liposorb TS-20®, which is available from Lipo Chemicals, Inc.;
Lumisorb PS®, which is available from Lambent Technologies Corp.;
Lumisorb SMO (T)®, which is available from Lambent Technologies Corp.;
Lumisorb SMS K®, which is available from Lambent Technologies Corp.;
Lumisorb SSO®, which is available from Lambent Technologies Corp.;
Lumisorb STS K®, which is available from Lambent Technologies Corp.;
Lumisorb STT®, which is available from Lambent Technologies Corp.;
Magrabar SMO®, which is available from Magrabar Chemical Corp.;
Magrabar SMO-VEG®, which is available from Magrabar Chemical Corp.;
Magrabar SMT®, which is available from Magrabar Chemical Corp.;
Magrabar STO®, which is available from Magrabar Chemical Corp.;
Miracare BC-27®, which is available from Rhodia, Inc.;
Ritabate 20®, which is available from RITA Corp.;
Ritabate 40®, which is available from RITA Corp.;
Ritabate 60®, which is available from RITA Corp.;
Ritabate 80®, which is available from RITA Corp.;
T-Maz®, which is available from BASF Corp.;
Tego SML®, which is available from Goldschmidt Chemical Corp.;
Tego SML 20®, which is available from Goldschmidt Chemical Corp.;
Tego SMO 80 V®, which is available from Goldschmidt Chemical Corp.;
Tego SMO V®, which is available from Goldschmidt Chemical Corp.;
Tego SMS®, which is available from Goldschmidt Chemical Corp.;
Tego STO V®, which is available from Goldschmidt Chemical Corp.;
Tween 21®, which is available from Uniqema;
Tween 40®, which is available from Uniqema;
Tween 60®, which is available from Uniqema;
Tween 60 K®, which is available from Uniqema;
Tween 61®, which is available from Uniqema;
Tween 65®, which is available from Uniqema;
Tween 80®, which is available from Uniqema;
Tween 80 K®, which is available from Uniqema;
Tween 81®, which is available from Uniqema; and
Tween 85®, which is available from Uniqema;

Sucrose and Glucose Esters and Derivatives, including but not limited to,
DeSulf GOS-P-60WCG®, which is available from DeForest Enterprises, Inc.;

Glucam E-20 Distearate®, which is available from Amerchol Corp.;
Glucamate DOE-120®, which is available from Amerchol Corp.;
Glucamate SSE-20®, which is available from Amerchol Corp.;
Glucate DO®, which is available from Amerchol Corp.;
Glucate SS®, which is available from Amerchol Corp.;
Glucopon 425 UP®, which is available from Cognis Corporation;
Isolan IS®, which is available from Goldschmidt Chemical Corp.;
Mazon 40®, which is available from BASF Corp.;
Montanov 82®, which is available from Seppic Inc.;
Montanov 202®, which is available from Seppic Inc.;
Montanov S®, which is available from Seppic Inc.;
Rheozan®, which is available from Rhodia, Inc.;
Simulsol AS 48®, which is available from Seppic Inc.;
Simulsol SL 4®, which is available from Seppic Inc.;
Simulsol SL 10®, which is available from Seppic Inc.;
Simulsol SL 11W®, which is available from Seppic Inc.;
Simulsol SL 55®, which is available from Seppic Inc.;
Suga Nate 100 and 160®, which is available from Colonial Chemical Co.;
Tego Care 450®, which is available from Goldschmidt Chemical Corp.;
Tego Care CG 90®, which is available from Goldschmidt Chemical Corp.;
Tego Care PS®, which is available from Goldschmidt Chemical Corp.;
Tegosoft PSE 141 G®, which is available from Goldschmidt Chemical Corp.;
Tegotens G 826®, which is available from Goldschmidt Chemical Corp.;
Triton BG-10 (70%)®, which is available from Dow Chemical Company;
Triton CG-110 (60%)®, which is available from Dow Chemical Company; and
Wickenol 545®, which is available from Alzo International, Inc.

Another embodiment comprises from 0.001% to 0.1% cyclosporin A, Anise oil, and a sorbitan ester.

Another embodiment comprises from 0.001% to 0.1% cyclosporin A, Anise oil, and Polysorbate 20.

Another embodiment comprises from 0.001% to 0.1% cyclosporin A, Anise oil, and Polysorbate 40.

Another embodiment comprises from 0.001% to 0.1% cyclosporin A, Anise oil, and Polysorbate 60.

Another embodiment comprises from 0.001% to 0.1% cyclosporin A, Anise oil, and Polysorbate 80.

Another embodiment comprises from 0.001% to 0.1% cyclosporin A, Anise oil, and a stearate.

Another embodiment comprises from 0.001% to 0.1% cyclosporin A, Anise oil, and glyceryl stearate.

Another embodiment comprises from 0.001% to 0.1% cyclosporin A, Anise oil, and isopropyl stearate.

Another embodiment comprises from 0.001% to 0.1% cyclosporin A, Anise oil, and polyoxyl stearate.

Another embodiment comprises from 0.001% to 0.1% cyclosporin A, Anise oil, and propylene glycol stearate.

Another embodiment comprises from 0.001% to 0.1% cyclosporin A, Anise oil, and sucrose stearate.

Another embodiment comprises from 0.001% to 0.1% cyclosporin A, Anise oil, and polyethylene glycol.

Another embodiment comprises from 0.001% to 0.1% cyclosporin A, Anise oil, and polyethylene oxide.

Another embodiment comprises from 0.001% to 0.1% cyclosporin A, Anise oil, and polypropylene oxide.

Another embodiment comprises from 0.001% to 0.1% cyclosporin A, Anise oil, and a polyethylene oxide-polypropylene oxide copolymer.

Another embodiment comprises from 0.001% to 0.1% cyclosporin A, Anise oil, and an alcohol ethoxylate.

Another embodiment comprises from 0.001% to 0.1% cyclosporin A, Anise oil, and an alkylphenol ethoxylate.

Another embodiment comprises from 0.001% to 0.1% cyclosporin A, Anise oil, and an alkyl glycoside.

Another embodiment comprises from 0.001% to 0.1% cyclosporin A, Anise oil, and alkyl polyglycoside.

Another embodiment comprises from 0.001% to 0.1% cyclosporin A, Anise oil, and a fatty alcohol.

Another embodiment comprises from 0.001% to 0.1% cyclosporin A, Anise oil, and hydroxypropylmethyl cellulose.

Another embodiment comprises from 0.001% to 0.1% cyclosporin A, Anise oil, and carboxymethyl cellulose.

Another embodiment comprises from 0.001% to 0.1% cyclosporin A, Anise oil, and a polyacrylic acid.

Another embodiment comprises from 0.001% to 0.1% cyclosporin A, Anise oil, and a Carbomer.

Another embodiment comprises from 0.001% to 0.1% cyclosporin A, Anise oil, and a phosphalipid.

Another embodiment comprises from 0.001% to 0.1% cyclosporin A, Anise oil, and phosphatidyl chloline.

Another embodiment comprises from 0.001% to 0.1% cyclosporin A, Anise oil, and phosphatidyl serine.

Another embodiment comprises from 0.001% to 0.1% cyclosporin A, Clove oil, and a sorbitan ester.

Another embodiment comprises from 0.001% to 0.1% cyclosporin A, Clove oil, and Polysorbate 20.

Another embodiment comprises from 0.001% to 0.1% cyclosporin A, Clove oil, and Polysorbate 40.

Another embodiment comprises from 0.001% to 0.1% cyclosporin A, Clove oil, and Polysorbate 60.

Another embodiment comprises from 0.001% to 0.1% cyclosporin A, Clove oil, and Polysorbate 80.

Another embodiment comprises from 0.001% to 0.1%cyclosporin A, Clove oil, and a stearate.

Another embodiment comprises from 0.001% to 0.1% cyclosporin A, Clove oil, and glyceryl stearate.

Another embodiment comprises from 0.001% to 0.1% cyclosporin A, Clove oil, and isopropyl stearate.

Another embodiment comprises from 0.001% to 0.1% cyclosporin A, Clove oil, and polyoxyl stearate.

Another embodiment comprises from 0.001% to 0.1% cyclosporin A, Clove oil, and propylene glycol stearate.

Another embodiment comprises from 0.001% to 0.1% cyclosporin A, Clove oil, and sucrose stearate.

Another embodiment comprises from 0.001% to 0.1% cyclosporin A, Clove oil, and polyethylene glycol.

Another embodiment comprises from 0.001% to 0.1% cyclosporin A, Clove oil, and polyethylene oxide.

Another embodiment comprises from 0.001% to 0.1% cyclosporin A, Clove oil, and polypropylene oxide.

Another embodiment comprises from 0.001% to 0.1% cyclosporin A, Clove oil, and a polyethylene oxide-polypropylene oxide copolymer.

Another embodiment comprises from 0.001% to 0.1% cyclosporin A, Clove oil, and an alcohol ethoxylate.

Another embodiment comprises from 0.001% to 0.1% cyclosporin A, Clove oil, and an alkylphenol ethoxylate.

Another embodiment comprises from 0.001% to 0.1% cyclosporin A, Clove oil, and an alkyl glycoside.

Another embodiment comprises from 0.001% to 0.1% cyclosporin A, Clove oil, and alkyl polyglycoside.

Another embodiment comprises from 0.001% to 0.1% cyclosporin A, Clove oil, and a fatty alcohol.

Another embodiment comprises from 0.001% to 0.1% cyclosporin A, Clove oil, and hydroxypropylmethyl cellulose.

Another embodiment comprises from 0.001% to 0.1% cyclosporin A, Clove oil, and carboxymethyl cellulose.

Another embodiment comprises from 0.001% to 0.1% cyclosporin A, Clove oil, and a polyacrylic acid.

Another embodiment comprises from 0.001% to 0.1% cyclosporin A, Clove oil, and a Carbomer.

Another embodiment comprises from 0.001% to 0.1% cyclosporin A, Clove oil, and a phosphalipid.

Another embodiment comprises from 0.001% to 0.1% cyclosporin A, Clove oil, and phosphatidyl chloline.

Another embodiment comprises from 0.001% to 0.1% cyclosporin A, Clove oil, and phosphatidyl serine.

Another embodiment comprises from 0.001% to 0.1% cyclosporin A, Cassia oil, and a sorbitan ester.

Another embodiment comprises from 0.001% to 0.1% cyclosporin A, Cassia oil, and Polysorbate 20.

Another embodiment comprises from 0.001% to 0.1% cyclosporin A, Cassia oil, and Polysorbate 40.

Another embodiment comprises from 0.001% to 0.1% cyclosporin A, Cassia oil, and Polysorbate 60.

Another embodiment comprises from 0.001% to 0.1% cyclosporin A, Cassia oil, and Polysorbate 80.

Another embodiment comprises from 0.001% to 0.1% cyclosporin A, Cassia oil, and a stearate.

Another embodiment comprises from 0.001% to 0.1% cyclosporin A, Cassia oil, and glyceryl stearate.

Another embodiment comprises from 0.001% to 0.1% cyclosporin A, Cassia oil, and isopropyl stearate.

Another embodiment comprises from 0.001% to 0.1% cyclosporin A, Cassia oil, and polyoxyl stearate.

Another embodiment comprises from 0.001% to 0.1% cyclosporin A, Cassia oil, and propylene glycol stearate.

Another embodiment comprises from 0.001% to 0.1% cyclosporin A, Cassia oil, and sucrose stearate.

Another embodiment comprises from 0.001% to 0.1% cyclosporin A, Cassia oil, and polyethylene glycol.

Another embodiment comprises from 0.001% to 0.1% cyclosporin A, Cassia oil, and polyethylene oxide.

Another embodiment comprises from 0.001% to 0.1% cyclosporin A, Cassia oil, and polypropylene oxide.

Another embodiment comprises from 0.001% to 0.1% cyclosporin A, Cassia oil, and a polyethylene oxide-polypropylene oxide copolymer.

Another embodiment comprises from 0.001% to 0.1% cyclosporin A, Cassia oil, and an alcohol ethoxylate.

Another embodiment comprises from 0.001% to 0.1% cyclosporin A, Cassia oil, and an alkylphenol ethoxylate.

Another embodiment comprises from 0.001% to 0.1% cyclosporin A, Cassia oil, and an alkyl glycoside.

Another embodiment comprises from 0.001% to 0.1% cyclosporin A, Cassia oil, and alkyl polyglycoside.

Another embodiment comprises from 0.001% to 0.1% cyclosporin A, Cassia oil, and a fatty alcohol.

Another embodiment comprises from 0.001% to 0.1% cyclosporin A, Cassia oil, and hydroxypropylmethyl cellulose.

Another embodiment comprises from 0.001% to 0.1% cyclosporin A, Cassia oil, and carboxymethyl cellulose.

Another embodiment comprises from 0.001% to 0.1% cyclosporin A, Cassia oil, and a polyacrylic acid.

Another embodiment comprises from 0.001% to 0.1% cyclosporin A, Cassia oil, and a Carbomer.

Another embodiment comprises from 0.001% to 0.1% cyclosporin A, Cassia oil, and a phosphalipid.

Another embodiment comprises from 0.001% to 0.1% cyclosporin A, Cassia oil, and phosphatidyl chloline.

Another embodiment comprises from 0.001% to 0.1% cyclosporin A, Cassia oil, and phosphatidyl serine.

Another embodiment comprises from 0.001% to 0.1% cyclosporin A, Cinnamon oil, and a sorbitan ester.

Another embodiment comprises from 0.001% to 0.1% cyclosporin A, Cinnamon oil, and Polysorbate 20.

Another embodiment comprises from 0.001% to 0.1% cyclosporin A, Cinnamon oil, and Polysorbate 40.

Another embodiment comprises from 0.001% to 0.1% cyclosporin A, Cinnamon oil, and Polysorbate 60.

Another embodiment comprises from 0.001% to 0.1% cyclosporin A, Cinnamon oil, and Polysorbate 80.

Another embodiment comprises from 0.001% to 0.1% cyclosporin A, Cinnamon oil, and a stearate.

Another embodiment comprises from 0.001% to 0.1% cyclosporin A, Cinnamon oil, and glyceryl stearate.

Another embodiment comprises from 0.001% to 0.1% cyclosporin A, Cinnamon oil, and isopropyl stearate.

Another embodiment comprises from 0.001% to 0.1% cyclosporin A, Cinnamon oil, and polyoxyl stearate.

Another embodiment comprises from 0.001% to 0.1% cyclosporin A, Cinnamon oil, and propylene glycol stearate.

Another embodiment comprises from 0.001% to 0.1% cyclosporin A, Cinnamon oil, and sucrose stearate.

Another embodiment comprises from 0.001% to 0.1% cyclosporin A, Cinnamon oil, and polyethylene glycol.

Another embodiment comprises from 0.001% to 0.1% cyclosporin A, Cinnamon oil, and polyethylene oxide.

Another embodiment comprises from 0.001% to 0.1% cyclosporin A, Cinnamon oil, and polypropylene oxide.

Another embodiment comprises from 0.001% to 0.1% cyclosporin A, Cinnamon oil, and a polyethylene oxide-polypropylene oxide copolymer.

Another embodiment comprises from 0.001% to 0.1% cyclosporin A, Cinnamon oil, and an alcohol ethoxylate.

Another embodiment comprises from 0.001% to 0.1% cyclosporin A, Cinnamon oil, and an alkylphenol ethoxylate.

Another embodiment comprises from 0.001% to 0.1% cyclosporin A, Cinnamon oil, and an alkyl glycoside.

Another embodiment comprises from 0.001% to 0.1% cyclosporin A, Cinnamon oil, and alkyl polyglycoside.

Another embodiment comprises from 0.001% to 0.1% cyclosporin A, Cinnamon oil, and a fatty alcohol.

Another embodiment comprises from 0.001% to 0.1% cyclosporin A, Cinnamon oil, and hydroxypropylmethyl cellulose.

Another embodiment comprises from 0.001% to 0.1% cyclosporin A, Cinnamon oil, and carboxymethyl cellulose.

Another embodiment comprises from 0.001% to 0.1% cyclosporin A, Cinnamon oil, and a polyacrylic acid.

Another embodiment comprises from 0.001% to 0.1% cyclosporin A, Cinnamon oil, and a Carbomer.

Another embodiment comprises from 0.001% to 0.1% cyclosporin A, Cinnamon oil, and a phosphalipid.

Another embodiment comprises from 0.001% to 0.1% cyclosporin A, Cinnamon oil, and phosphatidyl chloline.

Another embodiment comprises from 0.001% to 0.1% cyclosporin A, Cinnamon oil, and phosphatidyl serine.

Another embodiment comprises from 0.005% to about 0.05% cyclosporin A, Anise oil, and a sorbitan ester.

Another embodiment comprises from 0.005% to about 0.05% cyclosporin A, Anise oil, and Polysorbate 20.

Another embodiment comprises from 0.005% to about 0.05% cyclosporin A, Anise oil, and Polysorbate 40.

Another embodiment comprises from 0.005% to about 0.05% cyclosporin A, Anise oil, and Polysorbate 60.

Another embodiment comprises from 0.005% to about 0.05% cyclosporin A, Anise oil, and Polysorbate 80.

Another embodiment comprises from 0.005% to about 0.05% cyclosporin A, Anise oil, and a stearate.

Another embodiment comprises from 0.005% to about 0.05% cyclosporin A, Anise oil, and glyceryl stearate.

Another embodiment comprises from 0.005% to about 0.05% cyclosporin A, Anise oil, and isopropyl stearate.

Another embodiment comprises from 0.005% to about 0.05% cyclosporin A, Anise oil, and polyoxyl stearate.

Another embodiment comprises from 0.005% to about 0.05% cyclosporin A, Anise oil, and propylene glycol stearate.

Another embodiment comprises from 0.005% to about 0.05% cyclosporin A, Anise oil, and sucrose stearate.

Another embodiment comprises from 0.005% to about 0.05% cyclosporin A, Anise oil, and polyethylene glycol.

Another embodiment comprises from 0.005% to about 0.05% cyclosporin A, Anise oil, and polyethylene oxide.

Another embodiment comprises from 0.005% to about 0.05% cyclosporin A, Anise oil, and polypropylene oxide.

Another embodiment comprises from 0.005% to about 0.05% cyclosporin A, Anise oil, and a polyethylene oxide-polypropylene oxide copolymer.

Another embodiment comprises from 0.005% to about 0.05% cyclosporin A, Anise oil, and an alcohol ethoxylate.

Another embodiment comprises from 0.005% to about 0.05% cyclosporin A, Anise oil, and an alkylphenol ethoxylate.

Another embodiment comprises from 0.005% to about 0.05% cyclosporin A, Anise oil, and an alkyl glycoside.

Another embodiment comprises from 0.005% to about 0.05% cyclosporin A, Anise oil, and alkyl polyglycoside.

Another embodiment comprises from 0.005% to about 0.05% cyclosporin A, Anise oil, and a fatty alcohol.

Another embodiment comprises from 0.005% to about 0.05% cyclosporin A, Anise oil, and hydroxypropylmethyl cellulose.

Another embodiment comprises from 0.005% to about 0.05% cyclosporin A, Anise oil, and carboxymethyl cellulose.

Another embodiment comprises from 0.005% to about 0.05% cyclosporin A, Anise oil, and a polyacrylic acid.

Another embodiment comprises from 0.005% to about 0.05% cyclosporin A, Anise oil, and a Carbomer.

Another embodiment comprises from 0.005% to about 0.05% cyclosporin A, Anise oil, and a phosphalipid.

Another embodiment comprises from 0.005% to about 0.05% cyclosporin A, Anise oil, and phosphatidyl chloline.

Another embodiment comprises from 0.005% to about 0.05% cyclosporin A, Anise oil, and phosphatidyl serine.

Another embodiment comprises from 0.005% to about 0.05% cyclosporin A, Clove oil, and a sorbitan ester.

Another embodiment comprises from 0.005% to about 0.05% cyclosporin A, Clove oil, and Polysorbate 20.

Another embodiment comprises from 0.005% to about 0.05% cyclosporin A, Clove oil, and Polysorbate 40.

Another embodiment comprises from 0.005% to about 0.05% cyclosporin A, Clove oil, and Polysorbate 60.

Another embodiment comprises from 0.005% to about 0.05% cyclosporin A, Clove oil, and Polysorbate 80.

Another embodiment comprises from 0.005% to about 0.05% cyclosporin A, Clove oil, and a stearate.

Another embodiment comprises from 0.005% to about 0.05% cyclosporin A, Clove oil, and glyceryl stearate.

Another embodiment comprises from 0.005% to about 0.05% cyclosporin A, Clove oil, and isopropyl stearate.

Another embodiment comprises from 0.005% to about 0.05% cyclosporin A, Clove oil, and polyoxyl stearate.

Another embodiment comprises from 0.005% to about 0.05% cyclosporin A, Clove oil, and propylene glycol stearate.

Another embodiment comprises from 0.005% to about 0.05% cyclosporin A, Clove oil, and sucrose stearate.

Another embodiment comprises from 0.005% to about 0.05% cyclosporin A, Clove oil, and polyethylene glycol.

Another embodiment comprises from 0.005% to about 0.05% cyclosporin A, Clove oil, and polyethylene oxide.

Another embodiment comprises from 0.005% to about 0.05% cyclosporin A, Clove oil, and polypropylene oxide.

Another embodiment comprises from 0.005% to about 0.05% cyclosporin A, Clove oil, and a polyethylene oxide-polypropylene oxide copolymer.

Another embodiment comprises from 0.005% to about 0.05% cyclosporin A, Clove oil, and an alcohol ethoxylate.

Another embodiment comprises from 0.005% to about 0.05% cyclosporin A, Clove oil, and an alkylphenol ethoxylate.

Another embodiment comprises from 0.005% to about 0.05% cyclosporin A, Clove oil, and an alkyl glycoside.

Another embodiment comprises from 0.005% to about 0.05% cyclosporin A, Clove oil, and alkyl polyglycoside.

Another embodiment comprises from 0.005% to about 0.05% cyclosporin A, Clove oil, and a fatty alcohol.

Another embodiment comprises from 0.005% to about 0.05% cyclosporin A, Clove oil, and hydroxypropylmethyl cellulose.

Another embodiment comprises from 0.005% to about 0.05% cyclosporin A, Clove oil, and carboxymethyl cellulose.

Another embodiment comprises from 0.005% to about 0.05% cyclosporin A, Clove oil, and a polyacrylic acid.

Another embodiment comprises from 0.005% to about 0.05% cyclosporin A, Clove oil, and a Carbomer.

Another embodiment comprises from 0.005% to about 0.05% cyclosporin A, Clove oil, and a phosphalipid.

Another embodiment comprises from 0.005% to about 0.05% cyclosporin A, Clove oil, and phosphatidyl chloline.

Another embodiment comprises from 0.005% to about 0.05% cyclosporin A, Clove oil, and phosphatidyl serine.

Another embodiment comprises from 0.005% to about 0.05% cyclosporin A, Cassia oil, and a sorbitan ester.

Another embodiment comprises from 0.005% to about 0.05% cyclosporin A, Cassia oil, and Polysorbate 20.

Another embodiment comprises from 0.005% to about 0.05% cyclosporin A, Cassia oil, and Polysorbate 40.

Another embodiment comprises from 0.005% to about 0.05% cyclosporin A, Cassia oil, and Polysorbate 60.

Another embodiment comprises from 0.005% to about 0.05% cyclosporin A, Cassia oil, and Polysorbate 80.

Another embodiment comprises from 0.005% to about 0.05% cyclosporin A, Cassia oil, and a stearate.

Another embodiment comprises from 0.005% to about 0.05% cyclosporin A, Cassia oil, and glyceryl stearate.

Another embodiment comprises from 0.005% to about 0.05% cyclosporin A, Cassia oil, and isopropyl stearate.

Another embodiment comprises from 0.005% to about 0.05% cyclosporin A, Cassia oil, and polyoxyl stearate.

Another embodiment comprises from 0.005% to about 0.05% cyclosporin A, Cassia oil, and propylene glycol stearate.

Another embodiment comprises from 0.005% to about 0.05% cyclosporin A, Cassia oil, and sucrose stearate.

Another embodiment comprises from 0.005% to about 0.05% cyclosporin A, Cassia oil, and polyethylene glycol.

Another embodiment comprises from 0.005% to about 0.05% cyclosporin A, Cassia oil, and polyethylene oxide.

Another embodiment comprises from 0.005% to about 0.05% cyclosporin A, Cassia oil, and polypropylene oxide.

Another embodiment comprises from 0.005% to about 0.05% cyclosporin A, Cassia oil, and a polyethylene oxide-polypropylene oxide copolymer.

Another embodiment comprises from 0.005% to about 0.05% cyclosporin A, Cassia oil, and an alcohol ethoxylate.

Another embodiment comprises from 0.005% to about 0.05% cyclosporin A, Cassia oil, and an alkylphenol ethoxylate.

Another embodiment comprises from 0.005% to about 0.05% cyclosporin A, Cassia oil, and an alkyl glycoside.

Another embodiment comprises from 0.005% to about 0.05% cyclosporin A, Cassia oil, and alkyl polyglycoside.

Another embodiment comprises from 0.005% to about 0.05% cyclosporin A, Cassia oil, and a fatty alcohol.

Another embodiment comprises from 0.005% to about 0.05% cyclosporin A, Cassia oil, and hydroxypropylmethyl cellulose.

Another embodiment comprises from 0.005% to about 0.05% cyclosporin A, Cassia oil, and carboxymethyl cellulose.

Another embodiment comprises from 0.005% to about 0.05% cyclosporin A, Cassia oil, and a polyacrylic acid.

Another embodiment comprises from 0.005% to about 0.05% cyclosporin A, Cassia oil, and a Carbomer.

Another embodiment comprises from 0.005% to about 0.05% cyclosporin A, Cassia oil, and a phosphalipid.

Another embodiment comprises from 0.005% to about 0.05% cyclosporin A, Cassia oil, and phosphatidyl choline.

Another embodiment comprises from 0.005% to about 0.05% cyclosporin A, Cassia oil, and phosphatidyl serine.

Another embodiment comprises from 0.005% to about 0.05% cyclosporin A, Cinnamon oil, and a sorbitan ester.

Another embodiment comprises from 0.005% to about 0.05% cyclosporin A, Cinnamon oil, and Polysorbate 20.

Another embodiment comprises from 0.005% to about 0.05% cyclosporin A, Cinnamon oil, and Polysorbate 40.

Another embodiment comprises from 0.005% to about 0.05% cyclosporin A, Cinnamon oil, and Polysorbate 60.

Another embodiment comprises from 0.005% to about 0.05% cyclosporin A, Cinnamon oil, and Polysorbate 80.

Another embodiment comprises from 0.005% to about 0.05% cyclosporin A, Cinnamon oil, and a stearate.

Another embodiment comprises from 0.005% to about 0.05% cyclosporin A, Cinnamon oil, and glyceryl stearate.

Another embodiment comprises from 0.005% to about 0.05% cyclosporin A, Cinnamon oil, and isopropyl stearate.

Another embodiment comprises from 0.005% to about 0.05% cyclosporin A, Cinnamon oil, and polyoxyl stearate.

Another embodiment comprises from 0.005% to about 0.05% cyclosporin A, Cinnamon oil, and propylene glycol stearate.

Another embodiment comprises from 0.005% to about 0.05% cyclosporin A, Cinnamon oil, and sucrose stearate.

Another embodiment comprises from 0.005% to about 0.05% cyclosporin A, Cinnamon oil, and polyethylene glycol.

Another embodiment comprises from 0.005% to about 0.05% cyclosporin A, Cinnamon oil, and polyethylene oxide.

Another embodiment comprises from 0.005% to about 0.05% cyclosporin A, Cinnamon oil, and polypropylene oxide.

Another embodiment comprises from 0.005% to about 0.05% cyclosporin A, Cinnamon oil, and a polyethylene oxide-polypropylene oxide copolymer.

Another embodiment comprises from 0.005% to about 0.05% cyclosporin A, Cinnamon oil, and an alcohol ethoxylate.

Another embodiment comprises from 0.005% to about 0.05% cyclosporin A, Cinnamon oil, and an alkylphenol ethoxylate.

Another embodiment comprises from 0.005% to about 0.05% cyclosporin A, Cinnamon oil, and an alkyl glycoside.

Another embodiment comprises from 0.005% to about 0.05% cyclosporin A, Cinnamon oil, and alkyl polyglycoside.

Another embodiment comprises from 0.005% to about 0.05% cyclosporin A, Cinnamon oil, and a fatty alcohol.

Another embodiment comprises from 0.005% to about 0.05% cyclosporin A, Cinnamon oil, and hydroxypropylmethyl cellulose.

Another embodiment comprises from 0.005% to about 0.05% cyclosporin A, Cinnamon oil, and carboxymethyl cellulose.

Another embodiment comprises from 0.005% to about 0.05% cyclosporin A, Cinnamon oil, and a polyacrylic acid.

Another embodiment comprises from 0.005% to about 0.05% cyclosporin A, Cinnamon oil, and a Carbomer.

Another embodiment comprises from 0.005% to about 0.05% cyclosporin A, Cinnamon oil, and a phosphalipid.

Another embodiment comprises from 0.005% to about 0.05% cyclosporin A, Cinnamon oil, and phosphatidyl chlorine.

Another embodiment comprises from 0.005% to about 0.05% cyclosporin A, Cinnamon oil, and phosphatidyl serine.

Another embodiment comprises about 0.05% cyclosporin A, Anise oil, and a sorbitan ester.

Another embodiment comprises about 0.05% cyclosporin A, Anise oil, and Polysorbate 20.

Another embodiment comprises about 0.05% cyclosporin A, Anise oil, and Polysorbate 40.

Another embodiment comprises about 0.05% cyclosporin A, Anise oil, and Polysorbate 60.

Another embodiment comprises about 0.05% cyclosporin A, Anise oil, and Polysorbate 80.

Another embodiment comprises about 0.05% cyclosporin A, Anise oil, and a stearate.

Another embodiment comprises about 0.05% cyclosporin A, Anise oil, and glyceryl stearate.

Another embodiment comprises about 0.05% cyclosporin A, Anise oil, and isopropyl stearate.

Another embodiment comprises about 0.05% cyclosporin A, Anise oil, and polyoxyl stearate.

Another embodiment comprises about 0.05% cyclosporin A, Anise oil, and propylene glycol stearate.

Another embodiment comprises about 0.05% cyclosporin A, Anise oil, and sucrose stearate.

Another embodiment comprises about 0.05% cyclosporin A, Anise oil, and polyethylene glycol.

Another embodiment comprises about 0.05% cyclosporin A, Anise oil, and polyethylene oxide.

Another embodiment comprises about 0.05% cyclosporin A, Anise oil, and polypropylene oxide.

Another embodiment comprises about 0.05% cyclosporin A, Anise oil, and a polyethylene oxide-polypropylene oxide copolymer.

Another embodiment comprises about 0.05% cyclosporin A, Anise oil, and an alcohol ethoxylate.

Another embodiment comprises about 0.05% cyclosporin A, Anise oil, and an alkylphenol ethoxylate.

Another embodiment comprises about 0.05% cyclosporin A, Anise oil, and an alkyl glycoside.

Another embodiment comprises about 0.05% cyclosporin A, Anise oil, and alkyl polyglycoside.

Another embodiment comprises about 0.05% cyclosporin A, Anise oil, and a fatty alcohol.

Another embodiment comprises about 0.05% cyclosporin A, Anise oil, and hydroxypropylmethyl cellulose.

Another embodiment comprises about 0.05% cyclosporin A, Anise oil, and carboxymethyl cellulose.

Another embodiment comprises about 0.05% cyclosporin A, Anise oil, and a polyacrylic acid.

Another embodiment comprises about 0.05% cyclosporin A, Anise oil, and a Carbomer.

Another embodiment comprises about 0.05% cyclosporin A, Anise oil, and a phosphalipid.

Another embodiment comprises about 0.05% cyclosporin A, Anise oil, and phosphatidyl chloline.

Another embodiment comprises about 0.05% cyclosporin A, Anise oil, and phosphatidyl serine.

Another embodiment comprises about 0.05% cyclosporin A, Clove oil, and a sorbitan ester.

Another embodiment comprises about 0.05% cyclosporin A, Clove oil, and Polysorbate 20.

Another embodiment comprises about 0.05% cyclosporin A, Clove oil, and Polysorbate 40.

Another embodiment comprises about 0.05% cyclosporin A, Clove oil, and Polysorbate 60.

Another embodiment comprises about 0.05% cyclosporin A, Clove oil, and Polysorbate 80.

Another embodiment comprises about 0.05% cyclosporin A, Clove oil, and a stearate.

Another embodiment comprises about 0.05% cyclosporin A, Clove oil, and glyceryl stearate.

Another embodiment comprises about 0.05% cyclosporin A, Clove oil, and isopropyl stearate.

Another embodiment comprises about 0.05% cyclosporin A, Clove oil, and polyoxyl stearate.

Another embodiment comprises about 0.05% cyclosporin A, Clove oil, and propylene glycol stearate.

Another embodiment comprises about 0.05% cyclosporin A, Clove oil, and sucrose stearate.

Another embodiment comprises about 0.05% cyclosporin A, Clove oil, and polyethylene glycol.

Another embodiment comprises about 0.05% cyclosporin A, Clove oil, and polyethylene oxide.

Another embodiment comprises about 0.05% cyclosporin A, Clove oil, and polypropylene oxide.

Another embodiment comprises about 0.05% cyclosporin A, Clove oil, and a polyethylene oxide-polypropylene oxide copolymer.

Another embodiment comprises about 0.05% cyclosporin A, Clove oil, and an alcohol ethoxylate.

Another embodiment comprises about 0.05% cyclosporin A, Clove oil, and an alkylphenol ethoxylate.

Another embodiment comprises about 0.05% cyclosporin A, Clove oil, and an alkyl glycoside.

Another embodiment comprises about 0.05% cyclosporin A, Clove oil, and alkyl polyglycoside.

Another embodiment comprises about 0.05% cyclosporin A, Clove oil, and a fatty alcohol.

Another embodiment comprises about 0.05% cyclosporin A, Clove oil, and hydroxypropylmethyl cellulose.

Another embodiment comprises about 0.05% cyclosporin A, Clove oil, and carboxymethyl cellulose.

Another embodiment comprises about 0.05% cyclosporin A, Clove oil, and a polyacrylic acid.

Another embodiment comprises about 0.05% cyclosporin A, Clove oil, and a Carbomer.

Another embodiment comprises about 0.05% cyclosporin A, Clove oil, and a phosphalipid.

Another embodiment comprises about 0.05% cyclosporin A, Clove oil, and phosphatidyl chlorine.

Another embodiment comprises about 0.05% cyclosporin A, Clove oil, and phosphatidyl serine.

Another embodiment comprises about 0.05% cyclosporin A, Cassia oil, and a sorbitan ester.

Another embodiment comprises about 0.05% cyclosporin A, Cassia oil, and Polysorbate 20.

Another embodiment comprises about 0.05% cyclosporin A, Cassia oil, and Polysorbate 40.

Another embodiment comprises about 0.05% cyclosporin A, Cassia oil, and Polysorbate 60.

Another embodiment comprises about 0.05% cyclosporin A, Cassia oil, and Polysorbate 80.

Another embodiment comprises about 0.05% cyclosporin A, Cassia oil, and a stearate.

Another embodiment comprises about 0.05% cyclosporin A, Cassia oil, and glyceryl stearate.

Another embodiment comprises about 0.05% cyclosporin A, Cassia oil, and isopropyl stearate.

Another embodiment comprises about 0.05% cyclosporin A, Cassia oil, and polyoxyl stearate.

Another embodiment comprises about 0.05% cyclosporin A, Cassia oil, and propylene glycol stearate.

Another embodiment comprises about 0.05% cyclosporin A, Cassia oil, and sucrose stearate.

Another embodiment comprises about 0.05% cyclosporin A, Cassia oil, and polyethylene glycol.

Another embodiment comprises about 0.05% cyclosporin A, Cassia oil, and polyethylene oxide.

Another embodiment comprises about 0.05% cyclosporin A, Cassia oil, and polypropylene oxide.

Another embodiment comprises about 0.05% cyclosporin A, Cassia oil, and a polyethylene oxide-polypropylene oxide copolymer.

Another embodiment comprises about 0.05% cyclosporin A, Cassia oil, and an alcohol ethoxylate.

Another embodiment comprises about 0.05% cyclosporin A, Cassia oil, and an alkylphenol ethoxylate.

Another embodiment comprises about 0.05% cyclosporin A, Cassia oil, and an alkyl glycoside.

Another embodiment comprises about 0.05% cyclosporin A, Cassia oil, and alkyl polyglycoside.

Another embodiment comprises about 0.05% cyclosporin A, Cassia oil, and a fatty alcohol.

Another embodiment comprises about 0.05% cyclosporin A, Cassia oil, and hydroxypropylmethyl cellulose.

Another embodiment comprises about 0.05% cyclosporin A, Cassia oil, and carboxymethyl cellulose.

Another embodiment comprises about 0.05% cyclosporin A, Cassia oil, and a polyacrylic acid.

Another embodiment comprises about 0.05% cyclosporin A, Cassia oil, and a Carbomer.

Another embodiment comprises about 0.05% cyclosporin A, Cassia oil, and a phosphalipid.
Another embodiment comprises about 0.05% cyclosporin A, Cassia oil, and phosphatidyl chlorine.
Another embodiment comprises about 0.05% cyclosporin A, Cassia oil, and phosphatidyl serine.
Another embodiment comprises about 0.05% cyclosporin A, Cinnamon oil, and a sorbitan ester.
Another embodiment comprises about 0.05% cyclosporin A, Cinnamon oil, and Polysorbate 20.
Another embodiment comprises about 0.05% cyclosporin A, Cinnamon oil, and Polysorbate 40.
Another embodiment comprises about 0.05% cyclosporin A, Cinnamon oil, and Polysorbate 60.
Another embodiment comprises about 0.05% cyclosporin A, Cinnamon oil, and Polysorbate 80.
Another embodiment comprises about 0.05% cyclosporin A, Cinnamon oil, and a stearate.
Another embodiment comprises about 0.05% cyclosporin A, Cinnamon oil, and glyceryl stearate.
Another embodiment comprises about 0.05% cyclosporin A, Cinnamon oil, and isopropyl stearate.
Another embodiment comprises about 0.05% cyclosporin A, Cinnamon oil, and polyoxyl stearate.
Another embodiment comprises about 0.05% cyclosporin A, Cinnamon oil, and propylene glycol stearate.
Another embodiment comprises about 0.05% cyclosporin A, Cinnamon oil, and sucrose stearate.
Another embodiment comprises about 0.05% cyclosporin A, Cinnamon oil, and polyethylene glycol.
Another embodiment comprises about 0.05% cyclosporin A, Cinnamon oil, and polyethylene oxide.
Another embodiment comprises about 0.05% cyclosporin A, Cinnamon oil, and polypropylene oxide.
Another embodiment comprises about 0.05% cyclosporin A, Cinnamon oil, and a polyethylene oxide-polypropylene oxide copolymer.
Another embodiment comprises about 0.05% cyclosporin A, Cinnamon oil, and an alcohol ethoxylate.
Another embodiment comprises about 0.05% cyclosporin A, Cinnamon oil, and an alkylphenol ethoxylate.
Another embodiment comprises about 0.05% cyclosporin A, Cinnamon oil, and an alkyl glycoside.
Another embodiment comprises about 0.05% cyclosporin A, Cinnamon oil, and alkyl polyglycoside.
Another embodiment comprises about 0.05% cyclosporin A, Cinnamon oil, and a fatty alcohol.
Another embodiment comprises about 0.05% cyclosporin A, Cinnamon oil, and hydroxypropylmethyl cellulose.
Another embodiment comprises about 0.05% cyclosporin A, Cinnamon oil, and carboxymethyl cellulose.
Another embodiment comprises about 0.05% cyclosporin A, Cinnamon oil, and a polyacrylic acid.
Another embodiment comprises about 0.05% cyclosporin A, Cinnamon oil, and a Carbomer.
Another embodiment comprises about 0.05% cyclosporin A, Cinnamon oil, and a phosphalipid.
Another embodiment comprises about 0.05% cyclosporin A, Cinnamon oil, and phosphatidyl chloine.
Another embodiment comprises about 0.05% cyclosporin A, Cinnamon oil, and phosphatidyl serine.
Another embodiment comprises cyclosporin A, an alcohol, and Anise oil.
Another embodiment comprises cyclosporin A, Diglycerol®, and Anise oil.
Another embodiment comprises cyclosporin A, Hetoxide GT-80®, and Anise oil.
Another embodiment comprises cyclosporin A, Lexemul BEO®, and Anise oil.
Another embodiment comprises cyclosporin A, Polyglycerol-3®, and Anise oil.
Another embodiment comprises cyclosporin A, Redicote E Series®, and Anise oil.
Another embodiment comprises cyclosporin A, Simulsol OX 1005L®, and Anise oil.
Another embodiment comprises cyclosporin A, Stanfax 567®, and Anise oil.
Another embodiment comprises cyclosporin A, TA-1618®, and Anise oil.
Another embodiment comprises cyclosporin A, Witconol H-31A®, and Anise oil.
Another embodiment comprises cyclosporin A, Standard Div.®, and Anise oil.
Anise oil.
Another embodiment comprises cyclosporin A, an amine oxide, and Anise oil.
Another embodiment comprises cyclosporin A, AO-405®, and Anise oil.
Another embodiment comprises cyclosporin A, AO-455®, and Anise oil.
Another embodiment comprises cyclosporin A, AO 728 Special®, and Anise oil.
Another embodiment comprises cyclosporin A, Barlox 12®, and Anise oil.
Another embodiment comprises cyclosporin A, Barlox 14®, and Anise oil.
Another embodiment comprises cyclosporin A, Burcoxide Lo®, and Anise oil.
Another embodiment comprises cyclosporin A, Caloxamine LO®, and Anise oil.
Another embodiment comprises cyclosporin A, Chemoxide CAW®, and Anise oil.
Another embodiment comprises cyclosporin A, Chemoxide LM-30®, and Anise oil.
Another embodiment comprises cyclosporin A, Chemoxide LO®, and Anise oil.
Another embodiment comprises cyclosporin A, Chemoxide MO®, and Anise oil.
Another embodiment comprises cyclosporin A, Colalux CAO-35®, and Anise oil.
Another embodiment comprises cyclosporin A, Colalux LO®, and Anise oil.
Another embodiment comprises cyclosporin A, DeMox CAPO®, and Anise oil.
Another embodiment comprises cyclosporin A, DeMox CSG-30®, and Anise oil.
Another embodiment comprises cyclosporin A, DeMox LAO®, and Anise oil.
Another embodiment comprises cyclosporin A, Emcol L®, and Anise oil.
Another embodiment comprises cyclosporin A, Empigen OB®, and Anise oil.
Another embodiment comprises cyclosporin A, Empigen OS/A®, and Anise oil.
Another embodiment comprises cyclosporin A, Foamox CDO®, and Anise oil.
Another embodiment comprises cyclosporin A, Foamox DMM®, and Anise oil.
Another embodiment comprises cyclosporin A, Foamox DMS®, and Anise oil.
Another embodiment comprises cyclosporin A, Genaminox KC®, and Anise oil.
Another embodiment comprises cyclosporin A, Genaminox LA®, and Anise oil.

Another embodiment comprises cyclosporin A, Hartofoam SAO®, and Anise oil.

Another embodiment comprises cyclosporin A, Hartox DMCD®, and Anise oil.

Another embodiment comprises cyclosporin A, Lipowax DAT®, and Anise oil.

Another embodiment comprises cyclosporin A, Lipowax PB Pastilles®, and Anise oil.

Another embodiment comprises cyclosporin A, Mackamine C8®, and Anise oil.

Another embodiment comprises cyclosporin A, Mackamine C10®, and Anise oil.

Another embodiment comprises cyclosporin A, Mackamine C14®, and Anise oil.

Another embodiment comprises cyclosporin A, Mackamine CAO®, and Anise oil.

Another embodiment comprises cyclosporin A, Mackamine CO®, and Anise oil.

Another embodiment comprises cyclosporin A, Mackamine LO®, and Anise oil.

Another embodiment comprises cyclosporin A, Mackamine O2®, and Anise oil.

Another embodiment comprises cyclosporin A, Mackamine SAO®, and Anise oil.

Another embodiment comprises cyclosporin A, Mackamine SO®, and Anise oil.

Another embodiment comprises cyclosporin A, Mazox KCAO®, and Anise oil.

Another embodiment comprises cyclosporin A, Monalac MO®, and Anise oil.

Another embodiment comprises cyclosporin A, Norfox LDA®, and Anise oil.

Another embodiment comprises cyclosporin A, Rhodamox LO®, and Anise oil.

Another embodiment comprises cyclosporin A, Schercamox C-AA®, and Anise oil.

Another embodiment comprises cyclosporin A, Schercamox DMA®, and Anise oil.

Another embodiment comprises cyclosporin A, Schercamox DML®, and Anise oil.

Another embodiment comprises cyclosporin A, Schercamox DMM®, and Anise oil.

Another embodiment comprises cyclosporin A, Schercamox DMS®, and Anise oil.

Another embodiment comprises cyclosporin A, Tegotens DO®, and Anise oil.

Another embodiment comprises cyclosporin A, Tomah AO-14-2®, and Anise oil.

Another embodiment comprises cyclosporin A, Triaminox CDO®, and Anise oil., and Anise oil.

Another embodiment comprises cyclosporin A, a block polymer, and Anise oil.

Another embodiment comprises cyclosporin A, AL 2070®, and Anise oil.

Another embodiment comprises cyclosporin A, Antarox 17-R-2®, and Anise oil.

Another embodiment comprises cyclosporin A, Antarox 25-R-2®, and Anise oil.

Another embodiment comprises cyclosporin A, Antarox 31-R-1®, and Anise oil.

Another embodiment comprises cyclosporin A, Antarox P-84®, and Anise oil.

Another embodiment comprises cyclosporin A, Antarox P-104/H®, and Anise oil.

Another embodiment comprises cyclosporin A, Arnox BP-Series®, and Anise oil.

Another embodiment comprises cyclosporin A, Chemonic 435®, and Anise oil.

Another embodiment comprises cyclosporin A, Chemonic D-25®, and Anise oil.

Another embodiment comprises cyclosporin A, Chemonic PL Series®, and Anise oil.

Another embodiment comprises cyclosporin A, Ethox L-121®, and Anise oil.

Another embodiment comprises cyclosporin A, Ethox L-122®, and Anise oil.

Another embodiment comprises cyclosporin A, Genapol PF-10®, and Anise oil.

Another embodiment comprises cyclosporin A, Genapol PF-20®, and Anise oil.

Another embodiment comprises cyclosporin A, Genapol PF-40A®, and Anise oil.

Another embodiment comprises cyclosporin A, Norfox 2-LF®, and Anise oil.

Another embodiment comprises cyclosporin A, Simulsol NW 342®, and Anise oil.

Another embodiment comprises cyclosporin A, T-Det BP-1®, and Anise oil.

Another embodiment comprises cyclosporin A, T-Det XD®, and Anise oil.

Another embodiment comprises cyclosporin A, T-Det XH®, and Anise oil.

Another embodiment comprises cyclosporin A, Triton CF-32®, and Anise oil.

Another embodiment comprises cyclosporin A, Witconol 171®, and Anise oil.

Another embodiment comprises cyclosporin A, Witconol 324®, and Anise oil.

Another embodiment comprises cyclosporin A, Witconol 324D®, and Anise oil.

Another embodiment comprises cyclosporin A, Witconol PD-2000®, and Anise oil., and Anise oil.

a Carboxylated Alcohol or Alkylphenol Ethoxylate, and Anise oil.

Another embodiment comprises cyclosporin A, Emcol CN-6®, and Anise oil.

Another embodiment comprises cyclosporin A, Ethcarb®, and Anise oil.

Another embodiment comprises cyclosporin A, Gemtex WNT-Conc®, and Anise oil.

Another embodiment comprises cyclosporin A, Incrodet TD7-C®, and Anise oil.

Another embodiment comprises cyclosporin A, Marlinat CM 105/80®, and Anise oil.

Another embodiment comprises cyclosporin A, Marlowet 1072®, and Anise oil.

Another embodiment comprises cyclosporin A, Marlowet 4530®, and Anise oil.

Another embodiment comprises cyclosporin A, Marlowet 4530 LF®, and Anise oil.

Another embodiment comprises cyclosporin A, Marlowet 4534®, and Anise oil.

Another embodiment comprises cyclosporin A, Marlowet 4538®, and Anise oil.

Another embodiment comprises cyclosporin A, Marlowet 4539®, and Anise oil.

Another embodiment comprises cyclosporin A, Marlowet 4539 LF®, and Anise oil.

Another embodiment comprises cyclosporin A, Marlowet 4541®, and Anise oil.

Another embodiment comprises cyclosporin A, Miranate LEC-80®, and Anise oil.

Another embodiment comprises cyclosporin A, Sandopan B®, and Anise oil.

Another embodiment comprises cyclosporin A, Sandopan B Modified®, and Anise oil.

Another embodiment comprises cyclosporin A, Sandopan LS-24 Gel®, and Anise oil.

Another embodiment comprises cyclosporin A, Surfine T-A®, and Anise oil.

Another embodiment comprises cyclosporin A, and Anise oil.

Another embodiment comprises cyclosporin A, a Carboxylic Acid/Fatty Acid, and Anise oil.

Another embodiment comprises cyclosporin A, Colaterge RAM®, and Anise oil.

Another embodiment comprises cyclosporin A, Colatrope INC®, and Anise oil.

Another embodiment comprises cyclosporin A, Crodacid B®, and Anise oil.

Another embodiment comprises cyclosporin A, DeTrope CA-100®, and Anise oil.

Another embodiment comprises cyclosporin A, Latol MTO®, and Anise oil.

Another embodiment comprises cyclosporin A, Lumulse CC-33 K®, and Anise oil.

Another embodiment comprises cyclosporin A, Mulls 2218®, and Anise oil.

Another embodiment comprises cyclosporin A, OL-600®, and Anise oil.

Another embodiment comprises cyclosporin A, OL-800®, and Anise oil.

Another embodiment comprises cyclosporin A, R-910®, and Anise oil.

Another embodiment comprises cyclosporin A, S-210®, and Anise oil.

Another embodiment comprises cyclosporin A, Sandopan DTC Acid®, and Anise oil.

Another embodiment comprises cyclosporin A, Sandopan LS 24 N®, and Anise oil.

Another embodiment comprises cyclosporin A, Sandopan MA-18®, and Anise oil.

Another embodiment comprises cyclosporin A, and Anise oil.

Another embodiment comprises cyclosporin A, an Ethoxylated Alcohol, and Anise oil.

Another embodiment comprises cyclosporin A, Adsee 799®, and Anise oil.

Another embodiment comprises cyclosporin A, Adsee 799®, and Anise oil.

Another embodiment comprises cyclosporin A, Alfonic 610-3.5®, and Anise oil.

Another embodiment comprises cyclosporin A, Alfonic 810-2®, and Anise oil.

Another embodiment comprises cyclosporin A, Alfonic 810-6®, and Anise oil.

Another embodiment comprises cyclosporin A, Alfonic 1012-3®, and Anise oil.

Another embodiment comprises cyclosporin A, Alfonic 1012-5®, and Anise oil.

Another embodiment comprises cyclosporin A, Alfonic 1216CO-1.5®, and Anise oil.

Another embodiment comprises cyclosporin A, Alfonic 1216CO-7®, and Anise oil.

Another embodiment comprises cyclosporin A, Alfonic 1412-3®, and Anise oil.

Another embodiment comprises cyclosporin A, Alfonic 1412-7®, and Anise oil.

Another embodiment comprises cyclosporin A, Arlasolve 200®, and Anise oil.

Another embodiment comprises cyclosporin A, Arlasolve 200 Liquid®, and Anise oil.

Another embodiment comprises cyclosporin A, Armix 180-C®, and Anise oil.

Another embodiment comprises cyclosporin A, Armix 183®, and Anise oil.

Another embodiment comprises cyclosporin A, Armul 2404®, and Anise oil.

Another embodiment comprises cyclosporin A, Armul 2404®, and Anise oil.

Another embodiment comprises cyclosporin A, Atlas EMJ-C®, and Anise oil.

Another embodiment comprises cyclosporin A, Atlas G-2109®, and Anise oil.

Another embodiment comprises cyclosporin A, Atlas G-3886®, and Anise oil.

Another embodiment comprises cyclosporin A, Atlas G-3890®, and Anise oil.

Another embodiment comprises cyclosporin A, Bio Soft E-200®, and Anise oil.

Another embodiment comprises cyclosporin A, Bio Soft E-300®, and Anise oil.

Another embodiment comprises cyclosporin A, Bio Soft E-400®, and Anise oil.

Another embodiment comprises cyclosporin A, Bio Soft EN 600®, and Anise oil.

Another embodiment comprises cyclosporin A, Bio Soft TD-400®, and Anise oil.

Another embodiment comprises cyclosporin A, Bio Soft TD-630®, and Anise oil.

Another embodiment comprises cyclosporin A, Brij 30®, and Anise oil.

Another embodiment comprises cyclosporin A, Brij 52®, and Anise oil.

Another embodiment comprises cyclosporin A, Brij 56®, and Anise oil.

Another embodiment comprises cyclosporin A, Brij 58®, and Anise oil.

Another embodiment comprises cyclosporin A, Brij 72®, and Anise oil.

Another embodiment comprises cyclosporin A, Brij 76®, and Anise oil.

Another embodiment comprises cyclosporin A, Brij 78®, and Anise oil.

Another embodiment comprises cyclosporin A, Brij 93®, and Anise oil.

Another embodiment comprises cyclosporin A, Brij 97®, and Anise oil.

Another embodiment comprises cyclosporin A, Brij 98®, and Anise oil.

Another embodiment comprises cyclosporin A, Brij 700®, and Anise oil.

Another embodiment comprises cyclosporin A, Brij 700 S®, and Anise oil.

Another embodiment comprises cyclosporin A, Brij 721®, and Anise oil.

Another embodiment comprises cyclosporin A, Brij 721 S®, and Anise oil.

Another embodiment comprises cyclosporin A, Burcoterge CDG®, and Anise oil.

Another embodiment comprises cyclosporin A, Canasol AT 600®, and Anise oil.

Another embodiment comprises cyclosporin A, Canasol AT 800®, and Anise oil.

Another embodiment comprises cyclosporin A, Canasol AT 1200®, and Anise oil.
Another embodiment comprises cyclosporin A, Canasol BJ 35®, and Anise oil.
Another embodiment comprises cyclosporin A, Canasol BJ 36®, and Anise oil.
Another embodiment comprises cyclosporin A, Canasol BJ 52®, and Anise oil.
Another embodiment comprises cyclosporin A, Canasol BJ 58®, and Anise oil.
Another embodiment comprises cyclosporin A, Canasol BJ 72®, and Anise oil.
Another embodiment comprises cyclosporin A, Canasol BJ 78®, and Anise oil.
Another embodiment comprises cyclosporin A, Canasol BJ 98®, and Anise oil.
Another embodiment comprises cyclosporin A, Canasol BJ 307®, and Anise oil.
Another embodiment comprises cyclosporin A, Cerfak 1400®, and Anise oil.
Another embodiment comprises cyclosporin A, Cetomacrogol 1000 BP®, and Anise oil.
Another embodiment comprises cyclosporin A, Chemonic C-2®, and Anise oil.
Another embodiment comprises cyclosporin A, Chemonic C-10®, and Anise oil.
Another embodiment comprises cyclosporin A, Chemonic C-20®, and Anise oil.
Another embodiment comprises cyclosporin A, Chemonic CT-12®, and Anise oil.
Another embodiment comprises cyclosporin A, Chemonic CT-20®, and Anise oil.
Another embodiment comprises cyclosporin A, Chemonic CT-30®, and Anise oil.
Another embodiment comprises cyclosporin A, Chemonic CT-55®, and Anise oil.
Another embodiment comprises cyclosporin A, Chemonic G-7®, and Anise oil.
Another embodiment comprises cyclosporin A, Chemonic G-26®, and Anise oil.
Another embodiment comprises cyclosporin A, Chemonic L-4®, and Anise oil.
Another embodiment comprises cyclosporin A, Chemonic L-7®, and Anise oil.
Another embodiment comprises cyclosporin A, Chemonic L-12®, and Anise oil.
Another embodiment comprises cyclosporin A, Chemonic L-23®, and Anise oil.
Another embodiment comprises cyclosporin A, Chemonic O-2®, and Anise oil.
Another embodiment comprises cyclosporin A, Chemonic O-5®, and Anise oil.
Another embodiment comprises cyclosporin A, Chemonic O-10®, and Anise oil.
Another embodiment comprises cyclosporin A, Chemonic O-20®, and Anise oil.
Another embodiment comprises cyclosporin A, Chemonic S-2®, and Anise oil.
Another embodiment comprises cyclosporin A, Chemonic S-10®, and Anise oil.
Another embodiment comprises cyclosporin A, Chemonic S-20®, and Anise oil.
Another embodiment comprises cyclosporin A, Colamulse FE®, and Anise oil.
Another embodiment comprises cyclosporin A, Cremophor A 20®, and Anise oil.
Another embodiment comprises cyclosporin A, Cremophor SA 2®, and Anise oil.
Another embodiment comprises cyclosporin A, Dehydol 100®, and Anise oil.
Another embodiment comprises cyclosporin A, Dehydol O-4®, and Anise oil.
Another embodiment comprises cyclosporin A, Delonic C-18®, and Anise oil.
Another embodiment comprises cyclosporin A, DeSonic 6T®, and Anise oil.
Another embodiment comprises cyclosporin A, DeSonic 9D®, and Anise oil.
Another embodiment comprises cyclosporin A, DeSonic 9T®, and Anise oil.
Another embodiment comprises cyclosporin A, DeSonic 12D®, and Anise oil.
Another embodiment comprises cyclosporin A, DeSonic 12T®, and Anise oil.
Another embodiment comprises cyclosporin A, DeSonic 15T®, and Anise oil.
Another embodiment comprises cyclosporin A, DeSonic TDA-9®, and Anise oil.
Another embodiment comprises cyclosporin A, DeThox GLG-7®, and Anise oil.
Another embodiment comprises cyclosporin A, DeThox GLG-26®, and Anise oil.
Another embodiment comprises cyclosporin A, DeThox LA-4®, and Anise oil.
Another embodiment comprises cyclosporin A, DeThox LA-23®, and Anise oil.
Another embodiment comprises cyclosporin A, DeThox SA-80®, and Anise oil.
Another embodiment comprises cyclosporin A, Disponil O5®, and Anise oil.
Another embodiment comprises cyclosporin A, Eccoterge EO-41B®, and Anise oil.
Another embodiment comprises cyclosporin A, Empilan KA2.5/90®, and Anise oil.
Another embodiment comprises cyclosporin A, Empilan KA5/90®, and Anise oil.
Another embodiment comprises cyclosporin A, Empilan KM-20®, and Anise oil.
Another embodiment comprises cyclosporin A, Empilan KM-50®, and Anise oil.
Another embodiment comprises cyclosporin A, Empilan L-23®, and Anise oil.
Another embodiment comprises cyclosporin A, Ethylan 25-3®, and Anise oil.
Another embodiment comprises cyclosporin A, Ethylan 1204®, and Anise oil.
Another embodiment comprises cyclosporin A, Ethylan DA-4®, and Anise oil.
Another embodiment comprises cyclosporin A, Ethylan LA-230®, and Anise oil.
Another embodiment comprises cyclosporin A, Ethylan SN®, and Anise oil.
Another embodiment comprises cyclosporin A, Ethylan TD-60®, and Anise oil.
Another embodiment comprises cyclosporin A, Ethylan TD-100®, and Anise oil.
Another embodiment comprises cyclosporin A, Ethylan TD-1407®, and Anise oil.
Another embodiment comprises cyclosporin A, Eumulgin B1®, and Anise oil.
Another embodiment comprises cyclosporin A, Eumulgin B2®, and Anise oil.

Another embodiment comprises cyclosporin A, Eumulgin B3®, and Anise oil.

Another embodiment comprises cyclosporin A, Eumulgin O-10®, and Anise oil.

Another embodiment comprises cyclosporin A, Flo Mo 80/20®, and Anise oil.

Another embodiment comprises cyclosporin A, Flo Mo Low Foam®, and Anise oil.

Another embodiment comprises cyclosporin A, Forlan C-24®, and Anise oil.

Another embodiment comprises cyclosporin A, Genapol 1454®, and Anise oil.

Another embodiment comprises cyclosporin A, Genapol BA-020®, and Anise oil.

Another embodiment comprises cyclosporin A, Genapol BA-040®, and Anise oil.

Another embodiment comprises cyclosporin A, Genapol C-100®, and Anise oil.

Another embodiment comprises cyclosporin A, Genapol DA 060®, and Anise oil.

Another embodiment comprises cyclosporin A, Genapol HS 020®, and Anise oil.

Another embodiment comprises cyclosporin A, Genapol HS 200®, and Anise oil.

Another embodiment comprises cyclosporin A, Genapol ID-040®, and Anise oil.

Another embodiment comprises cyclosporin A, Genapol ID-060®, and Anise oil.

Another embodiment comprises cyclosporin A, Genapol ID-090®, and Anise oil.

Another embodiment comprises cyclosporin A, Genapol LA 010®, and Anise oil.

Another embodiment comprises cyclosporin A, Genapol LA 020®, and Anise oil.

Another embodiment comprises cyclosporin A, Genapol LA 030®, and Anise oil.

Another embodiment comprises cyclosporin A, Genapol LA 040®, and Anise oil.

Another embodiment comprises cyclosporin A, Genapol LA 050®, and Anise oil.

Another embodiment comprises cyclosporin A, Genapol LA 060®, and Anise oil.

Another embodiment comprises cyclosporin A, Genapol LA 070®, and Anise oil.

Another embodiment comprises cyclosporin A, Genapol LA 070S®, and Anise oil.

Another embodiment comprises cyclosporin A, Genapol LA 230®, and Anise oil.

Another embodiment comprises cyclosporin A, Genapol O 020®, and Anise oil.

Another embodiment comprises cyclosporin A, Genapol O 050®, and Anise oil.

Another embodiment comprises cyclosporin A, Genapol O 100®, and Anise oil.

Another embodiment comprises cyclosporin A, Genapol O 200®, and Anise oil.

Another embodiment comprises cyclosporin A, Genapol SA 030®, and Anise oil.

Another embodiment comprises cyclosporin A, Genapol SA 120®, and Anise oil.

Another embodiment comprises cyclosporin A, Genapol T-020®, and Anise oil.

Another embodiment comprises cyclosporin A, Genapol UD-030®, and Anise oil.

Another embodiment comprises cyclosporin A, Genapol UD-050®, and Anise oil.

Another embodiment comprises cyclosporin A, Genapol UD-070®, and Anise oil.

Another embodiment comprises cyclosporin A, Genapol UD-079®, and Anise oil.

Another embodiment comprises cyclosporin A, Genapol UD-080®, and Anise oil.

Another embodiment comprises cyclosporin A, Genapol UD-110®, and Anise oil.

Another embodiment comprises cyclosporin A, Genapol X 030®, and Anise oil.

Another embodiment comprises cyclosporin A, Genapol X 050®, and Anise oil.

Another embodiment comprises cyclosporin A, Genapol X 060®, and Anise oil.

Another embodiment comprises cyclosporin A, Genapol X 070®, and Anise oil.

Another embodiment comprises cyclosporin A, Genapol X 080®, and Anise oil.

Another embodiment comprises cyclosporin A, Genapol X 100®, and Anise oil.

Another embodiment comprises cyclosporin A, Genapol X159®, and Anise oil.

Another embodiment comprises cyclosporin A, Generol 122 E5®, and Anise oil.

Another embodiment comprises cyclosporin A, Generol 122 E25®, and Anise oil.

Another embodiment comprises cyclosporin A, Hostacerin T-3®, and Anise oil.

Another embodiment comprises cyclosporin A, Iconol LF 110®, and Anise oil.

Another embodiment comprises cyclosporin A, Incropol CS-20®, and Anise oil.

Another embodiment comprises cyclosporin A, Lexemul CS-20®, and Anise oil.

Another embodiment comprises cyclosporin A, Liponic EG-1®, and Anise oil.

Another embodiment comprises cyclosporin A, Lipowax D®, and Anise oil.

Another embodiment comprises cyclosporin A, Lipowax G®, and Anise oil.

Another embodiment comprises cyclosporin A, Lipowax NI®, and Anise oil.

Another embodiment comprises cyclosporin A, Lipowax P®, and Anise oil.

Another embodiment comprises cyclosporin A, Lipowax P-31®, and Anise oil.

Another embodiment comprises cyclosporin A, Lipowax PR®, and Anise oil.

Another embodiment comprises cyclosporin A, Lumulse CS-20®, and Anise oil.

Another embodiment comprises cyclosporin A, Macol CSA-20®, and Anise oil.

Another embodiment comprises cyclosporin A, Marlox B 24/50®, and Anise oil.

Another embodiment comprises cyclosporin A, Mazawet 77®, and Anise oil.

Another embodiment comprises cyclosporin A, Norfox 1713®, and Anise oil.

Another embodiment comprises cyclosporin A, Norfox 2579®, and Anise oil.

Another embodiment comprises cyclosporin A, Norfox Lo Foam®, and Anise oil.

Another embodiment comprises cyclosporin A, Promulgen D®, and Anise oil.

Another embodiment comprises cyclosporin A, Promulgen G®, and Anise oil.

Another embodiment comprises cyclosporin A, Renex 30®, and Anise oil.

Another embodiment comprises cyclosporin A, Renex 36®, and Anise oil.

Another embodiment comprises cyclosporin A, Rhodasurf A 24®, and Anise oil.

Another embodiment comprises cyclosporin A, Rhodasurf AAE-10®, and Anise oil.

Another embodiment comprises cyclosporin A, Rhodasurf BEH-25®, and Anise oil.

Another embodiment comprises cyclosporin A, Rhodasurf BEH-40®, and Anise oil.

Another embodiment comprises cyclosporin A, Rhodasurf DA 530®, and Anise oil.

Another embodiment comprises cyclosporin A, Rhodasurf DA 630®, and Anise oil.

Another embodiment comprises cyclosporin A, Rhodasurf DA 639®, and Anise oil.

Another embodiment comprises cyclosporin A, Rhodasurf LAN-23®, and Anise oil.

Another embodiment comprises cyclosporin A, Rhodasurf ON-870®, and Anise oil.

Another embodiment comprises cyclosporin A, Rhodasurf ON-877®, and Anise oil.

Another embodiment comprises cyclosporin A, Rhodasurf TB-970 FLK®, and Anise oil.

Another embodiment comprises cyclosporin A, Ritacet-20®, and Anise oil.

Another embodiment comprises cyclosporin A, Ritachol 1000®, and Anise oil.

Another embodiment comprises cyclosporin A, Ritachol 2000®, and Anise oil.

Another embodiment comprises cyclosporin A, Ritachol 5000®, and Anise oil.

Another embodiment comprises cyclosporin A, Ritox 35®, and Anise oil.

Another embodiment comprises cyclosporin A, Surfonic DA-4®, and Anise oil.

Another embodiment comprises cyclosporin A, Surfonic DA-6®, and Anise oil.

Another embodiment comprises cyclosporin A, Surfonic L46-7®, and Anise oil.

Another embodiment comprises cyclosporin A, Surfonic POA®, and Anise oil.

Another embodiment comprises cyclosporin A, Synthrapol KB®, and Anise oil.

Another embodiment comprises cyclosporin A, Teginacid®, and Anise oil.

Another embodiment comprises cyclosporin A, Teginacid C®, and Anise oil.

Another embodiment comprises cyclosporin A, Tegotens EC 11®, and Anise oil.

Another embodiment comprises cyclosporin A, Tinegal NA®, and Anise oil.

Another embodiment comprises cyclosporin A, Tomadol 400®, and Anise oil.

Another embodiment comprises cyclosporin A, Tomadol 600®, and Anise oil.

Another embodiment comprises cyclosporin A, Tomadol 900®, and Anise oil.

Another embodiment comprises cyclosporin A, Uniperol O®, and Anise oil.

Another embodiment comprises cyclosporin A, Witconol SN Series®, and Anise oil.

Another embodiment comprises cyclosporin A, and Anise oil.

Another embodiment comprises cyclosporin A, an Ethoxylated Alkylphenol, and Anise oil.

Another embodiment comprises cyclosporin A, Antarox LF-222®, and Anise oil.

Another embodiment comprises cyclosporin A, Atlox 775®, and Anise oil.

Another embodiment comprises cyclosporin A, Caloxylate N-9®, and Anise oil.

Another embodiment comprises cyclosporin A, Canasol NF-1000®, and Anise oil.

Another embodiment comprises cyclosporin A, Canasol NF-3000®, and Anise oil.

Another embodiment comprises cyclosporin A, Canasol NF-3070®, and Anise oil.

Another embodiment comprises cyclosporin A, Canasol OF 1670®, and Anise oil.

Another embodiment comprises cyclosporin A, Canasol OF 2570®, and Anise oil.

Another embodiment comprises cyclosporin A, Canasol OF 4070®, and Anise oil.

Another embodiment comprises cyclosporin A, Chemax DNP-8®, and Anise oil.

Another embodiment comprises cyclosporin A, Chemax DNP-18®, and Anise oil.

Another embodiment comprises cyclosporin A, Chemax DNP-150/50®, and Anise oil.

Another embodiment comprises cyclosporin A, DeSonic 1.5N®, and Anise oil.

Another embodiment comprises cyclosporin A, DeSonic 4N®, and Anise oil.

Another embodiment comprises cyclosporin A, DeSonic 5N®, and Anise oil.

Another embodiment comprises cyclosporin A, DeSonic 6D®, and Anise oil.

Another embodiment comprises cyclosporin A, DeSonic 6N®, and Anise oil.

Another embodiment comprises cyclosporin A, DeSonic 7N®, and Anise oil.

Another embodiment comprises cyclosporin A, DeSonic 9N®, and Anise oil.

Another embodiment comprises cyclosporin A, DeSonic 10D®, and Anise oil.

Another embodiment comprises cyclosporin A, DeSonic 11N®, and Anise oil.

Another embodiment comprises cyclosporin A, DeSonic 12N®, and Anise oil.

Another embodiment comprises cyclosporin A, DeSonic 15N®, and Anise oil.

Another embodiment comprises cyclosporin A, DeSonic 20N®, and Anise oil.

Another embodiment comprises cyclosporin A, Eccoscour RC®, and Anise oil.

Another embodiment comprises cyclosporin A, Eccoterge EO-100®, and Anise oil.

Another embodiment comprises cyclosporin A, Emulsifier 632/90%®, and Anise oil.

Another embodiment comprises cyclosporin A, Geronol AG-821®, and Anise oil.

Another embodiment comprises cyclosporin A, Gradonic N-95®, and Anise oil.

Another embodiment comprises cyclosporin A, Hetoxide NP-4®, and Anise oil.

Another embodiment comprises cyclosporin A, Hetoxide NP-30®, and Anise oil.

Another embodiment comprises cyclosporin A, Hostapal N-100®, and Anise oil.

Another embodiment comprises cyclosporin A, Hostapal N-110®, and Anise oil.

Another embodiment comprises cyclosporin A, Igepal CTA-639W®, and Anise oil.

Another embodiment comprises cyclosporin A, Igepal DAP-9®, and Anise oil.

Another embodiment comprises cyclosporin A, Igepal OD-410®, and Anise oil.

Another embodiment comprises cyclosporin A, Igepal SS-837®, and Anise oil.

Another embodiment comprises cyclosporin A, Lipocol NP-9 USP®, and Anise oil.

Another embodiment comprises cyclosporin A, Macol DNP-10®, and Anise oil.

Another embodiment comprises cyclosporin A, Marlophen NP 5®, and Anise oil.

Another embodiment comprises cyclosporin A, Marlophen P 1®, and Anise oil.

Another embodiment comprises cyclosporin A, Surfonic NB®, and Anise oil.

Another embodiment comprises cyclosporin A, Surfonic OPB-307®, and Anise oil.

Another embodiment comprises cyclosporin A, Surfonic OPB-407®, and Anise oil.

Another embodiment comprises cyclosporin A, Syn Fac 334®, and Anise oil.

Another embodiment comprises cyclosporin A, Syn Fac 8216®, and Anise oil.

Another embodiment comprises cyclosporin A, Triton N-57®, and Anise oil.

Another embodiment comprises cyclosporin A, Trycol 6956®, and Anise oil.

Another embodiment comprises cyclosporin A, Trycol 6961®, and Anise oil.

Another embodiment comprises cyclosporin A, Trycol 6964®, and Anise oil.

Another embodiment comprises cyclosporin A, Trycol 6969®, and Anise oil.

Another embodiment comprises cyclosporin A, Trycol 6974®, and Anise oil.

Another embodiment comprises cyclosporin A, Witbreak DRB-127®, and Anise oil.

Another embodiment comprises cyclosporin A, Witbreak DRB-127®, and Anise oil.

Another embodiment comprises cyclosporin A, Witconol NP Series®, and Anise oil.

Another embodiment comprises cyclosporin A, and Anise oil.

Another embodiment comprises cyclosporin A, an Ethoxylated Aryl Phenol, and Anise oil.

Another embodiment comprises cyclosporin A, Sporophor BSU®, and Anise oil.

Another embodiment comprises cyclosporin A, Sporophor CY/8®, and Anise oil.

Another embodiment comprises cyclosporin A, Sporophor S/25®, and Anise oil.

Another embodiment comprises cyclosporin A, Witconol NIO®, and Anise oil.

Another embodiment comprises cyclosporin A, Witconol NIW®, and Anise oil.

Another embodiment comprises cyclosporin A, Witconol S-100®, and Anise oil.

Another embodiment comprises cyclosporin A, and Anise oil.

Another embodiment comprises cyclosporin A, an Ethoxylated Fatty Acid, and Anise oil.

Another embodiment comprises cyclosporin A, Aldo PGHMS®, and Anise oil.

Another embodiment comprises cyclosporin A, Alkamuls TO-15/HR®, and Anise oil.

Another embodiment comprises cyclosporin A, Armotan AL-69-66®, and Anise oil.

Another embodiment comprises cyclosporin A, Cerasynt 840®, and Anise oil.

Another embodiment comprises cyclosporin A, Cerasynt 945®, and Anise oil.

Another embodiment comprises cyclosporin A, Crystal Inhibitor No. 5®, and Anise oil.

Another embodiment comprises cyclosporin A, DeThox Acid L-9®, and Anise oil.

Another embodiment comprises cyclosporin A, DeThox Acid S-8®, and Anise oil.

Another embodiment comprises cyclosporin A, Ethofat 242/25®, and Anise oil.

Another embodiment comprises cyclosporin A, Hydropalat 65®, and Anise oil.

Another embodiment comprises cyclosporin A, Lipo EGMS®, and Anise oil.

Another embodiment comprises cyclosporin A, Lipopeg 2 DL®, and Anise oil.

Another embodiment comprises cyclosporin A, Lipopeg 4 DL®, and Anise oil.

Another embodiment comprises cyclosporin A, Lipopeg 4-L®, and Anise oil.

Another embodiment comprises cyclosporin A, Lipopeg 39-S®, and Anise oil.

Another embodiment comprises cyclosporin A, Lipopeg 4-S®, and Anise oil.

Another embodiment comprises cyclosporin A, Lipopeg 10-S®, and Anise oil.

Another embodiment comprises cyclosporin A, Lipopeg 100-S®, and Anise oil.

Another embodiment comprises cyclosporin A, Lipopeg 6000 DS®, and Anise oil.

Another embodiment comprises cyclosporin A, Lumulse 40-L®, and Anise oil.

Another embodiment comprises cyclosporin A, Lumulse 40-S®, and Anise oil.

Another embodiment comprises cyclosporin A, Lumulse 42-L®, and Anise oil.

Another embodiment comprises cyclosporin A, Lumulse 42-S®, and Anise oil.

Another embodiment comprises cyclosporin A, Lumulse 100-S®, and Anise oil.

Another embodiment comprises cyclosporin A, Lumulse 602-S®, and Anise oil.

Another embodiment comprises cyclosporin A, Magrabar PGE-20-0®, and Anise oil.

Another embodiment comprises cyclosporin A, Magrabar PGE-20L®, and Anise oil.

Another embodiment comprises cyclosporin A, Magrabar PGE-20T®, and Anise oil.

Another embodiment comprises cyclosporin A, Magrabar PGE-22-0®, and Anise oil.

Another embodiment comprises cyclosporin A, Magrabar PGE-22L®, and Anise oil.

Another embodiment comprises cyclosporin A, Magrabar PGE-22T®, and Anise oil.

Another embodiment comprises cyclosporin A, Magrabar PGE-40-0®, and Anise oil.

Another embodiment comprises cyclosporin A, Magrabar PGE-40L®, and Anise oil.

Another embodiment comprises cyclosporin A, Magrabar PGE-40T®, and Anise oil.

Another embodiment comprises cyclosporin A, Magrabar PGE-42-0®, and Anise oil.

Another embodiment comprises cyclosporin A, Magrabar PGE-42L®, and Anise oil.

Another embodiment comprises cyclosporin A, Magrabar PGE-42T®, and Anise oil.

Another embodiment comprises cyclosporin A, Magrabar PGE-60-0®, and Anise oil.

Another embodiment comprises cyclosporin A, Magrabar PGE-60L®, and Anise oil.

Another embodiment comprises cyclosporin A, Magrabar PGE-60T®, and Anise oil.

Another embodiment comprises cyclosporin A, Magrabar PGE-62-0®, and Anise oil.

Another embodiment comprises cyclosporin A, Magrabar PGE-62L®, and Anise oil.

Another embodiment comprises cyclosporin A, Magrabar PGE-62T®, and Anise oil.

Another embodiment comprises cyclosporin A, Mapeg S-40K®, and Anise oil.

Another embodiment comprises cyclosporin A, Marlowet OTS®, and Anise oil.

Another embodiment comprises cyclosporin A, Naturechem PGR®, and Anise oil.

Another embodiment comprises cyclosporin A, PG No. 4®, and Anise oil.

Another embodiment comprises cyclosporin A, Renex 20®, and Anise oil.

Another embodiment comprises cyclosporin A, Ritox 52®, and Anise oil.

Another embodiment comprises cyclosporin A, Ritox 53®, and Anise oil.

Another embodiment comprises cyclosporin A, Ritox 59®, and Anise oil.

Another embodiment comprises cyclosporin A, Surtax 8916/A®, and Anise oil.

Another embodiment comprises cyclosporin A, Tego Acid S 40 P®, and Anise oil.

Another embodiment comprises cyclosporin A, Tego Acid S 100 P®, and Anise oil.

Another embodiment comprises cyclosporin A, Tween 20®, and Anise oil.

Another embodiment comprises cyclosporin A, Volpo 131®, and Anise oil.

Another embodiment comprises cyclosporin A, and Anise oil.

Another embodiment comprises cyclosporin A, an Ethoxylated Fatty Ester or Oil, and Anise oil.

Another embodiment comprises cyclosporin A, Acconon 6-C10®, and Anise oil.

Another embodiment comprises cyclosporin A, Acconon CC-6®, and Anise oil.

Another embodiment comprises cyclosporin A, Acconon CO-7®, and Anise oil.

Another embodiment comprises cyclosporin A, Aldosperse 40/60 FG®, and Anise oil.

Another embodiment comprises cyclosporin A, Aldosperse ML-23®, and Anise oil.

Another embodiment comprises cyclosporin A, Aldosperse MS-20 FG®, and Anise oil.

Another embodiment comprises cyclosporin A, Alkamuls EL-620®, and Anise oil.

Another embodiment comprises cyclosporin A, Alkamuls EL-719®, and Anise oil.

Another embodiment comprises cyclosporin A, Alkamuls EL-985®, and Anise oil.

Another embodiment comprises cyclosporin A, Arlatone G®, and Anise oil.

Another embodiment comprises cyclosporin A, Arlatone T®, and Anise oil.

Another embodiment comprises cyclosporin A, Atlas G-1045A®, and Anise oil.

Another embodiment comprises cyclosporin A, Atlas G-1086®, and Anise oil.

Another embodiment comprises cyclosporin A, Atlas G-1087®, and Anise oil.

Another embodiment comprises cyclosporin A, Atlas G-1089®, and Anise oil.

Another embodiment comprises cyclosporin A, Atlas G-1096®, and Anise oil.

Another embodiment comprises cyclosporin A, Atlas G-1292®, and Anise oil.

Another embodiment comprises cyclosporin A, Atlas G-1293®, and Anise oil.

Another embodiment comprises cyclosporin A, Atlas G-1300®, and Anise oil.

Another embodiment comprises cyclosporin A, Atlas G-7076®, and Anise oil.

Another embodiment comprises cyclosporin A, Capmul EMG®, and Anise oil.

Another embodiment comprises cyclosporin A, Chemonic CO-40®, and Anise oil.

Another embodiment comprises cyclosporin A, Chemonic LI-3®, and Anise oil.

Another embodiment comprises cyclosporin A, Chemonic LI-7®, and Anise oil.

Another embodiment comprises cyclosporin A, Cirrasol GM®, and Anise oil.

Another embodiment comprises cyclosporin A, Cremophor CO 40®, and Anise oil.

Another embodiment comprises cyclosporin A, Cremophor CO 410®, and Anise oil.

Another embodiment comprises cyclosporin A, Cremophor EL®, and Anise oil.

Another embodiment comprises cyclosporin A, Cremophor GC7®, and Anise oil.

Another embodiment comprises cyclosporin A, Cremophor RH-40®, and Anise oil.

Another embodiment comprises cyclosporin A, Crovol A-40®, and Anise oil.

Another embodiment comprises cyclosporin A, Crovol A-70®, and Anise oil.

Another embodiment comprises cyclosporin A, Crovol M-70®, and Anise oil.

Another embodiment comprises cyclosporin A, Crovol PK-70®, and Anise oil.

Another embodiment comprises cyclosporin A, Cutina E-24®, and Anise oil.

Another embodiment comprises cyclosporin A, Dacospin 12-R®, and Anise oil.

Another embodiment comprises cyclosporin A, Dehymuls HRE-7®, and Anise oil.

Another embodiment comprises cyclosporin A, DeSonic 30C®, and Anise oil.

Another embodiment comprises cyclosporin A, DeSonic 36C®, and Anise oil.

Another embodiment comprises cyclosporin A, DeSonic 40C®, and Anise oil.

Another embodiment comprises cyclosporin A, Durfax 60®, and Anise oil.

Another embodiment comprises cyclosporin A, Durfax 65®, and Anise oil.

Another embodiment comprises cyclosporin A, Durfax 80®, and Anise oil.

Another embodiment comprises cyclosporin A, Durfax EOM®, and Anise oil.

Another embodiment comprises cyclosporin A, Eccoterge NF-2®, and Anise oil.

Another embodiment comprises cyclosporin A, Emulpon CO-360®, and Anise oil.

Another embodiment comprises cyclosporin A, Emulpon CO-550®, and Anise oil.

Another embodiment comprises cyclosporin A, Emulsogen EL®, and Anise oil.

Another embodiment comprises cyclosporin A, Emulsogen HCO 040®, and Anise oil.

Another embodiment comprises cyclosporin A, Emulsogen HCO 060®, and Anise oil.

Another embodiment comprises cyclosporin A, Emulsynt 1055®, and Anise oil.

Another embodiment comprises cyclosporin A, Ethox 3095®, and Anise oil.

Another embodiment comprises cyclosporin A, Eumulgin RO-40®, and Anise oil.

Another embodiment comprises cyclosporin A, Genapol G-260®, and Anise oil.

Another embodiment comprises cyclosporin A, Glycosperse L-20®, and Anise oil.

Another embodiment comprises cyclosporin A, Glycosperse O-5®, and Anise oil.

Another embodiment comprises cyclosporin A, Glycosperse O-20®, and Anise oil.

Another embodiment comprises cyclosporin A, Glycosperse O-20 FG®, and Anise oil.

Another embodiment comprises cyclosporin A, Glycosperse S-20®, and Anise oil.

Another embodiment comprises cyclosporin A, Glycosperse S-20 FG®, and Anise oil.

Another embodiment comprises cyclosporin A, Glycosperse TS-20®, and Anise oil.

Another embodiment comprises cyclosporin A, Glycosperse TS-20 FG®, and Anise oil.

Another embodiment comprises cyclosporin A, Hetan SL®, and Anise oil.

Another embodiment comprises cyclosporin A, Hetan SO®, and Anise oil.

Another embodiment comprises cyclosporin A, Hetan SS®, and Anise oil.

Another embodiment comprises cyclosporin A, Hetoxide C-2®, and Anise oil.

Another embodiment comprises cyclosporin A, Hetoxide C-9®, and Anise oil.

Another embodiment comprises cyclosporin A, Hetoxide C-15®, and Anise oil.

Another embodiment comprises cyclosporin A, Hetoxide C-25®, and Anise oil.

Another embodiment comprises cyclosporin A, Hetoxide C-40®, and Anise oil.

Another embodiment comprises cyclosporin A, Hetoxide C-200®, and Anise oil.

Another embodiment comprises cyclosporin A, Hetoxide C-200-50%®, and Anise oil.

Another embodiment comprises cyclosporin A, Hetoxide GC-30®, and Anise oil.

Another embodiment comprises cyclosporin A, Hetoxide HC-60®, and Anise oil.

Another embodiment comprises cyclosporin A, Ice No. 2®, and Anise oil.

Another embodiment comprises cyclosporin A, Incrocas 30/40®, and Anise oil.

Another embodiment comprises cyclosporin A, Lexol EC®, and Anise oil.

Another embodiment comprises cyclosporin A, Lexol EO®, and Anise oil.

Another embodiment comprises cyclosporin A, Lipocol HCO-40®, and Anise oil.

Another embodiment comprises cyclosporin A, Lipocol HCO-60®, and Anise oil.

Another embodiment comprises cyclosporin A, Lipocol O-3 Special®, and Anise oil.

Another embodiment comprises cyclosporin A, Lipopeg 2-L®, and Anise oil.

Another embodiment comprises cyclosporin A, Lipopeg 4-DO®, and Anise oil.

Another embodiment comprises cyclosporin A, Lipopeg 4-DS®, and Anise oil.

Another embodiment comprises cyclosporin A, Lipovol GTB®, and Anise oil.

Another embodiment comprises cyclosporin A, Lonzest SML-20®, and Anise oil.

Another embodiment comprises cyclosporin A, Lonzest SMO-20®, and Anise oil.

Another embodiment comprises cyclosporin A, Lonzest SMS-20®, and Anise oil.

Another embodiment comprises cyclosporin A, Lonzest STO-20®, and Anise oil.

Another embodiment comprises cyclosporin A, Lonzest STS-20®, and Anise oil.

Another embodiment comprises cyclosporin A, Lumulse GR-40®, and Anise oil.

Another embodiment comprises cyclosporin A, Lumulse GRH-40®, and Anise oil.

Another embodiment comprises cyclosporin A, Lumulse POE (7) GML®, and Anise oil.

Another embodiment comprises cyclosporin A, Lumulse POE (12) Glyc®, and Anise oil.

Another embodiment comprises cyclosporin A, Lumulse POE (40) MS KP®, and Anise oil.

Another embodiment comprises cyclosporin A, Marlowet 4750®, and Anise oil.

Another embodiment comprises cyclosporin A, Marlowet LVS®, and Anise oil.

Another embodiment comprises cyclosporin A, Marlowet R 11®, and Anise oil.

Another embodiment comprises cyclosporin A, Marlowet R 40®, and Anise oil.

Another embodiment comprises cyclosporin A, Mazol 80 MGK®, and Anise oil.

Another embodiment comprises cyclosporin A, Nonionic Emulsifier T-9®, and Anise oil.

Another embodiment comprises cyclosporin A, Oronal LCG®, and Anise oil.

Another embodiment comprises cyclosporin A, Polyderm PPI-CO-200®, and Anise oil.

Another embodiment comprises cyclosporin A, Polyderm PPI-CO-40®, and Anise oil.

Another embodiment comprises cyclosporin A, Rewoderm LI 520-70®, and Anise oil.

Another embodiment comprises cyclosporin A, Ritapeg 150 DS®, and Anise oil.

Another embodiment comprises cyclosporin A, Softigen 767®, and Anise oil.

Another embodiment comprises cyclosporin A, Surfactol 318®, and Anise oil.

Another embodiment comprises cyclosporin A, Surfactol 365®, and Anise oil.

Another embodiment comprises cyclosporin A, Syn Lube 107®, and Anise oil.

Another embodiment comprises cyclosporin A, Syn Lube 728®, and Anise oil.

Another embodiment comprises cyclosporin A, Syn Lube 1632H®, and Anise oil.

Another embodiment comprises cyclosporin A, Syn Lube 6277-A®, and Anise oil.

Another embodiment comprises cyclosporin A, T-Det C-20®, and Anise oil.

Another embodiment comprises cyclosporin A, T-Det C-40®, and Anise oil.

Another embodiment comprises cyclosporin A, Tally 100 Plus®, and Anise oil.

Another embodiment comprises cyclosporin A, Uniperol EL®, and Anise oil.

Another embodiment comprises cyclosporin A, and Anise oil.

Another embodiment comprises cyclosporin A, a Fatty Ester, and Anise oil.

Another embodiment comprises cyclosporin A, Actralube-Syn 147®, and Anise oil.

Another embodiment comprises cyclosporin A, Atlas G-1556®, and Anise oil.

Another embodiment comprises cyclosporin A, Atlas G-1564®, and Anise oil.

Another embodiment comprises cyclosporin A, Atlasol Base Oil S®, and Anise oil.

Another embodiment comprises cyclosporin A, Base ML®, and Anise oil.

Another embodiment comprises cyclosporin A, Base MT®, and Anise oil.

Another embodiment comprises cyclosporin A, Cerasynt 303®, and Anise oil.

Another embodiment comprises cyclosporin A, Dermol 1012®, and Anise oil.

Another embodiment comprises cyclosporin A, Kemester 4000®, and Anise oil.

Another embodiment comprises cyclosporin A, Lactipol S®, and Anise oil.

Another embodiment comprises cyclosporin A, Magrabar PGO®, and Anise oil.

Another embodiment comprises cyclosporin A, Mayco Base BFO®, and Anise oil.

Another embodiment comprises cyclosporin A, Methyl Linoleate®, and Anise oil.

Another embodiment comprises cyclosporin A, Pationic 122A®, and Anise oil.

Another embodiment comprises cyclosporin A, Pationic 138C®, and Anise oil.

Another embodiment comprises cyclosporin A, Pationic CSL®, and Anise oil.

Another embodiment comprises cyclosporin A, Pationic ISL®, and Anise oil.

Another embodiment comprises cyclosporin A, Pationic SBL®, and Anise oil.

Another embodiment comprises cyclosporin A, Pationic SSL®, and Anise oil.

Another embodiment comprises cyclosporin A, Ritasol®, and Anise oil.

Another embodiment comprises cyclosporin A, Tego Alkanol CS 20®, and Anise oil.

Another embodiment comprises cyclosporin A, Tego Alkanol L23 P®, and Anise oil.

Another embodiment comprises cyclosporin A, Tego Alkanol S2®, and Anise oil.

Another embodiment comprises cyclosporin A, Tego Alkanol S20 P®, and Anise oil.

Another embodiment comprises cyclosporin A, Triemulsifier 600 MS®, and Anise oil.

Another embodiment comprises cyclosporin A, and Anise oil.

Another embodiment comprises cyclosporin A, a Glycerol Esters, and Anise oil.

Another embodiment comprises cyclosporin A, Agro #9 Wint SBO®, and Anise oil.

Another embodiment comprises cyclosporin A, Ahcovel Base 700®, and Anise oil.

Another embodiment comprises cyclosporin A, Aldo HMS FG®, and Anise oil.

Another embodiment comprises cyclosporin A, Aldo MLD®, and Anise oil.

Another embodiment comprises cyclosporin A, Aldo MLD FG®, and Anise oil.

Another embodiment comprises cyclosporin A, Aldo MO FG®, and Anise oil.

Another embodiment comprises cyclosporin A, Aldo MS®, and Anise oil.

Another embodiment comprises cyclosporin A, Aldo MS FG®, and Anise oil.

Another embodiment comprises cyclosporin A, Aldo MS LG FG®, and Anise oil.

Another embodiment comprises cyclosporin A, Aldo MSD®, and Anise oil.

Another embodiment comprises cyclosporin A, Aldo MSD FG®, and Anise oil.

Another embodiment comprises cyclosporin A, Aldosperse O-20 FG®, and Anise oil.

Another embodiment comprises cyclosporin A, Aldosperse TS-20 FG®, and Anise oil.

Another embodiment comprises cyclosporin A, Aldosperse TS-40 FG®, and Anise oil.

Another embodiment comprises cyclosporin A, Arlacel 165®, and Anise oil.

Another embodiment comprises cyclosporin A, Arlacel 186®, and Anise oil.

Another embodiment comprises cyclosporin A, Capmul GMO®, and Anise oil.

Another embodiment comprises cyclosporin A, Capmul GMS®, and Anise oil.

Another embodiment comprises cyclosporin A, Caprol 3GO®, and Anise oil.

Another embodiment comprises cyclosporin A, Caprol 3GVS®, and Anise oil.

Another embodiment comprises cyclosporin A, Caprol 6G2S®, and Anise oil.

Another embodiment comprises cyclosporin A, Caprol 10G40®, and Anise oil.

Another embodiment comprises cyclosporin A, Caprol 10G100®, and Anise oil.

Another embodiment comprises cyclosporin A, Caprol ET®, and Anise oil.

Another embodiment comprises cyclosporin A, Caprol PGE860®, and Anise oil.

Another embodiment comprises cyclosporin A, Cerasynt 945®, and Anise oil.

Another embodiment comprises cyclosporin A, Cerasynt GMS®, and Anise oil.

Another embodiment comprises cyclosporin A, Cerasynt Q®, and Anise oil.

Another embodiment comprises cyclosporin A, Cerasynt SD®, and Anise oil.

Another embodiment comprises cyclosporin A, Cerasynt WM®, and Anise oil.

Another embodiment comprises cyclosporin A, Chemsperse 14®, and Anise oil.

Another embodiment comprises cyclosporin A, Cremophor GO-32®, and Anise oil.

Another embodiment comprises cyclosporin A, Cremophor GS11®, and Anise oil.

Another embodiment comprises cyclosporin A, Cremophor GS-32®, and Anise oil.

Another embodiment comprises cyclosporin A, Cutina KD-16®, and Anise oil.

Another embodiment comprises cyclosporin A, Dehymuls PGPH®, and Anise oil.

Another embodiment comprises cyclosporin A, Dermol DGDIS®, and Anise oil.

Another embodiment comprises cyclosporin A, Dermol DGMIS®, and Anise oil.

Another embodiment comprises cyclosporin A, Dermol G-76®, and Anise oil.

Another embodiment comprises cyclosporin A, Dermol G-7DI®, and Anise oil.

Another embodiment comprises cyclosporin A, Dermol NGDI®, and Anise oil.

Another embodiment comprises cyclosporin A, Dermolan GLH®, and Anise oil.

Another embodiment comprises cyclosporin A, Drewmulse GMO®, and Anise oil.

Another embodiment comprises cyclosporin A, Drewpol 3-5-M®, and Anise oil.

Another embodiment comprises cyclosporin A, Durlac 100 W®, and Anise oil.

Another embodiment comprises cyclosporin A, Dur-Lo®, and Anise oil.

Another embodiment comprises cyclosporin A, Dynasan 118®, and Anise oil.

Another embodiment comprises cyclosporin A, EC-25®, and Anise oil.

Another embodiment comprises cyclosporin A, EM 40®, and Anise oil.

Another embodiment comprises cyclosporin A, Emerest 2400®, and Anise oil.

Another embodiment comprises cyclosporin A, Emerest 2452®, and Anise oil.

Another embodiment comprises cyclosporin A, Empilan G-26®, and Anise oil.

Another embodiment comprises cyclosporin A, Genapol TSM®, and Anise oil.

Another embodiment comprises cyclosporin A, Hostacerin DGI®, and Anise oil.

Another embodiment comprises cyclosporin A, Hostacerin DGL®, and Anise oil.

Another embodiment comprises cyclosporin A, Hostacerin DGMS®, and Anise oil.

Another embodiment comprises cyclosporin A, Hostacerin DGSB®, and Anise oil.

Another embodiment comprises cyclosporin A, Ice No. 2®, and Anise oil.

Another embodiment comprises cyclosporin A, Imwitor 742®, and Anise oil.

Another embodiment comprises cyclosporin A, Imwitor 780 K®, and Anise oil.

Another embodiment comprises cyclosporin A, Imwitor 960 Flakes®, and Anise oil.

Another embodiment comprises cyclosporin A, Isolan GI 34®, and Anise oil.

Another embodiment comprises cyclosporin A, Isolan GO 33®, and Anise oil.

Another embodiment comprises cyclosporin A, Kemester 1000®, and Anise oil.

Another embodiment comprises cyclosporin A, Kemester 2000®, and Anise oil.

Another embodiment comprises cyclosporin A, Kemester 2000®, and Anise oil.

Another embodiment comprises cyclosporin A, Kemester 6000SE®, and Anise oil.

Another embodiment comprises cyclosporin A, Lamecreme DGE 18®, and Anise oil.

Another embodiment comprises cyclosporin A, Lexemul 515®, and Anise oil.

Another embodiment comprises cyclosporin A, Lexemul 561®, and Anise oil.

Another embodiment comprises cyclosporin A, Lexemul AR®, and Anise oil.

Another embodiment comprises cyclosporin A, Lexemul AS®, and Anise oil.

Another embodiment comprises cyclosporin A, Lexemul GDL®, and Anise oil.

Another embodiment comprises cyclosporin A, Lexemul T®, and Anise oil.

Another embodiment comprises cyclosporin A, Lipomulse 165®, and Anise oil.

Another embodiment comprises cyclosporin A, Lumulse GML K®, and Anise oil.

Another embodiment comprises cyclosporin A, Lumulse GMO K®, and Anise oil.

Another embodiment comprises cyclosporin A, Lumulse GMR K®, and Anise oil.

Another embodiment comprises cyclosporin A, Lumulse GMT K®, and Anise oil.

Another embodiment comprises cyclosporin A, Magrabar GMC®, and Anise oil.

Another embodiment comprises cyclosporin A, Magrabar GMO-CK®, and Anise oil.

Another embodiment comprises cyclosporin A, Magrabar MDG-5050®, and Anise oil.

Another embodiment comprises cyclosporin A, Magrabar PGO-315®, and Anise oil.

Another embodiment comprises cyclosporin A, Magrabar PGO-1010®, and Anise oil.

Another embodiment comprises cyclosporin A, Mazol 300K®, and Anise oil.

Another embodiment comprises cyclosporin A, Mazol GMO-K®, and Anise oil.

Another embodiment comprises cyclosporin A, Mazol GMS-K®, and Anise oil.

Another embodiment comprises cyclosporin A, Mazol PG031-K®, and Anise oil.

Another embodiment comprises cyclosporin A, Miglyol 812®, and Anise oil.

Another embodiment comprises cyclosporin A, Norfox 165C®, and Anise oil.

Another embodiment comprises cyclosporin A, Schercemol GMIS®, and Anise oil.

Another embodiment comprises cyclosporin A, Tegin®, and Anise oil.

Another embodiment comprises cyclosporin A, Tegin 4100 Pellets®, and Anise oil.

Another embodiment comprises cyclosporin A, Tegin M Pellets®, and Anise oil.

Another embodiment comprises cyclosporin A, Tegin OV®, and Anise oil.

Another embodiment comprises cyclosporin A, Teginacid H®, and Anise oil.

Another embodiment comprises cyclosporin A, Tego Cosmo P813®, and Anise oil.

Another embodiment comprises cyclosporin A, Wickenol 535®, and Anise oil.

Another embodiment comprises cyclosporin A, Witconol 14®, and Anise oil.

Another embodiment comprises cyclosporin A, Witconol 14®, and Anise oil.

Another embodiment comprises cyclosporin A, Witconol 14F®, and Anise oil.

Another embodiment comprises cyclosporin A, Witconol 18L®, and Anise oil.

Another embodiment comprises cyclosporin A, Witconol GOT®, and Anise oil.

Another embodiment comprises cyclosporin A, Witconol MST®, and Anise oil.

Another embodiment comprises cyclosporin A, Witconol RHT®, and Anise oil.

Another embodiment comprises cyclosporin A, and Anise oil.

Another embodiment comprises cyclosporin A, a Glycol Ester, and Anise oil.

Another embodiment comprises cyclosporin A, Alkamuls 600 DO®, and Anise oil.

Another embodiment comprises cyclosporin A, Alkamuls SEG®, and Anise oil.

Another embodiment comprises cyclosporin A, Atlas EM-2®, and Anise oil.

Another embodiment comprises cyclosporin A, Cerasynt IP®, and Anise oil.

Another embodiment comprises cyclosporin A, Cerasynt M®, and Anise oil.

Another embodiment comprises cyclosporin A, Cerasynt MN®, and Anise oil.

Another embodiment comprises cyclosporin A, Cerasynt PA®, and Anise oil.

Another embodiment comprises cyclosporin A, Chemsperse EGDS®, and Anise oil.

Another embodiment comprises cyclosporin A, Chemsperse EGMS®, and Anise oil.

Another embodiment comprises cyclosporin A, Colonial Monolaurin®, and Anise oil.

Another embodiment comprises cyclosporin A, DeMuls SGE-95®, and Anise oil.

Another embodiment comprises cyclosporin A, Eccoterge 200®, and Anise oil.

Another embodiment comprises cyclosporin A, Emerest 2380®, and Anise oil.

Another embodiment comprises cyclosporin A, Ethox 2610®, and Anise oil.

Another embodiment comprises cyclosporin A, Ethox DO-9®, and Anise oil.

Another embodiment comprises cyclosporin A, Ethox DO-14®, and Anise oil.

Another embodiment comprises cyclosporin A, Ethox SO-9®, and Anise oil.

Another embodiment comprises cyclosporin A, Fizul MD-318®, and Anise oil.

Another embodiment comprises cyclosporin A, Genapol EGDS-VHP®, and Anise oil.

Another embodiment comprises cyclosporin A, Genapol TS Powder®, and Anise oil.

Another embodiment comprises cyclosporin A, Hostacerin WO®, and Anise oil.

Another embodiment comprises cyclosporin A, Inversol 140®, and Anise oil.

Another embodiment comprises cyclosporin A, Kemester 104®, and Anise oil.

Another embodiment comprises cyclosporin A, Kemester 205®, and Anise oil.

Another embodiment comprises cyclosporin A, Kemester 226®, and Anise oil.

Another embodiment comprises cyclosporin A, Kemester 5221SE®, and Anise oil.

Another embodiment comprises cyclosporin A, Kemester EGDS®, and Anise oil.

Another embodiment comprises cyclosporin A, Lexemul EGDS®, and Anise oil.

Another embodiment comprises cyclosporin A, Lexemul EGMS®, and Anise oil.

Another embodiment comprises cyclosporin A, Lexemul P®, and Anise oil.

Another embodiment comprises cyclosporin A, Lipo DGLS®, and Anise oil.

Another embodiment comprises cyclosporin A, Lipo EGDS®, and Anise oil.

Another embodiment comprises cyclosporin A, Lipo PGMS®, and Anise oil.

Another embodiment comprises cyclosporin A, Liposorb S-4®, and Anise oil.

Another embodiment comprises cyclosporin A, Liposorb TO-20®, and Anise oil.

Another embodiment comprises cyclosporin A, Lumulse PGO®, and Anise oil.

Another embodiment comprises cyclosporin A, Mackester EGDS®, and Anise oil.

Another embodiment comprises cyclosporin A, Mackester EGMS®, and Anise oil.

Another embodiment comprises cyclosporin A, Mackester GSTP®, and Anise oil.

Another embodiment comprises cyclosporin A, Mackester Series®, and Anise oil.

Another embodiment comprises cyclosporin A, Magrabar PDG-50®, and Anise oil.

Another embodiment comprises cyclosporin A, Mapeg 6000 DS®, and Anise oil.

Another embodiment comprises cyclosporin A, Marlowet 4702®, and Anise oil.

Another embodiment comprises cyclosporin A, Monalube 305®, and Anise oil.

Another embodiment comprises cyclosporin A, Monalube 310®, and Anise oil.

Another embodiment comprises cyclosporin A, Monalube 315®, and Anise oil.

Another embodiment comprises cyclosporin A, Monalube 320®, and Anise oil.

Another embodiment comprises cyclosporin A, Monalube 325®, and Anise oil.

Another embodiment comprises cyclosporin A, Monalube 330®, and Anise oil.

Another embodiment comprises cyclosporin A, Naturechem PGHS®, and Anise oil.

Another embodiment comprises cyclosporin A, Polycastorol PLO-840®, and Anise oil.

Another embodiment comprises cyclosporin A, Polytex 10M®, and Anise oil.

Another embodiment comprises cyclosporin A, Ritasynt IP®, and Anise oil.

Another embodiment comprises cyclosporin A, Ross Chem PEG 600 DT®, and Anise oil.

Another embodiment comprises cyclosporin A, Schercemol PGMS®, and Anise oil.

Another embodiment comprises cyclosporin A, Sponto H-44C®, and Anise oil.

Another embodiment comprises cyclosporin A, Tegin G®, and Anise oil.

Another embodiment comprises cyclosporin A, Witbreak DGE-182®, and Anise oil.

Another embodiment comprises cyclosporin A, Witbreak DGE-182®, and Anise oil.

Another embodiment comprises cyclosporin A, Witbreak DRA-21®, and Anise oil.

Another embodiment comprises cyclosporin A, Witbreak DRA-21®, and Anise oil.

Another embodiment comprises cyclosporin A, Witbreak DRA-50®, and Anise oil.

Another embodiment comprises cyclosporin A, Witbreak DRA-50®, and Anise oil.

Another embodiment comprises cyclosporin A, Witconol F26-46®, and Anise oil.

Another embodiment comprises cyclosporin A, Witconol H-32®, and Anise oil.

Another embodiment comprises cyclosporin A, Witconol H-33®, and Anise oil.

Another embodiment comprises cyclosporin A, Witconol H-35A®, and Anise oil.

Another embodiment comprises cyclosporin A, Witconol RHP®, and Anise oil.

Another embodiment comprises cyclosporin A, and Anise oil.

Another embodiment comprises cyclosporin A, a Lanolin-based Derivative, and Anise oil.

Another embodiment comprises cyclosporin A, Amerchol CAB®, and Anise oil.

Another embodiment comprises cyclosporin A, Amerchol L-101®, and Anise oil.

Another embodiment comprises cyclosporin A, Amerlate LFA-LO®, and Anise oil.

Another embodiment comprises cyclosporin A, Amerlate P®, and Anise oil.

Another embodiment comprises cyclosporin A, Barre Common Degras®, and Anise oil.

Another embodiment comprises cyclosporin A, Cholesterol NF®, and Anise oil.

Another embodiment comprises cyclosporin A, Crodalan AWS®, and Anise oil.

Another embodiment comprises cyclosporin A, Crodalan LA®, and Anise oil.

Another embodiment comprises cyclosporin A, Emery 1650®, and Anise oil.

Another embodiment comprises cyclosporin A, Emery 1650®, and Anise oil.

Another embodiment comprises cyclosporin A, Emery 1740®, and Anise oil.

Another embodiment comprises cyclosporin A, Emery 1740®, and Anise oil.

Another embodiment comprises cyclosporin A, Forlan 500®, and Anise oil.

Another embodiment comprises cyclosporin A, Forlan L®, and Anise oil.

Another embodiment comprises cyclosporin A, Laneto 50®, and Anise oil.

Another embodiment comprises cyclosporin A, Laneto 100®, and Anise oil.

Another embodiment comprises cyclosporin A, Laneto AWS®, and Anise oil.

Another embodiment comprises cyclosporin A, Lanfrax 1776®, and Anise oil.

Another embodiment comprises cyclosporin A, Lanfrax 1776®, and Anise oil.

Another embodiment comprises cyclosporin A, Lanogel 21®, and Anise oil.

Another embodiment comprises cyclosporin A, Lipolan®, and Anise oil.

Another embodiment comprises cyclosporin A, Lipolan 31®, and Anise oil.

Another embodiment comprises cyclosporin A, OHlan®, and Anise oil.

Another embodiment comprises cyclosporin A, Polychol 5®, and Anise oil.

Another embodiment comprises cyclosporin A, Polychol 15®, and Anise oil.

Another embodiment comprises cyclosporin A, Ritacetyl®, and Anise oil.

Another embodiment comprises cyclosporin A, Ritachol®, and Anise oil.

Another embodiment comprises cyclosporin A, Ritahydrox®, and Anise oil.

Another embodiment comprises cyclosporin A, Ritalafa®, and Anise oil.

Another embodiment comprises cyclosporin A, Ritalan®, and Anise oil.

Another embodiment comprises cyclosporin A, Ritalan AWS®, and Anise oil.

Another embodiment comprises cyclosporin A, Ritalan C®, and Anise oil.

Another embodiment comprises cyclosporin A, Ritawax®, and Anise oil.

Another embodiment comprises cyclosporin A, Ritawax AEO®, and Anise oil.

Another embodiment comprises cyclosporin A, Ritawax ALA®, and Anise oil.

Another embodiment comprises cyclosporin A, Solan/Solan 50/Super Solan®, and Anise oil.

Another embodiment comprises cyclosporin A, Super Hartolan/Hartolan®, and Anise oil.

Another embodiment comprises cyclosporin A, Supersat AWS-4®, and Anise oil.

Another embodiment comprises cyclosporin A, Supersat AWS-24®, and Anise oil.

Another embodiment comprises cyclosporin A, and Anise oil.

Another embodiment comprises cyclosporin A, a Lecithin or Lecithin Derivative, and Anise oil.

Another embodiment comprises cyclosporin A, Alcolec®, and Anise oil.

Another embodiment comprises cyclosporin A, Lecithin®, and Anise oil.

Another embodiment comprises cyclosporin A, Lexin K®, and Anise oil.

Another embodiment comprises cyclosporin A, Natipide®, and Anise oil.

Another embodiment comprises cyclosporin A, and Anise oil.

Another embodiment comprises cyclosporin A, a Lignin or Lignin Derivative, and Anise oil.

Another embodiment comprises cyclosporin A, Diwatex XP 9®, and Anise oil.

Another embodiment comprises cyclosporin A, Dynasperse LCD®, and Anise oil.

Another embodiment comprises cyclosporin A, Indulin SAL®, and Anise oil.

Another embodiment comprises cyclosporin A, Indulin W-1®, and Anise oil.

Another embodiment comprises cyclosporin A, Indulin W-5®, and Anise oil.

Another embodiment comprises cyclosporin A, Lignosol FTA®, and Anise oil.

Another embodiment comprises cyclosporin A, Lignosol SFX-65®, and Anise oil.

Another embodiment comprises cyclosporin A, Marasperse 52 CP®, and Anise oil.

Another embodiment comprises cyclosporin A, Marasperse AG®, and Anise oil.

Another embodiment comprises cyclosporin A, Marasperse CBOS-4®, and Anise oil.

Another embodiment comprises cyclosporin A, Ufoxane 2®, and Anise oil.

Another embodiment comprises cyclosporin A, and Anise oil.

Another embodiment comprises cyclosporin A, a Methyl Ester, and Anise oil.

Another embodiment comprises cyclosporin A, E.B. Cleaner AK®, and Anise oil.

Another embodiment comprises cyclosporin A, Oleocal ME-70®, and Anise oil.

Another embodiment comprises cyclosporin A, Trade Name Company®, and Anise oil.

Another embodiment comprises cyclosporin A, Methyl Esters (cont'd)®, and Anise oil.

Another embodiment comprises cyclosporin A, Oleocal ME-92®, and Anise oil.

Another embodiment comprises cyclosporin A, Oleocal ME-112®, and Anise oil.

Another embodiment comprises cyclosporin A, Oleocal ME-130®, and Anise oil.

Another embodiment comprises cyclosporin A, and Anise oil.

Another embodiment comprises cyclosporin A, a Monoglyceride or a Derivative thereof, and Anise oil.

Another embodiment comprises cyclosporin A, Dynacet 211®, and Anise oil.

Another embodiment comprises cyclosporin A, Hetsorb S-20®, and Anise oil.

Another embodiment comprises cyclosporin A, Imwitor 191®, and Anise oil.

Another embodiment comprises cyclosporin A, Imwitor 370®, and Anise oil.

Another embodiment comprises cyclosporin A, Imwitor 375®, and Anise oil.

Another embodiment comprises cyclosporin A, Imwitor 900®, and Anise oil.

Another embodiment comprises cyclosporin A, Imwitor 945®, and Anise oil.

Another embodiment comprises cyclosporin A, Imwitor 2020®, and Anise oil.

Another embodiment comprises cyclosporin A, Kemester 5500®; and Anise oil.

Another embodiment comprises cyclosporin A, Kemester 6000®, and Anise oil.

Another embodiment comprises cyclosporin A, Magrabar GMC®, and Anise oil.

Another embodiment comprises cyclosporin A, Magrabar GMO-CK®, and Anise oil.

Another embodiment comprises cyclosporin A, Magrabar GPC-10®, and Anise oil.

Another embodiment comprises cyclosporin A, Magrabar MDG-5050®, and Anise oil.

Another embodiment comprises cyclosporin A, Monalube 335®, and Anise oil.

Another embodiment comprises cyclosporin A, Monoglycerides Glyceryl Monestearate Archer Daniels Midland Company®, and Anise oil.

Another embodiment comprises cyclosporin A, Rita GMS®, and Anise oil.

Another embodiment comprises cyclosporin A, Ritamulse SCG®, and Anise oil.

Another embodiment comprises cyclosporin A, Softigen 701®, and Anise oil.

Another embodiment comprises cyclosporin A, Tally 100 Plus®, and Anise oil.

Another embodiment comprises cyclosporin A, and Anise oil.

Another embodiment comprises cyclosporin A, a Polyethylene Glycol, and Anise oil.

Another embodiment comprises cyclosporin A, Emulgade PL 68/50®, and Anise oil.

Another embodiment comprises cyclosporin A, Lumulse PEG®, and Anise oil.

Another embodiment comprises cyclosporin A, Rhodasurf PEG-400®, and Anise oil.

Another embodiment comprises cyclosporin A, Rhodasurf PEG-600®, and Anise oil.

Another embodiment comprises cyclosporin A, Witconol PEG-400®, and Anise oil.

Another embodiment comprises cyclosporin A, and Anise oil.

Another embodiment comprises cyclosporin A, a Polymeric Surfactant, and Anise oil.

Another embodiment comprises cyclosporin A, Acritamer PNC-EG®, and Anise oil.

Another embodiment comprises cyclosporin A, Ag-Rho DEP-775®, and Anise oil.

Another embodiment comprises cyclosporin A, APG 325N Glycoside®, and Anise oil.

Another embodiment comprises cyclosporin A, Aristoflex AVC®, and Anise oil.

Another embodiment comprises cyclosporin A, Aristoflex HMB®, and Anise oil.

Another embodiment comprises cyclosporin A, Burco NPS-225®, and Anise oil.

Another embodiment comprises cyclosporin A, Burco NPS-816®, and Anise oil.

Another embodiment comprises cyclosporin A, Chemccinate 5603®, and Anise oil.

Another embodiment comprises cyclosporin A, Cosmedia Guar C-261N®, and Anise oil.

Another embodiment comprises cyclosporin A, Gantrez S-95®, and Anise oil.

Another embodiment comprises cyclosporin A, Glucopon 220 UP®, and Anise oil.

Another embodiment comprises cyclosporin A, Glucopon 225 DK®, and Anise oil.

Another embodiment comprises cyclosporin A, Glucopon 425 N®, and Anise oil.

Another embodiment comprises cyclosporin A, Glucopon 600 UP®, and Anise oil.

Another embodiment comprises cyclosporin A, Glucopon 625 UP®, and Anise oil.

Another embodiment comprises cyclosporin A, Pemulen 1621®, and Anise oil.

Another embodiment comprises cyclosporin A, Pemulen 1622®, and Anise oil.

Another embodiment comprises cyclosporin A, Pemulen TR-1®, and Anise oil.

Another embodiment comprises cyclosporin A, Pemulen TR-2®, and Anise oil.

Another embodiment comprises cyclosporin A, Plantacare 818®, and Anise oil.

Another embodiment comprises cyclosporin A, Plantapon LGC Sorb®, and Anise oil.

Another embodiment comprises cyclosporin A, Plantaren 1200N®, and Anise oil.

Another embodiment comprises cyclosporin A, Plantaren 2000N®, and Anise oil.

Another embodiment comprises cyclosporin A, Viscolam AT 64®, and Anise oil.

Another embodiment comprises cyclosporin A, Viscolam AT 64P®, and Anise oil.

Another embodiment comprises cyclosporin A, Viscolam AT 100®, and Anise oil.

Another embodiment comprises cyclosporin A, Viscolam MAC 7®, and Anise oil.

Another embodiment comprises cyclosporin A, Viscolam SMC 20®, and Anise oil.

Another embodiment comprises cyclosporin A, Witbreak RTC-323®, and Anise oil.

Another embodiment comprises cyclosporin A, WSI 3700®, and Anise oil.

Another embodiment comprises cyclosporin A, and Anise oil.

Another embodiment comprises cyclosporin A, a Propoxylated or Ethoxylated Fatty Acid, Alcohol, or Alkyl Phenol, and Anise oil.

Another embodiment comprises cyclosporin A, Antarox AA-60®, and Anise oil.

Another embodiment comprises cyclosporin A, Antarox LF-224®, and Anise oil.

Another embodiment comprises cyclosporin A, Burcomul DFE-45®, and Anise oil.

Another embodiment comprises cyclosporin A, Burcoterge LFE-1000®, and Anise oil.

Another embodiment comprises cyclosporin A, Chemal LF-25B®, and Anise oil.

Another embodiment comprises cyclosporin A, Chemal LF-40B®, and Anise oil.

Another embodiment comprises cyclosporin A, Dehypon LS-36®, and Anise oil.

Another embodiment comprises cyclosporin A, Dehypon LS-36®, and Anise oil.

Another embodiment comprises cyclosporin A, Dehypon LS-54®, and Anise oil.

Another embodiment comprises cyclosporin A, Dehypon LS-54®, and Anise oil.

Another embodiment comprises cyclosporin A, Delonic 100 VLF®, and Anise oil.

Another embodiment comprises cyclosporin A, Delonic LF-60 MOD®, and Anise oil.

Another embodiment comprises cyclosporin A, Empiderm B®, and Anise oil.

Another embodiment comprises cyclosporin A, Ethylan 1206®, and Anise oil.

Another embodiment comprises cyclosporin A, Ethylan NS-500K®, and Anise oil.

Another embodiment comprises cyclosporin A, Ethylan NS-500LQ®, and Anise oil.

Another embodiment comprises cyclosporin A, Genapol 1392®, and Anise oil.

Another embodiment comprises cyclosporin A, Genapol 2317®, and Anise oil.

Another embodiment comprises cyclosporin A, Genapol 26EP710®, and Anise oil.

Another embodiment comprises cyclosporin A, Genapol EP 1022®, and Anise oil.

Another embodiment comprises cyclosporin A, Genapol EP 1024®, and Anise oil.

Another embodiment comprises cyclosporin A, Genapol EP 6068®, and Anise oil.

Another embodiment comprises cyclosporin A, Genapol NP915®, and Anise oil.

Another embodiment comprises cyclosporin A, Kieralon MFB®, and Anise oil.

Another embodiment comprises cyclosporin A, Lumisolve CSA-80 V®, and Anise oil.

Another embodiment comprises cyclosporin A, Marlowet 5001®, and Anise oil.

Another embodiment comprises cyclosporin A, Marlox FK 64®, and Anise oil.

Another embodiment comprises cyclosporin A, Marlox MO 124®, and Anise oil.

Another embodiment comprises cyclosporin A, Marlox S 58®, and Anise oil.

Another embodiment comprises cyclosporin A, Nonatell 1003®, and Anise oil.

Another embodiment comprises cyclosporin A, Nonatell 1038®, and Anise oil.

Another embodiment comprises cyclosporin A, Nonatell 1052®, and Anise oil.

Another embodiment comprises cyclosporin A, Nonatell 1061®, and Anise oil.

Another embodiment comprises cyclosporin A, Nonatell 1075®, and Anise oil.

Another embodiment comprises cyclosporin A, Nonatell 1088®, and Anise oil.

Another embodiment comprises cyclosporin A, Nonatell 1123®, and Anise oil.

Another embodiment comprises cyclosporin A, Nonatell 1153®, and Anise oil.

Another embodiment comprises cyclosporin A, Nonatell 1161®, and Anise oil.

Another embodiment comprises cyclosporin A, Nonatell 1172®, and Anise oil.

Another embodiment comprises cyclosporin A, Nonatell 1181®, and Anise oil.

Another embodiment comprises cyclosporin A, Norfox 36®, and Anise oil.

Another embodiment comprises cyclosporin A, Procetyl AWS®, and Anise oil.

Another embodiment comprises cyclosporin A, Sandoxylate SX 412®, and Anise oil.

Another embodiment comprises cyclosporin A, Sandoxylate SX 418®, and Anise oil.

Another embodiment comprises cyclosporin A, Surfonic JL-80X®, and Anise oil.

Another embodiment comprises cyclosporin A, Surfonic JL-80X-B1®, and Anise oil.

Another embodiment comprises cyclosporin A, Surfonic L4-29X®, and Anise oil.

Another embodiment comprises cyclosporin A, Surfonic LF®, and Anise oil.

Another embodiment comprises cyclosporin A, T-Det A826®, and Anise oil.

Another embodiment comprises cyclosporin A, T-Det LF-416®, and Anise oil.

Another embodiment comprises cyclosporin A, Tergitol Min-Foam 1X®, and Anise oil.

Another embodiment comprises cyclosporin A, Tergitol Min-Foam 2X®, and Anise oil.

Another embodiment comprises cyclosporin A, Triton CF-21®, and Anise oil.

Another embodiment comprises cyclosporin A, Triton CF-76®, and Anise oil.

Another embodiment comprises cyclosporin A, Triton XL-80N®, and Anise oil.

Another embodiment comprises cyclosporin A, Witconol NS-98®, and Anise oil.

Another embodiment comprises cyclosporin A, Witconol NS-108LQ®, and Anise oil.

Another embodiment comprises cyclosporin A, Witconol NS-145®, and Anise oil.

Another embodiment comprises cyclosporin A, Witconol NS-179®, and Anise oil.

Another embodiment comprises cyclosporin A, and Anise oil.

Another embodiment comprises cyclosporin A, a Protein-based Surfactant, and Anise oil.

Another embodiment comprises cyclosporin A, Amino-Foam W®, and Anise oil.

Another embodiment comprises cyclosporin A, Amiter LGOD-2®, and Anise oil.

Another embodiment comprises cyclosporin A, Amiter LGS-2®, and Anise oil.

Another embodiment comprises cyclosporin A, Amiter LGS-5®, and Anise oil.

Another embodiment comprises cyclosporin A, Lamepon S®, and Anise oil.

Another embodiment comprises cyclosporin A, Lamepon S®, and Anise oil.

Another embodiment comprises cyclosporin A, Maypon 4C®, and Anise oil.

Another embodiment comprises cyclosporin A, May-Tein C®, and Anise oil.

Another embodiment comprises cyclosporin A, May-Tein CT®, and Anise oil.

Another embodiment comprises cyclosporin A, May-Tein KTS®, and Anise oil.

Another embodiment comprises cyclosporin A, May-Tein SY®, and Anise oil.

Another embodiment comprises cyclosporin A, Plantapon S®, and Anise oil.

Another embodiment comprises cyclosporin A, Proteol APL®, and Anise oil.

Another embodiment comprises cyclosporin A, Proteol OAT®, and Anise oil.

Another embodiment comprises cyclosporin A, Pyroter CPI-40®, and Anise oil.

Another embodiment comprises cyclosporin A, Pyroter GPI-25®, and Anise oil.

Another embodiment comprises cyclosporin A, Supro-Tein S®, and Anise oil.

Another embodiment comprises cyclosporin A, Supro-Tein V®, and Anise oil.

Another embodiment comprises cyclosporin A, ®, and Anise oil.

Another embodiment comprises cyclosporin A, a Sarcosine Derivative®, and Anise oil.

Another embodiment comprises cyclosporin A, Crodasinic LS-30®, and Anise oil.

Another embodiment comprises cyclosporin A, Vanseal CS®, and Anise oil.

Another embodiment comprises cyclosporin A, Vanseal LS®, and Anise oil.

Another embodiment comprises cyclosporin A, Vanseal MS®, and Anise oil.

Another embodiment comprises cyclosporin A, Vanseal NACS-30®, and Anise oil.

Another embodiment comprises cyclosporin A, Vanseal NALS-95®, and Anise oil.

Another embodiment comprises cyclosporin A, Vanseal OS®, and Anise oil.

Another embodiment comprises cyclosporin A, ®, and Anise oil.

Another embodiment comprises cyclosporin A, a Silicone-based Surfactant®, and Anise oil.

Another embodiment comprises cyclosporin A, Abil-B-9950®, and Anise oil.

Another embodiment comprises cyclosporin A, Abil Care 85®, and Anise oil.

Another embodiment comprises cyclosporin A, Abil EM 90®, and Anise oil.

Another embodiment comprises cyclosporin A, Abil EM 97®, and Anise oil.

Another embodiment comprises cyclosporin A, Abil WE-09®, and Anise oil.

Another embodiment comprises cyclosporin A, Dow Corning 1248 Fluid®, and Anise oil.

Another embodiment comprises cyclosporin A, Dow Corning 3225C®, and Anise oil.

Another embodiment comprises cyclosporin A, Dow Corning 5200®, and Anise oil.

Another embodiment comprises cyclosporin A, Dow Corning Q4-3667®, and Anise oil.

Another embodiment comprises cyclosporin A, Monasil PCA®, and Anise oil.

Another embodiment comprises cyclosporin A, Monasil PDM®, and Anise oil.

Another embodiment comprises cyclosporin A, Monasil PLN®, and Anise oil.

Another embodiment comprises cyclosporin A, Polyderm PPI-SI-WS®, and Anise oil.

Another embodiment comprises cyclosporin A, Troysol 380W®, and Anise oil.

Another embodiment comprises cyclosporin A, Troysol S366®, and Anise oil.

Another embodiment comprises cyclosporin A, and Anise oil.

Another embodiment comprises cyclosporin A, a Sorbitan Derivative, and Anise oil.

Another embodiment comprises cyclosporin A, Alkamuls SML®, and Anise oil.

Another embodiment comprises cyclosporin A, Alkamuls SMO®, and Anise oil.

Another embodiment comprises cyclosporin A, Alkamuls STO®, and Anise oil.

Another embodiment comprises cyclosporin A, Arlacel 20®, and Anise oil.

Another embodiment comprises cyclosporin A, Arlacel 40®, and Anise oil.

Another embodiment comprises cyclosporin A, Arlacel 60®, and Anise oil.

Another embodiment comprises cyclosporin A, Arlacel 80®, and Anise oil.

Another embodiment comprises cyclosporin A, Arlacel C®, and Anise oil.

Another embodiment comprises cyclosporin A, Armul 21®, and Anise oil.

Another embodiment comprises cyclosporin A, Atlox 80®, and Anise oil.
Another embodiment comprises cyclosporin A, Atlox 847®, and Anise oil.
Another embodiment comprises cyclosporin A, Atlox 1045A®, and Anise oil.
Another embodiment comprises cyclosporin A, Canarcel 20®, and Anise oil.
Another embodiment comprises cyclosporin A, Canarcel 60®, and Anise oil.
Another embodiment comprises cyclosporin A, Canarcel 80®, and Anise oil.
Another embodiment comprises cyclosporin A, Canarcel TW 20®, and Anise oil.
Another embodiment comprises cyclosporin A, Canarcel TW 60®, and Anise oil.
Another embodiment comprises cyclosporin A, Canarcel TW 80®, and Anise oil.
Another embodiment comprises cyclosporin A, Coladet BSB-P®, and Anise oil.
Another embodiment comprises cyclosporin A, Customulse O-20®, and Anise oil.
Another embodiment comprises cyclosporin A, Dehymuls E®, and Anise oil.
Another embodiment comprises cyclosporin A, DeSotan SMO®, and Anise oil.
Another embodiment comprises cyclosporin A, DeSotan SMO-20®, and Anise oil.
Another embodiment comprises cyclosporin A, DeSotan SMT®, and Anise oil.
Another embodiment comprises cyclosporin A, DeSotan SMT-20®, and Anise oil.
Another embodiment comprises cyclosporin A, Durfax 60®, and Anise oil.
Another embodiment comprises cyclosporin A, Durfax 65®, and Anise oil.
Another embodiment comprises cyclosporin A, Durfax 80®, and Anise oil.
Another embodiment comprises cyclosporin A, Durtan 60®, and Anise oil.
Another embodiment comprises cyclosporin A, Durtan 65®, and Anise oil.
Another embodiment comprises cyclosporin A, Liposorb L®, and Anise oil.
Another embodiment comprises cyclosporin A, Liposorb L-10®, and Anise oil.
Another embodiment comprises cyclosporin A, Liposorb L-20®, and Anise oil.
Another embodiment comprises cyclosporin A, Liposorb O®, and Anise oil.
Another embodiment comprises cyclosporin A, Liposorb O-20®, and Anise oil.
Another embodiment comprises cyclosporin A, Liposorb P®, and Anise oil.
Another embodiment comprises cyclosporin A, Liposorb P-20®, and Anise oil.
Another embodiment comprises cyclosporin A, Liposorb S®, and Anise oil.
Another embodiment comprises cyclosporin A, Liposorb S-20®, and Anise oil.
Another embodiment comprises cyclosporin A, Liposorb SQO®, and Anise oil.
Another embodiment comprises cyclosporin A, Liposorb TO®, and Anise oil.
Another embodiment comprises cyclosporin A, Liposorb TS®, and Anise oil.
Another embodiment comprises cyclosporin A, Liposorb TS-20®, and Anise oil.
Another embodiment comprises cyclosporin A, Lumisorb PS®, and Anise oil.
Another embodiment comprises cyclosporin A, Lumisorb SMO (T)®, and Anise oil.
Another embodiment comprises cyclosporin A, Lumisorb SMS K®, and Anise oil.
Another embodiment comprises cyclosporin A, Lumisorb SSO®, and Anise oil.
Another embodiment comprises cyclosporin A, Lumisorb STS K®, and Anise oil.
Another embodiment comprises cyclosporin A, Lumisorb STT®, and Anise oil.
Another embodiment comprises cyclosporin A, Magrabar SMO®, and Anise oil.
Another embodiment comprises cyclosporin A, Magrabar SMO-VEG®, and Anise oil.
Another embodiment comprises cyclosporin A, Magrabar SMT®, and Anise oil.
Another embodiment comprises cyclosporin A, Magrabar STO®, and Anise oil.
Another embodiment comprises cyclosporin A, Miracare BC-27®, and Anise oil.
Another embodiment comprises cyclosporin A, Ritabate 20®, and Anise oil.
Another embodiment comprises cyclosporin A, Ritabate 40®, and Anise oil.
Another embodiment comprises cyclosporin A, Ritabate 60®, and Anise oil.
Another embodiment comprises cyclosporin A, Ritabate 80®, and Anise oil.
Another embodiment comprises cyclosporin A, T-Maz®, and Anise oil.
Another embodiment comprises cyclosporin A, Tego SML®, and Anise oil.
Another embodiment comprises cyclosporin A, Tego SML 20®, and Anise oil.
Another embodiment comprises cyclosporin A, Tego SMO 80 V®, and Anise oil.
Another embodiment comprises cyclosporin A, Tego SMO V®, and Anise oil.
Another embodiment comprises cyclosporin A, Tego SMS®, and Anise oil.
Another embodiment comprises cyclosporin A, Tego STO V®, and Anise oil.
Another embodiment comprises cyclosporin A, Tween 21®, and Anise oil.
Another embodiment comprises cyclosporin A, Tween 40®, and Anise oil.
Another embodiment comprises cyclosporin A, Tween 60®, and Anise oil.
Another embodiment comprises cyclosporin A, Tween 60 K®, and Anise oil.
Another embodiment comprises cyclosporin A, Tween 61®, and Anise oil.
Another embodiment comprises cyclosporin A, Tween 65®, and Anise oil.
Another embodiment comprises cyclosporin A, Tween 80®, and Anise oil.
Another embodiment comprises cyclosporin A, Tween 80 K®, and Anise oil.
Another embodiment comprises cyclosporin A, Tween 81®, and Anise oil.
Another embodiment comprises cyclosporin A, Tween 85®, and Anise oil.

Another embodiment comprises cyclosporin A, and Anise oil.

Another embodiment comprises cyclosporin A, a Sucrose or Glucose Ester, or Derivative thereof, and Anise oil.

Another embodiment comprises cyclosporin A, DeSulf GOS-P-60WCG®, and Anise oil.

Another embodiment comprises cyclosporin A, Glucam E-20 Distearate®, and Anise oil.

Another embodiment comprises cyclosporin A, Glucamate DOE-120®, and Anise oil.

Another embodiment comprises cyclosporin A, Glucamate SSE-20®, and Anise oil.

Another embodiment comprises cyclosporin A, Glucate DO®, and Anise oil.

Another embodiment comprises cyclosporin A, Glucate SS®, and Anise oil.

Another embodiment comprises cyclosporin A, Glucopon 425 UP®, and Anise oil.

Another embodiment comprises cyclosporin A, Isolan IS®, and Anise oil.

Another embodiment comprises cyclosporin A, Mazon 40®, and Anise oil.

Another embodiment comprises cyclosporin A, Montanov 82®, and Anise oil.

Another embodiment comprises cyclosporin A, Montanov 202®, and Anise oil.

Another embodiment comprises cyclosporin A, Montanov S®, and Anise oil.

Another embodiment comprises cyclosporin A, Rheozan®, and Anise oil.

Another embodiment comprises cyclosporin A, Simulsol AS 48®, and Anise oil.

Another embodiment comprises cyclosporin A, Simulsol SL 4®, and Anise oil.

Another embodiment comprises cyclosporin A, Simulsol SL 10®, and Anise oil.

Another embodiment comprises cyclosporin A, Simulsol SL 11W®, and Anise oil.

Another embodiment comprises cyclosporin A, Simulsol SL 55®, and Anise oil.

Another embodiment comprises cyclosporin A, Suga Nate 100 and 160®, and Anise oil.

Another embodiment comprises cyclosporin A, Tego Care 450®, and Anise oil.

Another embodiment comprises cyclosporin A, Tego Care CG 90®, and Anise oil.

Another embodiment comprises cyclosporin A, Tego Care PS®, and Anise oil.

Another embodiment comprises cyclosporin A, Tegosoft PSE 141 G®, and Anise oil.

Another embodiment comprises cyclosporin A, Tegotens G 826®, and Anise oil.

Another embodiment comprises cyclosporin A, Triton BG-10 (70%)®, and Anise oil.

Another embodiment comprises cyclosporin A, Triton CG-110 (60%)®, and Anise oil.

Another embodiment comprises cyclosporin A, Wickenol 545®, and Anise oil.

Another embodiment comprises cyclosporin A, an alcohol, and Clove oil.

Another embodiment comprises cyclosporin A, Diglycerol®, and Clove oil.

Another embodiment comprises cyclosporin A, Hetoxide GT-80®, and Clove oil.

Another embodiment comprises cyclosporin A, Lexemul BEO®, and Clove oil.

Another embodiment comprises cyclosporin A, Polyglycerol-3®, and Clove oil.

Another embodiment comprises cyclosporin A, Redicote E Series®, and Clove oil.

Another embodiment comprises cyclosporin A, Simulsol OX 1005L®, and Clove oil.

Another embodiment comprises cyclosporin A, Stanfax 567®, and Clove oil.

Another embodiment comprises cyclosporin A, TA-1618®, and Clove oil.

Another embodiment comprises cyclosporin A, Witconol H-31A®, and Clove oil.

Another embodiment comprises cyclosporin A, Standard Div.®, and Clove oil., and Clove oil.

Another embodiment comprises cyclosporin A, an amine oxide, and Clove oil.

Another embodiment comprises cyclosporin A, AO-405®, and Clove oil.

Another embodiment comprises cyclosporin A, AO-455®, and Clove oil.

Another embodiment comprises cyclosporin A, AO 728 Special®, and Clove oil.

Another embodiment comprises cyclosporin A, Barlox 12®, and Clove oil.

Another embodiment comprises cyclosporin A, Barlox 14®, and Clove oil.

Another embodiment comprises cyclosporin A, Burcoxide Lo®, and Clove oil.

Another embodiment comprises cyclosporin A, Caloxamine LO®, and Clove oil.

Another embodiment comprises cyclosporin A, Chemoxide CAW®, and Clove oil.

Another embodiment comprises cyclosporin A, Chemoxide LM-30®, and Clove oil.

Another embodiment comprises cyclosporin A, Chemoxide LO®, and Clove oil.

Another embodiment comprises cyclosporin A, Chemoxide MO®, and Clove oil.

Another embodiment comprises cyclosporin A, Colalux CAO-35®, and Clove oil.

Another embodiment comprises cyclosporin A, Colalux LO®, and Clove oil.

Another embodiment comprises cyclosporin A, DeMox CAPO®, and Clove oil.

Another embodiment comprises cyclosporin A, DeMox CSG-30®, and Clove oil.

Another embodiment comprises cyclosporin A, DeMox LAO®, and Clove oil.

Another embodiment comprises cyclosporin A, Emcol L®, and Clove oil.

Another embodiment comprises cyclosporin A, Empigen OB®, and Clove oil.

Another embodiment comprises cyclosporin A, Empigen OS/A®, and Clove oil.

Another embodiment comprises cyclosporin A, Foamox CDO®, and Clove oil.

Another embodiment comprises cyclosporin A, Foamox DMM®, and Clove oil.

Another embodiment comprises cyclosporin A, Foamox DMS®, and Clove oil.

Another embodiment comprises cyclosporin A, Genaminox KC®, and Clove oil.

Another embodiment comprises cyclosporin A, Genaminox LA®, and Clove oil.

Another embodiment comprises cyclosporin A, Hartofoam SAO®, and Clove oil.

Another embodiment comprises cyclosporin A, Hartox DMCD®, and Clove oil.

Another embodiment comprises cyclosporin A, Lipowax DAT®, and Clove oil.

Another embodiment comprises cyclosporin A, Lipowax PB Pastilles®, and Clove oil.

Another embodiment comprises cyclosporin A, Mackamine C8®, and Clove oil.

Another embodiment comprises cyclosporin A, Mackamine C10®, and Clove oil.

Another embodiment comprises cyclosporin A, Mackamine C14®, and Clove oil.

Another embodiment comprises cyclosporin A, Mackamine CAO®, and Clove oil.

Another embodiment comprises cyclosporin A, Mackamine CO®, and Clove oil.

Another embodiment comprises cyclosporin A, Mackamine LO®, and Clove oil.

Another embodiment comprises cyclosporin A, Mackamine O2®, and Clove oil.

Another embodiment comprises cyclosporin A, Mackamine SAO®, and Clove oil.

Another embodiment comprises cyclosporin A, Mackamine SO®, and Clove oil.

Another embodiment comprises cyclosporin A, Mazox KCAO®, and Clove oil.

Another embodiment comprises cyclosporin A, Monalac MO®, and Clove oil.

Another embodiment comprises cyclosporin A, Norfox LDA®, and Clove oil.

Another embodiment comprises cyclosporin A, Rhodamox LO®, and Clove oil.

Another embodiment comprises cyclosporin A, Schercamox C-AA®, and Clove oil.

Another embodiment comprises cyclosporin A, Schercamox DMA®, and Clove oil.

Another embodiment comprises cyclosporin A, Schercamox DML®, and Clove oil.

Another embodiment comprises cyclosporin A, Schercamox DMM®, and Clove oil.

Another embodiment comprises cyclosporin A, Schercamox DMS®, and Clove oil.

Another embodiment comprises cyclosporin A, Tegotens DO®, and Clove oil.

Another embodiment comprises cyclosporin A, Tomah AO-14-2®, and Clove oil.

Another embodiment comprises cyclosporin A, Triaminox CDO®, and Clove oil., and Clove oil.

Another embodiment comprises cyclosporin A, a block polymer, and Clove oil.

Another embodiment comprises cyclosporin A, AL 2070®, and Clove oil.

Another embodiment comprises cyclosporin A, Antarox 17-R-2®, and Clove oil.

Another embodiment comprises cyclosporin A, Antarox 25-R-2®, and Clove oil.

Another embodiment comprises cyclosporin A, Antarox 31-R-1®, and Clove oil.

Another embodiment comprises cyclosporin A, Antarox P-84®, and Clove oil.

Another embodiment comprises cyclosporin A, Antarox P-104/H®, and Clove oil.

Another embodiment comprises cyclosporin A, Arnox BP-Series®, and Clove oil.

Another embodiment comprises cyclosporin A, Chemonic 435®, and Clove oil.

Another embodiment comprises cyclosporin A, Chemonic D-25®, and Clove oil.

Another embodiment comprises cyclosporin A, Chemonic PL Series®, and Clove oil.

Another embodiment comprises cyclosporin A, Ethox L-121®, and Clove oil.

Another embodiment comprises cyclosporin A, Ethox L-122®, and Clove oil.

Another embodiment comprises cyclosporin A, Genapol PF-10®, and Clove oil.

Another embodiment comprises cyclosporin A, Genapol PF-20®, and Clove oil.

Another embodiment comprises cyclosporin A, Genapol PF-40A®, and Clove oil.

Another embodiment comprises cyclosporin A, Norfox 2-LF®, and Clove oil.

Another embodiment comprises cyclosporin A, Simulsol NW 342®, and Clove oil.

Another embodiment comprises cyclosporin A, T-Det BP-1®, and Clove oil.

Another embodiment comprises cyclosporin A, T-Det XD®, and Clove oil.

Another embodiment comprises cyclosporin A, T-Det XH®, and Clove oil.

Another embodiment comprises cyclosporin A, Triton CF-32®, and Clove oil.

Another embodiment comprises cyclosporin A, Witconol 171®, and Clove oil.

Another embodiment comprises cyclosporin A, Witconol 324®, and Clove oil.

Another embodiment comprises cyclosporin A, Witconol 324D®, and Clove oil.

Another embodiment comprises cyclosporin A, Witconol PD-2000®, and Clove oil., and Clove oil.

a Carboxylated Alcohol or Alkylphenol Ethoxylate, and Clove oil.

Another embodiment comprises cyclosporin A, Emcol CN-6®, and Clove oil.

Another embodiment comprises cyclosporin A, Ethcarb®, and Clove oil.

Another embodiment comprises cyclosporin A, Gemtex WNT-Conc®, and Clove oil.

Another embodiment comprises cyclosporin A, Incrodet TD7-C®, and Clove oil.

Another embodiment comprises cyclosporin A, Marlinat CM 105/80®, and Clove oil.

Another embodiment comprises cyclosporin A, Marlowet 1072®, and Clove oil.

Another embodiment comprises cyclosporin A, Marlowet 4530®, and Clove oil.

Another embodiment comprises cyclosporin A, Marlowet 4530 LF®, and Clove oil.

Another embodiment comprises cyclosporin A, Marlowet 4534®, and Clove oil.

Another embodiment comprises cyclosporin A, Marlowet 4538®, and Clove oil.

Another embodiment comprises cyclosporin A, Marlowet 4539®, and Clove oil.

Another embodiment comprises cyclosporin A, Marlowet 4539 LF®, and Clove oil.

Another embodiment comprises cyclosporin A, Marlowet 4541®, and Clove oil.

Another embodiment comprises cyclosporin A, Miranate LEC-80®, and Clove oil.

Another embodiment comprises cyclosporin A, Sandopan B®, and Clove oil.

Another embodiment comprises cyclosporin A, Sandopan B Modified®, and Clove oil.

Another embodiment comprises cyclosporin A, Sandopan LS-24 Gel®, and Clove oil.

Another embodiment comprises cyclosporin A, Surfine T-A®, and Clove oil.

Another embodiment comprises cyclosporin A, and Clove oil.

Another embodiment comprises cyclosporin A, a Carboxylic Acid/Fatty Acid, and Clove oil.

Another embodiment comprises cyclosporin A, Colaterge RAM®, and Clove oil.

Another embodiment comprises cyclosporin A, Colatrope INC®, and Clove oil.

Another embodiment comprises cyclosporin A, Crodacid B®, and Clove oil.

Another embodiment comprises cyclosporin A, DeTrope CA-100®, and Clove oil.

Another embodiment comprises cyclosporin A, Latol MTO®, and Clove oil.

Another embodiment comprises cyclosporin A, Lumulse CC-33 K®, and Clove oil.

Another embodiment comprises cyclosporin A, Mulls 2218®, and Clove oil.

Another embodiment comprises cyclosporin A, OL-600®, and Clove oil.

Another embodiment comprises cyclosporin A, OL-800®, and Clove oil.

Another embodiment comprises cyclosporin A, R-910®, and Clove oil.

Another embodiment comprises cyclosporin A, S-210®, and Clove oil.

Another embodiment comprises cyclosporin A, Sandopan DTC Acid®, and Clove oil.

Another embodiment comprises cyclosporin A, Sandopan LS 24 N®, and Clove oil.

Another embodiment comprises cyclosporin A, Sandopan MA-18®, and Clove oil.

Another embodiment comprises cyclosporin A, and Clove oil.

Another embodiment comprises cyclosporin A, an Ethoxylated Alcohol, and Clove oil.

Another embodiment comprises cyclosporin A, Adsee 799®, and Clove oil.

Another embodiment comprises cyclosporin A, Adsee 799®, and Clove oil.

Another embodiment comprises cyclosporin A, Alfonic 610-3.5®, and Clove oil.

Another embodiment comprises cyclosporin A, Alfonic 810-2®, and Clove oil.

Another embodiment comprises cyclosporin A, Alfonic 810-6®, and Clove oil.

Another embodiment comprises cyclosporin A, Alfonic 1012-3®, and Clove oil.

Another embodiment comprises cyclosporin A, Alfonic 1012-5®, and Clove oil.

Another embodiment comprises cyclosporin A, Alfonic 1216CO-1.5®, and Clove oil.

Another embodiment comprises cyclosporin A, Alfonic 1216CO-7®, and Clove oil.

Another embodiment comprises cyclosporin A, Alfonic 1412-3®, and Clove oil.

Another embodiment comprises cyclosporin A, Alfonic 1412-7®, and Clove oil.

Another embodiment comprises cyclosporin A, Arlasolve 200®, and Clove oil.

Another embodiment comprises cyclosporin A, Arlasolve 200 Liquid®, and Clove oil.

Another embodiment comprises cyclosporin A, Armix 180-C®, and Clove oil.

Another embodiment comprises cyclosporin A, Armix 183®, and Clove oil.

Another embodiment comprises cyclosporin A, Armul 2404®, and Clove oil.

Another embodiment comprises cyclosporin A, Armul 2404®, and Clove oil.

Another embodiment comprises cyclosporin A, Atlas EMJ-C®, and Clove oil.

Another embodiment comprises cyclosporin A, Atlas G-2109®, and Clove oil.

Another embodiment comprises cyclosporin A, Atlas G-3886®, and Clove oil.

Another embodiment comprises cyclosporin A, Atlas G-3890®, and Clove oil.

Another embodiment comprises cyclosporin A, Bio Soft E-200®, and Clove oil.

Another embodiment comprises cyclosporin A, Bio Soft E-300®, and Clove oil.

Another embodiment comprises cyclosporin A, Bio Soft E-400®, and Clove oil.

Another embodiment comprises cyclosporin A, Bio Soft EN 600®, and Clove oil.

Another embodiment comprises cyclosporin A, Bio Soft TD-400®, and Clove oil.

Another embodiment comprises cyclosporin A, Bio Soft TD-630®, and Clove oil.

Another embodiment comprises cyclosporin A, Brij 30®, and Clove oil.

Another embodiment comprises cyclosporin A, Brij 52®, and Clove oil.

Another embodiment comprises cyclosporin A, Brij 56®, and Clove oil.

Another embodiment comprises cyclosporin A, Brij 58®, and Clove oil.

Another embodiment comprises cyclosporin A, Brij 72®, and Clove oil.

Another embodiment comprises cyclosporin A, Brij 76®, and Clove oil.

Another embodiment comprises cyclosporin A, Brij 78®, and Clove oil.

Another embodiment comprises cyclosporin A, Brij 93®, and Clove oil.

Another embodiment comprises cyclosporin A, Brij 97®, and Clove oil.

Another embodiment comprises cyclosporin A, Brij 98®, and Clove oil.

Another embodiment comprises cyclosporin A, Brij 700®, and Clove oil.

Another embodiment comprises cyclosporin A, Brij 700 S®, and Clove oil.

Another embodiment comprises cyclosporin A, Brij 721®, and Clove oil.

Another embodiment comprises cyclosporin A, Brij 721 S®, and Clove oil.

Another embodiment comprises cyclosporin A, Burcoterge CDG®, and Clove oil.

Another embodiment comprises cyclosporin A, Canasol AT 600®, and Clove oil.

Another embodiment comprises cyclosporin A, Canasol AT 800®, and Clove oil.

Another embodiment comprises cyclosporin A, Canasol AT 1200®, and Clove oil.

Another embodiment comprises cyclosporin A, Canasol BJ 35®, and Clove oil.
Another embodiment comprises cyclosporin A, Canasol BJ 36®, and Clove oil.
Another embodiment comprises cyclosporin A, Canasol BJ 52®, and Clove oil.
Another embodiment comprises cyclosporin A, Canasol BJ 58®, and Clove oil.
Another embodiment comprises cyclosporin A, Canasol BJ 72®, and Clove oil.
Another embodiment comprises cyclosporin A, Canasol BJ 78®, and Clove oil.
Another embodiment comprises cyclosporin A, Canasol BJ 98®, and Clove oil.
Another embodiment comprises cyclosporin A, Canasol BJ 307®, and Clove oil.
Another embodiment comprises cyclosporin A, Cerfak 1400®, and Clove oil.
Another embodiment comprises cyclosporin A, Cetomacrogol 1000 BP®, and Clove oil.
Another embodiment comprises cyclosporin A, Chemonic C-2®, and Clove oil.
Another embodiment comprises cyclosporin A, Chemonic C-10®, and Clove oil.
Another embodiment comprises cyclosporin A, Chemonic C-20®, and Clove oil.
Another embodiment comprises cyclosporin A, Chemonic CT-12®, and Clove oil.
Another embodiment comprises cyclosporin A, Chemonic CT-20®, and Clove oil.
Another embodiment comprises cyclosporin A, Chemonic CT-30®, and Clove oil.
Another embodiment comprises cyclosporin A, Chemonic CT-55®, and Clove oil.
Another embodiment comprises cyclosporin A, Chemonic G-7®, and Clove oil.
Another embodiment comprises cyclosporin A, Chemonic G-26®, and Clove oil.
Another embodiment comprises cyclosporin A, Chemonic L-4®, and Clove oil.
Another embodiment comprises cyclosporin A, Chemonic L-7®, and Clove oil.
Another embodiment comprises cyclosporin A, Chemonic L-12®, and Clove oil.
Another embodiment comprises cyclosporin A, Chemonic L-23®, and Clove oil.
Another embodiment comprises cyclosporin A, Chemonic O-2®, and Clove oil.
Another embodiment comprises cyclosporin A, Chemonic O-5®, and Clove oil.
Another embodiment comprises cyclosporin A, Chemonic O-10®, and Clove oil.
Another embodiment comprises cyclosporin A, Chemonic O-20®, and Clove oil.
Another embodiment comprises cyclosporin A, Chemonic S-2®, and Clove oil.
Another embodiment comprises cyclosporin A, Chemonic S-10®, and Clove oil.
Another embodiment comprises cyclosporin A, Chemonic S-20®, and Clove oil.
Another embodiment comprises cyclosporin A, Colamulse FE®, and Clove oil.
Another embodiment comprises cyclosporin A, Cremophor A 20®, and Clove oil.
Another embodiment comprises cyclosporin A, Cremophor SA 2®, and Clove oil.
Another embodiment comprises cyclosporin A, Dehydol 100®, and Clove oil.
Another embodiment comprises cyclosporin A, Dehydol O-4®, and Clove oil.
Another embodiment comprises cyclosporin A, Delonic C-18®, and Clove oil.
Another embodiment comprises cyclosporin A, DeSonic 6T®, and Clove oil.
Another embodiment comprises cyclosporin A, DeSonic 9D®, and Clove oil.
Another embodiment comprises cyclosporin A, DeSonic 9T®, and Clove oil.
Another embodiment comprises cyclosporin A, DeSonic 12D®, and Clove oil.
Another embodiment comprises cyclosporin A, DeSonic 12T®, and Clove oil.
Another embodiment comprises cyclosporin A, DeSonic 15T®, and Clove oil.
Another embodiment comprises cyclosporin A, DeSonic TDA-9®, and Clove oil.
Another embodiment comprises cyclosporin A, DeThox GLG-7®, and Clove oil.
Another embodiment comprises cyclosporin A, DeThox GLG-26®, and Clove oil.
Another embodiment comprises cyclosporin A, DeThox LA-4®, and Clove oil.
Another embodiment comprises cyclosporin A, DeThox LA-23®, and Clove oil.
Another embodiment comprises cyclosporin A, DeThox SA-80®, and Clove oil.
Another embodiment comprises cyclosporin A, Disponil O5®, and Clove oil.
Another embodiment comprises cyclosporin A, Eccoterge EO-41B®, and Clove oil.
Another embodiment comprises cyclosporin A, Empilan KA2.5/90®, and Clove oil.
Another embodiment comprises cyclosporin A, Empilan KA5/90®, and Clove oil.
Another embodiment comprises cyclosporin A, Empilan KM-20®, and Clove oil.
Another embodiment comprises cyclosporin A, Empilan KM-50®, and Clove oil.
Another embodiment comprises cyclosporin A, Empilan L-23®, and Clove oil.
Another embodiment comprises cyclosporin A, Ethylan 25-3®, and Clove oil.
Another embodiment comprises cyclosporin A, Ethylan 1204®, and Clove oil.
Another embodiment comprises cyclosporin A, Ethylan DA-4®, and Clove oil.
Another embodiment comprises cyclosporin A, Ethylan LA-23®, and Clove oil.
Another embodiment comprises cyclosporin A, Ethylan SN®, and Clove oil.
Another embodiment comprises cyclosporin A, Ethylan TD-60®, and Clove oil.
Another embodiment comprises cyclosporin A, Ethylan TD-100®, and Clove oil.
Another embodiment comprises cyclosporin A, Ethylan TD-1407®, and Clove oil.
Another embodiment comprises cyclosporin A, Eumulgin B1®, and Clove oil.
Another embodiment comprises cyclosporin A, Eumulgin B2®, and Clove oil.
Another embodiment comprises cyclosporin A, Eumulgin B3®, and Clove oil.

Another embodiment comprises cyclosporin A, Eumulgin O-10®, and Clove oil.

Another embodiment comprises cyclosporin A, Flo Mo 80/20®, and Clove oil.

Another embodiment comprises cyclosporin A, Flo Mo Low Foam®, and Clove oil.

Another embodiment comprises cyclosporin A, Forlan C-24®, and Clove oil.

Another embodiment comprises cyclosporin A, Genapol 1454®, and Clove oil.

Another embodiment comprises cyclosporin A, Genapol BA-020®, and Clove oil.

Another embodiment comprises cyclosporin A, Genapol BA-040®, and Clove oil.

Another embodiment comprises cyclosporin A, Genapol C-100®, and Clove oil.

Another embodiment comprises cyclosporin A, Genapol DA 060®, and Clove oil.

Another embodiment comprises cyclosporin A, Genapol HS 020®, and Clove oil.

Another embodiment comprises cyclosporin A, Genapol HS 200®, and Clove oil.

Another embodiment comprises cyclosporin A, Genapol ID-040®, and Clove oil.

Another embodiment comprises cyclosporin A, Genapol ID-060®, and Clove oil.

Another embodiment comprises cyclosporin A, Genapol ID-090®, and Clove oil.

Another embodiment comprises cyclosporin A, Genapol LA 010®, and Clove oil.

Another embodiment comprises cyclosporin A, Genapol LA 020®, and Clove oil.

Another embodiment comprises cyclosporin A, Genapol LA 030®, and Clove oil.

Another embodiment comprises cyclosporin A, Genapol LA 040®, and Clove oil.

Another embodiment comprises cyclosporin A, Genapol LA 050®, and Clove oil.

Another embodiment comprises cyclosporin A, Genapol LA 060®, and Clove oil.

Another embodiment comprises cyclosporin A, Genapol LA 070®, and Clove oil.

Another embodiment comprises cyclosporin A, Genapol LA 070S®, and Clove oil.

Another embodiment comprises cyclosporin A, Genapol LA 230®, and Clove oil.

Another embodiment comprises cyclosporin A, Genapol O 020®, and Clove oil.

Another embodiment comprises cyclosporin A, Genapol O 050®, and Clove oil.

Another embodiment comprises cyclosporin A, Genapol O 100®, and Clove oil.

Another embodiment comprises cyclosporin A, Genapol O 200®, and Clove oil.

Another embodiment comprises cyclosporin A, Genapol SA 030®, and Clove oil.

Another embodiment comprises cyclosporin A, Genapol SA 120®, and Clove oil.

Another embodiment comprises cyclosporin A, Genapol T-020®, and Clove oil.

Another embodiment comprises cyclosporin A, Genapol UD-030®, and Clove oil.

Another embodiment comprises cyclosporin A, Genapol UD-050®, and Clove oil.

Another embodiment comprises cyclosporin A, Genapol UD-070®, and Clove oil.

Another embodiment comprises cyclosporin A, Genapol UD-079®, and Clove oil.

Another embodiment comprises cyclosporin A, Genapol UD-080®, and Clove oil.

Another embodiment comprises cyclosporin A, Genapol UD-110®, and Clove oil.

Another embodiment comprises cyclosporin A, Genapol X 030®, and Clove oil.

Another embodiment comprises cyclosporin A, Genapol X 050®, and Clove oil.

Another embodiment comprises cyclosporin A, Genapol X 060®, and Clove oil.

Another embodiment comprises cyclosporin A, Genapol X 070®, and Clove oil.

Another embodiment comprises cyclosporin A, Genapol X 080®, and Clove oil.

Another embodiment comprises cyclosporin A, Genapol X 100®, and Clove oil.

Another embodiment comprises cyclosporin A, Genapol X159®, and Clove oil.

Another embodiment comprises cyclosporin A, Generol 122 E5®, and Clove oil.

Another embodiment comprises cyclosporin A, Generol 122 E25®, and Clove oil.

Another embodiment comprises cyclosporin A, Hostacerin T-3®, and Clove oil.

Another embodiment comprises cyclosporin A, Iconol LF 110®, and Clove oil.

Another embodiment comprises cyclosporin A, Incropol CS-20®, and Clove oil.

Another embodiment comprises cyclosporin A, Lexemul CS-20®, and Clove oil.

Another embodiment comprises cyclosporin A, Liponic EG-1®, and Clove oil.

Another embodiment comprises cyclosporin A, Lipowax D®, and Clove oil.

Another embodiment comprises cyclosporin A, Lipowax G®, and Clove oil.

Another embodiment comprises cyclosporin A, Lipowax NI®, and Clove oil.

Another embodiment comprises cyclosporin A, Lipowax P®, and Clove oil.

Another embodiment comprises cyclosporin A, Lipowax P-31®, and Clove oil.

Another embodiment comprises cyclosporin A, Lipowax PR®, and Clove oil.

Another embodiment comprises cyclosporin A, Lumulse CS-20®, and Clove oil.

Another embodiment comprises cyclosporin A, Macol CSA-20®, and Clove oil.

Another embodiment comprises cyclosporin A, Marlox B 24/50®, and Clove oil.

Another embodiment comprises cyclosporin A, Mazawet 77®, and Clove oil.

Another embodiment comprises cyclosporin A, Norfox 1713®, and Clove oil.

Another embodiment comprises cyclosporin A, Norfox 2579®, and Clove oil.

Another embodiment comprises cyclosporin A, Norfox Lo Foam®, and Clove oil.

Another embodiment comprises cyclosporin A, Promulgen D®, and Clove oil.

Another embodiment comprises cyclosporin A, Promulgen G®, and Clove oil.

Another embodiment comprises cyclosporin A, Renex 30®, and Clove oil.

Another embodiment comprises cyclosporin A, Renex 36®, and Clove oil.

Another embodiment comprises cyclosporin A, Rhodasurf A 24®, and Clove oil.

Another embodiment comprises cyclosporin A, Rhodasurf AAE-10®, and Clove oil.

Another embodiment comprises cyclosporin A, Rhodasurf BEH-25®, and Clove oil.

Another embodiment comprises cyclosporin A, Rhodasurf BEH-40®, and Clove oil.

Another embodiment comprises cyclosporin A, Rhodasurf DA 530®, and Clove oil.

Another embodiment comprises cyclosporin A, Rhodasurf DA 630®, and Clove oil.

Another embodiment comprises cyclosporin A, Rhodasurf DA 639®, and Clove oil.

Another embodiment comprises cyclosporin A, Rhodasurf LAN-23®, and Clove oil.

Another embodiment comprises cyclosporin A, Rhodasurf ON-870®, and Clove oil.

Another embodiment comprises cyclosporin A, Rhodasurf ON-877®, and Clove oil.

Another embodiment comprises cyclosporin A, Rhodasurf TB-970 FLK®, and Clove oil.

Another embodiment comprises cyclosporin A, Ritacet-20®, and Clove oil.

Another embodiment comprises cyclosporin A, Ritachol 1000®, and Clove oil.

Another embodiment comprises cyclosporin A, Ritachol 2000®, and Clove oil.

Another embodiment comprises cyclosporin A, Ritachol 5000®, and Clove oil.

Another embodiment comprises cyclosporin A, Ritox 35®, and Clove oil.

Another embodiment comprises cyclosporin A, Surfonic DA-4®, and Clove oil.

Another embodiment comprises cyclosporin A, Surfonic DA-6®, and Clove oil.

Another embodiment comprises cyclosporin A, Surfonic L46-7®, and Clove oil.

Another embodiment comprises cyclosporin A, Surfonic POA®, and Clove oil.

Another embodiment comprises cyclosporin A, Synthrapol KB®, and Clove oil.

Another embodiment comprises cyclosporin A, Teginacid®, and Clove oil.

Another embodiment comprises cyclosporin A, Teginacid C®, and Clove oil.

Another embodiment comprises cyclosporin A, Tegotens EC 11®, and Clove oil.

Another embodiment comprises cyclosporin A, Tinegal NA®, and Clove oil.

Another embodiment comprises cyclosporin A, Tomadol 400®, and Clove oil.

Another embodiment comprises cyclosporin A, Tomadol 600®, and Clove oil.

Another embodiment comprises cyclosporin A, Tomadol 900®, and Clove oil.

Another embodiment comprises cyclosporin A, Uniperol O®, and Clove oil.

Another embodiment comprises cyclosporin A, Witconol SN Series®, and Clove oil.

Another embodiment comprises cyclosporin A, and Clove oil.

Another embodiment comprises cyclosporin A, an Ethoxylated Alkylphenol, and Clove oil.

Another embodiment comprises cyclosporin A, Antarox LF-222®, and Clove oil.

Another embodiment comprises cyclosporin A, Atlox 775®, and Clove oil.

Another embodiment comprises cyclosporin A, Caloxylate N-9®, and Clove oil.

Another embodiment comprises cyclosporin A, Canasol NF-1000®, and Clove oil.

Another embodiment comprises cyclosporin A, Canasol NF-3000®, and Clove oil.

Another embodiment comprises cyclosporin A, Canasol NF-3070®, and Clove oil.

Another embodiment comprises cyclosporin A, Canasol OF 1670®, and Clove oil.

Another embodiment comprises cyclosporin A, Canasol OF 2570®, and Clove oil.

Another embodiment comprises cyclosporin A, Canasol OF 4070®, and Clove oil.

Another embodiment comprises cyclosporin A, Chemax DNP-8®, and Clove oil.

Another embodiment comprises cyclosporin A, Chemax DNP-18®, and Clove oil.

Another embodiment comprises cyclosporin A, Chemax DNP-150/50®, and Clove oil.

Another embodiment comprises cyclosporin A, DeSonic 1.5N®, and Clove oil.

Another embodiment comprises cyclosporin A, DeSonic 4N®, and Clove oil.

Another embodiment comprises cyclosporin A, DeSonic 5N®, and Clove oil.

Another embodiment comprises cyclosporin A, DeSonic 6D®, and Clove oil.

Another embodiment comprises cyclosporin A, DeSonic 6N®, and Clove oil.

Another embodiment comprises cyclosporin A, DeSonic 7N®, and Clove oil.

Another embodiment comprises cyclosporin A, DeSonic 9N®, and Clove oil.

Another embodiment comprises cyclosporin A, DeSonic 10D®, and Clove oil.

Another embodiment comprises cyclosporin A, DeSonic 11N®, and Clove oil.

Another embodiment comprises cyclosporin A, DeSonic 12N®, and Clove oil.

Another embodiment comprises cyclosporin A, DeSonic 15N®, and Clove oil.

Another embodiment comprises cyclosporin A, DeSonic 20N®, and Clove oil.

Another embodiment comprises cyclosporin A, Eccoscour RC®, and Clove oil.

Another embodiment comprises cyclosporin A, Eccoterge EO-100®, and Clove oil.

Another embodiment comprises cyclosporin A, Emulsifier 632/90%®, and Clove oil.

Another embodiment comprises cyclosporin A, Geronol AG-821®, and Clove oil.

Another embodiment comprises cyclosporin A, Gradonic N-95®, and Clove oil.

Another embodiment comprises cyclosporin A, Hetoxide NP-4®, and Clove oil.

Another embodiment comprises cyclosporin A, Hetoxide NP-30®, and Clove oil.

Another embodiment comprises cyclosporin A, Hostapal N-100®, and Clove oil.

Another embodiment comprises cyclosporin A, Hostapal N-110®, and Clove oil.

Another embodiment comprises cyclosporin A, Igepal CTA-639W®, and Clove oil.

Another embodiment comprises cyclosporin A, Igepal DAP-9®, and Clove oil.

Another embodiment comprises cyclosporin A, Igepal OD-410®, and Clove oil.

Another embodiment comprises cyclosporin A, Igepal SS-837®, and Clove oil.

Another embodiment comprises cyclosporin A, Lipocol NP-9 USP®, and Clove oil.

Another embodiment comprises cyclosporin A, Macol DNP-10®, and Clove oil.

Another embodiment comprises cyclosporin A, Marlophen NP 5®, and Clove oil.

Another embodiment comprises cyclosporin A, Marlophen P 1®, and Clove oil.

Another embodiment comprises cyclosporin A, Surfonic NB®, and Clove oil.

Another embodiment comprises cyclosporin A, Surfonic OPB-307®, and Clove oil.

Another embodiment comprises cyclosporin A, Surfonic OPB-407®, and Clove oil.

Another embodiment comprises cyclosporin A, Syn Fac 334®, and Clove oil.

Another embodiment comprises cyclosporin A, Syn Fac 8216®, and Clove oil.

Another embodiment comprises cyclosporin A, Triton N-57®, and Clove oil.

Another embodiment comprises cyclosporin A, Trycol 6956®, and Clove oil.

Another embodiment comprises cyclosporin A, Trycol 6961®, and Clove oil.

Another embodiment comprises cyclosporin A, Trycol 6964®, and Clove oil.

Another embodiment comprises cyclosporin A, Trycol 6969®, and Clove oil.

Another embodiment comprises cyclosporin A, Trycol 6974®, and Clove oil.

Another embodiment comprises cyclosporin A, Witbreak DRB-127®, and Clove oil.

Another embodiment comprises cyclosporin A, Witbreak DRB-127®, and Clove oil.

Another embodiment comprises cyclosporin A, Witconol NP Series®, and Clove oil.

Another embodiment comprises cyclosporin A, and Clove oil.

Another embodiment comprises cyclosporin A, an Ethoxylated Aryl Phenol, and Clove oil.

Another embodiment comprises cyclosporin A, Sprophor BSU®, and Clove oil.

Another embodiment comprises cyclosporin A, Sprophor CY/8®, and Clove oil.

Another embodiment comprises cyclosporin A, Sprophor S/25®, and Clove oil.

Another embodiment comprises cyclosporin A, Witconol NIO®, and Clove oil.

Another embodiment comprises cyclosporin A, Witconol NIW®, and Clove oil.

Another embodiment comprises cyclosporin A, Witconol S-100®, and Clove oil.

Another embodiment comprises cyclosporin A, and Clove oil.

Another embodiment comprises cyclosporin A, an Ethoxylated Fatty Acid, and Clove oil.

Another embodiment comprises cyclosporin A, Aldo PGHMS®, and Clove oil.

Another embodiment comprises cyclosporin A, Alkamuls TO-15/HR®, and Clove oil.

Another embodiment comprises cyclosporin A, Armotan AL-69-66®, and Clove oil.

Another embodiment comprises cyclosporin A, Cerasynt 840®, and Clove oil.

Another embodiment comprises cyclosporin A, Cerasynt 945®, and Clove oil.

Another embodiment comprises cyclosporin A, Crystal Inhibitor No. 5®, and Clove oil.

Another embodiment comprises cyclosporin A, DeThox Acid L-9®, and Clove oil.

Another embodiment comprises cyclosporin A, DeThox Acid S-8®, and Clove oil.

Another embodiment comprises cyclosporin A, Ethofat 242/25®, and Clove oil.

Another embodiment comprises cyclosporin A, Hydropalat 65®, and Clove oil;

Another embodiment comprises cyclosporin A, Lipo EGMS®, and Clove oil.

Another embodiment comprises cyclosporin A, Lipopeg 2 DL®, and Clove oil.

Another embodiment comprises cyclosporin A, Lipopeg 4 DL®, and Clove oil.

Another embodiment comprises cyclosporin A, Lipopeg 4-L®, and Clove oil.

Another embodiment comprises cyclosporin A, Lipopeg 39-S®, and Clove oil.

Another embodiment comprises cyclosporin A, Lipopeg 4-S®, and Clove oil.

Another embodiment comprises cyclosporin A, Lipopeg 10-S®, and Clove oil.

Another embodiment comprises cyclosporin A, Lipopeg 100-S®, and Clove oil.

Another embodiment comprises cyclosporin A, Lipopeg 6000 DS®, and Clove oil.

Another embodiment comprises cyclosporin A, Lumulse 40-L®, and Clove oil.

Another embodiment comprises cyclosporin A, Lumulse 40-S®, and Clove oil.

Another embodiment comprises cyclosporin A, Lumulse 42-L®, and Clove oil.

Another embodiment comprises cyclosporin A, Lumulse 42-S®, and Clove oil.

Another embodiment comprises cyclosporin A, Lumulse 100-S®, and Clove oil.

Another embodiment comprises cyclosporin A, Lumulse 602-S®, and Clove oil.

Another embodiment comprises cyclosporin A, Magrabar PGE-20-0®, and Clove oil.

Another embodiment comprises cyclosporin A, Magrabar PGE-20L®, and Clove oil.

Another embodiment comprises cyclosporin A, Magrabar PGE-20T®, and Clove oil.

Another embodiment comprises cyclosporin A, Magrabar PGE-22-0®, and Clove oil.

Another embodiment comprises cyclosporin A, Magrabar PGE-22L®, and Clove oil.

Another embodiment comprises cyclosporin A, Magrabar PGE-22T®, and Clove oil.

Another embodiment comprises cyclosporin A, Magrabar PGE-40-0®, and Clove oil.

Another embodiment comprises cyclosporin A, Magrabar PGE-40L®, and Clove oil.

Another embodiment comprises cyclosporin A, Magrabar PGE-40T®, and Clove oil.

Another embodiment comprises cyclosporin A, Magrabar PGE-42-O®, and Clove oil.

Another embodiment comprises cyclosporin A, Magrabar PGE-42L®, and Clove oil.

Another embodiment comprises cyclosporin A, Magrabar PGE-42T®, and Clove oil.

Another embodiment comprises cyclosporin A, Magrabar PGE-60-O®, and Clove oil.

Another embodiment comprises cyclosporin A, Magrabar PGE-60L®, and Clove oil.

Another embodiment comprises cyclosporin A, Magrabar PGE-60T®, and Clove oil.

Another embodiment comprises cyclosporin A, Magrabar PGE-62-O®, and Clove oil.

Another embodiment comprises cyclosporin A, Magrabar PGE-62L®, and Clove oil.

Another embodiment comprises cyclosporin A, Magrabar PGE-62T®, and Clove oil.

Another embodiment comprises cyclosporin A, Mapeg S-40K®, and Clove oil.

Another embodiment comprises cyclosporin A, Marlowet OTS®, and Clove oil.

Another embodiment comprises cyclosporin A, Naturechem PGR®, and Clove oil.

Another embodiment comprises cyclosporin A, PG No. 4®, and Clove oil.

Another embodiment comprises cyclosporin A, Renex 20®, and Clove oil.

Another embodiment comprises cyclosporin A, Ritox 52®, and Clove oil.

Another embodiment comprises cyclosporin A, Ritox 53®, and Clove oil.

Another embodiment comprises cyclosporin A, Ritox 59®, and Clove oil.

Another embodiment comprises cyclosporin A, Surtax 8916/A®, and Clove oil.

Another embodiment comprises cyclosporin A, Tego Acid S 40 P®, and Clove oil.

Another embodiment comprises cyclosporin A, Tego Acid S 100 P®, and Clove oil.

Another embodiment comprises cyclosporin A, Tween 20®, and Clove oil.

Another embodiment comprises cyclosporin A, Volpo 131®, and Clove oil.

Another embodiment comprises cyclosporin A, and Clove oil.

Another embodiment comprises cyclosporin A, an Ethoxylated Fatty Ester or Oil, and Clove oil.

Another embodiment comprises cyclosporin A, Acconon 6-C10®, and Clove oil.

Another embodiment comprises cyclosporin A, Acconon CC-6®, and Clove oil.

Another embodiment comprises cyclosporin A, Acconon CO-7®, and Clove oil.

Another embodiment comprises cyclosporin A, Aldosperse 40/60 FG®, and Clove oil.

Another embodiment comprises cyclosporin A, Aldosperse ML-23®, and Clove oil.

Another embodiment comprises cyclosporin A, Aldosperse MS-20 FG®, and Clove oil.

Another embodiment comprises cyclosporin A, Alkamuls EL-620®, and Clove oil.

Another embodiment comprises cyclosporin A, Alkamuls EL-719®, and Clove oil.

Another embodiment comprises cyclosporin A, Alkamuls EL-985®, and Clove oil.

Another embodiment comprises cyclosporin A, Arlatone G®, and Clove oil.

Another embodiment comprises cyclosporin A, Arlatone T®, and Clove oil.

Another embodiment comprises cyclosporin A, Atlas G-1045A®, and Clove oil.

Another embodiment comprises cyclosporin A, Atlas G-1086®, and Clove oil.

Another embodiment comprises cyclosporin A, Atlas G-1087®, and Clove oil.

Another embodiment comprises cyclosporin A, Atlas G-1089®, and Clove oil.

Another embodiment comprises cyclosporin A, Atlas G-1096®, and Clove oil.

Another embodiment comprises cyclosporin A, Atlas G-1292®, and Clove oil.

Another embodiment comprises cyclosporin A, Atlas G-1293®, and Clove oil.

Another embodiment comprises cyclosporin A, Atlas G-1300®, and Clove oil.

Another embodiment comprises cyclosporin A, Atlas G-7076®, and Clove oil.

Another embodiment comprises cyclosporin A, Capmul EMG®, and Clove oil.

Another embodiment comprises cyclosporin A, Chemonic CO-40®, and Clove oil.

Another embodiment comprises cyclosporin A, Chemonic LI-3®, and Clove oil.

Another embodiment comprises cyclosporin A, Chemonic LI-7®, and Clove oil.

Another embodiment comprises cyclosporin A, Cirrasol GM®, and Clove oil.

Another embodiment comprises cyclosporin A, Cremophor CO 40®, and Clove oil.

Another embodiment comprises cyclosporin A, Cremophor CO 410®, and Clove oil.

Another embodiment comprises cyclosporin A, Cremophor EL®, and Clove oil.

Another embodiment comprises cyclosporin A, Cremophor GC7®, and Clove oil.

Another embodiment comprises cyclosporin A, Cremophor RH-40®, and Clove oil.

Another embodiment comprises cyclosporin A, Crovol A-40®, and Clove oil.

Another embodiment comprises cyclosporin A, Crovol A-70®, and Clove oil.

Another embodiment comprises cyclosporin A, Crovol M-70®, and Clove oil.

Another embodiment comprises cyclosporin A, Crovol PK-70®, and Clove oil.

Another embodiment comprises cyclosporin A, Cutina E-24®, and Clove oil.

Another embodiment comprises cyclosporin A, Dacospin 12-R®, and Clove oil.

Another embodiment comprises cyclosporin A, Dehymuls HRE-7®, and Clove oil.

Another embodiment comprises cyclosporin A, DeSonic 30C®, and Clove oil.

Another embodiment comprises cyclosporin A, DeSonic 36C®, and Clove oil.

Another embodiment comprises cyclosporin A, DeSonic 40C®, and Clove oil.

Another embodiment comprises cyclosporin A, Durfax 60®, and Clove oil.

Another embodiment comprises cyclosporin A, Durfax 65®, and Clove oil.

Another embodiment comprises cyclosporin A, Durfax 80®, and Clove oil.

Another embodiment comprises cyclosporin A, Durfax EOM®, and Clove oil.

Another embodiment comprises cyclosporin A, Eccoterge NF-2®, and Clove oil.

Another embodiment comprises cyclosporin A, Emulpon CO-360®, and Clove oil.

Another embodiment comprises cyclosporin A, Emulpon CO-550®, and Clove oil.

Another embodiment comprises cyclosporin A, Emulsogen EL®, and Clove oil.

Another embodiment comprises cyclosporin A, Emulsogen HCO 040®, and Clove oil.

Another embodiment comprises cyclosporin A, Emulsogen HCO 060®, and Clove oil.

Another embodiment comprises cyclosporin A, Emulsynt 1055®, and Clove oil.

Another embodiment comprises cyclosporin A, Ethox 3095®, and Clove oil.

Another embodiment comprises cyclosporin A, Eumulgin RO-40®, and Clove oil.

Another embodiment comprises cyclosporin A, Genapol G-260®, and Clove oil.

Another embodiment comprises cyclosporin A, Glycosperse L-20®, and Clove oil.

Another embodiment comprises cyclosporin A, Glycosperse O-5®, and Clove oil.

Another embodiment comprises cyclosporin A, Glycosperse O-20®, and Clove oil.

Another embodiment comprises cyclosporin A, Glycosperse O-20 FG®, and Clove oil.

Another embodiment comprises cyclosporin A, Glycosperse S-20®, and Clove oil.

Another embodiment comprises cyclosporin A, Glycosperse S-20 FG®, and Clove oil.

Another embodiment comprises cyclosporin A, Glycosperse TS-20®, and Clove oil.

Another embodiment comprises cyclosporin A, Glycosperse TS-20 FG®, and Clove oil.

Another embodiment comprises cyclosporin A, Hetan SL®, and Clove oil.

Another embodiment comprises cyclosporin A, Hetan SO®, and Clove oil.

Another embodiment comprises cyclosporin A, Hetan SS®, and Clove oil.

Another embodiment comprises cyclosporin A, Hetoxide C-2®, and Clove oil.

Another embodiment comprises cyclosporin A, Hetoxide C-9®, and Clove oil.

Another embodiment comprises cyclosporin A, Hetoxide C-15®, and Clove oil.

Another embodiment comprises cyclosporin A, Hetoxide C-25®, and Clove oil.

Another embodiment comprises cyclosporin A, Hetoxide C-40®, and Clove oil.

Another embodiment comprises cyclosporin A, Hetoxide C-200®, and Clove oil.

Another embodiment comprises cyclosporin A, Hetoxide C-200-50%®, and Clove oil.

Another embodiment comprises cyclosporin A, Hetoxide GC-30®, and Clove oil.

Another embodiment comprises cyclosporin A, Hetoxide HC-60®, and Clove oil.

Another embodiment comprises cyclosporin A, Ice No. 2®, and Clove oil.

Another embodiment comprises cyclosporin A, Incrocas 30/40®, and Clove oil.

Another embodiment comprises cyclosporin A, Lexol EC®, and Clove oil.

Another embodiment comprises cyclosporin A, Lexol EO®, and Clove oil.

Another embodiment comprises cyclosporin A, Lipocol HCO-40®, and Clove oil.

Another embodiment comprises cyclosporin A, Lipocol HCO-60®, and Clove oil.

Another embodiment comprises cyclosporin A, Lipocol O-3 Special®, and Clove oil.

Another embodiment comprises cyclosporin A, Lipopeg 2-L®, and Clove oil.

Another embodiment comprises cyclosporin A, Lipopeg 4-DO®, and Clove oil.

Another embodiment comprises cyclosporin A, Lipopeg 4-DS®, and Clove oil.

Another embodiment comprises cyclosporin A, Lipovol GTB®, and Clove oil.

Another embodiment comprises cyclosporin A, Lonzest SML-20®, and Clove oil.

Another embodiment comprises cyclosporin A, Lonzest SMO-20®, and Clove oil.

Another embodiment comprises cyclosporin A, Lonzest SMS-20®, and Clove oil.

Another embodiment comprises cyclosporin A, Lonzest STO-20®, and Clove oil.

Another embodiment comprises cyclosporin A, Lonzest STS-20®, and Clove oil.

Another embodiment comprises cyclosporin A, Lumulse GR-40®, and Clove oil.

Another embodiment comprises cyclosporin A, Lumulse GRH-40®, and Clove oil.

Another embodiment comprises cyclosporin A, Lumulse POE (7) GML®, and Clove oil.

Another embodiment comprises cyclosporin A, Lumulse POE (12) Glyc®, and Clove oil.

Another embodiment comprises cyclosporin A, Lumulse POE (40) MS KP®, and Clove oil.

Another embodiment comprises cyclosporin A, Marlowet 4750®, and Clove oil.

Another embodiment comprises cyclosporin A, Marlowet LVS®, and Clove oil.

Another embodiment comprises cyclosporin A, Marlowet R 11®, and Clove oil.

Another embodiment comprises cyclosporin A, Marlowet R 40®, and Clove oil.

Another embodiment comprises cyclosporin A, Mazol 80 MGK®, and Clove oil.

Another embodiment comprises cyclosporin A, Nonionic Emulsifier T-9®, and Clove oil.

Another embodiment comprises cyclosporin A, Oronal LCG®, and Clove oil.

Another embodiment comprises cyclosporin A, Polyderm PPI-CO-200®, and Clove oil.

Another embodiment comprises cyclosporin A, Polyderm PPI-CO-40®, and Clove oil.

Another embodiment comprises cyclosporin A, Rewoderm LI 520-70®, and Clove oil.

Another embodiment comprises cyclosporin A, Ritapeg 150 DS®, and Clove oil.

Another embodiment comprises cyclosporin A, Softigen 767®, and Clove oil.

Another embodiment comprises cyclosporin A, Surfactol 318®, and Clove oil.

Another embodiment comprises cyclosporin A, Surfactol 365®, and Clove oil.

Another embodiment comprises cyclosporin A, Syn Lube 107®, and Clove oil.

Another embodiment comprises cyclosporin A, Syn Lube 728®, and Clove oil.

Another embodiment comprises cyclosporin A, Syn Lube 1632H®, and Clove oil.

Another embodiment comprises cyclosporin A, Syn Lube 6277-A®, and Clove oil.

Another embodiment comprises cyclosporin A, T-Det C-20®, and Clove oil.

Another embodiment comprises cyclosporin A, T-Det C-40®, and Clove oil.

Another embodiment comprises cyclosporin A, Tally 100 Plus®, and Clove oil.

Another embodiment comprises cyclosporin A, Uniperol EL®, and Clove oil.

Another embodiment comprises cyclosporin A, and Clove oil.

Another embodiment comprises cyclosporin A, a Fatty Ester, and Clove oil.

Another embodiment comprises cyclosporin A, Actralube-Syn 147®, and Clove oil.

Another embodiment comprises cyclosporin A, Atlas G-1556®, and Clove oil.

Another embodiment comprises cyclosporin A, Atlas G-1564®, and Clove oil.

Another embodiment comprises cyclosporin A, Atlasol Base Oil S®, and Clove oil.

Another embodiment comprises cyclosporin A, Base ML®, and Clove oil.

Another embodiment comprises cyclosporin A, Base MT®, and Clove oil.

Another embodiment comprises cyclosporin A, Cerasynt 303®, and Clove oil.

Another embodiment comprises cyclosporin A, Dermol 1012®, and Clove oil.

Another embodiment comprises cyclosporin A, Kemester 4000®, and Clove oil.

Another embodiment comprises cyclosporin A, Lactipol S®, and Clove oil.

Another embodiment comprises cyclosporin A, Magrabar PGO®, and Clove oil.

Another embodiment comprises cyclosporin A, Mayco Base BFO®, and Clove oil.

Another embodiment comprises cyclosporin A, Methyl Linoleate®, and Clove oil.

Another embodiment comprises cyclosporin A, Pationic 122A®, and Clove oil.

Another embodiment comprises cyclosporin A, Pationic 138C®, and Clove oil.

Another embodiment comprises cyclosporin A, Pationic CSL®, and Clove oil.

Another embodiment comprises cyclosporin A, Pationic ISL®, and Clove oil.

Another embodiment comprises cyclosporin A, Pationic SBL®, and Clove oil.

Another embodiment comprises cyclosporin A, Pationic SSL®, and Clove oil.

Another embodiment comprises cyclosporin A, Ritasol®, and Clove oil.

Another embodiment comprises cyclosporin A, Tego Alkanol CS 20®, and Clove oil.

Another embodiment comprises cyclosporin A, Tego Alkanol L23 P®, and Clove oil.

Another embodiment comprises cyclosporin A, Tego Alkanol S2®, and Clove oil.

Another embodiment comprises cyclosporin A, Tego Alkanol S20 P®, and Clove oil.

Another embodiment comprises cyclosporin A, Triemulsifier 600 MS®, and Clove oil.

Another embodiment comprises cyclosporin A, and Clove oil.

Another embodiment comprises cyclosporin A, a Glycerol Esters, and Clove oil.

Another embodiment comprises cyclosporin A, Agro #9 Wint SBO®, and Clove oil.

Another embodiment comprises cyclosporin A, Ahcovel Base 700®, and Clove oil.

Another embodiment comprises cyclosporin A, Aldo HMS FG®, and Clove oil.

Another embodiment comprises cyclosporin A, Aldo MLD®, and Clove oil.

Another embodiment comprises cyclosporin A, Aldo MLD FG®, and Clove oil.

Another embodiment comprises cyclosporin A, Aldo MO FG®, and Clove oil.

Another embodiment comprises cyclosporin A, Aldo MS®, and Clove oil.

Another embodiment comprises cyclosporin A, Aldo MS FG®, and Clove oil.

Another embodiment comprises cyclosporin A, Aldo MS LG FG®, and Clove oil.

Another embodiment comprises cyclosporin A, Aldo MSD®, and Clove oil.

Another embodiment comprises cyclosporin A, Aldo MSD FG®, and Clove oil.

Another embodiment comprises cyclosporin A, Aldosperse O-20 FG®, and Clove oil.

Another embodiment comprises cyclosporin A, Aldosperse TS-20 FG®, and Clove oil.

Another embodiment comprises cyclosporin A, Aldosperse TS-40 FG®, and Clove oil.

Another embodiment comprises cyclosporin A, Arlacel 165®, and Clove oil.

Another embodiment comprises cyclosporin A, Arlacel 186®, and Clove oil.

Another embodiment comprises cyclosporin A, Capmul GMO®, and Clove oil.

Another embodiment comprises cyclosporin A, Capmul GMS®, and Clove oil.

Another embodiment comprises cyclosporin A, Caprol 3GO®, and Clove oil.

Another embodiment comprises cyclosporin A, Caprol 3GVS®, and Clove oil.

Another embodiment comprises cyclosporin A, Caprol 6G2S®, and Clove oil.

Another embodiment comprises cyclosporin A, Caprol 10G40®, and Clove oil.

Another embodiment comprises cyclosporin A, Caprol 10G100®, and Clove oil.

Another embodiment comprises cyclosporin A, Caprol ET®, and Clove oil.

Another embodiment comprises cyclosporin A, Caprol PGE860®, and Clove oil.

Another embodiment comprises cyclosporin A, Cerasynt 945®, and Clove oil.

Another embodiment comprises cyclosporin A, Cerasynt GMS®, and Clove oil.

Another embodiment comprises cyclosporin A, Cerasynt Q®, and Clove oil.

Another embodiment comprises cyclosporin A, Cerasynt SD®, and Clove oil.

Another embodiment comprises cyclosporin A, Cerasynt WM®, and Clove oil.

Another embodiment comprises cyclosporin A, Chemsperse 14®, and Clove oil.

Another embodiment comprises cyclosporin A, Cremophor GO-32®, and Clove oil.

Another embodiment comprises cyclosporin A, Cremophor GS11®, and Clove oil.

Another embodiment comprises cyclosporin A, Cremophor GS-32®, and Clove oil.

Another embodiment comprises cyclosporin A, Cutina KD-16®, and Clove oil.

Another embodiment comprises cyclosporin A, Dehymuls PGPH®, and Clove oil.

Another embodiment comprises cyclosporin A, Dermol DGDIS®, and Clove oil.

Another embodiment comprises cyclosporin A, Dermol DGMIS®, and Clove oil.

Another embodiment comprises cyclosporin A, Dermol G-76®, and Clove oil.

Another embodiment comprises cyclosporin A, Dermol G-7DI®, and Clove oil.

Another embodiment comprises cyclosporin A, Dermol NGDI®, and Clove oil.

Another embodiment comprises cyclosporin A, Dermolan GLH®, and Clove oil.

Another embodiment comprises cyclosporin A, Drewmulse GMO®, and Clove oil.

Another embodiment comprises cyclosporin A, Drewpol 3-5-M®, and Clove oil.

Another embodiment comprises cyclosporin A, Durlac 100 W®, and Clove oil.

Another embodiment comprises cyclosporin A, Dur-Lo®, and Clove oil.

Another embodiment comprises cyclosporin A, Dynasan 118®, and Clove oil.

Another embodiment comprises cyclosporin A, EC-25®, and Clove oil.

Another embodiment comprises cyclosporin A, EM 40®, and Clove oil.

Another embodiment comprises cyclosporin A, Emerest 2400®, and Clove oil.

Another embodiment comprises cyclosporin A, Emerest 2452®, and Clove oil.

Another embodiment comprises cyclosporin A, Empilan G-26®, and Clove oil.

Another embodiment comprises cyclosporin A, Genapol TSM®, and Clove oil.

Another embodiment comprises cyclosporin A, Hostacerin DGI®, and Clove oil.

Another embodiment comprises cyclosporin A, Hostacerin DGL®, and Clove oil.

Another embodiment comprises cyclosporin A, Hostacerin DGMS®, and Clove oil.

Another embodiment comprises cyclosporin A, Hostacerin DGSB®, and Clove oil.

Another embodiment comprises cyclosporin A, Ice No. 2®, and Clove oil.

Another embodiment comprises cyclosporin A, Imwitor 742®, and Clove oil.

Another embodiment comprises cyclosporin A, Imwitor 780 K®, and Clove oil.

Another embodiment comprises cyclosporin A, Imwitor 960 Flakes®, and Clove oil.

Another embodiment comprises cyclosporin A, Isolan GI 34®, and Clove oil.

Another embodiment comprises cyclosporin A, Isolan GO 33®, and Clove oil.

Another embodiment comprises cyclosporin A, Kemester 1000®, and Clove oil.

Another embodiment comprises cyclosporin A, Kemester 2000®, and Clove oil.

Another embodiment comprises cyclosporin A, Kemester 2000®, and Clove oil.

Another embodiment comprises cyclosporin A, Kemester 6000SE®, and Clove oil.

Another embodiment comprises cyclosporin A, Lamecreme DGE 18®, and Clove oil.

Another embodiment comprises cyclosporin A, Lexemul 515®, and Clove oil.

Another embodiment comprises cyclosporin A, Lexemul 561®, and Clove oil.

Another embodiment comprises cyclosporin A, Lexemul AR®, and Clove oil.

Another embodiment comprises cyclosporin A, Lexemul AS®, and Clove oil.

Another embodiment comprises cyclosporin A, Lexemul GDL®, and Clove oil.

Another embodiment comprises cyclosporin A, Lexemul T®, and Clove oil.

Another embodiment comprises cyclosporin A, Lipomulse 165®, and Clove oil.

Another embodiment comprises cyclosporin A, Lumulse GML K®, and Clove oil.

Another embodiment comprises cyclosporin A, Lumulse GMO K®, and Clove oil.

Another embodiment comprises cyclosporin A, Lumulse GMR K®, and Clove oil.

Another embodiment comprises cyclosporin A, Lumulse GMT K®, and Clove oil.

Another embodiment comprises cyclosporin A, Magrabar GMC®, and Clove oil.

Another embodiment comprises cyclosporin A, Magrabar GMO-CK®, and Clove oil.

Another embodiment comprises cyclosporin A, Magrabar MDG-5050®, and Clove oil.

Another embodiment comprises cyclosporin A, Magrabar PGO-315®, and Clove oil.

Another embodiment comprises cyclosporin A, Magrabar PGO-1010®, and Clove oil.

Another embodiment comprises cyclosporin A, Mazol 300K®, and Clove oil.

Another embodiment comprises cyclosporin A, Mazol GMO-K®, and Clove oil.

Another embodiment comprises cyclosporin A, Mazol GMS-K®, and Clove oil.

Another embodiment comprises cyclosporin A, Mazol PGO31-K®, and Clove oil.

Another embodiment comprises cyclosporin A, Miglyol 812®, and Clove oil.

Another embodiment comprises cyclosporin A, Norfox 165C®, and Clove oil.

Another embodiment comprises cyclosporin A, Schercemol GMIS®, and Clove oil.

Another embodiment comprises cyclosporin A, Tegin®, and Clove oil.

Another embodiment comprises cyclosporin A, Tegin 4100 Pellets®, and Clove oil.

Another embodiment comprises cyclosporin A, Tegin M Pellets®, and Clove oil.

Another embodiment comprises cyclosporin A, Tegin OV®, and Clove oil.

Another embodiment comprises cyclosporin A, Teginacid H®, and Clove oil.

Another embodiment comprises cyclosporin A, Tego Cosmo P813®, and Clove oil.

Another embodiment comprises cyclosporin A, Wickenol 535®, and Clove oil.

Another embodiment comprises cyclosporin A, Witconol 14®, and Clove oil.

Another embodiment comprises cyclosporin A, Witconol 14®, and Clove oil.

Another embodiment comprises cyclosporin A, Witconol 14F®, and Clove oil.

Another embodiment comprises cyclosporin A, Witconol 18L®, and Clove oil.

Another embodiment comprises cyclosporin A, Witconol GOT®, and Clove oil.

Another embodiment comprises cyclosporin A, Witconol MST®, and Clove oil.

Another embodiment comprises cyclosporin A, Witconol RHT®, and Clove oil.

Another embodiment comprises cyclosporin A, and Clove oil.

Another embodiment comprises cyclosporin A, a Glycol Ester, and Clove oil.

Another embodiment comprises cyclosporin A, Alkamuls 600 DO®, and Clove oil.

Another embodiment comprises cyclosporin A, Alkamuls SEG®, and Clove oil.

Another embodiment comprises cyclosporin A, Atlas EM-2®, and Clove oil.

Another embodiment comprises cyclosporin A, Cerasynt IP®, and Clove oil.

Another embodiment comprises cyclosporin A, Cerasynt M®, and Clove oil.

Another embodiment comprises cyclosporin A, Cerasynt MN®, and Clove oil.

Another embodiment comprises cyclosporin A, Cerasynt PA®, and Clove oil.

Another embodiment comprises cyclosporin A, Chemsperse EGDS®, and Clove oil.

Another embodiment comprises cyclosporin A, Chemsperse EGMS®, and Clove oil.

Another embodiment comprises cyclosporin A, Colonial Monolaurin®, and Clove oil.

Another embodiment comprises cyclosporin A, DeMuls SGE-95®, and Clove oil.

Another embodiment comprises cyclosporin A, Eccoterge 200®, and Clove oil.

Another embodiment comprises cyclosporin A, Emerest 2380®, and Clove oil.

Another embodiment comprises cyclosporin A, Ethox 2610®, and Clove oil.

Another embodiment comprises cyclosporin A, Ethox DO-9®, and Clove oil.

Another embodiment comprises cyclosporin A, Ethox DO-14®, and Clove oil.

Another embodiment comprises cyclosporin A, Ethox SO-9®, and Clove oil.

Another embodiment comprises cyclosporin A, Fizul MD-318®, and Clove oil.

Another embodiment comprises cyclosporin A, Genapol EGDS-VHP®, and Clove oil.

Another embodiment comprises cyclosporin A, Genapol TS Powder®, and Clove oil.

Another embodiment comprises cyclosporin A, Hostacerin WO®, and Clove oil.

Another embodiment comprises cyclosporin A, Inversol 140®, and Clove oil.

Another embodiment comprises cyclosporin A, Kemester 104®, and Clove oil.

Another embodiment comprises cyclosporin A, Kemester 205®, and Clove oil.

Another embodiment comprises cyclosporin A, Kemester 226®, and Clove oil.

Another embodiment comprises cyclosporin A, Kemester 5221SE®, and Clove oil.

Another embodiment comprises cyclosporin A, Kemester EGDS®, and Clove oil.

Another embodiment comprises cyclosporin A, Lexemul EGDS®, and Clove oil.

Another embodiment comprises cyclosporin A, Lexemul EGMS®, and Clove oil.

Another embodiment comprises cyclosporin A, Lexemul P®, and Clove oil.

Another embodiment comprises cyclosporin A, Lipo DGLS®, and Clove oil.

Another embodiment comprises cyclosporin A, Lipo EGDS®, and Clove oil.

Another embodiment comprises cyclosporin A, Lipo PGMS®, and Clove oil.

Another embodiment comprises cyclosporin A, Liposorb S-4®, and Clove oil.

Another embodiment comprises cyclosporin A, Liposorb TO-20®, and Clove oil.

Another embodiment comprises cyclosporin A, Lumulse PGO®, and Clove oil.

Another embodiment comprises cyclosporin A, Mackester EGDS®, and Clove oil.

Another embodiment comprises cyclosporin A, Mackester EGMS®, and Clove oil.

Another embodiment comprises cyclosporin A, Mackester GSTP®, and Clove oil.

Another embodiment comprises cyclosporin A, Mackester Series®, and Clove oil.

Another embodiment comprises cyclosporin A, Magrabar PDG-50®, and Clove oil.

Another embodiment comprises cyclosporin A, Mapeg 6000 DS®, and Clove oil.

Another embodiment comprises cyclosporin A, Marlowet 4702®, and Clove oil.

Another embodiment comprises cyclosporin A, Monalube 305®, and Clove oil.

Another embodiment comprises cyclosporin A, Monalube 310®, and Clove oil.

Another embodiment comprises cyclosporin A, Monalube 315®, and Clove oil.

Another embodiment comprises cyclosporin A, Monalube 320®, and Clove oil.

Another embodiment comprises cyclosporin A, Monalube 325®, and Clove oil.

Another embodiment comprises cyclosporin A, Monalube 330®, and Clove oil.

Another embodiment comprises cyclosporin A, Naturechem PGHS®, and Clove oil.

Another embodiment comprises cyclosporin A, Polycastorol PLO-840®, and Clove oil.

Another embodiment comprises cyclosporin A, Polytex 10M®, and Clove oil.

Another embodiment comprises cyclosporin A, Ritasynt IP®, and Clove oil.

Another embodiment comprises cyclosporin A, Ross Chem PEG 600 DT®, and Clove oil.

Another embodiment comprises cyclosporin A, Schercemol PGMS®, and Clove oil.

Another embodiment comprises cyclosporin A, Sponto H-44C®, and Clove oil.

Another embodiment comprises cyclosporin A, Tegin G®, and Clove oil.

Another embodiment comprises cyclosporin A, Witbreak DGE-182®, and Clove oil.

Another embodiment comprises cyclosporin A, Witbreak DGE-182®, and Clove oil.

Another embodiment comprises cyclosporin A, Witbreak DRA-21®, and Clove oil.

Another embodiment comprises cyclosporin A, Witbreak DRA-21®, and Clove oil.

Another embodiment comprises cyclosporin A, Witbreak DRA-50®, and Clove oil.

Another embodiment comprises cyclosporin A, Witbreak DRA-50®, and Clove oil.

Another embodiment comprises cyclosporin A, Witconol F26-46®, and Clove oil.

Another embodiment comprises cyclosporin A, Witconol H-32®, and Clove oil.

Another embodiment comprises cyclosporin A, Witconol H-33®, and Clove oil.

Another embodiment comprises cyclosporin A, Witconol H-35A®, and Clove oil.

Another embodiment comprises cyclosporin A, Witconol RHP®, and Clove oil.

Another embodiment comprises cyclosporin A, and Clove oil.

Another embodiment comprises cyclosporin A, a Lanolin-based Derivative, and Clove oil.

Another embodiment comprises cyclosporin A, Amerchol CAB®, and Clove oil.

Another embodiment comprises cyclosporin A, Amerchol L-101®, and Clove oil.

Another embodiment comprises cyclosporin A, Amerlate LFA-LO®, and Clove oil.

Another embodiment comprises cyclosporin A, Amerlate P®, and Clove oil.

Another embodiment comprises cyclosporin A, Barre Common Degras®, and Clove oil.

Another embodiment comprises cyclosporin A, Cholesterol NF®, and Clove oil.

Another embodiment comprises cyclosporin A, Crodalan AWS®, and Clove oil.

Another embodiment comprises cyclosporin A, Crodalan LA®, and Clove oil.

Another embodiment comprises cyclosporin A, Emery 1650®, and Clove oil.

Another embodiment comprises cyclosporin A, Emery 1650®, and Clove oil.

Another embodiment comprises cyclosporin A, Emery 1740®, and Clove oil.

Another embodiment comprises cyclosporin A, Emery 1740®, and Clove oil.

Another embodiment comprises cyclosporin A, Forlan 500®, and Clove oil.

Another embodiment comprises cyclosporin A, Forlan L®, and Clove oil.

Another embodiment comprises cyclosporin A, Laneto 50®, and Clove oil.

Another embodiment comprises cyclosporin A, Laneto 100®, and Clove oil.

Another embodiment comprises cyclosporin A, Laneto AWS®, and Clove oil.

Another embodiment comprises cyclosporin A, Lanfrax 1776®, and Clove oil.

Another embodiment comprises cyclosporin A, Lanfrax 1776®, and Clove oil.

Another embodiment comprises cyclosporin A, Lanogel 21®, and Clove oil.

Another embodiment comprises cyclosporin A, Lipolan®, and Clove oil.

Another embodiment comprises cyclosporin A, Lipolan 31®, and Clove oil.

Another embodiment comprises cyclosporin A, OHlan®, and Clove oil.

Another embodiment comprises cyclosporin A, Polychol 5®, and Clove oil.

Another embodiment comprises cyclosporin A, Polychol 15®, and Clove oil.

Another embodiment comprises cyclosporin A, Ritacetyl®, and Clove oil.

Another embodiment comprises cyclosporin A, Ritachol®, and Clove oil.

Another embodiment comprises cyclosporin A, Ritahydrox®, and Clove oil.

Another embodiment comprises cyclosporin A, Ritalafa®, and Clove oil.

Another embodiment comprises cyclosporin A, Ritalan®, and Clove oil.

Another embodiment comprises cyclosporin A, Ritalan AWS®, and Clove oil.

Another embodiment comprises cyclosporin A, Ritalan C®, and Clove oil.

Another embodiment comprises cyclosporin A, Ritawax®, and Clove oil.

Another embodiment comprises cyclosporin A, Ritawax AEO®, and Clove oil.

Another embodiment comprises cyclosporin A, Ritawax ALA®, and Clove oil.

Another embodiment comprises cyclosporin A, Solan/Solan 50/Super Solan®, and Clove oil.

Another embodiment comprises cyclosporin A, Super Hartolan/Hartolan®, and Clove oil.

Another embodiment comprises cyclosporin A, Supersat AWS-4®, and Clove oil.

Another embodiment comprises cyclosporin A, Supersat AWS-24®, and Clove oil.

Another embodiment comprises cyclosporin A, and Clove oil.

Another embodiment comprises cyclosporin A, a Lecithin or Lecithin Derivative, and Clove oil.

Another embodiment comprises cyclosporin A, Alcolec®, and Clove oil.

Another embodiment comprises cyclosporin A, Lecithin®, and Clove oil.

Another embodiment comprises cyclosporin A, Lexin K®, and Clove oil.

Another embodiment comprises cyclosporin A, Natipide®, and Clove oil.

Another embodiment comprises cyclosporin A, and Clove oil.

Another embodiment comprises cyclosporin A, a Lignin or Lignin Derivative, and Clove oil.

Another embodiment comprises cyclosporin A, Diwatex XP 9®, and Clove oil.

Another embodiment comprises cyclosporin A, Dynasperse LCD®, and Clove oil.

Another embodiment comprises cyclosporin A, Indulin SAL®, and Clove oil.

Another embodiment comprises cyclosporin A, Indulin W-1®, and Clove oil.

Another embodiment comprises cyclosporin A, Indulin W-5®, and Clove oil.

Another embodiment comprises cyclosporin A, Lignosol FTA®, and Clove oil.

Another embodiment comprises cyclosporin A, Lignosol SFX-65®, and Clove oil.

Another embodiment comprises cyclosporin A, Marasperse 52 CP®, and Clove oil.

Another embodiment comprises cyclosporin A, Marasperse AG®, and Clove oil.

Another embodiment comprises cyclosporin A, Marasperse CBOS-4®, and Clove oil.

Another embodiment comprises cyclosporin A, Ufoxane 2®, and Clove oil.

Another embodiment comprises cyclosporin A, and Clove oil.

Another embodiment comprises cyclosporin A, a Methyl Ester, and Clove oil.

Another embodiment comprises cyclosporin A, E.B. Cleaner AK®, and Clove oil.

Another embodiment comprises cyclosporin A, Oleocal ME-70®, and Clove oil.

Another embodiment comprises cyclosporin A, Trade Name Company®, and Clove oil.

Another embodiment comprises cyclosporin A, Methyl Esters (cont'd)®, and Clove oil.

Another embodiment comprises cyclosporin A, Oleocal ME-92®, and Clove oil.

Another embodiment comprises cyclosporin A, Oleocal ME-112®, and Clove oil.

Another embodiment comprises cyclosporin A, Oleocal ME-130®, and Clove oil.

Another embodiment comprises cyclosporin A, and Clove oil.

Another embodiment comprises cyclosporin A, a Monoglyceride or a Derivative thereof, and Clove oil.

Another embodiment comprises cyclosporin A, Dynacet 211®, and Clove oil.

Another embodiment comprises cyclosporin A, Hetsorb S-20®, and Clove oil.

Another embodiment comprises cyclosporin A, Imwitor 191®, and Clove oil.

Another embodiment comprises cyclosporin A, Imwitor 370®, and Clove oil.

Another embodiment comprises cyclosporin A, Imwitor 375®, and Clove oil.

Another embodiment comprises cyclosporin A, Imwitor 900®, and Clove oil.

Another embodiment comprises cyclosporin A, Imwitor 945®, and Clove oil.

Another embodiment comprises cyclosporin A, Imwitor 2020®, and Clove oil.

Another embodiment comprises cyclosporin A, Kemester 5500®, and Clove oil.

Another embodiment comprises cyclosporin A, Kemester 6000®, and Clove oil.

Another embodiment comprises cyclosporin A, Magrabar GMC®, and Clove oil.

Another embodiment comprises cyclosporin A, Magrabar GMO-CK®, and Clove oil.

Another embodiment comprises cyclosporin A, Magrabar GPC-10®, and Clove oil.

Another embodiment comprises cyclosporin A, Magrabar MDG-5050®, and Clove oil.

Another embodiment comprises cyclosporin A, Monalube 335®, and Clove oil.

Another embodiment comprises cyclosporin A, Monoglycerides Glyceryl Monestearate Archer Daniels Midland Company®, and Clove oil.

Another embodiment comprises cyclosporin A, Rita GMS®, and Clove oil.

Another embodiment comprises cyclosporin A, Ritamulse SCG®, and Clove oil.

Another embodiment comprises cyclosporin A, Softigen 701®, and Clove oil.

Another embodiment comprises cyclosporin A, Tally 100 Plus®, and Clove oil.

Another embodiment comprises cyclosporin A, and Clove oil.

Another embodiment comprises cyclosporin A, a Polyethylene Glycol, and Clove oil.

Another embodiment comprises cyclosporin A, Emulgade PL 68/50®, and Clove oil.

Another embodiment comprises cyclosporin A, Lumulse PEG®, and Clove oil.

Another embodiment comprises cyclosporin A, Rhodasurf PEG-400®, and Clove oil.

Another embodiment comprises cyclosporin A, Rhodasurf PEG-600®, and Clove oil.

Another embodiment comprises cyclosporin A, Witconol PEG-400®, and Clove oil.

Another embodiment comprises cyclosporin A, and Clove oil.

Another embodiment comprises cyclosporin A, a Polymeric Surfactant, and Clove oil.

Another embodiment comprises cyclosporin A, Acritamer PNC-EG®, and Clove oil.

Another embodiment comprises cyclosporin A, Ag-Rho DEP-775®, and Clove oil.

Another embodiment comprises cyclosporin A, APG 325N Glycoside®, and Clove oil.

Another embodiment comprises cyclosporin A, Aristoflex AVC®, and Clove oil.

Another embodiment comprises cyclosporin A, Aristoflex HMB®, and Clove oil.

Another embodiment comprises cyclosporin A, Burco NPS-225®, and Clove oil.

Another embodiment comprises cyclosporin A, Burco NPS-816®, and Clove oil.

Another embodiment comprises cyclosporin A, Chemccinate 5603®, and Clove oil.

Another embodiment comprises cyclosporin A, Cosmedia Guar C-261N®, and Clove oil.

Another embodiment comprises cyclosporin A, Gantrez S-95®, and Clove oil.

Another embodiment comprises cyclosporin A, Glucopon 220 UP®, and Clove oil.

Another embodiment comprises cyclosporin A, Glucopon 225 DK®, and Clove oil.

Another embodiment comprises cyclosporin A, Glucopon 425 N®, and Clove oil.

Another embodiment comprises cyclosporin A, Glucopon 600 UP®, and Clove oil.

Another embodiment comprises cyclosporin A, Glucopon 625 UP®, and Clove oil.

Another embodiment comprises cyclosporin A, Pemulen 1621®, and Clove oil.

Another embodiment comprises cyclosporin A, Pemulen 1622®, and Clove oil.

Another embodiment comprises cyclosporin A, Pemulen TR-1®, and Clove oil.

Another embodiment comprises cyclosporin A, Pemulen TR-2®, and Clove oil.

Another embodiment comprises cyclosporin A, Plantacare 818®, and Clove oil.

Another embodiment comprises cyclosporin A, Plantapon LGC Sorb®, and Clove oil.

Another embodiment comprises cyclosporin A, Plantaren 1200N®, and Clove oil.

Another embodiment comprises cyclosporin A, Plantaren 2000N®, and Clove oil.

Another embodiment comprises cyclosporin A, Viscolam AT 64®, and Clove oil.

Another embodiment comprises cyclosporin A, Viscolam AT 64P®, and Clove oil.

Another embodiment comprises cyclosporin A, Viscolam AT 100®, and Clove oil.

Another embodiment comprises cyclosporin A, Viscolam MAC 7®, and Clove oil.

Another embodiment comprises cyclosporin A, Viscolam SMC 20®, and Clove oil.

Another embodiment comprises cyclosporin A, Witbreak RTC-323®, and Clove oil.

Another embodiment comprises cyclosporin A, WSI 3700®, and Clove oil.

Another embodiment comprises cyclosporin A, and Clove oil.

Another embodiment comprises cyclosporin A, a Propoxylated or Ethoxylated Fatty Acid, Alcohol, or Alkyl Phenol, and Clove oil.

Another embodiment comprises cyclosporin A, Antarox AA-60®, and Clove oil.

Another embodiment comprises cyclosporin A, Antarox LF-224®, and Clove oil.

Another embodiment comprises cyclosporin A, Burcomul DFE-45®, and Clove oil.

Another embodiment comprises cyclosporin A, Burcoterge LFE-1000®, and Clove oil.

Another embodiment comprises cyclosporin A, Chemal LF-25B®, and Clove oil.

Another embodiment comprises cyclosporin A, Chemal LF-40B®, and Clove oil.

Another embodiment comprises cyclosporin A, Dehypon LS-36®, and Clove oil.

Another embodiment comprises cyclosporin A, Dehypon LS-36®, and Clove oil.

Another embodiment comprises cyclosporin A, Dehypon LS-54®, and Clove oil.

Another embodiment comprises cyclosporin A, Dehypon LS-54®, and Clove oil.

Another embodiment comprises cyclosporin A, Delonic 100 VLF®, and Clove oil.

Another embodiment comprises cyclosporin A, Delonic LF-60 MOD®, and Clove oil.

Another embodiment comprises cyclosporin A, Empiderm B®, and Clove oil.

Another embodiment comprises cyclosporin A, Ethylan 1206®, and Clove oil.

Another embodiment comprises cyclosporin A, Ethylan NS-500K®, and Clove oil.

Another embodiment comprises cyclosporin A, Ethylan NS-500LQ®, and Clove oil.

Another embodiment comprises cyclosporin A, Genapol 1392®, and Clove oil.

Another embodiment comprises cyclosporin A, Genapol 2317®, and Clove oil.

Another embodiment comprises cyclosporin A, Genapol 26EP710®, and Clove oil.

Another embodiment comprises cyclosporin A, Genapol EP 1022®, and Clove oil.

Another embodiment comprises cyclosporin A, Genapol EP 1024®, and Clove oil.

Another embodiment comprises cyclosporin A, Genapol EP 6068®, and Clove oil.

Another embodiment comprises cyclosporin A, Genapol NP915®, and Clove oil.

Another embodiment comprises cyclosporin A, Kieralon MFB®, and Clove oil.

Another embodiment comprises cyclosporin A, Lumisolve CSA-80 V®, and Clove oil.

Another embodiment comprises cyclosporin A, Marlowet 5001®, and Clove oil.

Another embodiment comprises cyclosporin A, Marlox FK 64®, and Clove oil.

Another embodiment comprises cyclosporin A, Marlox MO 124®, and Clove oil.

Another embodiment comprises cyclosporin A, Marlox S 58®, and Clove oil.

Another embodiment comprises cyclosporin A, Nonatell 1003®, and Clove oil.

Another embodiment comprises cyclosporin A, Nonatell 1038®, and Clove oil.

Another embodiment comprises cyclosporin A, Nonatell 1052®, and Clove oil.

Another embodiment comprises cyclosporin A, Nonatell 1061®, and Clove oil.

Another embodiment comprises cyclosporin A, Nonatell 1075®, and Clove oil.

Another embodiment comprises cyclosporin A, Nonatell 1088®, and Clove oil.

Another embodiment comprises cyclosporin A, Nonatell 1123®, and Clove oil.

Another embodiment comprises cyclosporin A, Nonatell 1153®, and Clove oil.

Another embodiment comprises cyclosporin A, Nonatell 1161®, and Clove oil.

Another embodiment comprises cyclosporin A, Nonatell 1172®, and Clove oil.

Another embodiment comprises cyclosporin A, Nonatell 1181®, and Clove oil.

Another embodiment comprises cyclosporin A, Norfox 36®, and Clove oil.

Another embodiment comprises cyclosporin A, Procetyl AWS®, and Clove oil.

Another embodiment comprises cyclosporin A, Sandoxylate SX 412®, and Clove oil.

Another embodiment comprises cyclosporin A, Sandoxylate SX 418®, and Clove oil.

Another embodiment comprises cyclosporin A, Surfonic JL-80X®, and Clove oil.

Another embodiment comprises cyclosporin A, Surfonic JL-80X-B1®, and Clove oil.

Another embodiment comprises cyclosporin A, Surfonic L4-29X®, and Clove oil.

Another embodiment comprises cyclosporin A, Surfonic LF®, and Clove oil.

Another embodiment comprises cyclosporin A, T-Det A826®, and Clove oil.

Another embodiment comprises cyclosporin A, T-Det LF-416®, and Clove oil.

Another embodiment comprises cyclosporin A, Tergitol Min-Foam 1X®, and Clove oil.

Another embodiment comprises cyclosporin A, Tergitol Min-Foam 2X®, and Clove oil.

Another embodiment comprises cyclosporin A, Triton CF-21®, and Clove oil.

Another embodiment comprises cyclosporin A, Triton CF-76®, and Clove oil.

Another embodiment comprises cyclosporin A, Triton XL-80N®, and Clove oil.

Another embodiment comprises cyclosporin A, Witconol NS-98®, and Clove oil.

Another embodiment comprises cyclosporin A, Witconol NS-108LQ®, and Clove oil.

Another embodiment comprises cyclosporin A, Witconol NS-145®, and Clove oil.

Another embodiment comprises cyclosporin A, Witconol NS-179®, and Clove oil.

Another embodiment comprises cyclosporin A, and Clove oil.

Another embodiment comprises cyclosporin A, a Protein-based Surfactant, and Clove oil.

Another embodiment comprises cyclosporin A, Amino-Foam W®, and Clove oil.

Another embodiment comprises cyclosporin A, Amiter LGOD-2®, and Clove oil.

Another embodiment comprises cyclosporin A, Amiter LGS-2®, and Clove oil.

Another embodiment comprises cyclosporin A, Amiter LGS-5®, and Clove oil.

Another embodiment comprises cyclosporin A, Lamepon S®, and Clove oil.

Another embodiment comprises cyclosporin A, Lamepon S®, and Clove oil.

Another embodiment comprises cyclosporin A, Maypon 4C®, and Clove oil.

Another embodiment comprises cyclosporin A, May-Tein C®, and Clove oil.

Another embodiment comprises cyclosporin A, May-Tein CT®, and Clove oil.

Another embodiment comprises cyclosporin A, May-Tein KTS®, and Clove oil.

Another embodiment comprises cyclosporin A, May-Tein SY®, and Clove oil.

Another embodiment comprises cyclosporin A, Plantapon S®, and Clove oil.

Another embodiment comprises cyclosporin A, Proteol APL®, and Clove oil.

Another embodiment comprises cyclosporin A, Proteol OAT®, and Clove oil.

Another embodiment comprises cyclosporin A, Pyroter CPI-40®, and Clove oil.

Another embodiment comprises cyclosporin A, Pyroter GPI-25®, and Clove oil.

Another embodiment comprises cyclosporin A, Supro-Tein S®, and Clove oil.

Another embodiment comprises cyclosporin A, Supro-Tein V®, and Clove oil.

Another embodiment comprises cyclosporin A, ®, and Clove oil.

Another embodiment comprises cyclosporin A, a Sarcosine Derivative®, and Clove oil.

Another embodiment comprises cyclosporin A, Crodasinic LS-30®, and Clove oil.

Another embodiment comprises cyclosporin A, Vanseal CS®, and Clove oil.

Another embodiment comprises cyclosporin A, Vanseal LS®, and Clove oil.

Another embodiment comprises cyclosporin A, Vanseal MS®, and Clove oil.

Another embodiment comprises cyclosporin A, Vanseal NACS-30®, and Clove oil.

Another embodiment comprises cyclosporin A, Vanseal NALS-95®, and Clove oil.

Another embodiment comprises cyclosporin A, Vanseal OS®, and Clove oil.

Another embodiment comprises cyclosporin A, ®, and Clove oil.

Another embodiment comprises cyclosporin A, a Silicone-based Surfactant®, and Clove oil.

Another embodiment comprises cyclosporin A, Abil-B-9950®, and Clove oil.

Another embodiment comprises cyclosporin A, Abil Care 85®, and Clove oil.

Another embodiment comprises cyclosporin A, Abil EM 90®, and Clove oil.

Another embodiment comprises cyclosporin A, Abil EM 97®, and Clove oil.

Another embodiment comprises cyclosporin A, Abil WE-09®, and Clove oil.

Another embodiment comprises cyclosporin A, Dow Corning 1248 Fluid®, and Clove oil.

Another embodiment comprises cyclosporin A, Dow Corning 3225C®, and Clove oil.

Another embodiment comprises cyclosporin A, Dow Corning 5200®, and Clove oil.

Another embodiment comprises cyclosporin A, Dow Corning Q4-3667®, and Clove oil.

Another embodiment comprises cyclosporin A, Monasil PCA®, and Clove oil.

Another embodiment comprises cyclosporin A, Monasil PDM®, and Clove oil.

Another embodiment comprises cyclosporin A, Monasil PLN®, and Clove oil.

Another embodiment comprises cyclosporin A, Polyderm PPI-SI-WS®, and Clove oil.

Another embodiment comprises cyclosporin A, Troysol 380W®, and Clove oil.

Another embodiment comprises cyclosporin A, Troysol S366®, and Clove oil.

Another embodiment comprises cyclosporin A, and Clove oil.

Another embodiment comprises cyclosporin A, a Sorbitan Derivative, and Clove oil.

Another embodiment comprises cyclosporin A, Alkamuls SML®, and Clove oil.

Another embodiment comprises cyclosporin A, Alkamuls SMO®, and Clove oil.

Another embodiment comprises cyclosporin A, Alkamuls STO®, and Clove oil.

Another embodiment comprises cyclosporin A, Arlacel 20®, and Clove oil.

Another embodiment comprises cyclosporin A, Arlacel 40®, and Clove oil.

Another embodiment comprises cyclosporin A, Arlacel 60®, and Clove oil.

Another embodiment comprises cyclosporin A, Arlacel 80®, and Clove oil.

Another embodiment comprises cyclosporin A, Arlacel C®, and Clove oil.

Another embodiment comprises cyclosporin A, Armul 21®, and Clove oil.

Another embodiment comprises cyclosporin A, Atlox 80®, and Clove oil.

Another embodiment comprises cyclosporin A, Atlox 847®, and Clove oil.
Another embodiment comprises cyclosporin A, Atlox 1045A®, and Clove oil.
Another embodiment comprises cyclosporin A, Canarcel 20®, and Clove oil.
Another embodiment comprises cyclosporin A, Canarcel 60®, and Clove oil.
Another embodiment comprises cyclosporin A, Canarcel 80®, and Clove oil.
Another embodiment comprises cyclosporin A, Canarcel TW 20®, and Clove oil.
Another embodiment comprises cyclosporin A, Canarcel TW 60®, and Clove oil.
Another embodiment comprises cyclosporin A, Canarcel TW 80®, and Clove oil.
Another embodiment comprises cyclosporin A, Coladet BSB-P®, and Clove oil.
Another embodiment comprises cyclosporin A, Customulse O-20®, and Clove oil.
Another embodiment comprises cyclosporin A, Dehymuls E®, and Clove oil.
Another embodiment comprises cyclosporin A, DeSotan SMO®, and Clove oil.
Another embodiment comprises cyclosporin A, DeSotan SMO-20®, and Clove oil.
Another embodiment comprises cyclosporin A, DeSotan SMT®, and Clove oil.
Another embodiment comprises cyclosporin A, DeSotan SMT-20®, and Clove oil.
Another embodiment comprises cyclosporin A, Durfax 60®, and Clove oil.
Another embodiment comprises cyclosporin A, Durfax 65®, and Clove oil.
Another embodiment comprises cyclosporin A, Durfax 80®, and Clove oil.
Another embodiment comprises cyclosporin A, Durtan 60®, and Clove oil.
Another embodiment comprises cyclosporin A, Durtan 65®, and Clove oil.
Another embodiment comprises cyclosporin A, Liposorb L®, and Clove oil.
Another embodiment comprises cyclosporin A, Liposorb L-10®, and Clove oil.
Another embodiment comprises cyclosporin A, Liposorb L-20®, and Clove oil.
Another embodiment comprises cyclosporin A, Liposorb O®, and Clove oil.
Another embodiment comprises cyclosporin A, Liposorb O-20®, and Clove oil.
Another embodiment comprises cyclosporin A, Liposorb P®, and Clove oil.
Another embodiment comprises cyclosporin A, Liposorb P-20®, and Clove oil.
Another embodiment comprises cyclosporin A, Liposorb S®, and Clove oil.
Another embodiment comprises cyclosporin A, Liposorb S-20®, and Clove oil.
Another embodiment comprises cyclosporin A, Liposorb SQO®, and Clove oil.
Another embodiment comprises cyclosporin A, Liposorb TO®, and Clove oil.
Another embodiment comprises cyclosporin A, Liposorb TS®, and Clove oil.
Another embodiment comprises cyclosporin A, Liposorb TS-20®, and Clove oil.
Another embodiment comprises cyclosporin A, Lumisorb PS®, and Clove oil.
Another embodiment comprises cyclosporin A, Lumisorb SMO (T)®, and Clove oil.
Another embodiment comprises cyclosporin A, Lumisorb SMS K®, and Clove oil.
Another embodiment comprises cyclosporin A, Lumisorb SSO®, and Clove oil.
Another embodiment comprises cyclosporin A, Lumisorb STS K®, and Clove oil.
Another embodiment comprises cyclosporin A, Lumisorb STT®, and Clove oil.
Another embodiment comprises cyclosporin A, Magrabar SMO®, and Clove oil.
Another embodiment comprises cyclosporin A, Magrabar SMO-VEG®, and Clove oil.
Another embodiment comprises cyclosporin A, Magrabar SMT®, and Clove oil.
Another embodiment comprises cyclosporin A, Magrabar STO®, and Clove oil.
Another embodiment comprises cyclosporin A, Miracare BC-27®, and Clove oil.
Another embodiment comprises cyclosporin A, Ritabate 20®, and Clove oil.
Another embodiment comprises cyclosporin A, Ritabate 40®, and Clove oil.
Another embodiment comprises cyclosporin A, Ritabate 60®, and Clove oil.
Another embodiment comprises cyclosporin A, Ritabate 80®, and Clove oil.
Another embodiment comprises cyclosporin A, T-Maz®, and Clove oil.
Another embodiment comprises cyclosporin A, Tego SML®, and Clove oil.
Another embodiment comprises cyclosporin A, Tego SML 20®, and Clove oil.
Another embodiment comprises cyclosporin A, Tego SMO 80 V®, and Clove oil.
Another embodiment comprises cyclosporin A, Tego SMO V®, and Clove oil.
Another embodiment comprises cyclosporin A, Tego SMS®, and Clove oil.
Another embodiment comprises cyclosporin A, Tego STO V®, and Clove oil.
Another embodiment comprises cyclosporin A, Tween 21®, and Clove oil.
Another embodiment comprises cyclosporin A, Tween 40®, and Clove oil.
Another embodiment comprises cyclosporin A, Tween 60®, and Clove oil.
Another embodiment comprises cyclosporin A, Tween 60 K®, and Clove oil.
Another embodiment comprises cyclosporin A, Tween 61®, and Clove oil.
Another embodiment comprises cyclosporin A, Tween 65®, and Clove oil.
Another embodiment comprises cyclosporin A, Tween 80®, and Clove oil.
Another embodiment comprises cyclosporin A, Tween 80 K®, and Clove oil.
Another embodiment comprises cyclosporin A, Tween 81®, and Clove oil.
Another embodiment comprises cyclosporin A, Tween 85®, and Clove oil.
Another embodiment comprises cyclosporin A, and Clove oil.

Another embodiment comprises cyclosporin A, a Sucrose or Glucose Ester, or Derivative thereof, and Clove oil.

Another embodiment comprises cyclosporin A, DeSulf GOS-P-60WCG®, and Clove oil.

Another embodiment comprises cyclosporin A, Glucam E-20 Distearate®, and Clove oil.

Another embodiment comprises cyclosporin A, Glucamate DOE-120®, and Clove oil.

Another embodiment comprises cyclosporin A, Glucamate SSE-20®, and Clove oil.

Another embodiment comprises cyclosporin A, Glucate DO®, and Clove oil.

Another embodiment comprises cyclosporin A, Glucate SS®, and Clove oil.

Another embodiment comprises cyclosporin A, Glucopon 425 UP®, and Clove oil.

Another embodiment comprises cyclosporin A, Isolan IS®, and Clove oil.

Another embodiment comprises cyclosporin A, Mazon 40®, and Clove oil.

Another embodiment comprises cyclosporin A, Montanov 82®, and Clove oil.

Another embodiment comprises cyclosporin A, Montanov 202®, and Clove oil.

Another embodiment comprises cyclosporin A, Montanov S®, and Clove oil.

Another embodiment comprises cyclosporin A, Rheozan®, and Clove oil.

Another embodiment comprises cyclosporin A, Simulsol AS 48®, and Clove oil.

Another embodiment comprises cyclosporin A, Simulsol SL 4®, and Clove oil.

Another embodiment comprises cyclosporin A, Simulsol SL 10®, and Clove oil.

Another embodiment comprises cyclosporin A, Simulsol SL 11W®, and Clove oil.

Another embodiment comprises cyclosporin A, Simulsol SL 55®, and Clove oil.

Another embodiment comprises cyclosporin A, Suga Nate 100 and 160®, and Clove oil.

Another embodiment comprises cyclosporin A, Tego Care 450®, and Clove oil.

Another embodiment comprises cyclosporin A, Tego Care CG 90®, and Clove oil.

Another embodiment comprises cyclosporin A, Tego Care PS®, and Clove oil.

Another embodiment comprises cyclosporin A, Tegosoft PSE 141 G®, and Clove oil.

Another embodiment comprises cyclosporin A, Tegotens G 826®, and Clove oil.

Another embodiment comprises cyclosporin A, Triton BG-10 (70%)®, and Clove oil.

Another embodiment comprises cyclosporin A, Triton CG-110 (60%)®, and Clove oil.

Another embodiment comprises cyclosporin A, Wickenol 545®, and Clove oil.

Another embodiment comprises cyclosporin A, an alcohol, and Cassia oil.

Another embodiment comprises cyclosporin A, Diglycerol®, and Cassia oil.

Another embodiment comprises cyclosporin A, Hetoxide GT-80®, and Cassia oil.

Another embodiment comprises cyclosporin A, Lexemul BEO®, and Cassia oil.

Another embodiment comprises cyclosporin A, Polyglycerol-3®, and Cassia oil.

Another embodiment comprises cyclosporin A, Redicote E Series®, and Cassia oil.

Another embodiment comprises cyclosporin A, Simulsol OX 1005L®, and Cassia oil.

Another embodiment comprises cyclosporin A, Stanfax 567®, and Cassia oil.

Another embodiment comprises cyclosporin A, TA-1618®, and Cassia oil.

Another embodiment comprises cyclosporin A, Witconol H-31A®, and Cassia oil.

Another embodiment comprises cyclosporin A, Standard Div.®, and Cassia oil., and Cassia oil.

Another embodiment comprises cyclosporin A, an amine oxide, and Cassia oil.

Another embodiment comprises cyclosporin A, AO-405®, and Cassia oil.

Another embodiment comprises cyclosporin A, AO-455®, and Cassia oil.

Another embodiment comprises cyclosporin A, AO 728 Special®, and Cassia oil.

Another embodiment comprises cyclosporin A, Barlox 12®, and Cassia oil.

Another embodiment comprises cyclosporin A, Barlox 14®, and Cassia oil.

Another embodiment comprises cyclosporin A, Burcoxide Lo®, and Cassia oil.

Another embodiment comprises cyclosporin A, Caloxamine LO®, and Cassia oil.

Another embodiment comprises cyclosporin A, Chemoxide CAW®, and Cassia oil.

Another embodiment comprises cyclosporin A, Chemoxide LM-30®, and Cassia oil.

Another embodiment comprises cyclosporin A, Chemoxide LO®, and Cassia oil.

Another embodiment comprises cyclosporin A, Chemoxide MO®, and Cassia oil.

Another embodiment comprises cyclosporin A, Colalux CAO-35®, and Cassia oil.

Another embodiment comprises cyclosporin A, Colalux LO®, and Cassia oil.

Another embodiment comprises cyclosporin A, DeMox CAPO®, and Cassia oil.

Another embodiment comprises cyclosporin A, DeMox CSG-30®, and Cassia oil.

Another embodiment comprises cyclosporin A, DeMox LAO®, and Cassia oil.

Another embodiment comprises cyclosporin A, Emcol L®, and Cassia oil.

Another embodiment comprises cyclosporin A, Empigen OB®, and Cassia oil.

Another embodiment comprises cyclosporin A, Empigen OS/A®, and Cassia oil.

Another embodiment comprises cyclosporin A, Foamox CDO®, and Cassia oil.

Another embodiment comprises cyclosporin A, Foamox DMM®, and Cassia oil.

Another embodiment comprises cyclosporin A, Foamox DMS®, and Cassia oil.

Another embodiment comprises cyclosporin A, Genaminox KC®, and Cassia oil.

Another embodiment comprises cyclosporin A, Genaminox LA®, and Cassia oil.

Another embodiment comprises cyclosporin A, Hartofoam SAO®, and Cassia oil.

Another embodiment comprises cyclosporin A, Hartox DMCD®, and Cassia oil.

Another embodiment comprises cyclosporin A, Lipowax DAT®, and Cassia oil.

Another embodiment comprises cyclosporin A, Lipowax PB Pastilles®, and Cassia oil.

Another embodiment comprises cyclosporin A, Mackamine C8®, and Cassia oil.

Another embodiment comprises cyclosporin A, Mackamine C10®, and Cassia oil.

Another embodiment comprises cyclosporin A, Mackamine C14®, and Cassia oil.

Another embodiment comprises cyclosporin A, Mackamine CAO®, and Cassia oil.

Another embodiment comprises cyclosporin A, Mackamine CO®, and Cassia oil.

Another embodiment comprises cyclosporin A, Mackamine LO®, and Cassia oil.

Another embodiment comprises cyclosporin A, Mackamine O2®, and Cassia oil.

Another embodiment comprises cyclosporin A, Mackamine SAO®, and Cassia oil.

Another embodiment comprises cyclosporin A, Mackamine SO®, and Cassia oil.

Another embodiment comprises cyclosporin A, Mazox KCAO®, and Cassia oil.

Another embodiment comprises cyclosporin A, Monalac MO®, and Cassia oil.

Another embodiment comprises cyclosporin A, Norfox LDA®, and Cassia oil.

Another embodiment comprises cyclosporin A, Rhodamox LO®, and Cassia oil.

Another embodiment comprises cyclosporin A, Schercamox C-AA®, and Cassia oil.

Another embodiment comprises cyclosporin A, Schercamox DMA®, and Cassia oil.

Another embodiment comprises cyclosporin A, Schercamox DML®, and Cassia oil.

Another embodiment comprises cyclosporin A, Schercamox DMM®, and Cassia oil.

Another embodiment comprises cyclosporin A, Schercamox DMS®, and Cassia oil.

Another embodiment comprises cyclosporin A, Tegotens DO®, and Cassia oil.

Another embodiment comprises cyclosporin A, Tomah AO-14-2®, and Cassia oil.

Another embodiment comprises cyclosporin A, Triaminox CDO®, and Cassia oil., and Cassia oil.

Another embodiment comprises cyclosporin A, a block polymer, and Cassia oil.

Another embodiment comprises cyclosporin A, AL 2070®, and Cassia oil.

Another embodiment comprises cyclosporin A, Antarox 17-R-2®, and Cassia oil.

Another embodiment comprises cyclosporin A, Antarox 25-R-2®, and Cassia oil.

Another embodiment comprises cyclosporin A, Antarox 31-R-1®, and Cassia oil.

Another embodiment comprises cyclosporin A, Antarox P-84®, and Cassia oil.

Another embodiment comprises cyclosporin A, Antarox P-104/H®, and Cassia oil.

Another embodiment comprises cyclosporin A, Arnox BP-Series®, and Cassia oil.

Another embodiment comprises cyclosporin A, Chemonic 435®, and Cassia oil.

Another embodiment comprises cyclosporin A, Chemonic D-25®, and Cassia oil.

Another embodiment comprises cyclosporin A, Chemonic PL Series®, and Cassia oil.

Another embodiment comprises cyclosporin A, Ethox L-121®, and Cassia oil.

Another embodiment comprises cyclosporin A, Ethox L-122®, and Cassia oil.

Another embodiment comprises cyclosporin A, Genapol PF-10®, and Cassia oil.

Another embodiment comprises cyclosporin A, Genapol PF-20®, and Cassia oil.

Another embodiment comprises cyclosporin A, Genapol PF-40A®, and Cassia oil.

Another embodiment comprises cyclosporin A, Norfox 2-LF®, and Cassia oil.

Another embodiment comprises cyclosporin A, Simulsol NW 342®, and Cassia oil.

Another embodiment comprises cyclosporin A, T-Det BP-1®, and Cassia oil.

Another embodiment comprises cyclosporin A, T-Det XD®, and Cassia oil.

Another embodiment comprises cyclosporin A, T-Det XH®, and Cassia oil.

Another embodiment comprises cyclosporin A, Triton CF-32®, and Cassia oil.

Another embodiment comprises cyclosporin A, Witconol 171®, and Cassia oil.

Another embodiment comprises cyclosporin A, Witconol 324®, and Cassia oil.

Another embodiment comprises cyclosporin A, Witconol 324D®, and Cassia oil.

Another embodiment comprises cyclosporin A, Witconol PD-2000®, and Cassia oil., and Cassia oil.

a Carboxylated Alcohol or Alkylphenol Ethoxylate, and Cassia oil.

Another embodiment comprises cyclosporin A, Emcol CN-6®, and Cassia oil.

Another embodiment comprises cyclosporin A, Ethcarb®, and Cassia oil.

Another embodiment comprises cyclosporin A, Gemtex WNT-Conc®, and Cassia oil.

Another embodiment comprises cyclosporin A, Incrodet TD7-C®, and Cassia oil.

Another embodiment comprises cyclosporin A, Marlinat CM 105/80®, and Cassia oil.

Another embodiment comprises cyclosporin A, Marlowet 1072®, and Cassia oil.

Another embodiment comprises cyclosporin A, Marlowet 4530®, and Cassia oil.

Another embodiment comprises cyclosporin A, Marlowet 4530 LF®, and Cassia oil.

Another embodiment comprises cyclosporin A, Marlowet 4534®, and Cassia oil.

Another embodiment comprises cyclosporin A, Marlowet 4538®, and Cassia oil.

Another embodiment comprises cyclosporin A, Marlowet 4539®, and Cassia oil.

Another embodiment comprises cyclosporin A, Marlowet 4539 LF®, and Cassia oil.

Another embodiment comprises cyclosporin A, Marlowet 4541®, and Cassia oil.

Another embodiment comprises cyclosporin A, Miranate LEC-80®, and Cassia oil.

Another embodiment comprises cyclosporin A, Sandopan B®, and Cassia oil.

Another embodiment comprises cyclosporin A, Sandopan B Modified®, and Cassia oil.

Another embodiment comprises cyclosporin A, Sandopan LS-24 Gel®, and Cassia oil.
Another embodiment comprises cyclosporin A, Surfine T-A®, and Cassia oil.
Another embodiment comprises cyclosporin A, and Cassia oil.
Another embodiment comprises cyclosporin A, a Carboxylic Acid/Fatty Acid, and Cassia oil.
Another embodiment comprises cyclosporin A, Colaterge RAM®, and Cassia oil.
Another embodiment comprises cyclosporin A, Colatrope INC®, and Cassia oil.
Another embodiment comprises cyclosporin A, Crodacid B®, and Cassia oil.
Another embodiment comprises cyclosporin A, DeTrope CA-100®, and Cassia oil.
Another embodiment comprises cyclosporin A, Latol MTO®, and Cassia oil.
Another embodiment comprises cyclosporin A, Lumulse CC-33 K®, and Cassia oil.
Another embodiment comprises cyclosporin A, Mulls 2218®, and Cassia oil.
Another embodiment comprises cyclosporin A, OL-600®, and Cassia oil.
Another embodiment comprises cyclosporin A, OL-800®, and Cassia oil.
Another embodiment comprises cyclosporin A, R-910®, and Cassia oil.
Another embodiment comprises cyclosporin A, S-210®, and Cassia oil.
Another embodiment comprises cyclosporin A, Sandopan DTC Acid®, and Cassia oil.
Another embodiment comprises cyclosporin A, Sandopan LS 24 N®, and Cassia oil.
Another embodiment comprises cyclosporin A, Sandopan MA-18®, and Cassia oil.
Another embodiment comprises cyclosporin A, and Cassia oil.
Another embodiment comprises cyclosporin A, an Ethoxylated Alcohol, and Cassia oil.
Another embodiment comprises cyclosporin A, Adsee 799®, and Cassia oil.
Another embodiment comprises cyclosporin A, Adsee 799®, and Cassia oil.
Another embodiment comprises cyclosporin A, Alfonic 610-3.5®, and Cassia oil.
Another embodiment comprises cyclosporin A, Alfonic 810-2®, and Cassia oil.
Another embodiment comprises cyclosporin A, Alfonic 810-6®, and Cassia oil.
Another embodiment comprises cyclosporin A, Alfonic 1012-3®, and Cassia oil.
Another embodiment comprises cyclosporin A, Alfonic 1012-5®, and Cassia oil.
Another embodiment comprises cyclosporin A, Alfonic 1216CO-1.5®, and Cassia oil.
Another embodiment comprises cyclosporin A, Alfonic 1216CO-7®, and Cassia oil.
Another embodiment comprises cyclosporin A, Alfonic 1412-3®, and Cassia oil.
Another embodiment comprises cyclosporin A, Alfonic 1412-7®, and Cassia oil.
Another embodiment comprises cyclosporin A, Arlasolve 200®, and Cassia oil.
Another embodiment comprises cyclosporin A, Arlasolve 200 Liquid®, and Cassia oil.
Another embodiment comprises cyclosporin A, Armix 180-C®, and Cassia oil.
Another embodiment comprises cyclosporin A, Armix 183®, and Cassia oil.
Another embodiment comprises cyclosporin A, Armul 2404®, and Cassia oil.
Another embodiment comprises cyclosporin A, Armul 2404®, and Cassia oil.
Another embodiment comprises cyclosporin A, Atlas EMJ-C®, and Cassia oil.
Another embodiment comprises cyclosporin A, Atlas G-2109®, and Cassia oil.
Another embodiment comprises cyclosporin A, Atlas G-3886®, and Cassia oil.
Another embodiment comprises cyclosporin A, Atlas G-3890®, and Cassia oil.
Another embodiment comprises cyclosporin A, Bio Soft E-200®, and Cassia oil.
Another embodiment comprises cyclosporin A, Bio Soft E-300®, and Cassia oil.
Another embodiment comprises cyclosporin A, Bio Soft E-400®, and Cassia oil.
Another embodiment comprises cyclosporin A, Bio Soft EN 600®, and Cassia oil.
Another embodiment comprises cyclosporin A, Bio Soft TD-400®, and Cassia oil.
Another embodiment comprises cyclosporin A, Bio Soft TD-630®, and Cassia oil.
Another embodiment comprises cyclosporin A, Brij 30®, and Cassia oil.
Another embodiment comprises cyclosporin A, Brij 52®, and Cassia oil.
Another embodiment comprises cyclosporin A, Brij 56®, and Cassia oil.
Another embodiment comprises cyclosporin A, Brij 58®, and Cassia oil.
Another embodiment comprises cyclosporin A, Brij 72®, and Cassia oil.
Another embodiment comprises cyclosporin A, Brij 76®, and Cassia oil.
Another embodiment comprises cyclosporin A, Brij 78®, and Cassia oil.
Another embodiment comprises cyclosporin A, Brij 93®, and Cassia oil.
Another embodiment comprises cyclosporin A, Brij 97®, and Cassia oil.
Another embodiment comprises cyclosporin A, Brij 98®, and Cassia oil.
Another embodiment comprises cyclosporin A, Brij 700®, and Cassia oil.
Another embodiment comprises cyclosporin A, Brij 700 S®, and Cassia oil.
Another embodiment comprises cyclosporin A, Brij 721®, and Cassia oil.
Another embodiment comprises cyclosporin A, Brij 721 S®, and Cassia oil.
Another embodiment comprises cyclosporin A, Burcoterge CDG®, and Cassia oil.
Another embodiment comprises cyclosporin A, Canasol AT 600®, and Cassia oil.
Another embodiment comprises cyclosporin A, Canasol AT 800®, and Cassia oil.
Another embodiment comprises cyclosporin A, Canasol AT 1200®, and Cassia oil.
Another embodiment comprises cyclosporin A, Canasol BJ 35®, and Cassia oil.

Another embodiment comprises cyclosporin A, Canasol BJ 36®, and Cassia oil.
Another embodiment comprises cyclosporin A, Canasol BJ 52®, and Cassia oil.
Another embodiment comprises cyclosporin A, Canasol BJ 58®, and Cassia oil.
Another embodiment comprises cyclosporin A, Canasol BJ 72®, and Cassia oil.
Another embodiment comprises cyclosporin A, Canasol BJ 78®, and Cassia oil.
Another embodiment comprises cyclosporin A, Canasol BJ 98®, and Cassia oil.
Another embodiment comprises cyclosporin A, Canasol BJ 307®, and Cassia oil.
Another embodiment comprises cyclosporin A, Certak 1400®, and Cassia oil.
Another embodiment comprises cyclosporin A, Cetomacrogol 1000 BP®, and Cassia oil.
Another embodiment comprises cyclosporin A, Chemonic C-2®, and Cassia oil.
Another embodiment comprises cyclosporin A, Chemonic C-10®, and Cassia oil.
Another embodiment comprises cyclosporin A, Chemonic C-20®, and Cassia oil.
Another embodiment comprises cyclosporin A, Chemonic CT-12®, and Cassia oil.
Another embodiment comprises cyclosporin A, Chemonic CT-20®, and Cassia oil.
Another embodiment comprises cyclosporin A, Chemonic CT-30®, and Cassia oil.
Another embodiment comprises cyclosporin A, Chemonic CT-55®, and Cassia oil.
Another embodiment comprises cyclosporin A, Chemonic G-7®, and Cassia oil.
Another embodiment comprises cyclosporin A, Chemonic G-26®, and Cassia oil.
Another embodiment comprises cyclosporin A, Chemonic L-4®, and Cassia oil.
Another embodiment comprises cyclosporin A, Chemonic L-7®, and Cassia oil.
Another embodiment comprises cyclosporin A, Chemonic L-12®, and Cassia oil.
Another embodiment comprises cyclosporin A, Chemonic L-23®, and Cassia oil.
Another embodiment comprises cyclosporin A, Chemonic O-2®, and Cassia oil.
Another embodiment comprises cyclosporin A, Chemonic O-5®, and Cassia oil.
Another embodiment comprises cyclosporin A, Chemonic O-10®, and Cassia oil.
Another embodiment comprises cyclosporin A, Chemonic O-20®, and Cassia oil.
Another embodiment comprises cyclosporin A, Chemonic S-2®, and Cassia oil.
Another embodiment comprises cyclosporin A, Chemonic S-10®, and Cassia oil.
Another embodiment comprises cyclosporin A, Chemonic S-20®, and Cassia oil.
Another embodiment comprises cyclosporin A, Colamulse FE®, and Cassia oil.
Another embodiment comprises cyclosporin A, Cremophor A 20®, and Cassia oil.
Another embodiment comprises cyclosporin A, Cremophor SA 2®, and Cassia oil.
Another embodiment comprises cyclosporin A, Dehydol 100®, and Cassia oil.
Another embodiment comprises cyclosporin A, Dehydol O-4®, and Cassia oil.
Another embodiment comprises cyclosporin A, Delonic C-18®, and Cassia oil.
Another embodiment comprises cyclosporin A, DeSonic 6T®, and Cassia oil.
Another embodiment comprises cyclosporin A, DeSonic 9D®, and Cassia oil.
Another embodiment comprises cyclosporin A, DeSonic 9T®, and Cassia oil.
Another embodiment comprises cyclosporin A, DeSonic 12D®, and Cassia oil.
Another embodiment comprises cyclosporin A, DeSonic 12T®, and Cassia oil.
Another embodiment comprises cyclosporin A, DeSonic 15T®, and Cassia oil.
Another embodiment comprises cyclosporin A, DeSonic TDA-9®, and Cassia oil.
Another embodiment comprises cyclosporin A, DeThox GLG-7®, and Cassia oil.
Another embodiment comprises cyclosporin A, DeThox GLG-26®, and Cassia oil.
Another embodiment comprises cyclosporin A, DeThox LA-4®, and Cassia oil.
Another embodiment comprises cyclosporin A, DeThox LA-23®, and Cassia oil.
Another embodiment comprises cyclosporin A, DeThox SA-80®, and Cassia oil.
Another embodiment comprises cyclosporin A, Disponil O5®, and Cassia oil.
Another embodiment comprises cyclosporin A, Eccoterge EO-41B®, and Cassia oil.
Another embodiment comprises cyclosporin A, Empilan KA2.5/90®, and Cassia oil.
Another embodiment comprises cyclosporin A, Empilan KA5/90®, and Cassia oil.
Another embodiment comprises cyclosporin A, Empilan KM-20®, and Cassia oil.
Another embodiment comprises cyclosporin A, Empilan KM-50®, and Cassia oil.
Another embodiment comprises cyclosporin A, Empilan L-23®, and Cassia oil.
Another embodiment comprises cyclosporin A, Ethylan 25-3®, and Cassia oil.
Another embodiment comprises cyclosporin A, Ethylan 1204®, and Cassia oil.
Another embodiment comprises cyclosporin A, Ethylan DA-4®, and Cassia oil.
Another embodiment comprises cyclosporin A, Ethylan LA-230®, and Cassia oil.
Another embodiment comprises cyclosporin A, Ethylan SN®, and Cassia oil.
Another embodiment comprises cyclosporin A, Ethylan TD-60®, and Cassia oil.
Another embodiment comprises cyclosporin A, Ethylan TD-100®, and Cassia oil.
Another embodiment comprises cyclosporin A, Ethylan TD-1407®, and Cassia oil.
Another embodiment comprises cyclosporin A, Eumulgin B1®, and Cassia oil.
Another embodiment comprises cyclosporin A, Eumulgin B2®, and Cassia oil.
Another embodiment comprises cyclosporin A, Eumulgin B3®, and Cassia oil.
Another embodiment comprises cyclosporin A, Eumulgin O-10®, and Cassia oil.

Another embodiment comprises cyclosporin A, Flo Mo 80/20®, and Cassia oil.

Another embodiment comprises cyclosporin A, Flo Mo Low Foam®, and Cassia oil.

Another embodiment comprises cyclosporin A, Forlan C-24®, and Cassia oil.

Another embodiment comprises cyclosporin A, Genapol 1454®, and Cassia oil.

Another embodiment comprises cyclosporin A, Genapol BA-020®, and Cassia oil.

Another embodiment comprises cyclosporin A, Genapol BA-040®, and Cassia oil.

Another embodiment comprises cyclosporin A, Genapol C-100®, and Cassia oil.

Another embodiment comprises cyclosporin A, Genapol DA 060®, and Cassia oil.

Another embodiment comprises cyclosporin A, Genapol HS 020®, and Cassia oil.

Another embodiment comprises cyclosporin A, Genapol HS 200®, and Cassia oil.

Another embodiment comprises cyclosporin A, Genapol ID-040®, and Cassia oil.

Another embodiment comprises cyclosporin A, Genapol ID-060®, and Cassia oil.

Another embodiment comprises cyclosporin A, Genapol ID-090®, and Cassia oil.

Another embodiment comprises cyclosporin A, Genapol LA 010®, and Cassia oil.

Another embodiment comprises cyclosporin A, Genapol LA 020®, and Cassia oil.

Another embodiment comprises cyclosporin A, Genapol LA 030®, and Cassia oil.

Another embodiment comprises cyclosporin A, Genapol LA 040®, and Cassia oil.

Another embodiment comprises cyclosporin A, Genapol LA 050®, and Cassia oil.

Another embodiment comprises cyclosporin A, Genapol LA 060®, and Cassia oil.

Another embodiment comprises cyclosporin A, Genapol LA 070®, and Cassia oil.

Another embodiment comprises cyclosporin A, Genapol LA 070S®, and Cassia oil.

Another embodiment comprises cyclosporin A, Genapol LA 230®, and Cassia oil.

Another embodiment comprises cyclosporin A, Genapol O 020®, and Cassia oil.

Another embodiment comprises cyclosporin A, Genapol O 050®, and Cassia oil.

Another embodiment comprises cyclosporin A, Genapol O 100®, and Cassia oil.

Another embodiment comprises cyclosporin A, Genapol O 200®, and Cassia oil.

Another embodiment comprises cyclosporin A, Genapol SA 030®, and Cassia oil.

Another embodiment comprises cyclosporin A, Genapol SA 120®, and Cassia oil.

Another embodiment comprises cyclosporin A, Genapol T-020®, and Cassia oil.

Another embodiment comprises cyclosporin A, Genapol UD-030®, and Cassia oil.

Another embodiment comprises cyclosporin A, Genapol UD-050®, and Cassia oil.

Another embodiment comprises cyclosporin A, Genapol UD-070®, and Cassia oil.

Another embodiment comprises cyclosporin A, Genapol UD-079®, and Cassia oil.

Another embodiment comprises cyclosporin A, Genapol UD-080®, and Cassia oil.

Another embodiment comprises cyclosporin A, Genapol UD-110®, and Cassia oil.

Another embodiment comprises cyclosporin A, Genapol X 030®, and Cassia oil.

Another embodiment comprises cyclosporin A, Genapol X 050®, and Cassia oil.

Another embodiment comprises cyclosporin A, Genapol X 060®, and Cassia oil.

Another embodiment comprises cyclosporin A, Genapol X 070®, and Cassia oil.

Another embodiment comprises cyclosporin A, Genapol X 080®, and Cassia oil.

Another embodiment comprises cyclosporin A, Genapol X 100®, and Cassia oil.

Another embodiment comprises cyclosporin A, Genapol X159®, and Cassia oil.

Another embodiment comprises cyclosporin A, Generol 122 E5®, and Cassia oil.

Another embodiment comprises cyclosporin A, Generol 122 E25®, and Cassia oil.

Another embodiment comprises cyclosporin A, Hostacerin T-3®, and Cassia oil.

Another embodiment comprises cyclosporin A, Iconol LF 110®, and Cassia oil.

Another embodiment comprises cyclosporin A, Incropol CS-20®, and Cassia oil.

Another embodiment comprises cyclosporin A, Lexemul CS-20®, and Cassia oil.

Another embodiment comprises cyclosporin A, Liponic EG-1®, and Cassia oil.

Another embodiment comprises cyclosporin A, Lipowax D®, and Cassia oil.

Another embodiment comprises cyclosporin A, Lipowax G®, and Cassia oil.

Another embodiment comprises cyclosporin A, Lipowax NI®, and Cassia oil.

Another embodiment comprises cyclosporin A, Lipowax P®, and Cassia oil.

Another embodiment comprises cyclosporin A, Lipowax P-31®, and Cassia oil.

Another embodiment comprises cyclosporin A, Lipowax PR®, and Cassia oil.

Another embodiment comprises cyclosporin A, Lumulse CS-20®, and Cassia oil.

Another embodiment comprises cyclosporin A, Macol CSA-20®, and Cassia oil.

Another embodiment comprises cyclosporin A, Marlox B 24/50®, and Cassia oil.

Another embodiment comprises cyclosporin A, Mazawet 77®, and Cassia oil.

Another embodiment comprises cyclosporin A, Norfox 1713®, and Cassia oil.

Another embodiment comprises cyclosporin A, Norfox 2579®, and Cassia oil.

Another embodiment comprises cyclosporin A, Norfox Lo Foam®, and Cassia oil.

Another embodiment comprises cyclosporin A, Promulgen D®, and Cassia oil.

Another embodiment comprises cyclosporin A, Promulgen G®, and Cassia oil.

Another embodiment comprises cyclosporin A, Renex 30®, and Cassia oil.

Another embodiment comprises cyclosporin A, Renex 36®, and Cassia oil.

Another embodiment comprises cyclosporin A, Rhodasurf A 24®, and Cassia oil.
Another embodiment comprises cyclosporin A, Rhodasurf AAE-10®, and Cassia oil.
Another embodiment comprises cyclosporin A, Rhodasurf BEH-25®, and Cassia oil.
Another embodiment comprises cyclosporin A, Rhodasurf BEH-40®, and Cassia oil.
Another embodiment comprises cyclosporin A, Rhodasurf DA 530®, and Cassia oil.
Another embodiment comprises cyclosporin A, Rhodasurf DA 630®, and Cassia oil.
Another embodiment comprises cyclosporin A, Rhodasurf DA 639®, and Cassia oil.
Another embodiment comprises cyclosporin A, Rhodasurf LAN-23®, and Cassia oil.
Another embodiment comprises cyclosporin A, Rhodasurf ON-870®, and Cassia oil.
Another embodiment comprises cyclosporin A, Rhodasurf ON-877®, and Cassia oil.
Another embodiment comprises cyclosporin A, Rhodasurf TB-970 FLK®, and Cassia oil.
Another embodiment comprises cyclosporin A, Ritacet-20®, and Cassia oil.
Another embodiment comprises cyclosporin A, Ritachol 1000®, and Cassia oil.
Another embodiment comprises cyclosporin A, Ritachol 2000®, and Cassia oil.
Another embodiment comprises cyclosporin A, Ritachol 5000®, and Cassia oil.
Another embodiment comprises cyclosporin A, Ritox 35®, and Cassia oil.
Another embodiment comprises cyclosporin A, Surfonic DA-4®, and Cassia oil.
Another embodiment comprises cyclosporin A, Surfonic DA-6®, and Cassia oil.
Another embodiment comprises cyclosporin A, Surfonic L46-7®, and Cassia oil.
Another embodiment comprises cyclosporin A, Surfonic POA®, and Cassia oil.
Another embodiment comprises cyclosporin A, Synthrapol KB®, and Cassia oil.
Another embodiment comprises cyclosporin A, Teginacid®, and Cassia oil.
Another embodiment comprises cyclosporin A, Teginacid C®, and Cassia oil.
Another embodiment comprises cyclosporin A, Tegotens EC 11®, and Cassia oil.
Another embodiment comprises cyclosporin A, Tinegal NA®, and Cassia oil.
Another embodiment comprises cyclosporin A, Tomadol 400®, and Cassia oil.
Another embodiment comprises cyclosporin A, Tomadol 600®, and Cassia oil.
Another embodiment comprises cyclosporin A, Tomadol 900®, and Cassia oil.
Another embodiment comprises cyclosporin A, Uniperol O®, and Cassia oil.
Another embodiment comprises cyclosporin A, Witconol SN Series®, and Cassia oil.
Another embodiment comprises cyclosporin A, and Cassia oil.
Another embodiment comprises cyclosporin A, an Ethoxylated Alkylphenol, and Cassia oil.
Another embodiment comprises cyclosporin A, Antarox LF-222®, and Cassia oil.
Another embodiment comprises cyclosporin A, Atlox 775®, and Cassia oil.
Another embodiment comprises cyclosporin A, Caloxylate N-9®, and Cassia oil.
Another embodiment comprises cyclosporin A, Canasol NF-1000®, and Cassia oil.
Another embodiment comprises cyclosporin A, Canasol NF-3000®, and Cassia oil.
Another embodiment comprises cyclosporin A, Canasol NF-3070®, and Cassia oil.
Another embodiment comprises cyclosporin A, Canasol OF 1670®, and Cassia oil.
Another embodiment comprises cyclosporin A, Canasol OF 2570®, and Cassia oil.
Another embodiment comprises cyclosporin A, Canasol OF 4070®, and Cassia oil.
Another embodiment comprises cyclosporin A, Chemax DNP-8®, and Cassia oil.
Another embodiment comprises cyclosporin A, Chemax DNP-18®, and Cassia oil.
Another embodiment comprises cyclosporin A, Chemax DNP-150/50®, and Cassia oil.
Another embodiment comprises cyclosporin A, DeSonic 1.5N®, and Cassia oil.
Another embodiment comprises cyclosporin A, DeSonic 4N®, and Cassia oil.
Another embodiment comprises cyclosporin A, DeSonic 5N®, and Cassia oil.
Another embodiment comprises cyclosporin A, DeSonic 6D®, and Cassia oil.
Another embodiment comprises cyclosporin A, DeSonic 6N®, and Cassia oil.
Another embodiment comprises cyclosporin A, DeSonic 7N®, and Cassia oil.
Another embodiment comprises cyclosporin A, DeSonic 9N®, and Cassia oil.
Another embodiment comprises cyclosporin A, DeSonic 10D®, and Cassia oil.
Another embodiment comprises cyclosporin A, DeSonic 11N®, and Cassia oil.
Another embodiment comprises cyclosporin A, DeSonic 12N®, and Cassia oil.
Another embodiment comprises cyclosporin A, DeSonic 15N®, and Cassia oil.
Another embodiment comprises cyclosporin A, DeSonic 20N®, and Cassia oil.
Another embodiment comprises cyclosporin A, Eccoscour RC®, and Cassia oil.
Another embodiment comprises cyclosporin A, Eccoterge EO-100®, and Cassia oil.
Another embodiment comprises cyclosporin A, Emulsifier 632/90%®, and Cassia oil.
Another embodiment comprises cyclosporin A, Geronol AG-821®, and Cassia oil.
Another embodiment comprises cyclosporin A, Gradonic N-95®, and Cassia oil.
Another embodiment comprises cyclosporin A, Hetoxide NP-4®, and Cassia oil.
Another embodiment comprises cyclosporin A, Hetoxide NP-30®, and Cassia oil.
Another embodiment comprises cyclosporin A, Hostapal N-100®, and Cassia oil.
Another embodiment comprises cyclosporin A, Hostapal N-110®, and Cassia oil.
Another embodiment comprises cyclosporin A, Igepal CTA-639W®, and Cassia oil.

Another embodiment comprises cyclosporin A, Igepal DAP-9®, and Cassia oil.

Another embodiment comprises cyclosporin A, Igepal OD-410®, and Cassia oil.

Another embodiment comprises cyclosporin A, Igepal SS-837®, and Cassia oil.

Another embodiment comprises cyclosporin A, Lipocol NP-9 USP®, and Cassia oil.

Another embodiment comprises cyclosporin A, Macol DNP-10®, and Cassia oil.

Another embodiment comprises cyclosporin A, Marlophen NP 5®, and Cassia oil.

Another embodiment comprises cyclosporin A, Marlophen P 1®, and Cassia oil.

Another embodiment comprises cyclosporin A, Surfonic NB®, and Cassia oil.

Another embodiment comprises cyclosporin A, Surfonic OPB-307®, and Cassia oil.

Another embodiment comprises cyclosporin A, Surfonic OPB-407®, and Cassia oil.

Another embodiment comprises cyclosporin A, Syn Fac 334®, and Cassia oil.

Another embodiment comprises cyclosporin A, Syn Fac 8216®, and Cassia oil.

Another embodiment comprises cyclosporin A, Triton N-57®, and Cassia oil.

Another embodiment comprises cyclosporin A, Trycol 6956®, and Cassia oil.

Another embodiment comprises cyclosporin A, Trycol 6961®, and Cassia oil.

Another embodiment comprises cyclosporin A, Trycol 6964®, and Cassia oil.

Another embodiment comprises cyclosporin A, Trycol 6969®, and Cassia oil.

Another embodiment comprises cyclosporin A, Trycol 6974®, and Cassia oil.

Another embodiment comprises cyclosporin A, Witbreak DRB-127®, and Cassia oil.

Another embodiment comprises cyclosporin A, Witbreak DRB-127®, and Cassia oil.

Another embodiment comprises cyclosporin A, Witconol NP Series®, and Cassia oil.

Another embodiment comprises cyclosporin A, and Cassia oil.

Another embodiment comprises cyclosporin A, an Ethoxylated Aryl Phenol, and Cassia oil.

Another embodiment comprises cyclosporin A, Sorophor BSU®, and Cassia oil.

Another embodiment comprises cyclosporin A, Sorophor CY/8®, and Cassia oil.

Another embodiment comprises cyclosporin A, Sorophor S/25®, and Cassia oil.

Another embodiment comprises cyclosporin A, Witconol NIO®, and Cassia oil.

Another embodiment comprises cyclosporin A, Witconol NIW®, and Cassia oil.

Another embodiment comprises cyclosporin A, Witconol S-100®, and Cassia oil.

Another embodiment comprises cyclosporin A, and Cassia oil.

Another embodiment comprises cyclosporin A, an Ethoxylated Fatty Acid, and Cassia oil.

Another embodiment comprises cyclosporin A, Aldo PGHMS®, and Cassia oil.

Another embodiment comprises cyclosporin A, Alkamuls TO-15/HR®, and Cassia oil.

Another embodiment comprises cyclosporin A, Armotan AL-69-66®, and Cassia oil.

Another embodiment comprises cyclosporin A, Cerasynt 840®, and Cassia oil.

Another embodiment comprises cyclosporin A, Cerasynt 945®, and Cassia oil.

Another embodiment comprises cyclosporin A, Crystal Inhibitor No. 5®, and Cassia oil.

Another embodiment comprises cyclosporin A, DeThox Acid L-9®, and Cassia oil.

Another embodiment comprises cyclosporin A, DeThox Acid S-8®, and Cassia oil.

Another embodiment comprises cyclosporin A, Ethofat 242/25®, and Cassia oil.

Another embodiment comprises cyclosporin A, Hydropalat 65®, and Cassia oil.

Another embodiment comprises cyclosporin A, Lipo EGMS®, and Cassia oil.

Another embodiment comprises cyclosporin A, Lipopeg 2 DL®, and Cassia oil.

Another embodiment comprises cyclosporin A, Lipopeg 4 DL®, and Cassia oil.

Another embodiment comprises cyclosporin A, Lipopeg 4-L®, and Cassia oil.

Another embodiment comprises cyclosporin A, Lipopeg 39-S®, and Cassia oil.

Another embodiment comprises cyclosporin A, Lipopeg 4-S®, and Cassia oil.

Another embodiment comprises cyclosporin A, Lipopeg 10-S®, and Cassia oil.

Another embodiment comprises cyclosporin A, Lipopeg 100-S®, and Cassia oil.

Another embodiment comprises cyclosporin A, Lipopeg 6000 DS®, and Cassia oil.

Another embodiment comprises cyclosporin A, Lumulse 40-L®, and Cassia oil.

Another embodiment comprises cyclosporin A, Lumulse 40-S®, and Cassia oil.

Another embodiment comprises cyclosporin A, Lumulse 42-L®, and Cassia oil.

Another embodiment comprises cyclosporin A, Lumulse 42-S®, and Cassia oil.

Another embodiment comprises cyclosporin A, Lumulse 100-S®, and Cassia oil.

Another embodiment comprises cyclosporin A, Lumulse 602-S®, and Cassia oil.

Another embodiment comprises cyclosporin A, Magrabar PGE-20-0®, and Cassia oil.

Another embodiment comprises cyclosporin A, Magrabar PGE-20L®, and Cassia oil.

Another embodiment comprises cyclosporin A, Magrabar PGE-20T®, and Cassia oil.

Another embodiment comprises cyclosporin A, Magrabar PGE-22-0®, and Cassia oil.

Another embodiment comprises cyclosporin A, Magrabar PGE-22L®, and Cassia oil.

Another embodiment comprises cyclosporin A, Magrabar PGE-22T®, and Cassia oil.

Another embodiment comprises cyclosporin A, Magrabar PGE-40-0®, and Cassia oil.

Another embodiment comprises cyclosporin A, Magrabar PGE-40L®, and Cassia oil.

Another embodiment comprises cyclosporin A, Magrabar PGE-40T®, and Cassia oil.

Another embodiment comprises cyclosporin A, Magrabar PGE-42-0®, and Cassia oil.

Another embodiment comprises cyclosporin A, Magrabar PGE-42L®, and Cassia oil.
Another embodiment comprises cyclosporin A, Magrabar PGE-42T®, and Cassia oil.
Another embodiment comprises cyclosporin A, Magrabar PGE-60-0®, and Cassia oil.
Another embodiment comprises cyclosporin A, Magrabar PGE-60L®, and Cassia oil.
Another embodiment comprises cyclosporin A, Magrabar PGE-60T®, and Cassia oil.
Another embodiment comprises cyclosporin A, Magrabar PGE-62-0®, and Cassia oil.
Another embodiment comprises cyclosporin A, Magrabar PGE-62L®, and Cassia oil.
Another embodiment comprises cyclosporin A, Magrabar PGE-62T®, and Cassia oil.
Another embodiment comprises cyclosporin A, Mapeg S-40K®, and Cassia oil.
Another embodiment comprises cyclosporin A, Marlowet OTS®, and Cassia oil.
Another embodiment comprises cyclosporin A, Naturechem PGR®, and Cassia oil.
Another embodiment comprises cyclosporin A, PG No. 4®, and Cassia oil.
Another embodiment comprises cyclosporin A, Renex 20®, and Cassia oil.
Another embodiment comprises cyclosporin A, Ritox 52®, and Cassia oil.
Another embodiment comprises cyclosporin A, Ritox 53®, and Cassia oil.
Another embodiment comprises cyclosporin A, Ritox 59®, and Cassia oil.
Another embodiment comprises cyclosporin A, Surfax 8916/A®, and Cassia oil.
Another embodiment comprises cyclosporin A, Tego Acid S 40 P®, and Cassia oil.
Another embodiment comprises cyclosporin A, Tego Acid S 100 P®, and Cassia oil.
Another embodiment comprises cyclosporin A, Tween 20®, and Cassia oil.
Another embodiment comprises cyclosporin A, Volpo 131®, and Cassia oil.
Another embodiment comprises cyclosporin A, and Cassia oil.
Another embodiment comprises cyclosporin A, an Ethoxylated Fatty Ester or Oil, and Cassia oil.
Another embodiment comprises cyclosporin A, Acconon 6-C10®, and Cassia oil.
Another embodiment comprises cyclosporin A, Acconon CC-6®, and Cassia oil.
Another embodiment comprises cyclosporin A, Acconon CO-7®, and Cassia oil.
Another embodiment comprises cyclosporin A, Aldosperse 40/60 FG®, and Cassia oil.
Another embodiment comprises cyclosporin A, Aldosperse ML-23®, and Cassia oil.
Another embodiment comprises cyclosporin A, Aldosperse MS-20 FG®, and Cassia oil.
Another embodiment comprises cyclosporin A, Alkamuls EL-620®, and Cassia oil.
Another embodiment comprises cyclosporin A, Alkamuls EL-719®, and Cassia oil.
Another embodiment comprises cyclosporin A, Alkamuls EL-985®, and Cassia oil.
Another embodiment comprises cyclosporin A, Arlatone G®, and Cassia oil.
Another embodiment comprises cyclosporin A, Arlatone T®, and Cassia oil.
Another embodiment comprises cyclosporin A, Atlas G-1045A®, and Cassia oil.
Another embodiment comprises cyclosporin A, Atlas G-1086®, and Cassia oil.
Another embodiment comprises cyclosporin A, Atlas G-1087®, and Cassia oil.
Another embodiment comprises cyclosporin A, Atlas G-1089®, and Cassia oil.
Another embodiment comprises cyclosporin A, Atlas G-1096®, and Cassia oil.
Another embodiment comprises cyclosporin A, Atlas G-1292®, and Cassia oil.
Another embodiment comprises cyclosporin A, Atlas G-1293®, and Cassia oil.
Another embodiment comprises cyclosporin A, Atlas G-1300®, and Cassia oil.
Another embodiment comprises cyclosporin A, Atlas G-7076®, and Cassia oil.
Another embodiment comprises cyclosporin A, Capmul EMG®, and Cassia oil.
Another embodiment comprises cyclosporin A, Chemonic CO-40®, and Cassia oil.
Another embodiment comprises cyclosporin A, Chemonic LI-3®, and Cassia oil.
Another embodiment comprises cyclosporin A, Chemonic LI-7®, and Cassia oil.
Another embodiment comprises cyclosporin A, Cirrasol GM®, and Cassia oil.
Another embodiment comprises cyclosporin A, Cremophor CO 40®, and Cassia oil.
Another embodiment comprises cyclosporin A, Cremophor CO 410®, and Cassia oil.
Another embodiment comprises cyclosporin A, Cremophor EL®, and Cassia oil.
Another embodiment comprises cyclosporin A, Cremophor GC7®, and Cassia oil.
Another embodiment comprises cyclosporin A, Cremophor RH-40®, and Cassia oil.
Another embodiment comprises cyclosporin A, Crovol A-40®, and Cassia oil.
Another embodiment comprises cyclosporin A, Crovol A-70®, and Cassia oil.
Another embodiment comprises cyclosporin A, Crovol M-70®, and Cassia oil.
Another embodiment comprises cyclosporin A, Crovol PK-70®, and Cassia oil.
Another embodiment comprises cyclosporin A, Cutina E-24®, and Cassia oil.
Another embodiment comprises cyclosporin A, Dacospin 12-R®, and Cassia oil.
Another embodiment comprises cyclosporin A, Dehymuls HRE-7®, and Cassia oil.
Another embodiment comprises cyclosporin A, DeSonic 30C®, and Cassia oil.
Another embodiment comprises cyclosporin A, DeSonic 36C®, and Cassia oil.
Another embodiment comprises cyclosporin A, DeSonic 40C®, and Cassia oil.
Another embodiment comprises cyclosporin A, Durfax 60®, and Cassia oil.
Another embodiment comprises cyclosporin A, Durfax 65®, and Cassia oil.
Another embodiment comprises cyclosporin A, Durfax 80®, and Cassia oil.

Another embodiment comprises cyclosporin A, Durfax EOM®, and Cassia oil.

Another embodiment comprises cyclosporin A, Eccoterge NF-2®, and Cassia oil.

Another embodiment comprises cyclosporin A, Emulpon CO-360®, and Cassia oil.

Another embodiment comprises cyclosporin A, Emulpon CO-550®, and Cassia oil.

Another embodiment comprises cyclosporin A, Emulsogen EL®, and Cassia oil.

Another embodiment comprises cyclosporin A, Emulsogen HCO 040®, and Cassia oil.

Another embodiment comprises cyclosporin A, Emulsogen HCO 060®, and Cassia oil.

Another embodiment comprises cyclosporin A, Emulsynt 1055®, and Cassia oil.

Another embodiment comprises cyclosporin A, Ethox 3095®, and Cassia oil.

Another embodiment comprises cyclosporin A, Eumulgin RO-40®, and Cassia oil.

Another embodiment comprises cyclosporin A, Genapol G-260®, and Cassia oil.

Another embodiment comprises cyclosporin A, Glycosperse L-20®, and Cassia oil.

Another embodiment comprises cyclosporin A, Glycosperse O-5®, and Cassia oil.

Another embodiment comprises cyclosporin A, Glycosperse O-20®, and Cassia oil.

Another embodiment comprises cyclosporin A, Glycosperse O-20 FG®, and Cassia oil.

Another embodiment comprises cyclosporin A, Glycosperse S-20®, and Cassia oil.

Another embodiment comprises cyclosporin A, Glycosperse S-20 FG®, and Cassia oil.

Another embodiment comprises cyclosporin A, Glycosperse TS-20®, and Cassia oil.

Another embodiment comprises cyclosporin A, Glycosperse TS-20 FG®, and Cassia oil.

Another embodiment comprises cyclosporin A, Hetan SL®, and Cassia oil.

Another embodiment comprises cyclosporin A, Hetan SO®, and Cassia oil.

Another embodiment comprises cyclosporin A, Hetan SS®, and Cassia oil.

Another embodiment comprises cyclosporin A, Hetoxide C-2®, and Cassia oil.

Another embodiment comprises cyclosporin A, Hetoxide C-9®, and Cassia oil.

Another embodiment comprises cyclosporin A, Hetoxide C-15®, and Cassia oil.

Another embodiment comprises cyclosporin A, Hetoxide C-25®, and Cassia oil.

Another embodiment comprises cyclosporin A, Hetoxide C-40®, and Cassia oil.

Another embodiment comprises cyclosporin A, Hetoxide C-200®, and Cassia oil.

Another embodiment comprises cyclosporin A, Hetoxide C-200-50%®, and Cassia oil.

Another embodiment comprises cyclosporin A, Hetoxide GC-30®, and Cassia oil.

Another embodiment comprises cyclosporin A, Hetoxide HC-60®, and Cassia oil.

Another embodiment comprises cyclosporin A, Ice No. 2®, and Cassia oil.

Another embodiment comprises cyclosporin A, Incrocas 30/40®, and Cassia oil.

Another embodiment comprises cyclosporin A, Lexol EC®, and Cassia oil.

Another embodiment comprises cyclosporin A, Lexol EO®, and Cassia oil.

Another embodiment comprises cyclosporin A, Lipocol HCO-40®, and Cassia oil.

Another embodiment comprises cyclosporin A, Lipocol HCO-60®, and Cassia oil.

Another embodiment comprises cyclosporin A, Lipocol O-3 Special®, and Cassia oil.

Another embodiment comprises cyclosporin A, Lipopeg 2-L®, and Cassia oil.

Another embodiment comprises cyclosporin A, Lipopeg 4-DO®, and Cassia oil.

Another embodiment comprises cyclosporin A, Lipopeg 4-DS®, and Cassia oil.

Another embodiment comprises cyclosporin A, Lipovol GTB®, and Cassia oil.

Another embodiment comprises cyclosporin A, Lonzest SML-20®, and Cassia oil.

Another embodiment comprises cyclosporin A, Lonzest SMO-20®, and Cassia oil.

Another embodiment comprises cyclosporin A, Lonzest SMS-20®, and Cassia oil.

Another embodiment comprises cyclosporin A, Lonzest STO-20®, and Cassia oil.

Another embodiment comprises cyclosporin A, Lonzest STS-20®, and Cassia oil.

Another embodiment comprises cyclosporin A, Lumulse GR-40®, and Cassia oil.

Another embodiment comprises cyclosporin A, Lumulse GRH-40®, and Cassia oil.

Another embodiment comprises cyclosporin A, Lumulse POE (7) GML®, and Cassia oil.

Another embodiment comprises cyclosporin A, Lumulse POE (12) Glyc®, and Cassia oil.

Another embodiment comprises cyclosporin A, Lumulse POE (40) MS KP®, and Cassia oil.

Another embodiment comprises cyclosporin A, Marlowet 4750®, and Cassia oil.

Another embodiment comprises cyclosporin A, Marlowet LVS®, and Cassia oil.

Another embodiment comprises cyclosporin A, Marlowet R 11®, and Cassia oil.

Another embodiment comprises cyclosporin A, Marlowet R 40®, and Cassia oil.

Another embodiment comprises cyclosporin A, Mazol 80 MGK®, and Cassia oil.

Another embodiment comprises cyclosporin A, Nonionic Emulsifier T-9®, and Cassia oil.

Another embodiment comprises cyclosporin A, Oronal LCG®, and Cassia oil.

Another embodiment comprises cyclosporin A, Polyderm PPI-CO-200®, and Cassia oil.

Another embodiment comprises cyclosporin A, Polyderm PPI-CO-40®, and Cassia oil.

Another embodiment comprises cyclosporin A, Rewoderm LI 520-70®, and Cassia oil.

Another embodiment comprises cyclosporin A, Ritapeg 150 DS®, and Cassia oil.

Another embodiment comprises cyclosporin A, Softigen 767®, and Cassia oil.

Another embodiment comprises cyclosporin A, Surfactol 318®, and Cassia oil.

Another embodiment comprises cyclosporin A, Surfactol 365®, and Cassia oil.

Another embodiment comprises cyclosporin A, Syn Lube 107®, and Cassia oil.

Another embodiment comprises cyclosporin A, Syn Lube 728®, and Cassia oil.

Another embodiment comprises cyclosporin A, Syn Lube 1632H®, and Cassia oil.

Another embodiment comprises cyclosporin A, Syn Lube 6277-A®, and Cassia oil.

Another embodiment comprises cyclosporin A, T-Det C-20®, and Cassia oil.

Another embodiment comprises cyclosporin A, T-Det C-40®, and Cassia oil.

Another embodiment comprises cyclosporin A, Tally 100 Plus®, and Cassia oil.

Another embodiment comprises cyclosporin A, Uniperol EL®, and Cassia oil.

Another embodiment comprises cyclosporin A, and Cassia oil.

Another embodiment comprises cyclosporin A, a Fatty Ester, and Cassia oil.

Another embodiment comprises cyclosporin A, Actralube-Syn 147®, and Cassia oil.

Another embodiment comprises cyclosporin A, Atlas G-1556®, and Cassia oil.

Another embodiment comprises cyclosporin A, Atlas G-1564®, and Cassia oil.

Another embodiment comprises cyclosporin A, Atlasol Base Oil S®, and Cassia oil.

Another embodiment comprises cyclosporin A, Base ML®, and Cassia oil.

Another embodiment comprises cyclosporin A, Base MT®, and Cassia oil.

Another embodiment comprises cyclosporin A, Cerasynt 303®, and Cassia oil.

Another embodiment comprises cyclosporin A, Dermol 1012®, and Cassia oil.

Another embodiment comprises cyclosporin A, Kemester 4000®, and Cassia oil.

Another embodiment comprises cyclosporin A, Lactipol S®, and Cassia oil.

Another embodiment comprises cyclosporin A, Magrabar PGO®, and Cassia oil.

Another embodiment comprises cyclosporin A, Mayco Base BFO®, and Cassia oil.

Another embodiment comprises cyclosporin A, Methyl Linoleate®, and Cassia oil.

Another embodiment comprises cyclosporin A, Pationic 122A®, and Cassia oil.

Another embodiment comprises cyclosporin A, Pationic 138C®, and Cassia oil.

Another embodiment comprises cyclosporin A, Pationic CSL®, and Cassia oil.

Another embodiment comprises cyclosporin A, Pationic ISL®, and Cassia oil.

Another embodiment comprises cyclosporin A, Pationic SBL®, and Cassia oil.

Another embodiment comprises cyclosporin A, Pationic SSL®, and Cassia oil.

Another embodiment comprises cyclosporin A, Ritasol®, and Cassia oil.

Another embodiment comprises cyclosporin A, Tego Alkanol CS 20®, and Cassia oil.

Another embodiment comprises cyclosporin A, Tego Alkanol L23 P®, and Cassia oil.

Another embodiment comprises cyclosporin A, Tego Alkanol S2®, and Cassia oil.

Another embodiment comprises cyclosporin A, Tego Alkanol S20 P®, and Cassia oil.

Another embodiment comprises cyclosporin A, Triemulsifier 600 MS®, and Cassia oil.

Another embodiment comprises cyclosporin A, and Cassia oil.

Another embodiment comprises cyclosporin A, a Glycerol Esters, and Cassia oil.

Another embodiment comprises cyclosporin A, Agro #9 Wint SBO®, and Cassia oil.

Another embodiment comprises cyclosporin A, Ahcovel Base 700®, and Cassia oil.

Another embodiment comprises cyclosporin A, Aldo HMS FG®, and Cassia oil.

Another embodiment comprises cyclosporin A, Aldo MLD®, and Cassia oil.

Another embodiment comprises cyclosporin A, Aldo MLD FG®, and Cassia oil.

Another embodiment comprises cyclosporin A, Aldo MO FG®, and Cassia oil.

Another embodiment comprises cyclosporin A, Aldo MS®, and Cassia oil.

Another embodiment comprises cyclosporin A, Aldo MS FG®, and Cassia oil.

Another embodiment comprises cyclosporin A, Aldo MS LG FG®, and Cassia oil.

Another embodiment comprises cyclosporin A, Aldo MSD®, and Cassia oil.

Another embodiment comprises cyclosporin A, Aldo MSD FG®, and Cassia oil.

Another embodiment comprises cyclosporin A, Aldosperse O-20 FG®, and Cassia oil.

Another embodiment comprises cyclosporin A, Aldosperse TS-20 FG®, and Cassia oil.

Another embodiment comprises cyclosporin A, Aldosperse TS-40 FG®, and Cassia oil.

Another embodiment comprises cyclosporin A, Arlacel 165®, and Cassia oil.

Another embodiment comprises cyclosporin A, Arlacel 186®, and Cassia oil.

Another embodiment comprises cyclosporin A, Capmul GMO®, and Cassia oil.

Another embodiment comprises cyclosporin A, Capmul GMS®, and Cassia oil.

Another embodiment comprises cyclosporin A, Caprol 3GO®, and Cassia oil.

Another embodiment comprises cyclosporin A, Caprol 3GVS®, and Cassia oil.

Another embodiment comprises cyclosporin A, Caprol 6G2S, and Cassia oil.

Another embodiment comprises cyclosporin A, Caprol 10G40®, and Cassia oil.

Another embodiment comprises cyclosporin A, Caprol 10G100®, and Cassia oil.

Another embodiment comprises cyclosporin A, Caprol ET®, and Cassia oil.

Another embodiment comprises cyclosporin A, Caprol PGE860®, and Cassia oil.

Another embodiment comprises cyclosporin A, Cerasynt 945®, and Cassia oil.

Another embodiment comprises cyclosporin A, Cerasynt GMS®, and Cassia oil.

Another embodiment comprises cyclosporin A, Cerasynt Q®, and Cassia oil.

Another embodiment comprises cyclosporin A, Cerasynt SD®, and Cassia oil.

Another embodiment comprises cyclosporin A, Cerasynt WM®, and Cassia oil.

Another embodiment comprises cyclosporin A, Chemsperse 14®, and Cassia oil.

Another embodiment comprises cyclosporin A, Cremophor GO-32®, and Cassia oil.

Another embodiment comprises cyclosporin A, Cremophor GS11®, and Cassia oil.

Another embodiment comprises cyclosporin A, Cremophor GS-32®, and Cassia oil.

Another embodiment comprises cyclosporin A, Cutina KD-16®, and Cassia oil.

Another embodiment comprises cyclosporin A, Dehymuls PGPH®, and Cassia oil.

Another embodiment comprises cyclosporin A, Dermol DGDIS®, and Cassia oil.

Another embodiment comprises cyclosporin A, Dermol DGMIS®, and Cassia oil.

Another embodiment comprises cyclosporin A, Dermol G-76®, and Cassia oil.

Another embodiment comprises cyclosporin A, Dermol G-7DI®, and Cassia oil.

Another embodiment comprises cyclosporin A, Dermol NGDI®, and Cassia oil.

Another embodiment comprises cyclosporin A, Dermolan GLH®, and Cassia oil.

Another embodiment comprises cyclosporin A, Drewmulse GMO®, and Cassia oil.

Another embodiment comprises cyclosporin A, Drewpol 3-5-M®, and Cassia oil.

Another embodiment comprises cyclosporin A, Durlac 100 W®, and Cassia oil.

Another embodiment comprises cyclosporin A, Dur-Lo®, and Cassia oil.

Another embodiment comprises cyclosporin A, Dynasan 118®, and Cassia oil.

Another embodiment comprises cyclosporin A, EC-25®, and Cassia oil.

Another embodiment comprises cyclosporin A, EM 40®, and Cassia oil.

Another embodiment comprises cyclosporin A, Emerest 2400®, and Cassia oil.

Another embodiment comprises cyclosporin A, Emerest 2452®, and Cassia oil.

Another embodiment comprises cyclosporin A, Empilan G-26®, and Cassia oil.

Another embodiment comprises cyclosporin A, Genapol TSM®, and Cassia oil.

Another embodiment comprises cyclosporin A, Hostacerin DGI®, and Cassia oil.

Another embodiment comprises cyclosporin A, Hostacerin DGL®, and Cassia oil.

Another embodiment comprises cyclosporin A, Hostacerin DGMS®, and Cassia oil.

Another embodiment comprises cyclosporin A, Hostacerin DGSB®, and Cassia oil.

Another embodiment comprises cyclosporin A, Ice No. 2®, and Cassia oil.

Another embodiment comprises cyclosporin A, Imwitor 742®, and Cassia oil.

Another embodiment comprises cyclosporin A, Imwitor 780 K®, and Cassia oil.

Another embodiment comprises cyclosporin A, Imwitor 960 Flakes®, and Cassia oil.

Another embodiment comprises cyclosporin A, Isolan GI 34®, and Cassia oil.

Another embodiment comprises cyclosporin A, Isolan GO 33®, and Cassia oil.

Another embodiment comprises cyclosporin A, Kemester 1000®, and Cassia oil.

Another embodiment comprises cyclosporin A, Kemester 2000®, and Cassia oil.

Another embodiment comprises cyclosporin A, Kemester 2000®, and Cassia oil.

Another embodiment comprises cyclosporin A, Kemester 6000SE®, and Cassia oil.

Another embodiment comprises cyclosporin A, Lamecreme DGE 18®, and Cassia oil.

Another embodiment comprises cyclosporin A, Lexemul 515®, and Cassia oil.

Another embodiment comprises cyclosporin A, Lexemul 561®, and Cassia oil.

Another embodiment comprises cyclosporin A, Lexemul AR®, and Cassia oil.

Another embodiment comprises cyclosporin A, Lexemul AS®, and Cassia oil.

Another embodiment comprises cyclosporin A, Lexemul GDL®, and Cassia oil.

Another embodiment comprises cyclosporin A, Lexemul T®, and Cassia oil.

Another embodiment comprises cyclosporin A, Lipomulse 165®, and Cassia oil.

Another embodiment comprises cyclosporin A, Lumulse GML K®, and Cassia oil.

Another embodiment comprises cyclosporin A, Lumulse GMO K®, and Cassia oil.

Another embodiment comprises cyclosporin A, Lumulse GMR K®, and Cassia oil.

Another embodiment comprises cyclosporin A, Lumulse GMT K®, and Cassia oil.

Another embodiment comprises cyclosporin A, Magrabar GMC®, and Cassia oil.

Another embodiment comprises cyclosporin A, Magrabar GMO-CK®, and Cassia oil.

Another embodiment comprises cyclosporin A, Magrabar MDG-5050®, and Cassia oil.

Another embodiment comprises cyclosporin A, Magrabar PGO-315®, and Cassia oil.

Another embodiment comprises cyclosporin A, Magrabar PGO-1010®, and Cassia oil.

Another embodiment comprises cyclosporin A, Mazol 300K®, and Cassia oil.

Another embodiment comprises cyclosporin A, Mazol GMO-K®, and Cassia oil.

Another embodiment comprises cyclosporin A, Mazol GMS-K®, and Cassia oil.

Another embodiment comprises cyclosporin A, Mazol PGO31-K®, and Cassia oil.

Another embodiment comprises cyclosporin A, Miglyol 812®, and Cassia oil.

Another embodiment comprises cyclosporin A, Norfox 165C®, and Cassia oil.

Another embodiment comprises cyclosporin A, Schercemol GMIS®, and Cassia oil.

Another embodiment comprises cyclosporin A, Tegin®, and Cassia oil.

Another embodiment comprises cyclosporin A, Tegin 4100 Pellets®, and Cassia oil.

Another embodiment comprises cyclosporin A, Tegin M Pellets®, and Cassia oil.

Another embodiment comprises cyclosporin A, Tegin OV®, and Cassia oil.

Another embodiment comprises cyclosporin A, Teginacid H®, and Cassia oil.

Another embodiment comprises cyclosporin A, Tego Cosmo P813®, and Cassia oil.

Another embodiment comprises cyclosporin A, Wickenol 535®, and Cassia oil.

Another embodiment comprises cyclosporin A, Witconol 14®, and Cassia oil.

Another embodiment comprises cyclosporin A, Witconol 14®, and Cassia oil.

Another embodiment comprises cyclosporin A, Witconol 14F®, and Cassia oil.

Another embodiment comprises cyclosporin A, Witconol 18L®, and Cassia oil.

Another embodiment comprises cyclosporin A, Witconol GOT®, and Cassia oil.

Another embodiment comprises cyclosporin A, Witconol MST®, and Cassia oil.

Another embodiment comprises cyclosporin A, Witconol RHT®, and Cassia oil.

Another embodiment comprises cyclosporin A, and Cassia oil.

Another embodiment comprises cyclosporin A, a Glycol Ester, and Cassia oil.

Another embodiment comprises cyclosporin A, Alkamuls 600 DO®, and Cassia oil.

Another embodiment comprises cyclosporin A, Alkamuls SEG®, and Cassia oil.

Another embodiment comprises cyclosporin A, Atlas EM-2®, and Cassia oil.

Another embodiment comprises cyclosporin A, Cerasynt IP®, and Cassia oil.

Another embodiment comprises cyclosporin A, Cerasynt M®, and Cassia oil.

Another embodiment comprises cyclosporin A, Cerasynt MN®, and Cassia oil.

Another embodiment comprises cyclosporin A, Cerasynt PA®, and Cassia oil.

Another embodiment comprises cyclosporin A, Chemsperse EGDS®, and Cassia oil.

Another embodiment comprises cyclosporin A, Chemsperse EGMS®, and Cassia oil.

Another embodiment comprises cyclosporin A, Colonial Monolaurin®, and Cassia oil.

Another embodiment comprises cyclosporin A, DeMuls SGE-95®, and Cassia oil.

Another embodiment comprises cyclosporin A, Eccoterge 200®, and Cassia oil.

Another embodiment comprises cyclosporin A, Emerest 2380®, and Cassia oil.

Another embodiment comprises cyclosporin A, Ethox 2610®, and Cassia oil.

Another embodiment comprises cyclosporin A, Ethox DO-9®, and Cassia oil.

Another embodiment comprises cyclosporin A, Ethox DO-14®, and Cassia oil.

Another embodiment comprises cyclosporin A, Ethox SO-9®, and Cassia oil.

Another embodiment comprises cyclosporin A, Fizul MD-318®, and Cassia oil.

Another embodiment comprises cyclosporin A, Genapol EGDS-VHP®, and Cassia oil.

Another embodiment comprises cyclosporin A, Genapol TS Powder®, and Cassia oil.

Another embodiment comprises cyclosporin A, Hostacerin WO®, and Cassia oil.

Another embodiment comprises cyclosporin A, Inversol 140®, and Cassia oil.

Another embodiment comprises cyclosporin A, Kemester 104®, and Cassia oil.

Another embodiment comprises cyclosporin A, Kemester 205®, and Cassia oil.

Another embodiment comprises cyclosporin A, Kemester 226®, and Cassia oil.

Another embodiment comprises cyclosporin A, Kemester 5221SE®, and Cassia oil.

Another embodiment comprises cyclosporin A, Kemester EGDS®, and Cassia oil.

Another embodiment comprises cyclosporin A, Lexemul EGDS®, and Cassia oil.

Another embodiment comprises cyclosporin A, Lexemul EGMS®, and Cassia oil.

Another embodiment comprises cyclosporin A, Lexemul P®, and Cassia oil.

Another embodiment comprises cyclosporin A, Lipo DGLS®, and Cassia oil.

Another embodiment comprises cyclosporin A, Lipo EGDS®, and Cassia oil.

Another embodiment comprises cyclosporin A, Lipo PGMS®, and Cassia oil.

Another embodiment comprises cyclosporin A, Liposorb S-4®, and Cassia oil.

Another embodiment comprises cyclosporin A, Liposorb TO-20®, and Cassia oil.

Another embodiment comprises cyclosporin A, Lumulse PGO®, and Cassia oil.

Another embodiment comprises cyclosporin A, Mackester EGDS®, and Cassia oil.

Another embodiment comprises cyclosporin A, Mackester EGMS®, and Cassia oil.

Another embodiment comprises cyclosporin A, Mackester GSTP®, and Cassia oil.

Another embodiment comprises cyclosporin A, Mackester Series®, and Cassia oil.

Another embodiment comprises cyclosporin A, Magrabar PDG-50®, and Cassia oil.

Another embodiment comprises cyclosporin A, Mapeg 6000 DS®, and Cassia oil.

Another embodiment comprises cyclosporin A, Marlowet 4702®, and Cassia oil.

Another embodiment comprises cyclosporin A, Monalube 305®, and Cassia oil.

Another embodiment comprises cyclosporin A, Monalube 310®, and Cassia oil.

Another embodiment comprises cyclosporin A, Monalube 315®, and Cassia oil.

Another embodiment comprises cyclosporin A, Monalube 320®, and Cassia oil.

Another embodiment comprises cyclosporin A, Monalube 325®, and Cassia oil.

Another embodiment comprises cyclosporin A, Monalube 330®, and Cassia oil.

Another embodiment comprises cyclosporin A, Naturechem PGHS®, and Cassia oil.

Another embodiment comprises cyclosporin A, Polycastorol PLO-840®, and Cassia oil.

Another embodiment comprises cyclosporin A, Polytex 10M®, and Cassia oil.

Another embodiment comprises cyclosporin A, Ritasynt IP®, and Cassia oil.

Another embodiment comprises cyclosporin A, Ross Chem PEG 600 DT®, and Cassia oil.

Another embodiment comprises cyclosporin A, Schercemol PGMS®, and Cassia oil.

Another embodiment comprises cyclosporin A, Sponto H-44C®, and Cassia oil.

Another embodiment comprises cyclosporin A, Tegin G®, and Cassia oil.

Another embodiment comprises cyclosporin A, Witbreak DGE-182®, and Cassia oil.

Another embodiment comprises cyclosporin A, Witbreak DGE-182®, and Cassia oil.

Another embodiment comprises cyclosporin A, Witbreak DRA-21®, and Cassia oil.

Another embodiment comprises cyclosporin A, Witbreak DRA-21®, and Cassia oil.

Another embodiment comprises cyclosporin A, Witbreak DRA-50®, and Cassia oil.

Another embodiment comprises cyclosporin A, Witbreak DRA-50®, and Cassia oil.

Another embodiment comprises cyclosporin A, Witconol F26-46®, and Cassia oil.

Another embodiment comprises cyclosporin A, Witconol H-32®, and Cassia oil.

Another embodiment comprises cyclosporin A, Witconol H-33®, and Cassia oil.

Another embodiment comprises cyclosporin A, Witconol H-35A®, and Cassia oil.

Another embodiment comprises cyclosporin A, Witconol RHP®, and Cassia oil.

Another embodiment comprises cyclosporin A, and Cassia oil.

Another embodiment comprises cyclosporin A, a Lanolin-based Derivative, and Cassia oil.

Another embodiment comprises cyclosporin A, Amerchol CAB®, and Cassia oil.

Another embodiment comprises cyclosporin A, Amerchol L-101®, and Cassia oil.

Another embodiment comprises cyclosporin A, Amerlate LFA-LO®, and Cassia oil.

Another embodiment comprises cyclosporin A, Amerlate P®, and Cassia oil.

Another embodiment comprises cyclosporin A, Barre Common Degras®, and Cassia oil.

Another embodiment comprises cyclosporin A, Cholesterol NF®, and Cassia oil.

Another embodiment comprises cyclosporin A, Crodalan AWS®, and Cassia oil.

Another embodiment comprises cyclosporin A, Crodalan LA®, and Cassia oil.

Another embodiment comprises cyclosporin A, Emery 1650®, and Cassia oil.

Another embodiment comprises cyclosporin A, Emery 1650®, and Cassia oil.

Another embodiment comprises cyclosporin A, Emery 1740®, and Cassia oil.

Another embodiment comprises cyclosporin A, Emery 1740®, and Cassia oil.

Another embodiment comprises cyclosporin A, Forlan 500®, and Cassia oil.

Another embodiment comprises cyclosporin A, Forlan L®, and Cassia oil.

Another embodiment comprises cyclosporin A, Laneto 50®, and Cassia oil.

Another embodiment comprises cyclosporin A, Laneto 100®, and Cassia oil.

Another embodiment comprises cyclosporin A, Laneto AWS®, and Cassia oil.

Another embodiment comprises cyclosporin A, Lanfrax 1776®, and Cassia oil.

Another embodiment comprises cyclosporin A, Lanfrax 1776®, and Cassia oil.

Another embodiment comprises cyclosporin A, Lanogel 21®, and Cassia oil.

Another embodiment comprises cyclosporin A, Lipolan®, and Cassia oil.

Another embodiment comprises cyclosporin A, Lipolan 31®, and Cassia oil.

Another embodiment comprises cyclosporin A, OHlan®, and Cassia oil.

Another embodiment comprises cyclosporin A, Polychol 5®, and Cassia oil.

Another embodiment comprises cyclosporin A, Polychol 15®, and Cassia oil.

Another embodiment comprises cyclosporin A, Ritacetyl®, and Cassia oil.

Another embodiment comprises cyclosporin A, Ritachol®, and Cassia oil.

Another embodiment comprises cyclosporin A, Ritahydrox®, and Cassia oil.

Another embodiment comprises cyclosporin A, Ritalafa®, and Cassia oil.

Another embodiment comprises cyclosporin A, Ritalan®, and Cassia oil.

Another embodiment comprises cyclosporin A, Ritalan AWS®, and Cassia oil.

Another embodiment comprises cyclosporin A, Ritalan C®, and Cassia oil.

Another embodiment comprises cyclosporin A, Ritawax®, and Cassia oil.

Another embodiment comprises cyclosporin A, Ritawax AEO®, and Cassia oil.

Another embodiment comprises cyclosporin A, Ritawax ALA®, and Cassia oil.

Another embodiment comprises cyclosporin A, Solan/Solan 50/Super Solan®, and Cassia oil.

Another embodiment comprises cyclosporin A, Super Hartolan/Hartolan®, and Cassia oil.

Another embodiment comprises cyclosporin A, Supersat AWS-4®, and Cassia oil.

Another embodiment comprises cyclosporin A, Supersat AWS-24®, and Cassia oil.

Another embodiment comprises cyclosporin A, and Cassia oil.

Another embodiment comprises cyclosporin A, a Lecithin or Lecithin Derivative, and Cassia oil.

Another embodiment comprises cyclosporin A, Alcolec®, and Cassia oil.

Another embodiment comprises cyclosporin A, Lecithin®, and Cassia oil.

Another embodiment comprises cyclosporin A, Lexin K®, and Cassia oil.

Another embodiment comprises cyclosporin A, Natipide®, and Cassia oil.

Another embodiment comprises cyclosporin A, and Cassia oil.

Another embodiment comprises cyclosporin A, a Lignin or Lignin Derivative, and Cassia oil.

Another embodiment comprises cyclosporin A, Diwatex XP 9®, and Cassia oil.

Another embodiment comprises cyclosporin A, Dynasperse LCD®, and Cassia oil.

Another embodiment comprises cyclosporin A, Indulin SAL®, and Cassia oil.

Another embodiment comprises cyclosporin A, Indulin W-1®, and Cassia oil.

Another embodiment comprises cyclosporin A, Indulin W-5®, and Cassia oil.

Another embodiment comprises cyclosporin A, Lignosol FTA®, and Cassia oil.

Another embodiment comprises cyclosporin A, Lignosol SFX-65®, and Cassia oil.

Another embodiment comprises cyclosporin A, Marasperse 52 CP®, and Cassia oil.

Another embodiment comprises cyclosporin A, Marasperse AG®, and Cassia oil.

Another embodiment comprises cyclosporin A, Marasperse CBOS-4®, and Cassia oil.

Another embodiment comprises cyclosporin A, Ufoxane 2®, and Cassia oil.

Another embodiment comprises cyclosporin A, and Cassia oil.

Another embodiment comprises cyclosporin A, a Methyl Ester, and Cassia oil.

Another embodiment comprises cyclosporin A, E.B. Cleaner AK®, and Cassia oil.

Another embodiment comprises cyclosporin A, Oleocal ME-70®, and Cassia oil.

Another embodiment comprises cyclosporin A, Trade Name Company®, and Cassia oil.

Another embodiment comprises cyclosporin A, Methyl Esters (cont'd)®, and Cassia oil.

Another embodiment comprises cyclosporin A, Oleocal ME-92®, and Cassia oil.

Another embodiment comprises cyclosporin A, Oleocal ME-112®, and Cassia oil.

Another embodiment comprises cyclosporin A, Oleocal ME-130®, and Cassia oil.

Another embodiment comprises cyclosporin A, and Cassia oil.

Another embodiment comprises cyclosporin A, a Monoglyceride or a Derivative thereof, and Cassia oil.

Another embodiment comprises cyclosporin A, Dynacet 211®, and Cassia oil.

Another embodiment comprises cyclosporin A, Hetsorb S-20®, and Cassia oil.

Another embodiment comprises cyclosporin A, Imwitor 191®, and Cassia oil.

Another embodiment comprises cyclosporin A, Imwitor 370®, and Cassia oil.

Another embodiment comprises cyclosporin A, Imwitor 375®, and Cassia oil.

Another embodiment comprises cyclosporin A, Imwitor 900®, and Cassia oil.

Another embodiment comprises cyclosporin A, Imwitor 945®, and Cassia oil.

Another embodiment comprises cyclosporin A, Imwitor 2020®, and Cassia oil.

Another embodiment comprises cyclosporin A, Kemester 5500®, and Cassia oil.

Another embodiment comprises cyclosporin A, Kemester 6000®, and Cassia oil.

Another embodiment comprises cyclosporin A, Magrabar GMC®, and Cassia oil.

Another embodiment comprises cyclosporin A, Magrabar GMO-CK®, and Cassia oil.

Another embodiment comprises cyclosporin A, Magrabar GPC-10®, and Cassia oil.

Another embodiment comprises cyclosporin A, Magrabar MDG-5050®, and Cassia oil.

Another embodiment comprises cyclosporin A, Monalube 335®, and Cassia oil.

Another embodiment comprises cyclosporin A, Monoglycerides Glyceryl Monestearate Archer Daniels Midland Company®, and Cassia oil.

Another embodiment comprises cyclosporin A, Rita GMS®, and Cassia oil.

Another embodiment comprises cyclosporin A, Ritamulse SCG®, and Cassia oil.

Another embodiment comprises cyclosporin A, Softigen 701®, and Cassia oil.

Another embodiment comprises cyclosporin A, Tally 100 Plus®, and Cassia oil.

Another embodiment comprises cyclosporin A, and Cassia oil.

Another embodiment comprises cyclosporin A, a Polyethylene Glycol, and Cassia oil.

Another embodiment comprises cyclosporin A, Emulgade PL 68/50®, and Cassia oil.

Another embodiment comprises cyclosporin A, Lumulse PEG®, and Cassia oil.

Another embodiment comprises cyclosporin A, Rhodasurf PEG-400®, and Cassia oil.

Another embodiment comprises cyclosporin A, Rhodasurf PEG-600®, and Cassia oil.

Another embodiment comprises cyclosporin A, Witconol PEG-400®, and Cassia oil.

Another embodiment comprises cyclosporin A, and Cassia oil.

Another embodiment comprises cyclosporin A, a Polymeric Surfactant, and Cassia oil.

Another embodiment comprises cyclosporin A, Acritamer PNC-EG®, and Cassia oil.

Another embodiment comprises cyclosporin A, Ag-Rho DEP-775®, and Cassia oil.

Another embodiment comprises cyclosporin A, APG 325N Glycoside®, and Cassia oil.

Another embodiment comprises cyclosporin A, Aristoflex AVC®, and Cassia oil.

Another embodiment comprises cyclosporin A, Aristoflex HMB®, and Cassia oil.

Another embodiment comprises cyclosporin A, Burco NPS-225®, and Cassia oil.

Another embodiment comprises cyclosporin A, Burco NPS-816®, and Cassia oil.

Another embodiment comprises cyclosporin A, Chemccinate 5603®, and Cassia oil.

Another embodiment comprises cyclosporin A, Cosmedia Guar C-261N®, and Cassia oil.

Another embodiment comprises cyclosporin A, Gantrez S-95®, and Cassia oil.

Another embodiment comprises cyclosporin A, Glucopon 220 UP®, and Cassia oil.

Another embodiment comprises cyclosporin A, Glucopon 225 DK®, and Cassia oil.

Another embodiment comprises cyclosporin A, Glucopon 425 N®, and Cassia oil.

Another embodiment comprises cyclosporin A, Glucopon 600 UP®, and Cassia oil.

Another embodiment comprises cyclosporin A, Glucopon 625 UP®, and Cassia oil.

Another embodiment comprises cyclosporin A, Pemulen 1621®, and Cassia oil.

Another embodiment comprises cyclosporin A, Pemulen 1622®, and Cassia oil.

Another embodiment comprises cyclosporin A, Pemulen TR-1®, and Cassia oil.

Another embodiment comprises cyclosporin A, Pemulen TR-2®, and Cassia oil.

Another embodiment comprises cyclosporin A, Plantacare 818®, and Cassia oil.

Another embodiment comprises cyclosporin A, Plantapon LGC Sorb®, and Cassia oil.

Another embodiment comprises cyclosporin A, Plantaren 1200N®, and Cassia oil.

Another embodiment comprises cyclosporin A, Plantaren 2000N®, and Cassia oil.

Another embodiment comprises cyclosporin A, Viscolam AT 64®, and Cassia oil.

Another embodiment comprises cyclosporin A, Viscolam AT 64P®, and Cassia oil.

Another embodiment comprises cyclosporin A, Viscolam AT 100®, and Cassia oil.

Another embodiment comprises cyclosporin A, Viscolam MAC 7®, and Cassia oil.

Another embodiment comprises cyclosporin A, Viscolam SMC 20®, and Cassia oil.

Another embodiment comprises cyclosporin A, Witbreak RTC-323®, and Cassia oil.

Another embodiment comprises cyclosporin A, WSI 3700®, and Cassia oil.

Another embodiment comprises cyclosporin A, and Cassia oil.

Another embodiment comprises cyclosporin A, a Propoxylated or Ethoxylated Fatty Acid, Alcohol, or Alkyl Phenol, and Cassia oil.

Another embodiment comprises cyclosporin A, Antarox AA-60®, and Cassia oil.

Another embodiment comprises cyclosporin A, Antarox LF-224®, and Cassia oil.

Another embodiment comprises cyclosporin A, Burcomul DFE-45®, and Cassia oil.

Another embodiment comprises cyclosporin A, Burcoterge LFE-1000®, and Cassia oil.

Another embodiment comprises cyclosporin A, Chemal LF-25B®, and Cassia oil.

Another embodiment comprises cyclosporin A, Chemal LF-40B®, and Cassia oil.

Another embodiment comprises cyclosporin A, Dehypon LS-36®, and Cassia oil.

Another embodiment comprises cyclosporin A, Dehypon LS-36®, and Cassia oil.

Another embodiment comprises cyclosporin A, Dehypon LS-54®, and Cassia oil.

Another embodiment comprises cyclosporin A, Dehypon LS-54®, and Cassia oil.

Another embodiment comprises cyclosporin A, Delonic 100 VLF®, and Cassia oil.

Another embodiment comprises cyclosporin A, Delonic LF-60 MOD®, and Cassia oil.

Another embodiment comprises cyclosporin A, Empiderm B®, and Cassia oil.

Another embodiment comprises cyclosporin A, Ethylan 1206®, and Cassia oil.

Another embodiment comprises cyclosporin A, Ethylan NS-500K®, and Cassia oil.

Another embodiment comprises cyclosporin A, Ethylan NS-500LQ®, and Cassia oil.

Another embodiment comprises cyclosporin A, Genapol 1392®, and Cassia oil.

Another embodiment comprises cyclosporin A, Genapol 2317®, and Cassia oil.

Another embodiment comprises cyclosporin A, Genapol 26EP710®, and Cassia oil.

Another embodiment comprises cyclosporin A, Genapol EP 1022®, and Cassia oil.

Another embodiment comprises cyclosporin A, Genapol EP 1024®, and Cassia oil.

Another embodiment comprises cyclosporin A, Genapol EP 6068®, and Cassia oil.

Another embodiment comprises cyclosporin A, Genapol NP915®, and Cassia oil.

Another embodiment comprises cyclosporin A, Kieralon MFB®, and Cassia oil.

Another embodiment comprises cyclosporin A, Lumisolve CSA-80 V®, and Cassia oil.

Another embodiment comprises cyclosporin A, Marlowet 5001®, and Cassia oil.

Another embodiment comprises cyclosporin A, Marlox FK 64®, and Cassia oil.

Another embodiment comprises cyclosporin A, Marlox MO 124®, and Cassia oil.

Another embodiment comprises cyclosporin A, Marlox S 58®, and Cassia oil.

Another embodiment comprises cyclosporin A, Nonatell 1003®, and Cassia oil.

Another embodiment comprises cyclosporin A, Nonatell 1038®, and Cassia oil.

Another embodiment comprises cyclosporin A, Nonatell 1052®, and Cassia oil.

Another embodiment comprises cyclosporin A, Nonatell 1061®, and Cassia oil.

Another embodiment comprises cyclosporin A, Nonatell 1075®, and Cassia oil.

Another embodiment comprises cyclosporin A, Nonatell 1088®, and Cassia oil.

Another embodiment comprises cyclosporin A, Nonatell 1123®, and Cassia oil.

Another embodiment comprises cyclosporin A, Nonatell 1153®, and Cassia oil.

Another embodiment comprises cyclosporin A, Nonatell 1161®, and Cassia oil.

Another embodiment comprises cyclosporin A, Nonatell 1172®, and Cassia oil.

Another embodiment comprises cyclosporin A, Nonatell 1181®, and Cassia oil.

Another embodiment comprises cyclosporin A, Norfox 36®, and Cassia oil.

Another embodiment comprises cyclosporin A, Procetyl AWS®, and Cassia oil.

Another embodiment comprises cyclosporin A, Sandoxylate SX 412®, and Cassia oil.

Another embodiment comprises cyclosporin A, Sandoxylate SX 418®, and Cassia oil.

Another embodiment comprises cyclosporin A, Surfonic JL-80X®, and Cassia oil.

Another embodiment comprises cyclosporin A, Surfonic JL-80X-B1®, and Cassia oil.

Another embodiment comprises cyclosporin A, Surfonic L4-29X®, and Cassia oil.

Another embodiment comprises cyclosporin A, Surfonic LF®, and Cassia oil.

Another embodiment comprises cyclosporin A, T-Det A826®, and Cassia oil.

Another embodiment comprises cyclosporin A, T-Det LF-416®, and Cassia oil.

Another embodiment comprises cyclosporin A, Tergitol Min-Foam 1X®, and Cassia oil.

Another embodiment comprises cyclosporin A, Tergitol Min-Foam 2X®, and Cassia oil.

Another embodiment comprises cyclosporin A, Triton CF-21®, and Cassia oil.

Another embodiment comprises cyclosporin A, Triton CF-76®, and Cassia oil.

Another embodiment comprises cyclosporin A, Triton XL-80N®, and Cassia oil.

Another embodiment comprises cyclosporin A, Witconol NS-98®, and Cassia oil.

Another embodiment comprises cyclosporin A, Witconol NS-108LQ®, and Cassia oil.

Another embodiment comprises cyclosporin A, Witconol NS-145®, and Cassia oil.

Another embodiment comprises cyclosporin A, Witconol NS-179®, and Cassia oil.

Another embodiment comprises cyclosporin A, and Cassia oil.

Another embodiment comprises cyclosporin A, a Protein-based Surfactant, and Cassia oil.

Another embodiment comprises cyclosporin A, Amino-Foam W®, and Cassia oil.

Another embodiment comprises cyclosporin A, Amiter LGOD-2®, and Cassia oil.

Another embodiment comprises cyclosporin A, Amiter LGS-2®, and Cassia oil.

Another embodiment comprises cyclosporin A, Amiter LGS-5®, and Cassia oil.

Another embodiment comprises cyclosporin A, Lamepon S®, and Cassia oil.

Another embodiment comprises cyclosporin A, Lamepon S®, and Cassia oil.

Another embodiment comprises cyclosporin A, Maypon 4C®, and Cassia oil.

Another embodiment comprises cyclosporin A, May-Tein C®, and Cassia oil.

Another embodiment comprises cyclosporin A, May-Tein CT®, and Cassia oil.

Another embodiment comprises cyclosporin A, May-Tein KTS®, and Cassia oil.

Another embodiment comprises cyclosporin A, May-Tein SY®, and Cassia oil.

Another embodiment comprises cyclosporin A, Plantapon S®, and Cassia oil.

Another embodiment comprises cyclosporin A, Proteol APL®, and Cassia oil.

Another embodiment comprises cyclosporin A, Proteol OAT®, and Cassia oil.

Another embodiment comprises cyclosporin A, Pyroter CPI-40®, and Cassia oil.

Another embodiment comprises cyclosporin A, Pyroter GPI-25®, and Cassia oil.

Another embodiment comprises cyclosporin A, Supro-Tein S®, and Cassia oil.

Another embodiment comprises cyclosporin A, Supro-Tein V®, and Cassia oil.

Another embodiment comprises cyclosporin A, ®, and Cassia oil.

Another embodiment comprises cyclosporin A, a Sarcosine Derivative®, and Cassia oil.

Another embodiment comprises cyclosporin A, Crodasinic LS-30®, and Cassia oil.

Another embodiment comprises cyclosporin A, Vanseal CS®, and Cassia oil.

Another embodiment comprises cyclosporin A, Vanseal LS®, and Cassia oil.

Another embodiment comprises cyclosporin A, Vanseal MS®, and Cassia oil.

Another embodiment comprises cyclosporin A, Vanseal NACS-30®, and Cassia oil.

Another embodiment comprises cyclosporin A, Vanseal NALS-95®, and Cassia oil.

Another embodiment comprises cyclosporin A, Vanseal OS®, and Cassia oil.

Another embodiment comprises cyclosporin A, ®, and Cassia oil.

Another embodiment comprises cyclosporin A, a Silicone-based Surfactant®, and Cassia oil.

Another embodiment comprises cyclosporin A, Abil-B-9950®, and Cassia oil.

Another embodiment comprises cyclosporin A, Abil Care 85®, and Cassia oil.

Another embodiment comprises cyclosporin A, Abil EM 90®, and Cassia oil.

Another embodiment comprises cyclosporin A, Abil EM 97®, and Cassia oil.

Another embodiment comprises cyclosporin A, Abil WE-09®, and Cassia oil.

Another embodiment comprises cyclosporin A, Dow Corning 1248 Fluid®, and Cassia oil.

Another embodiment comprises cyclosporin A, Dow Corning 3225C®, and Cassia oil.

Another embodiment comprises cyclosporin A, Dow Corning 5200®, and Cassia oil.

Another embodiment comprises cyclosporin A, Dow Corning Q4-3667®, and Cassia oil.

Another embodiment comprises cyclosporin A, Monasil PCA®, and Cassia oil.

Another embodiment comprises cyclosporin A, Monasil PDM®, and Cassia oil.

Another embodiment comprises cyclosporin A, Monasil PLN®, and Cassia oil.

Another embodiment comprises cyclosporin A, Polyderm PPI-SI-WS®, and Cassia oil.

Another embodiment comprises cyclosporin A, Troysol 380W®, and Cassia oil.

Another embodiment comprises cyclosporin A, Troysol S366®, and Cassia oil.

Another embodiment comprises cyclosporin A, and Cassia oil.

Another embodiment comprises cyclosporin A, a Sorbitan Derivative, and Cassia oil.

Another embodiment comprises cyclosporin A, Alkamuls SML®, and Cassia oil.

Another embodiment comprises cyclosporin A, Alkamuls SMO®, and Cassia oil.

Another embodiment comprises cyclosporin A, Alkamuls STO®, and Cassia oil.

Another embodiment comprises cyclosporin A, Arlacel 20®, and Cassia oil.

Another embodiment comprises cyclosporin A, Arlacel 40®, and Cassia oil.

Another embodiment comprises cyclosporin A, Arlacel 60®, and Cassia oil.

Another embodiment comprises cyclosporin A, Arlacel 80®, and Cassia oil.

Another embodiment comprises cyclosporin A, Arlacel C®, and Cassia oil.

Another embodiment comprises cyclosporin A, Armul 21®, and Cassia oil.

Another embodiment comprises cyclosporin A, Atlox 80®, and Cassia oil.

Another embodiment comprises cyclosporin A, Atlox 847®, and Cassia oil.

Another embodiment comprises cyclosporin A, Atlox 1045A®, and Cassia oil.

Another embodiment comprises cyclosporin A, Canarcel 20®, and Cassia oil.

Another embodiment comprises cyclosporin A, Canarcel 60®, and Cassia oil.

Another embodiment comprises cyclosporin A, Canarcel 80®, and Cassia oil.

Another embodiment comprises cyclosporin A, Canarcel TW 20®, and Cassia oil.

Another embodiment comprises cyclosporin A, Canarcel TW 60®, and Cassia oil.

Another embodiment comprises cyclosporin A, Canarcel TW 80®, and Cassia oil.

Another embodiment comprises cyclosporin A, Coladet BSB-P®, and Cassia oil.

Another embodiment comprises cyclosporin A, Customulse O-20®, and Cassia oil.

Another embodiment comprises cyclosporin A, Dehymuls E®, and Cassia oil.

Another embodiment comprises cyclosporin A, DeSotan SMO®, and Cassia oil.

Another embodiment comprises cyclosporin A, DeSotan SMO-20®, and Cassia oil.

Another embodiment comprises cyclosporin A, DeSotan SMT®, and Cassia oil.

Another embodiment comprises cyclosporin A, DeSotan SMT-20®, and Cassia oil.

Another embodiment comprises cyclosporin A, Durfax 60®, and Cassia oil.

Another embodiment comprises cyclosporin A, Durfax 65®, and Cassia oil.

Another embodiment comprises cyclosporin A, Durfax 80®, and Cassia oil.

Another embodiment comprises cyclosporin A, Durtan 60®, and Cassia oil.

Another embodiment comprises cyclosporin A, Durtan 65®, and Cassia oil.

Another embodiment comprises cyclosporin A, Liposorb L®, and Cassia oil.

Another embodiment comprises cyclosporin A, Liposorb L-10®, and Cassia oil.

Another embodiment comprises cyclosporin A, Liposorb L-20®, and Cassia oil.

Another embodiment comprises cyclosporin A, Liposorb O®, and Cassia oil.

Another embodiment comprises cyclosporin A, Liposorb O-20®, and Cassia oil.

Another embodiment comprises cyclosporin A, Liposorb P®, and Cassia oil.

Another embodiment comprises cyclosporin A, Liposorb P-20®, and Cassia oil.

Another embodiment comprises cyclosporin A, Liposorb S®, and Cassia oil.

Another embodiment comprises cyclosporin A, Liposorb S-20®, and Cassia oil.

Another embodiment comprises cyclosporin A, Liposorb SQO®, and Cassia oil.

Another embodiment comprises cyclosporin A, Liposorb TO®, and Cassia oil.

Another embodiment comprises cyclosporin A, Liposorb TS®, and Cassia oil.

Another embodiment comprises cyclosporin A, Liposorb TS-20®, and Cassia oil.

Another embodiment comprises cyclosporin A, Lumisorb PS®, and Cassia oil.

Another embodiment comprises cyclosporin A, Lumisorb SMO (T)®, and Cassia oil.

Another embodiment comprises cyclosporin A, Lumisorb SMS K®, and Cassia oil.

Another embodiment comprises cyclosporin A, Lumisorb SSO®, and Cassia oil.

Another embodiment comprises cyclosporin A, Lumisorb STS K®, and Cassia oil.

Another embodiment comprises cyclosporin A, Lumisorb STT®, and Cassia oil.

Another embodiment comprises cyclosporin A, Magrabar SMO®, and Cassia oil.

Another embodiment comprises cyclosporin A, Magrabar SMO-VEG®, and Cassia oil.

Another embodiment comprises cyclosporin A, Magrabar SMT®, and Cassia oil.

Another embodiment comprises cyclosporin A, Magrabar STO®, and Cassia oil.

Another embodiment comprises cyclosporin A, Miracare BC-27®, and Cassia oil.

Another embodiment comprises cyclosporin A, Ritabate 20®, and Cassia oil.

Another embodiment comprises cyclosporin A, Ritabate 40®, and Cassia oil.

Another embodiment comprises cyclosporin A, Ritabate 60®, and Cassia oil.

Another embodiment comprises cyclosporin A, Ritabate 80®, and Cassia oil.

Another embodiment comprises cyclosporin A, T-Maz®, and Cassia oil.

Another embodiment comprises cyclosporin A, Tego SML®, and Cassia oil.

Another embodiment comprises cyclosporin A, Tego SML 20®, and Cassia oil.

Another embodiment comprises cyclosporin A, Tego SMO 80 V®, and Cassia oil.

Another embodiment comprises cyclosporin A, Tego SMO V®, and Cassia oil.

Another embodiment comprises cyclosporin A, Tego SMS®, and Cassia oil.

Another embodiment comprises cyclosporin A, Tego STO V®, and Cassia oil.

Another embodiment comprises cyclosporin A, Tween 21®, and Cassia oil.

Another embodiment comprises cyclosporin A, Tween 40®, and Cassia oil.

Another embodiment comprises cyclosporin A, Tween 60®, and Cassia oil.

Another embodiment comprises cyclosporin A, Tween 60 K®, and Cassia oil.

Another embodiment comprises cyclosporin A, Tween 61®, and Cassia oil.

Another embodiment comprises cyclosporin A, Tween 65®, and Cassia oil.

Another embodiment comprises cyclosporin A, Tween 80®, and Cassia oil.

Another embodiment comprises cyclosporin A, Tween 80 K®, and Cassia oil.

Another embodiment comprises cyclosporin A, Tween 81®, and Cassia oil.

Another embodiment comprises cyclosporin A, Tween 85®, and Cassia oil.

Another embodiment comprises cyclosporin A, and Cassia oil.

Another embodiment comprises cyclosporin A, a Sucrose or Glucose Ester, or Derivative thereof, and Cassia oil.

Another embodiment comprises cyclosporin A, DeSulf GOS-P-60WCG®, and Cassia oil.

Another embodiment comprises cyclosporin A, Glucam E-20 Distearate®, and Cassia oil.

Another embodiment comprises cyclosporin A, Glucamate DOE-120®, and Cassia oil.

Another embodiment comprises cyclosporin A, Glucamate SSE-20®, and Cassia oil.

Another embodiment comprises cyclosporin A, Glucate DO®, and Cassia oil.

Another embodiment comprises cyclosporin A, Glucate SS®, and Cassia oil.

Another embodiment comprises cyclosporin A, Glucopon 425 UP®, and Cassia oil.

Another embodiment comprises cyclosporin A, Isolan IS®, and Cassia oil.

Another embodiment comprises cyclosporin A, Mazon 40®, and Cassia oil.

Another embodiment comprises cyclosporin A, Montanov 82®, and Cassia oil.

Another embodiment comprises cyclosporin A, Montanov 202®, and Cassia oil.

Another embodiment comprises cyclosporin A, Montanov S®, and Cassia oil.

Another embodiment comprises cyclosporin A, Rheozan®, and Cassia oil.

Another embodiment comprises cyclosporin A, Simulsol AS 48®, and Cassia oil.

Another embodiment comprises cyclosporin A, Simulsol SL 4®, and Cassia oil.

Another embodiment comprises cyclosporin A, Simulsol SL 10®, and Cassia oil.

Another embodiment comprises cyclosporin A, Simulsol SL 11W®, and Cassia oil.

Another embodiment comprises cyclosporin A, Simulsol SL 55®, and Cassia oil.

Another embodiment comprises cyclosporin A, Suga Nate 100 and 160®, and Cassia oil.

Another embodiment comprises cyclosporin A, Tego Care 450®, and Cassia oil.

Another embodiment comprises cyclosporin A, Tego Care CG 90®, and Cassia oil.

Another embodiment comprises cyclosporin A, Tego Care PS®, and Cassia oil.

Another embodiment comprises cyclosporin A, Tegosoft PSE 141 G®, and Cassia oil.

Another embodiment comprises cyclosporin A, Tegotens G 826®, and Cassia oil.

Another embodiment comprises cyclosporin A, Triton BG-10 (70%)®, and Cassia oil.

Another embodiment comprises cyclosporin A, Triton CG-110 (60%)®, and Cassia oil.

Another embodiment comprises cyclosporin A, Wickenol 545®, and Cassia oil.

Another embodiment comprises cyclosporin A, an alcohol, and Cinnamon oil.

Another embodiment comprises cyclosporin A, Diglycerol®, and Cinnamon oil.

Another embodiment comprises cyclosporin A, Hetoxide GT-80®, and Cinnamon oil.

Another embodiment comprises cyclosporin A, Lexemul BEO®, and Cinnamon oil.

Another embodiment comprises cyclosporin A, Polyglycerol-3®, and Cinnamon oil.

Another embodiment comprises cyclosporin A, Redicote E Series®, and Cinnamon oil.

Another embodiment comprises cyclosporin A, Simulsol OX 1005L®, and Cinnamon oil.

Another embodiment comprises cyclosporin A, Stanfax 567®, and Cinnamon oil.

Another embodiment comprises cyclosporin A, TA-1618®, and Cinnamon oil.

Another embodiment comprises cyclosporin A, Witconol H-31A®, and Cinnamon oil.

Another embodiment comprises cyclosporin A, Standard Div.®, and Cinnamon oil., and Cinnamon oil.

Another embodiment comprises cyclosporin A, an amine oxide, and Cinnamon oil.

Another embodiment comprises cyclosporin A, AO-405®, and Cinnamon oil.

Another embodiment comprises cyclosporin A, AO-455®, and Cinnamon oil.

Another embodiment comprises cyclosporin A, AO 728 Special®, and Cinnamon oil.

Another embodiment comprises cyclosporin A, Barlox 12®, and Cinnamon oil.

Another embodiment comprises cyclosporin A, Barlox 14®, and Cinnamon oil.

Another embodiment comprises cyclosporin A, Burcoxide Lo®, and Cinnamon oil.

Another embodiment comprises cyclosporin A, Caloxamine LO®, and Cinnamon oil.

Another embodiment comprises cyclosporin A, Chemoxide CAW®, and Cinnamon oil.

Another embodiment comprises cyclosporin A, Chemoxide LM-30®, and Cinnamon oil.

Another embodiment comprises cyclosporin A, Chemoxide LO®, and Cinnamon oil.

Another embodiment comprises cyclosporin A, Chemoxide MO®, and Cinnamon oil.

Another embodiment comprises cyclosporin A, Colalux CAO-35®, and Cinnamon oil.

Another embodiment comprises cyclosporin A, Colalux LO®, and Cinnamon oil.

Another embodiment comprises cyclosporin A, DeMox CAPO®, and Cinnamon oil.

Another embodiment comprises cyclosporin A, DeMox CSG-30®, and Cinnamon oil.

Another embodiment comprises cyclosporin A, DeMox LAO®, and Cinnamon oil.

Another embodiment comprises cyclosporin A, Emcol L®, and Cinnamon oil.

Another embodiment comprises cyclosporin A, Empigen OB®, and Cinnamon oil.

Another embodiment comprises cyclosporin A, Empigen OS/A®, and Cinnamon oil.

Another embodiment comprises cyclosporin A, Foamox CDO®, and Cinnamon oil.

Another embodiment comprises cyclosporin A, Foamox DMM®, and Cinnamon oil.

Another embodiment comprises cyclosporin A, Foamox DMS®, and Cinnamon oil.

Another embodiment comprises cyclosporin A, Genaminox KC®, and Cinnamon oil.

Another embodiment comprises cyclosporin A, Genaminox LA®, and Cinnamon oil.

Another embodiment comprises cyclosporin A, Hartofoam SAO®, and Cinnamon oil.

Another embodiment comprises cyclosporin A, Hartox DMCD®, and Cinnamon oil.

Another embodiment comprises cyclosporin A, Lipowax DAT®, and Cinnamon oil.

Another embodiment comprises cyclosporin A, Lipowax PB Pastilles®, and Cinnamon oil.

Another embodiment comprises cyclosporin A, Mackamine C8®, and Cinnamon oil.

Another embodiment comprises cyclosporin A, Mackamine C10®, and Cinnamon oil.

Another embodiment comprises cyclosporin A, Mackamine C14®, and Cinnamon oil.

Another embodiment comprises cyclosporin A, Mackamine CAO®, and Cinnamon oil.

Another embodiment comprises cyclosporin A, Mackamine CO®, and Cinnamon oil.

Another embodiment comprises cyclosporin A, Mackamine LO®, and Cinnamon oil.

Another embodiment comprises cyclosporin A, Mackamine O2®, and Cinnamon oil.

Another embodiment comprises cyclosporin A, Mackamine SAO®, and Cinnamon oil.

Another embodiment comprises cyclosporin A, Mackamine SO®, and Cinnamon oil.

Another embodiment comprises cyclosporin A, Mazox KCAO®, and Cinnamon oil.

Another embodiment comprises cyclosporin A, Monalac MO®, and Cinnamon oil.

Another embodiment comprises cyclosporin A, Norfox LDA®, and Cinnamon oil.

Another embodiment comprises cyclosporin A, Rhodamox LO®, and Cinnamon oil.

Another embodiment comprises cyclosporin A, Schercamox C-AA®, and Cinnamon oil.

Another embodiment comprises cyclosporin A, Schercamox DMA®, and Cinnamon oil.

Another embodiment comprises cyclosporin A, Schercamox DML®, and Cinnamon oil.

Another embodiment comprises cyclosporin A, Schercamox DMM®, and Cinnamon oil.

Another embodiment comprises cyclosporin A, Schercamox DMS®, and Cinnamon oil.

Another embodiment comprises cyclosporin A, Tegotens DO®, and Cinnamon oil.

Another embodiment comprises cyclosporin A, Tomah AO-14-2®, and Cinnamon oil.

Another embodiment comprises cyclosporin A, Triaminox CDO®, and Cinnamon oil., and Cinnamon oil.

Another embodiment comprises cyclosporin A, a block polymer, and Cinnamon oil.

Another embodiment comprises cyclosporin A, AL 2070®, and Cinnamon oil.

Another embodiment comprises cyclosporin A, Antarox 17-R-2®, and Cinnamon oil.

Another embodiment comprises cyclosporin A, Antarox 25-R-2®, and Cinnamon oil.

Another embodiment comprises cyclosporin A, Antarox 31-R-1®, and Cinnamon oil.

Another embodiment comprises cyclosporin A, Antarox P-84®, and Cinnamon oil.

Another embodiment comprises cyclosporin A, Antarox P-104/H®, and Cinnamon oil.

Another embodiment comprises cyclosporin A, Arnox BP-Series®, and Cinnamon oil.

Another embodiment comprises cyclosporin A, Chemonic 435®, and Cinnamon oil.

Another embodiment comprises cyclosporin A, Chemonic D-25®, and Cinnamon oil.

Another embodiment comprises cyclosporin A, Chemonic PL Series®, and Cinnamon oil.

Another embodiment comprises cyclosporin A, Ethox L-121®, and Cinnamon oil.

Another embodiment comprises cyclosporin A, Ethox L-122®, and Cinnamon oil.

Another embodiment comprises cyclosporin A, Genapol PF-10®, and Cinnamon oil.

Another embodiment comprises cyclosporin A, Genapol PF-20®, and Cinnamon oil.

Another embodiment comprises cyclosporin A, Genapol PF-40A®, and Cinnamon oil.

Another embodiment comprises cyclosporin A, Norfox 2-LF®, and Cinnamon oil.

Another embodiment comprises cyclosporin A, Simulsol NW 342®, and Cinnamon oil.

Another embodiment comprises cyclosporin A, T-Det BP-1®, and Cinnamon oil.

Another embodiment comprises cyclosporin A, T-Det XD®, and Cinnamon oil.

Another embodiment comprises cyclosporin A, T-Det XH®, and Cinnamon oil.

Another embodiment comprises cyclosporin A, Triton CF-32®, and Cinnamon oil.

Another embodiment comprises cyclosporin A, Witconol 171®, and Cinnamon oil.

Another embodiment comprises cyclosporin A, Witconol 324®, and Cinnamon oil.

Another embodiment comprises cyclosporin A, Witconol 324D®, and Cinnamon oil.

Another embodiment comprises cyclosporin A, Witconol PD-2000®, and Cinnamon oil., and Cinnamon oil.

a Carboxylated Alcohol or Alkylphenol Ethoxylate, and Cinnamon oil.

Another embodiment comprises cyclosporin A, Emcol CN-6®, and Cinnamon oil.

Another embodiment comprises cyclosporin A, Ethcarb®, and Cinnamon oil.

Another embodiment comprises cyclosporin A, Gemtex WNT-Conc®, and Cinnamon oil.

Another embodiment comprises cyclosporin A, Incrodet TD7-C®, and Cinnamon oil.

Another embodiment comprises cyclosporin A, Marlinat CM 105/80®, and Cinnamon oil.

Another embodiment comprises cyclosporin A, Marlowet 1072®, and Cinnamon oil.

Another embodiment comprises cyclosporin A, Marlowet 4530®, and Cinnamon oil.

Another embodiment comprises cyclosporin A, Marlowet 4530 LF®, and Cinnamon oil.

Another embodiment comprises cyclosporin A, Marlowet 4534®, and Cinnamon oil.

Another embodiment comprises cyclosporin A, Marlowet 4538®, and Cinnamon oil.

Another embodiment comprises cyclosporin A, Marlowet 4539®, and Cinnamon oil.

Another embodiment comprises cyclosporin A, Marlowet 4539 LF®, and Cinnamon oil.

Another embodiment comprises cyclosporin A, Marlowet 4541®, and Cinnamon oil.

Another embodiment comprises cyclosporin A, Miranate LEC-80®, and Cinnamon oil.

Another embodiment comprises cyclosporin A, Sandopan B®, and Cinnamon oil.

Another embodiment comprises cyclosporin A, Sandopan B Modified®, and Cinnamon oil.

Another embodiment comprises cyclosporin A, Sandopan LS-24 Gel®, and Cinnamon oil.

Another embodiment comprises cyclosporin A, Surfine T-A®, and Cinnamon oil.

Another embodiment comprises cyclosporin A, and Cinnamon oil.

Another embodiment comprises cyclosporin A, a Carboxylic Acid/Fatty Acid, and Cinnamon oil.

Another embodiment comprises cyclosporin A, Colaterge RAM®, and Cinnamon oil.

Another embodiment comprises cyclosporin A, Colatrope INC®, and Cinnamon oil.

Another embodiment comprises cyclosporin A, Crodacid B®, and Cinnamon oil.

Another embodiment comprises cyclosporin A, DeTrope CA-100®, and Cinnamon oil.

Another embodiment comprises cyclosporin A, Latol MTO®, and Cinnamon oil.

Another embodiment comprises cyclosporin A, Lumulse CC-33 K®, and Cinnamon oil.

Another embodiment comprises cyclosporin A, Mulls 2218®; and Cinnamon oil.

Another embodiment comprises cyclosporin A, OL-600®, and Cinnamon oil.

Another embodiment comprises cyclosporin A, OL-800®, and Cinnamon oil.

Another embodiment comprises cyclosporin A, R-910®, and Cinnamon oil.

Another embodiment comprises cyclosporin A, S-210®, and Cinnamon oil.

Another embodiment comprises cyclosporin A, Sandopan DTC Acid®, and Cinnamon oil.

Another embodiment comprises cyclosporin A, Sandopan LS 24 N®, and Cinnamon oil.

Another embodiment comprises cyclosporin A, Sandopan MA-18®, and Cinnamon oil.

Another embodiment comprises cyclosporin A, and Cinnamon oil.

Another embodiment comprises cyclosporin A, an Ethoxylated Alcohol, and Cinnamon oil.

Another embodiment comprises cyclosporin A, Adsee 799®, and Cinnamon oil.

Another embodiment comprises cyclosporin A, Adsee 799®, and Cinnamon oil.

Another embodiment comprises cyclosporin A, Alfonic 610-3.5®, and Cinnamon oil.

Another embodiment comprises cyclosporin A, Alfonic 810-2®, and Cinnamon oil.

Another embodiment comprises cyclosporin A, Alfonic 810-6®, and Cinnamon oil.

Another embodiment comprises cyclosporin A, Alfonic 1012-3®, and Cinnamon oil.

Another embodiment comprises cyclosporin A, Alfonic 1012-5®, and Cinnamon oil.

Another embodiment comprises cyclosporin A, Alfonic 1216CO-1.5®, and Cinnamon oil.

Another embodiment comprises cyclosporin A, Alfonic 1216CO-7®, and Cinnamon oil.

Another embodiment comprises cyclosporin A, Alfonic 1412-3®, and Cinnamon oil.

Another embodiment comprises cyclosporin A, Alfonic 1412-7®, and Cinnamon oil.

Another embodiment comprises cyclosporin A, Arlasolve 200®, and Cinnamon oil.

Another embodiment comprises cyclosporin A, Arlasolve 200 Liquid®, and Cinnamon oil.

Another embodiment comprises cyclosporin A, Armix 180-C®, and Cinnamon oil.

Another embodiment comprises cyclosporin A, Armix 183®, and Cinnamon oil.

Another embodiment comprises cyclosporin A, Armul 2404®, and Cinnamon oil.

Another embodiment comprises cyclosporin A, Armul 2404®, and Cinnamon oil.

Another embodiment comprises cyclosporin A, Atlas EMJ-C®, and Cinnamon oil.

Another embodiment comprises cyclosporin A, Atlas G-2109®, and Cinnamon oil.

Another embodiment comprises cyclosporin A, Atlas G-3886®, and Cinnamon oil.

Another embodiment comprises cyclosporin A, Atlas G-3890®, and Cinnamon oil.

Another embodiment comprises cyclosporin A, Bio Soft E-200®, and Cinnamon oil.

Another embodiment comprises cyclosporin A, Bio Soft E-300®, and Cinnamon oil.

Another embodiment comprises cyclosporin A, Bio Soft E-400®, and Cinnamon oil.

Another embodiment comprises cyclosporin A, Bio Soft EN 600®, and Cinnamon oil.

Another embodiment comprises cyclosporin A, Bio Soft TD-400®, and Cinnamon oil.

Another embodiment comprises cyclosporin A, Bio Soft TD-630®, and Cinnamon oil.

Another embodiment comprises cyclosporin A, Brij 30®, and Cinnamon oil.

Another embodiment comprises cyclosporin A, Brij 52®, and Cinnamon oil.

Another embodiment comprises cyclosporin A, Brij 56®, and Cinnamon oil.

Another embodiment comprises cyclosporin A, Brij 58®, and Cinnamon oil.

Another embodiment comprises cyclosporin A, Brij 72®, and Cinnamon oil.

Another embodiment comprises cyclosporin A, Brij 76®, and Cinnamon oil.

Another embodiment comprises cyclosporin A, Brij 78®, and Cinnamon oil.

Another embodiment comprises cyclosporin A, Brij 93®, and Cinnamon oil.

Another embodiment comprises cyclosporin A, Brij 97®, and Cinnamon oil.

Another embodiment comprises cyclosporin A, Brij 98®, and Cinnamon oil.

Another embodiment comprises cyclosporin A, Brij 700®, and Cinnamon oil.

Another embodiment comprises cyclosporin A, Brij 700 S®, and Cinnamon oil.

Another embodiment comprises cyclosporin A, Brij 721®, and Cinnamon oil.

Another embodiment comprises cyclosporin A, Brij 721 S®, and Cinnamon oil.

Another embodiment comprises cyclosporin A, Burcoterge CDG®, and Cinnamon oil.

Another embodiment comprises cyclosporin A, Canasol AT 600®, and Cinnamon oil.

Another embodiment comprises cyclosporin A, Canasol AT 800®, and Cinnamon oil.

Another embodiment comprises cyclosporin A, Canasol AT 1200®, and Cinnamon oil.

Another embodiment comprises cyclosporin A, Canasol BJ 35®, and Cinnamon oil.

Another embodiment comprises cyclosporin A, Canasol BJ 36®, and Cinnamon oil.

Another embodiment comprises cyclosporin A, Canasol BJ 52®, and Cinnamon oil.
Another embodiment comprises cyclosporin A, Canasol BJ 58®, and Cinnamon oil.
Another embodiment comprises cyclosporin A, Canasol BJ 72®, and Cinnamon oil.
Another embodiment comprises cyclosporin A, Canasol BJ 78®, and Cinnamon oil.
Another embodiment comprises cyclosporin A, Canasol BJ 98®, and Cinnamon oil.
Another embodiment comprises cyclosporin A, Canasol BJ 307®, and Cinnamon oil.
Another embodiment comprises cyclosporin A, Cerfak 1400®, and Cinnamon oil.
Another embodiment comprises cyclosporin A, Cetomacrogol 1000 BP®, and Cinnamon oil.
Another embodiment comprises cyclosporin A, Chemonic C-2®, and Cinnamon oil.
Another embodiment comprises cyclosporin A, Chemonic C-10®, and Cinnamon oil.
Another embodiment comprises cyclosporin A, Chemonic C-20®, and Cinnamon oil.
Another embodiment comprises cyclosporin A, Chemonic CT-12®, and Cinnamon oil.
Another embodiment comprises cyclosporin A, Chemonic CT-20®, and Cinnamon oil.
Another embodiment comprises cyclosporin A, Chemonic CT-30®, and Cinnamon oil.
Another embodiment comprises cyclosporin A, Chemonic CT-55®, and Cinnamon oil.
Another embodiment comprises cyclosporin A, Chemonic G-7®, and Cinnamon oil.
Another embodiment comprises cyclosporin A, Chemonic G-26®, and Cinnamon oil.
Another embodiment comprises cyclosporin A, Chemonic L-4®, and Cinnamon oil.
Another embodiment comprises cyclosporin A, Chemonic L-7®, and Cinnamon oil.
Another embodiment comprises cyclosporin A, Chemonic L-12®, and Cinnamon oil.
Another embodiment comprises cyclosporin A, Chemonic L-23®, and Cinnamon oil.
Another embodiment comprises cyclosporin A, Chemonic O-2®, and Cinnamon oil.
Another embodiment comprises cyclosporin A, Chemonic O-5®, and Cinnamon oil.
Another embodiment comprises cyclosporin A, Chemonic O-10®, and Cinnamon oil.
Another embodiment comprises cyclosporin A, Chemonic O-20®, and Cinnamon oil.
Another embodiment comprises cyclosporin A, Chemonic S-2®, and Cinnamon oil.
Another embodiment comprises cyclosporin A, Chemonic S-10®, and Cinnamon oil.
Another embodiment comprises cyclosporin A, Chemonic S-20®, and Cinnamon oil.
Another embodiment comprises cyclosporin A, Colamulse FE®, and Cinnamon oil.
Another embodiment comprises cyclosporin A, Cremophor A 20®, and Cinnamon oil.
Another embodiment comprises cyclosporin A, Cremophor SA 2®, and Cinnamon oil.
Another embodiment comprises cyclosporin A, Dehydol 100®, and Cinnamon oil.
Another embodiment comprises cyclosporin A, Dehydol O-4®, and Cinnamon oil.
Another embodiment comprises cyclosporin A, Delonic C-18®, and Cinnamon oil.
Another embodiment comprises cyclosporin A, DeSonic 6T®, and Cinnamon oil.
Another embodiment comprises cyclosporin A, DeSonic 9D®, and Cinnamon oil.
Another embodiment comprises cyclosporin A, DeSonic 9T®, and Cinnamon oil.
Another embodiment comprises cyclosporin A, DeSonic 12D®, and Cinnamon oil.
Another embodiment comprises cyclosporin A, DeSonic 12T®, and Cinnamon oil.
Another embodiment comprises cyclosporin A, DeSonic 15T®, and Cinnamon oil.
Another embodiment comprises cyclosporin A, DeSonic TDA-9®, and Cinnamon oil.
Another embodiment comprises cyclosporin A, DeThox GLG-7®, and Cinnamon oil.
Another embodiment comprises cyclosporin A, DeThox GLG-26®, and Cinnamon oil.
Another embodiment comprises cyclosporin A, DeThox LA-4®, and Cinnamon oil.
Another embodiment comprises cyclosporin A, DeThox LA-23®, and Cinnamon oil.
Another embodiment comprises cyclosporin A, DeThox SA-80®, and Cinnamon oil.
Another embodiment comprises cyclosporin A, Disponil O5®, and Cinnamon oil.
Another embodiment comprises cyclosporin A, Eccoterge EO-41B®, and Cinnamon oil.
Another embodiment comprises cyclosporin A, Empilan KA2.5/90®, and Cinnamon oil.
Another embodiment comprises cyclosporin A, Empilan KA5/90®, and Cinnamon oil.
Another embodiment comprises cyclosporin A, Empilan KM-20®, and Cinnamon oil.
Another embodiment comprises cyclosporin A, Empilan KM-50®, and Cinnamon oil.
Another embodiment comprises cyclosporin A, Empilan L-23®, and Cinnamon oil.
Another embodiment comprises cyclosporin A, Ethylan 25-3®, and Cinnamon oil.
Another embodiment comprises cyclosporin A, Ethylan 1204®, and Cinnamon oil.
Another embodiment comprises cyclosporin A, Ethylan DA-4®, and Cinnamon oil.
Another embodiment comprises cyclosporin A, Ethylan LA-230®, and Cinnamon oil.
Another embodiment comprises cyclosporin A, Ethylan SN®, and Cinnamon oil.
Another embodiment comprises cyclosporin A, Ethylan TD-60®, and Cinnamon oil.
Another embodiment comprises cyclosporin A, Ethylan TD-100®, and Cinnamon oil.
Another embodiment comprises cyclosporin A, Ethylan TD-1407®, and Cinnamon oil.
Another embodiment comprises cyclosporin A, Eumulgin B1®, and Cinnamon oil.
Another embodiment comprises cyclosporin A, Eumulgin B2®, and Cinnamon oil.
Another embodiment comprises cyclosporin A, Eumulgin B3®, and Cinnamon oil.
Another embodiment comprises cyclosporin A, Eumulgin O-10®, and Cinnamon oil.
Another embodiment comprises cyclosporin A, Flo Mo 80/20®, and Cinnamon oil.

Another embodiment comprises cyclosporin A, Flo Mo Low Foam®, and Cinnamon oil.
Another embodiment comprises cyclosporin A, Forlan C-24®, and Cinnamon oil.
Another embodiment comprises cyclosporin A, Genapol 1454®, and Cinnamon oil.
Another embodiment comprises cyclosporin A, Genapol BA-020®, and Cinnamon oil.
Another embodiment comprises cyclosporin A, Genapol BA-040®, and Cinnamon oil.
Another embodiment comprises cyclosporin A, Genapol C-100®, and Cinnamon oil.
Another embodiment comprises cyclosporin A, Genapol DA 060®, and Cinnamon oil.
Another embodiment comprises cyclosporin A, Genapol HS 020®, and Cinnamon oil.
Another embodiment comprises cyclosporin A, Genapol HS 200®, and Cinnamon oil.
Another embodiment comprises cyclosporin A, Genapol ID-040®, and Cinnamon oil.
Another embodiment comprises cyclosporin A, Genapol ID-060®, and Cinnamon oil.
Another embodiment comprises cyclosporin A, Genapol ID-090®, and Cinnamon oil.
Another embodiment comprises cyclosporin A, Genapol LA 010®, and Cinnamon oil.
Another embodiment comprises cyclosporin A, Genapol LA 020®, and Cinnamon oil.
Another embodiment comprises cyclosporin A, Genapol LA 030®, and Cinnamon oil.
Another embodiment comprises cyclosporin A, Genapol LA 040®, and Cinnamon oil.
Another embodiment comprises cyclosporin A, Genapol LA 050®, and Cinnamon oil.
Another embodiment comprises cyclosporin A, Genapol LA 060®, and Cinnamon oil.
Another embodiment comprises cyclosporin A, Genapol LA 070®, and Cinnamon oil.
Another embodiment comprises cyclosporin A, Genapol LA 070S®, and Cinnamon oil.
Another embodiment comprises cyclosporin A, Genapol LA 230®, and Cinnamon oil.
Another embodiment comprises cyclosporin A, Genapol O 020®, and Cinnamon oil.
Another embodiment comprises cyclosporin A, Genapol O 050®, and Cinnamon oil.
Another embodiment comprises cyclosporin A, Genapol O 100®, and Cinnamon oil.
Another embodiment comprises cyclosporin A, Genapol O 200®, and Cinnamon oil.
Another embodiment comprises cyclosporin A, Genapol SA 030®, and Cinnamon oil.
Another embodiment comprises cyclosporin A, Genapol SA 120®, and Cinnamon oil.
Another embodiment comprises cyclosporin A, Genapol T-020®, and Cinnamon oil.
Another embodiment comprises cyclosporin A, Genapol UD-030®, and Cinnamon oil.
Another embodiment comprises cyclosporin A, Genapol UD-050®, and Cinnamon oil.
Another embodiment comprises cyclosporin A, Genapol UD-070®, and Cinnamon oil.
Another embodiment comprises cyclosporin A, Genapol UD-079®, and Cinnamon oil.
Another embodiment comprises cyclosporin A, Genapol UD-080®, and Cinnamon oil.
Another embodiment comprises cyclosporin A, Genapol UD-110®, and Cinnamon oil.
Another embodiment comprises cyclosporin A, Genapol X 030®, and Cinnamon oil.
Another embodiment comprises cyclosporin A, Genapol X 050®, and Cinnamon oil.
Another embodiment comprises cyclosporin A, Genapol X 060®, and Cinnamon oil.
Another embodiment comprises cyclosporin A, Genapol X 070®, and Cinnamon oil.
Another embodiment comprises cyclosporin A, Genapol X 080®, and Cinnamon oil.
Another embodiment comprises cyclosporin A, Genapol X 100®, and Cinnamon oil.
Another embodiment comprises cyclosporin A, Genapol X159®, and Cinnamon oil.
Another embodiment comprises cyclosporin A, Generol 122 E5®, and Cinnamon oil.
Another embodiment comprises cyclosporin A, Generol 122 E25®, and Cinnamon oil.
Another embodiment comprises cyclosporin A, Hostacerin T-3®, and Cinnamon oil.
Another embodiment comprises cyclosporin A, Iconol LF 110®, and Cinnamon oil.
Another embodiment comprises cyclosporin A, Incropol CS-20®, and Cinnamon oil.
Another embodiment comprises cyclosporin A, Lexemul CS-20®, and Cinnamon oil.
Another embodiment comprises cyclosporin A, Liponic EG-1®, and Cinnamon oil.
Another embodiment comprises cyclosporin A, Lipowax D®, and Cinnamon oil.
Another embodiment comprises cyclosporin A, Lipowax G®, and Cinnamon oil.
Another embodiment comprises cyclosporin A, Lipowax NI®, and Cinnamon oil.
Another embodiment comprises cyclosporin A, Lipowax P®, and Cinnamon oil;
Another embodiment comprises cyclosporin A, Lipowax P-31®, and Cinnamon oil.
Another embodiment comprises cyclosporin A, Lipowax PR®, and Cinnamon oil.
Another embodiment comprises cyclosporin A, Lumulse CS-20®, and Cinnamon oil.
Another embodiment comprises cyclosporin A, Macol CSA-20®, and Cinnamon oil.
Another embodiment comprises cyclosporin A, Marlox B 24/50S, and Cinnamon oil.
Another embodiment comprises cyclosporin A, Mazawet 77®, and Cinnamon oil.
Another embodiment comprises cyclosporin A, Norfox 1713®, and Cinnamon oil.
Another embodiment comprises cyclosporin A, Norfox 2579®, and Cinnamon oil.
Another embodiment comprises cyclosporin A, Norfox Lo Foam®, and Cinnamon oil.
Another embodiment comprises cyclosporin A, Promulgen D®, and Cinnamon oil.
Another embodiment comprises cyclosporin A, Promulgen G®, and Cinnamon oil.
Another embodiment comprises cyclosporin A, Renex 30®, and Cinnamon oil.
Another embodiment comprises cyclosporin A, Renex 36®, and Cinnamon oil.
Another embodiment comprises cyclosporin A, Rhodasurf A 24®, and Cinnamon oil.

Another embodiment comprises cyclosporin A, Rhodasurf AAE-10®, and Cinnamon oil.
Another embodiment comprises cyclosporin A, Rhodasurf BEH-25®, and Cinnamon oil.
Another embodiment comprises cyclosporin A, Rhodasurf BEH-40®, and Cinnamon oil.
Another embodiment comprises cyclosporin A, Rhodasurf DA 530®, and Cinnamon oil.
Another embodiment comprises cyclosporin A, Rhodasurf DA 630®, and Cinnamon oil.
Another embodiment comprises cyclosporin A, Rhodasurf DA 639®, and Cinnamon oil.
Another embodiment comprises cyclosporin A, Rhodasurf LAN-23®, and Cinnamon oil.
Another embodiment comprises cyclosporin A, Rhodasurf ON-870®, and Cinnamon oil.
Another embodiment comprises cyclosporin A, Rhodasurf ON-877®, and Cinnamon oil.
Another embodiment comprises cyclosporin A, Rhodasurf TB-970 FLK®, and Cinnamon oil.
Another embodiment comprises cyclosporin A, Ritacet-20®, and Cinnamon oil.
Another embodiment comprises cyclosporin A, Ritachol 1000®, and Cinnamon oil.
Another embodiment comprises cyclosporin A, Ritachol 2000®, and Cinnamon oil.
Another embodiment comprises cyclosporin A, Ritachol 5000®, and Cinnamon oil.
Another embodiment comprises cyclosporin A, Ritox 35®, and Cinnamon oil.
Another embodiment comprises cyclosporin A, Surfonic DA-4®, and Cinnamon oil.
Another embodiment comprises cyclosporin A, Surfonic DA-6®, and Cinnamon oil.
Another embodiment comprises cyclosporin A, Surfonic L46-7®, and Cinnamon oil.
Another embodiment comprises cyclosporin A, Surfonic POA®, and Cinnamon oil.
Another embodiment comprises cyclosporin A, Synthrapol KB®, and Cinnamon oil.
Another embodiment comprises cyclosporin A, Teginacid®, and Cinnamon oil.
Another embodiment comprises cyclosporin A, Teginacid C®, and Cinnamon oil.
Another embodiment comprises cyclosporin A, Tegotens EC 11®, and Cinnamon oil.
Another embodiment comprises cyclosporin A, Tinegal NA®, and Cinnamon oil.
Another embodiment comprises cyclosporin A, Tomadol 400®, and Cinnamon oil.
Another embodiment comprises cyclosporin A, Tomadol 600®, and Cinnamon oil.
Another embodiment comprises cyclosporin A, Tomadol 900®, and Cinnamon oil.
Another embodiment comprises cyclosporin A, Uniperol O®, and Cinnamon oil.
Another embodiment comprises cyclosporin A, Witconol SN Series®, and Cinnamon oil.
Another embodiment comprises cyclosporin A, and Cinnamon oil.
Another embodiment comprises cyclosporin A, an Ethoxylated Alkylphenol, and Cinnamon oil.
Another embodiment comprises cyclosporin A, Antarox LF-222®, and Cinnamon oil.
Another embodiment comprises cyclosporin A, Atlox 775®, and Cinnamon oil.
Another embodiment comprises cyclosporin A, Caloxylate N-9®, and Cinnamon oil.
Another embodiment comprises cyclosporin A, Canasol NF-1000®, and Cinnamon oil.
Another embodiment comprises cyclosporin A, Canasol NF-3000®, and Cinnamon oil.
Another embodiment comprises cyclosporin A, Canasol NF-3070®, and Cinnamon oil.
Another embodiment comprises cyclosporin A, Canasol OF 1670®, and Cinnamon oil.
Another embodiment comprises cyclosporin A, Canasol OF 2570®, and Cinnamon oil.
Another embodiment comprises cyclosporin A, Canasol OF 4070®, and Cinnamon oil.
Another embodiment comprises cyclosporin A, Chemax DNP-83, and Cinnamon oil.
Another embodiment comprises cyclosporin A, Chemax DNP-18®, and Cinnamon oil.
Another embodiment comprises cyclosporin A, Chemax DNP-150/50®, and Cinnamon oil.
Another embodiment comprises cyclosporin A, DeSonic 1.5N®, and Cinnamon oil.
Another embodiment comprises cyclosporin A, DeSonic 4N®, and Cinnamon oil.
Another embodiment comprises cyclosporin A, DeSonic 5N®, and Cinnamon oil.
Another embodiment comprises cyclosporin A, DeSonic 6D®, and Cinnamon oil.
Another embodiment comprises cyclosporin A, DeSonic 6N®, and Cinnamon oil.
Another embodiment comprises cyclosporin A, DeSonic 7N®, and Cinnamon oil.
Another embodiment comprises cyclosporin A, DeSonic 9N®, and Cinnamon oil.
Another embodiment comprises cyclosporin A, DeSonic 10D®, and Cinnamon oil.
Another embodiment comprises cyclosporin A, DeSonic 11N®, and Cinnamon oil.
Another embodiment comprises cyclosporin A, DeSonic 12N®, and Cinnamon oil.
Another embodiment comprises cyclosporin A, DeSonic 15N®, and Cinnamon oil.
Another embodiment comprises cyclosporin A, DeSonic 20N®, and Cinnamon oil.
Another embodiment comprises cyclosporin A, Eccoscour RC®, and Cinnamon oil.
Another embodiment comprises cyclosporin A, Eccoterge EO-100®, and Cinnamon oil.
Another embodiment comprises cyclosporin A, Emulsifier 632/90%®, and Cinnamon oil.
Another embodiment comprises cyclosporin A, Geronol AG-821®, and Cinnamon oil.
Another embodiment comprises cyclosporin A, Gradonic N-95®, and Cinnamon oil.
Another embodiment comprises cyclosporin A, Hetoxide NP-4®, and Cinnamon oil.
Another embodiment comprises cyclosporin A, Hetoxide NP-30®, and Cinnamon oil.
Another embodiment comprises cyclosporin A, Hostapal N-100®, and Cinnamon oil.
Another embodiment comprises cyclosporin A, Hostapal N-110®, and Cinnamon oil.
Another embodiment comprises cyclosporin A, Igepal CTA-639W®, and Cinnamon oil.
Another embodiment comprises cyclosporin A, Igepal DAP-9®, and Cinnamon oil.

Another embodiment comprises cyclosporin A, Igepal OD-410®, and Cinnamon oil.

Another embodiment comprises cyclosporin A, Igepal SS-837®, and Cinnamon oil.

Another embodiment comprises cyclosporin A, Lipocol NP-9 USP®, and Cinnamon oil.

Another embodiment comprises cyclosporin A, Macol DNP-10®, and Cinnamon oil.

Another embodiment comprises cyclosporin A, Marlophen NP 5®, and Cinnamon oil.

Another embodiment comprises cyclosporin A, Marlophen P 1®, and Cinnamon oil.

Another embodiment comprises cyclosporin A, Surfonic NB®, and Cinnamon oil.

Another embodiment comprises cyclosporin A, Surfonic OPB-307®, and Cinnamon oil.

Another embodiment comprises cyclosporin A, Surfonic OPB-407®, and Cinnamon oil.

Another embodiment comprises cyclosporin A, Syn Fac 334®, and Cinnamon oil.

Another embodiment comprises cyclosporin A, Syn Fac 8216®, and Cinnamon oil.

Another embodiment comprises cyclosporin A, Triton N-57®, and Cinnamon oil.

Another embodiment comprises cyclosporin A, Trycol 6956®, and Cinnamon oil.

Another embodiment comprises cyclosporin A, Trycol 6961®, and Cinnamon oil.

Another embodiment comprises cyclosporin A, Trycol 6964®, and Cinnamon oil.

Another embodiment comprises cyclosporin A, Trycol 6969®, and Cinnamon oil.

Another embodiment comprises cyclosporin A, Trycol 6974®, and Cinnamon oil.

Another embodiment comprises cyclosporin A, Witbreak DRB-127®, and Cinnamon oil.

Another embodiment comprises cyclosporin A, Witbreak DRB-127®, and Cinnamon oil.

Another embodiment comprises cyclosporin A, Witconol NP Series®, and Cinnamon oil.

Another embodiment comprises cyclosporin A, and Cinnamon oil.

Another embodiment comprises cyclosporin A, an Ethoxylated Aryl Phenol, and Cinnamon oil.

Another embodiment comprises cyclosporin A, Soprophor BSU®, and Cinnamon oil.

Another embodiment comprises cyclosporin A, Soprophor CY/8®, and Cinnamon oil.

Another embodiment comprises cyclosporin A, Soprophor S/25®, and Cinnamon oil.

Another embodiment comprises cyclosporin A, Witconol NIO®, and Cinnamon oil.

Another embodiment comprises cyclosporin A, Witconol NIW®, and Cinnamon oil.

Another embodiment comprises cyclosporin A, Witconol S-100®, and Cinnamon oil.

Another embodiment comprises cyclosporin A, and Cinnamon oil.

Another embodiment comprises cyclosporin A, an Ethoxylated Fatty Acid, and Cinnamon oil.

Another embodiment comprises cyclosporin A, Aldo PGHMS®, and Cinnamon oil.

Another embodiment comprises cyclosporin A, Alkamuls TO-15/HR®, and Cinnamon oil.

Another embodiment comprises cyclosporin A, Armotan AL-69-66®, and Cinnamon oil.

Another embodiment comprises cyclosporin A, Cerasynt 840®, and Cinnamon oil.

Another embodiment comprises cyclosporin A, Cerasynt 945®, and Cinnamon oil.

Another embodiment comprises cyclosporin A, Crystal Inhibitor No. 5®, and Cinnamon oil.

Another embodiment comprises cyclosporin A, DeThox Acid L-9®, and Cinnamon oil.

Another embodiment comprises cyclosporin A, DeThox Acid S-8®, and Cinnamon oil.

Another embodiment comprises cyclosporin A, Ethofat 242/25®, and Cinnamon oil.

Another embodiment comprises cyclosporin A, Hydropalat 65®, and Cinnamon oil.

Another embodiment comprises cyclosporin A, Lipo EGMS®, and Cinnamon oil.

Another embodiment comprises cyclosporin A, Lipopeg 2 DL®, and Cinnamon oil.

Another embodiment comprises cyclosporin A, Lipopeg 4 DL®, and Cinnamon oil.

Another embodiment comprises cyclosporin A, Lipopeg 4-L®, and Cinnamon oil.

Another embodiment comprises cyclosporin A, Lipopeg 39-S®, and Cinnamon oil.

Another embodiment comprises cyclosporin A, Lipopeg 4-S®, and Cinnamon oil.

Another embodiment comprises cyclosporin A, Lipopeg 10-S®, and Cinnamon oil.

Another embodiment comprises cyclosporin A, Lipopeg 100-S®, and Cinnamon oil.

Another embodiment comprises cyclosporin A, Lipopeg 6000 DS®, and Cinnamon oil.

Another embodiment comprises cyclosporin A, Lumulse 40-L®, and Cinnamon oil.

Another embodiment comprises cyclosporin A, Lumulse 40-S®, and Cinnamon oil.

Another embodiment comprises cyclosporin A, Lumulse 42-L®, and Cinnamon oil.

Another embodiment comprises cyclosporin A, Lumulse 42-S®, and Cinnamon oil.

Another embodiment comprises cyclosporin A, Lumulse 100-S®, and Cinnamon oil.

Another embodiment comprises cyclosporin A, Lumulse 602-S®, and Cinnamon oil.

Another embodiment comprises cyclosporin A, Magrabar PGE-20-0®, and Cinnamon oil.

Another embodiment comprises cyclosporin A, Magrabar PGE-20L®, and Cinnamon oil.

Another embodiment comprises cyclosporin A, Magrabar PGE-20T®, and Cinnamon oil.

Another embodiment comprises cyclosporin A, Magrabar PGE-22-0®, and Cinnamon oil.

Another embodiment comprises cyclosporin A, Magrabar PGE-22L®, and Cinnamon oil.

Another embodiment comprises cyclosporin A, Magrabar PGE-22T®, and Cinnamon oil.

Another embodiment comprises cyclosporin A, Magrabar PGE-40-0®, and Cinnamon oil.

Another embodiment comprises cyclosporin A, Magrabar PGE-40L®, and Cinnamon oil.

Another embodiment comprises cyclosporin A, Magrabar PGE-40T®, and Cinnamon oil.

Another embodiment comprises cyclosporin A, Magrabar PGE-42-0®, and Cinnamon oil.

Another embodiment comprises cyclosporin A, Magrabar PGE-42L®, and Cinnamon oil.

Another embodiment comprises cyclosporin A, Magrabar PGE-42T®, and Cinnamon oil.

Another embodiment comprises cyclosporin A, Magrabar PGE-60-0®, and Cinnamon oil.

Another embodiment comprises cyclosporin A, Magrabar PGE-60L®, and Cinnamon oil.

Another embodiment comprises cyclosporin A, Magrabar PGE-60T®, and Cinnamon oil.

Another embodiment comprises cyclosporin A, Magrabar PGE-62-0®, and Cinnamon oil.

Another embodiment comprises cyclosporin A, Magrabar PGE-62L®, and Cinnamon oil.

Another embodiment comprises cyclosporin A, Magrabar PGE-62T®, and Cinnamon oil.

Another embodiment comprises cyclosporin A, Mapeg S-40K®, and Cinnamon oil.

Another embodiment comprises cyclosporin A, Marlowet OTS®, and Cinnamon oil.

Another embodiment comprises cyclosporin A, Naturechem PGR®, and Cinnamon oil.

Another embodiment comprises cyclosporin A, PG No. 4®, and Cinnamon oil.

Another embodiment comprises cyclosporin A, Renex 20®, and Cinnamon oil.

Another embodiment comprises cyclosporin A, Ritox 52®, and Cinnamon oil.

Another embodiment comprises cyclosporin A, Ritox 53®, and Cinnamon oil.

Another embodiment comprises cyclosporin A, Ritox 59®, and Cinnamon oil.

Another embodiment comprises cyclosporin A, Sunax 8916/A®, and Cinnamon oil.

Another embodiment comprises cyclosporin A, Tego Acid S 40 P®, and Cinnamon oil.

Another embodiment comprises cyclosporin A, Tego Acid S 100 P®, and Cinnamon oil.

Another embodiment comprises cyclosporin A, Tween 20®, and Cinnamon oil.

Another embodiment comprises cyclosporin A, Volpo 131®, and Cinnamon oil.

Another embodiment comprises cyclosporin A, and Cinnamon oil.

Another embodiment comprises cyclosporin A, an Ethoxylated Fatty Ester or Oil, and Cinnamon oil.

Another embodiment comprises cyclosporin A, Acconon 6-C10®, and Cinnamon oil.

Another embodiment comprises cyclosporin A, Acconon CC-6®, and Cinnamon oil.

Another embodiment comprises cyclosporin A, Acconon CO-7®, and Cinnamon oil.

Another embodiment comprises cyclosporin A, Aldosperse 40/60 FG®, and Cinnamon oil.

Another embodiment comprises cyclosporin A, Aldosperse ML-23®, and Cinnamon oil.

Another embodiment comprises cyclosporin A, Aldosperse MS-20 FG®, and Cinnamon oil.

Another embodiment comprises cyclosporin A, Alkamuls EL-620®, and Cinnamon oil.

Another embodiment comprises cyclosporin A, Alkamuls EL-719®, and Cinnamon oil.

Another embodiment comprises cyclosporin A, Alkamuls EL-985®, and Cinnamon oil.

Another embodiment comprises cyclosporin A, Arlatone G®, and Cinnamon oil.

Another embodiment comprises cyclosporin A, Arlatone T®, and Cinnamon oil.

Another embodiment comprises cyclosporin A, Atlas G-1045A®, and Cinnamon oil.

Another embodiment comprises cyclosporin A, Atlas G-1086®, and Cinnamon oil.

Another embodiment comprises cyclosporin A, Atlas G-1087®, and Cinnamon oil.

Another embodiment comprises cyclosporin A, Atlas G-1089®, and Cinnamon oil.

Another embodiment comprises cyclosporin A, Atlas G-1096®, and Cinnamon oil.

Another embodiment comprises cyclosporin A, Atlas G-1292®, and Cinnamon oil.

Another embodiment comprises cyclosporin A, Atlas G-1293®, and Cinnamon oil.

Another embodiment comprises cyclosporin A, Atlas G-1300®, and Cinnamon oil.

Another embodiment comprises cyclosporin A, Atlas G-7076®, and Cinnamon oil.

Another embodiment comprises cyclosporin A, Capmul EMG®, and Cinnamon oil.

Another embodiment comprises cyclosporin A, Chemonic CO-40®, and Cinnamon oil.

Another embodiment comprises cyclosporin A, Chemonic LI-3®, and Cinnamon oil.

Another embodiment comprises cyclosporin A, Chemonic LI-7®, and Cinnamon oil.

Another embodiment comprises cyclosporin A, Cirrasol GM®, and Cinnamon oil.

Another embodiment comprises cyclosporin A, Cremophor CO 40®, and Cinnamon oil.

Another embodiment comprises cyclosporin A, Cremophor CO 410®, and Cinnamon oil.

Another embodiment comprises cyclosporin A, Cremophor EL®, and Cinnamon oil.

Another embodiment comprises cyclosporin A, Cremophor GC7®, and Cinnamon oil.

Another embodiment comprises cyclosporin A, Cremophor RH-40®, and Cinnamon oil.

Another embodiment comprises cyclosporin A, Crovol A-40®, and Cinnamon oil.

Another embodiment comprises cyclosporin A, Crovol A-70®, and Cinnamon oil.

Another embodiment comprises cyclosporin A, Crovol M-70®, and Cinnamon oil.

Another embodiment comprises cyclosporin A, Crovol PK-70®, and Cinnamon oil.

Another embodiment comprises cyclosporin A, Cutina E-24®, and Cinnamon oil.

Another embodiment comprises cyclosporin A, Dacospin 12-R®, and Cinnamon oil.

Another embodiment comprises cyclosporin A, Dehymuls HRE-7®, and Cinnamon oil.

Another embodiment comprises cyclosporin A, DeSonic 30C®, and Cinnamon oil.

Another embodiment comprises cyclosporin A, DeSonic 36C®, and Cinnamon oil.

Another embodiment comprises cyclosporin A, DeSonic 40C®, and Cinnamon oil.

Another embodiment comprises cyclosporin A, Durfax 60®, and Cinnamon oil.

Another embodiment comprises cyclosporin A, Durfax 65®, and Cinnamon oil.

Another embodiment comprises cyclosporin A, Durfax 80®, and Cinnamon oil.

Another embodiment comprises cyclosporin A, Durfax EOM®, and Cinnamon oil.

Another embodiment comprises cyclosporin A, Eccoterge NF-2®, and Cinnamon oil.

Another embodiment comprises cyclosporin A, Emulpon CO-360®, and Cinnamon oil.

Another embodiment comprises cyclosporin A, Emulpon CO-550®, and Cinnamon oil.

Another embodiment comprises cyclosporin A, Emulsogen EL®, and Cinnamon oil.

Another embodiment comprises cyclosporin A, Emulsogen HCO 040®, and Cinnamon oil.

Another embodiment comprises cyclosporin A, Emulsogen HCO 060®, and Cinnamon oil.

Another embodiment comprises cyclosporin A, Emulsynt 1055®, and Cinnamon oil.

Another embodiment comprises cyclosporin A, Ethox 3095®, and Cinnamon oil.

Another embodiment comprises cyclosporin A, Eumulgin RO-40®, and Cinnamon oil.

Another embodiment comprises cyclosporin A, Genapol G-260®, and Cinnamon oil.

Another embodiment comprises cyclosporin A, Glycosperse L-20®, and Cinnamon oil.

Another embodiment comprises cyclosporin A, Glycosperse O-5®, and Cinnamon oil.

Another embodiment comprises cyclosporin A, Glycosperse O-20®, and Cinnamon oil.

Another embodiment comprises cyclosporin A, Glycosperse O-20 FG®, and Cinnamon oil.

Another embodiment comprises cyclosporin A, Glycosperse S-20®, and Cinnamon oil.

Another embodiment comprises cyclosporin A, Glycosperse S-20 FG®, and Cinnamon oil.

Another embodiment comprises cyclosporin A, Glycosperse TS-20®, and Cinnamon oil.

Another embodiment comprises cyclosporin A, Glycosperse TS-20 FG®, and Cinnamon oil.

Another embodiment comprises cyclosporin A, Hetan SL®, and Cinnamon oil.

Another embodiment comprises cyclosporin A, Hetan SO®, and Cinnamon oil.

Another embodiment comprises cyclosporin A, Hetan SS®, and Cinnamon oil.

Another embodiment comprises cyclosporin A, Hetoxide C-2®, and Cinnamon oil.

Another embodiment comprises cyclosporin A, Hetoxide C-9®, and Cinnamon oil.

Another embodiment comprises cyclosporin A, Hetoxide C-15®, and Cinnamon oil.

Another embodiment comprises cyclosporin A, Hetoxide C-25®, and Cinnamon oil.

Another embodiment comprises cyclosporin A, Hetoxide C-40®, and Cinnamon oil.

Another embodiment comprises cyclosporin A, Hetoxide C-200®, and Cinnamon oil.

Another embodiment comprises cyclosporin A, Hetoxide C-200-50%®, and Cinnamon oil.

Another embodiment comprises cyclosporin A, Hetoxide GC-30®, and Cinnamon oil.

Another embodiment comprises cyclosporin A, Hetoxide HC-60®, and Cinnamon oil.

Another embodiment comprises cyclosporin A, Ice No. 2®, and Cinnamon oil.

Another embodiment comprises cyclosporin A, Incrocas 30/40®, and Cinnamon oil.

Another embodiment comprises cyclosporin A, Lexol EC®, and Cinnamon oil.

Another embodiment comprises cyclosporin A, Lexol EO®, and Cinnamon oil.

Another embodiment comprises cyclosporin A, Lipocol HCO-40®, and Cinnamon oil.

Another embodiment comprises cyclosporin A, Lipocol HCO-60®, and Cinnamon oil.

Another embodiment comprises cyclosporin A, Lipocol O-3 Special®, and Cinnamon oil.

Another embodiment comprises cyclosporin A, Lipopeg 2-L®, and Cinnamon oil.

Another embodiment comprises cyclosporin A, Lipopeg 4-DO®, and Cinnamon oil.

Another embodiment comprises cyclosporin A, Lipopeg 4-DS®, and Cinnamon oil.

Another embodiment comprises cyclosporin A, Lipovol GTB®, and Cinnamon oil.

Another embodiment comprises cyclosporin A, Lonzest SML-20®, and Cinnamon oil.

Another embodiment comprises cyclosporin A, Lonzest SMO-20®, and Cinnamon oil.

Another embodiment comprises cyclosporin A, Lonzest SMS-20®, and Cinnamon oil.

Another embodiment comprises cyclosporin A, Lonzest STO-20®, and Cinnamon oil.

Another embodiment comprises cyclosporin A, Lonzest STS-20®, and Cinnamon oil.

Another embodiment comprises cyclosporin A, Lumulse GR-40®, and Cinnamon oil.

Another embodiment comprises cyclosporin A, Lumulse GRH-40®, and Cinnamon oil.

Another embodiment comprises cyclosporin A, Lumulse POE (7) GML®, and Cinnamon oil.

Another embodiment comprises cyclosporin A, Lumulse POE (12) Glyc®, and Cinnamon oil.

Another embodiment comprises cyclosporin A, Lumulse POE (40) MS KP®, and Cinnamon oil.

Another embodiment comprises cyclosporin A, Marlowet 4750®, and Cinnamon oil.

Another embodiment comprises cyclosporin A, Marlowet LVS®, and Cinnamon oil.

Another embodiment comprises cyclosporin A, Marlowet R 11®, and Cinnamon oil.

Another embodiment comprises cyclosporin A, Marlowet R 40®, and Cinnamon oil.

Another embodiment comprises cyclosporin A, Mazol 80 MGK®, and Cinnamon oil.

Another embodiment comprises cyclosporin A, Nonionic Emulsifier T-9®, and Cinnamon oil.

Another embodiment comprises cyclosporin A, Oronal LCG®, and Cinnamon oil.

Another embodiment comprises cyclosporin A, Polyderm PPI-CO-200®, and Cinnamon oil.

Another embodiment comprises cyclosporin A, Polyderm PPI-CO-40®, and Cinnamon oil.

Another embodiment comprises cyclosporin A, Rewoderm LI 520-70®, and Cinnamon oil.

Another embodiment comprises cyclosporin A, Ritapeg 150 DS®, and Cinnamon oil.

Another embodiment comprises cyclosporin A, Softigen 767®, and Cinnamon oil.

Another embodiment comprises cyclosporin A, Surfactol 318®, and Cinnamon oil.

Another embodiment comprises cyclosporin A, Surfactol 365®, and Cinnamon oil.

Another embodiment comprises cyclosporin A, Syn Lube 107®, and Cinnamon oil.

Another embodiment comprises cyclosporin A, Syn Lube 728®, and Cinnamon oil.

Another embodiment comprises cyclosporin A, Syn Lube 1632H®, and Cinnamon oil.

Another embodiment comprises cyclosporin A, Syn Lube 6277-A®, and Cinnamon oil.

Another embodiment comprises cyclosporin A, T-Det C-20®, and Cinnamon oil.

Another embodiment comprises cyclosporin A, T-Det C-40®, and Cinnamon oil.

Another embodiment comprises cyclosporin A, Tally 100 Plus®, and Cinnamon oil.

Another embodiment comprises cyclosporin A, Uniperol EL®, and Cinnamon oil.

Another embodiment comprises cyclosporin A, and Cinnamon oil.

Another embodiment comprises cyclosporin A, a Fatty Ester, and Cinnamon oil.

Another embodiment comprises cyclosporin A, Actralube-Syn 147®, and Cinnamon oil.

Another embodiment comprises cyclosporin A, Atlas G-1556®, and Cinnamon oil.

Another embodiment comprises cyclosporin A, Atlas G-1564®, and Cinnamon oil.

Another embodiment comprises cyclosporin A, Atlasol Base Oil S®, and Cinnamon oil.

Another embodiment comprises cyclosporin A, Base ML®, and Cinnamon oil.

Another embodiment comprises cyclosporin A, Base MT®, and Cinnamon oil.

Another embodiment comprises cyclosporin A, Cerasynt 303®, and Cinnamon oil.

Another embodiment comprises cyclosporin A, Dermol 1012®, and Cinnamon oil.

Another embodiment comprises cyclosporin A, Kemester 4000®, and Cinnamon oil.

Another embodiment comprises cyclosporin A, Lactipol S®, and Cinnamon oil.

Another embodiment comprises cyclosporin A, Magrabar PGO®, and Cinnamon oil.

Another embodiment comprises cyclosporin A, Mayco Base BFO®, and Cinnamon oil.

Another embodiment comprises cyclosporin A, Methyl Linoleate®, and Cinnamon oil.

Another embodiment comprises cyclosporin A, Pationic 122A®, and Cinnamon oil.

Another embodiment comprises cyclosporin A, Pationic 138C®, and Cinnamon oil.

Another embodiment comprises cyclosporin A, Pationic CSL®, and Cinnamon oil.

Another embodiment comprises cyclosporin A, Pationic ISL®, and Cinnamon oil.

Another embodiment comprises cyclosporin A, Pationic SBL®, and Cinnamon oil.

Another embodiment comprises cyclosporin A, Pationic SSL®, and Cinnamon oil.

Another embodiment comprises cyclosporin A, Ritasol®, and Cinnamon oil.

Another embodiment comprises cyclosporin A, Tego Alkanol CS 20®, and Cinnamon oil.

Another embodiment comprises cyclosporin A, Tego Alkanol L23 P®, and Cinnamon oil.

Another embodiment comprises cyclosporin A, Tego Alkanol S2®, and Cinnamon oil.

Another embodiment comprises cyclosporin A, Tego Alkanol S20 P®, and Cinnamon oil.

Another embodiment comprises cyclosporin A, Triemulsifier 600 MS®, and Cinnamon oil.

Another embodiment comprises cyclosporin A, and Cinnamon oil.

Another embodiment comprises cyclosporin A, a Glycerol Esters, and Cinnamon oil.

Another embodiment comprises cyclosporin A, Agro #9 Wint SBO®, and Cinnamon oil.

Another embodiment comprises cyclosporin A, Ahcovel Base 700®, and Cinnamon oil.

Another embodiment comprises cyclosporin A, Aldo HMS FG®, and Cinnamon oil.

Another embodiment comprises cyclosporin A, Aldo MLD®, and Cinnamon oil.

Another embodiment comprises cyclosporin A, Aldo MLD FG®, and Cinnamon oil.

Another embodiment comprises cyclosporin A, Aldo MO FG®, and Cinnamon oil.

Another embodiment comprises cyclosporin A, Aldo MS®, and Cinnamon oil.

Another embodiment comprises cyclosporin A, Aldo MS FG®, and Cinnamon oil.

Another embodiment comprises cyclosporin A, Aldo MS LG FG®, and Cinnamon oil.

Another embodiment comprises cyclosporin A, Aldo MSD®, and Cinnamon oil.

Another embodiment comprises cyclosporin A, Aldo MSD FG®, and Cinnamon oil.

Another embodiment comprises cyclosporin A, Aldosperse O-20 FG®, and Cinnamon oil.

Another embodiment comprises cyclosporin A, Aldosperse TS-20 FG®, and Cinnamon oil.

Another embodiment comprises cyclosporin A, Aldosperse TS-40 FG®, and Cinnamon oil.

Another embodiment comprises cyclosporin A, Arlacel 165®, and Cinnamon oil.

Another embodiment comprises cyclosporin A, Arlacel 186®, and Cinnamon oil.

Another embodiment comprises cyclosporin A, Capmul GMO®, and Cinnamon oil.

Another embodiment comprises cyclosporin A, Capmul GMS®, and Cinnamon oil.

Another embodiment comprises cyclosporin A, Caprol 3GO®, and Cinnamon oil.

Another embodiment comprises cyclosporin A, Caprol 3GVS®, and Cinnamon oil.

Another embodiment comprises cyclosporin A, Caprol 6G2S®, and Cinnamon oil.

Another embodiment comprises cyclosporin A, Caprol 10G4O®, and Cinnamon oil.

Another embodiment comprises cyclosporin A, Caprol 10G100®, and Cinnamon oil.

Another embodiment comprises cyclosporin A, Caprol ET®, and Cinnamon oil.

Another embodiment comprises cyclosporin A, Caprol PGE860®, and Cinnamon oil.

Another embodiment comprises cyclosporin A, Cerasynt 945®, and Cinnamon oil.

Another embodiment comprises cyclosporin A, Cerasynt GMS®, and Cinnamon oil.

Another embodiment comprises cyclosporin A, Cerasynt Q®, and Cinnamon oil.

Another embodiment comprises cyclosporin A, Cerasynt SD®, and Cinnamon oil.

Another embodiment comprises cyclosporin A, Cerasynt WM®, and Cinnamon oil.

Another embodiment comprises cyclosporin A, Chemsperse 14®, and Cinnamon oil.

Another embodiment comprises cyclosporin A, Cremophor GO-32®, and Cinnamon oil.

Another embodiment comprises cyclosporin A, Cremophor GS11®, and Cinnamon oil.

Another embodiment comprises cyclosporin A, Cremophor GS-32®, and Cinnamon oil.

Another embodiment comprises cyclosporin A, Cutina KD-16®, and Cinnamon oil.

Another embodiment comprises cyclosporin A, Dehymuls PGPH®, and Cinnamon oil.

Another embodiment comprises cyclosporin A, Dermol DGDIS®, and Cinnamon oil.

Another embodiment comprises cyclosporin A, Dermol DGMIS®, and Cinnamon oil.

Another embodiment comprises cyclosporin A, Dermol G-76®, and Cinnamon oil.

Another embodiment comprises cyclosporin A, Dermol G-7DI®, and Cinnamon oil.

Another embodiment comprises cyclosporin A, Dermol NGDI®, and Cinnamon oil.

Another embodiment comprises cyclosporin A, Dermolan GLH®, and Cinnamon oil.

Another embodiment comprises cyclosporin A, Drewmulse GMO®, and Cinnamon oil.

Another embodiment comprises cyclosporin A, Drewpol 3-5-M®, and Cinnamon oil.

Another embodiment comprises cyclosporin A, Durlac 100 W®, and Cinnamon oil.

Another embodiment comprises cyclosporin A, Dur-Lo®, and Cinnamon oil.

Another embodiment comprises cyclosporin A, Dynasan 118®, and Cinnamon oil.

Another embodiment comprises cyclosporin A, EC-25®, and Cinnamon oil.

Another embodiment comprises cyclosporin A, EM 40®, and Cinnamon oil.

Another embodiment comprises cyclosporin A, Emerest 2400®, and Cinnamon oil.

Another embodiment comprises cyclosporin A, Emerest 2452®, and Cinnamon oil.

Another embodiment comprises cyclosporin A, Empilan G-26®, and Cinnamon oil.

Another embodiment comprises cyclosporin A, Genapol TSM®, and Cinnamon oil.

Another embodiment comprises cyclosporin A, Hostacerin DGI®, and Cinnamon oil.

Another embodiment comprises cyclosporin A, Hostacerin DGL®, and Cinnamon oil.

Another embodiment comprises cyclosporin A, Hostacerin DGMS®, and Cinnamon oil.

Another embodiment comprises cyclosporin A, Hostacerin DGSB®, and Cinnamon oil.

Another embodiment comprises cyclosporin A, Ice No. 2®, and Cinnamon oil.

Another embodiment comprises cyclosporin A, Imwitor 742®, and Cinnamon oil.

Another embodiment comprises cyclosporin A, Imwitor 780 K®, and Cinnamon oil.

Another embodiment comprises cyclosporin A, Imwitor 960 Flakes®, and Cinnamon oil.

Another embodiment comprises cyclosporin A, Isolan GI 34®, and Cinnamon oil.

Another embodiment comprises cyclosporin A, Isolan GO 33®, and Cinnamon oil.

Another embodiment comprises cyclosporin A, Kemester 1000®, and Cinnamon oil.

Another embodiment comprises cyclosporin A, Kemester 2000®, and Cinnamon oil.

Another embodiment comprises cyclosporin A, Kemester 2000®, and Cinnamon oil.

Another embodiment comprises cyclosporin A, Kemester 6000SE®, and Cinnamon oil.

Another embodiment comprises cyclosporin A, Lamecreme DGE 18®, and Cinnamon oil.

Another embodiment comprises cyclosporin A, Lexemul 515®, and Cinnamon oil.

Another embodiment comprises cyclosporin A, Lexemul 561®, and Cinnamon oil.

Another embodiment comprises cyclosporin A, Lexemul AR®, and Cinnamon oil.

Another embodiment comprises cyclosporin A, Lexemul AS®, and Cinnamon oil.

Another embodiment comprises cyclosporin A, Lexemul GDL®, and Cinnamon oil.

Another embodiment comprises cyclosporin A, Lexemul T®, and Cinnamon oil.

Another embodiment comprises cyclosporin A, Lipomulse 165®, and Cinnamon oil.

Another embodiment comprises cyclosporin A, Lumulse GML K®, and Cinnamon oil.

Another embodiment comprises cyclosporin A, Lumulse GMO K®, and Cinnamon oil.

Another embodiment comprises cyclosporin A, Lumulse GMR K®, and Cinnamon oil.

Another embodiment comprises cyclosporin A, Lumulse GMT K®, and Cinnamon oil.

Another embodiment comprises cyclosporin A, Magrabar GMC®, and Cinnamon oil.

Another embodiment comprises cyclosporin A, Magrabar GMO-CK®, and Cinnamon oil.

Another embodiment comprises cyclosporin A, Magrabar MDG-5050®, and Cinnamon oil.

Another embodiment comprises cyclosporin A, Magrabar PGO-315®, and Cinnamon oil.

Another embodiment comprises cyclosporin A, Magrabar PGO-1010®, and Cinnamon oil.

Another embodiment comprises cyclosporin A, Mazol 300K®, and Cinnamon oil.

Another embodiment comprises cyclosporin A, Mazol GMO-K®, and Cinnamon oil.

Another embodiment comprises cyclosporin A, Mazol GMS-K®, and Cinnamon oil.

Another embodiment comprises cyclosporin A, Mazol PG031-K®, and Cinnamon oil.

Another embodiment comprises cyclosporin A, Miglyol 812®, and Cinnamon oil.

Another embodiment comprises cyclosporin A, Nonox 165C®, and Cinnamon oil.

Another embodiment comprises cyclosporin A, Schercemol GMIS®, and Cinnamon oil.

Another embodiment comprises cyclosporin A, Tegin®, and Cinnamon oil.

Another embodiment comprises cyclosporin A, Tegin 4100 Pellets®, and Cinnamon oil.

Another embodiment comprises cyclosporin A, Tegin M Pellets®, and Cinnamon oil.

Another embodiment comprises cyclosporin A, Tegin OV®, and Cinnamon oil.

Another embodiment comprises cyclosporin A, Teginacid H®, and Cinnamon oil.

Another embodiment comprises cyclosporin A, Tego Cosmo P813®, and Cinnamon oil.
Another embodiment comprises cyclosporin A, Wickenol 535®, and Cinnamon oil.
Another embodiment comprises cyclosporin A, Witconol 14®, and Cinnamon oil.
Another embodiment comprises cyclosporin A, Witconol 14®, and Cinnamon oil.
Another embodiment comprises cyclosporin A, Witconol 14F®, and Cinnamon oil.
Another embodiment comprises cyclosporin A, Witconol 18L®, and Cinnamon oil.
Another embodiment comprises cyclosporin A, Witconol GOT®, and Cinnamon oil.
Another embodiment comprises cyclosporin A, Witconol MST®, and Cinnamon oil.
Another embodiment comprises cyclosporin A, Witconol RHT®, and Cinnamon oil.
Another embodiment comprises cyclosporin A, and Cinnamon oil.
Another embodiment comprises cyclosporin A, a Glycol Ester, and Cinnamon oil.
Another embodiment comprises cyclosporin A, Alkamuls 600 DO®, and Cinnamon oil.
Another embodiment comprises cyclosporin A, Alkamuls SEG®, and Cinnamon oil.
Another embodiment comprises cyclosporin A, Atlas EM-2®, and Cinnamon oil.
Another embodiment comprises cyclosporin A, Cerasynt IP®, and Cinnamon oil.
Another embodiment comprises cyclosporin A, Cerasynt M®, and Cinnamon oil.
Another embodiment comprises cyclosporin A, Cerasynt MN®, and Cinnamon oil.
Another embodiment comprises cyclosporin A, Cerasynt PA®, and Cinnamon oil.
Another embodiment comprises cyclosporin A, Chemsperse EGDS®, and Cinnamon oil.
Another embodiment comprises cyclosporin A, Chemsperse EGMS®, and Cinnamon oil.
Another embodiment comprises cyclosporin A, Colonial Monolaurin®, and Cinnamon oil.
Another embodiment comprises cyclosporin A, DeMuls SGE-95®, and Cinnamon oil.
Another embodiment comprises cyclosporin A, Eccoterge 200®, and Cinnamon oil.
Another embodiment comprises cyclosporin A, Emerest 2380®, and Cinnamon oil.
Another embodiment comprises cyclosporin A, Ethox 2610®, and Cinnamon oil.
Another embodiment comprises cyclosporin A, Ethox DO-9®, and Cinnamon oil.
Another embodiment comprises cyclosporin A, Ethox DO-14®, and Cinnamon oil.
Another embodiment comprises cyclosporin A, Ethox SO-9®, and Cinnamon oil.
Another embodiment comprises cyclosporin A, Fizul MD-318®, and Cinnamon oil.
Another embodiment comprises cyclosporin A, Genapol EGDS-VHP®, and Cinnamon oil.
Another embodiment comprises cyclosporin A, Genapol TS Powder®, and Cinnamon oil.
Another embodiment comprises cyclosporin A, Hostacerin WO®, and Cinnamon oil.
Another embodiment comprises cyclosporin A, Inversol 140®, and Cinnamon oil.
Another embodiment comprises cyclosporin A, Kemester 104®, and Cinnamon oil.
Another embodiment comprises cyclosporin A, Kemester 205®, and Cinnamon oil.
Another embodiment comprises cyclosporin A, Kemester 226®, and Cinnamon oil.
Another embodiment comprises cyclosporin A, Kemester 5221SE®, and Cinnamon oil.
Another embodiment comprises cyclosporin A, Kemester EGDS®, and Cinnamon oil.
Another embodiment comprises cyclosporin A, Lexemul EGDS®, and Cinnamon oil.
Another embodiment comprises cyclosporin A, Lexemul EGMS®, and Cinnamon oil.
Another embodiment comprises cyclosporin A, Lexemul P®, and Cinnamon oil.
Another embodiment comprises cyclosporin A, Lipo DGLS®, and Cinnamon oil.
Another embodiment comprises cyclosporin A, Lipo EGDS®, and Cinnamon oil.
Another embodiment comprises cyclosporin A, Lipo PGMS®, and Cinnamon oil.
Another embodiment comprises cyclosporin A, Liposorb S-4®, and Cinnamon oil.
Another embodiment comprises cyclosporin A, Liposorb TO-20®, and Cinnamon oil.
Another embodiment comprises cyclosporin A, Lumulse PGO®, and Cinnamon oil.
Another embodiment comprises cyclosporin A, Mackester EGDS®, and Cinnamon oil.
Another embodiment comprises cyclosporin A, Mackester EGMS®, and Cinnamon oil.
Another embodiment comprises cyclosporin A, Mackester GSTP®, and Cinnamon oil.
Another embodiment comprises cyclosporin A, Mackester Series®, and Cinnamon oil.
Another embodiment comprises cyclosporin A, Magrabar PDG-50®, and Cinnamon oil.
Another embodiment comprises cyclosporin A, Mapeg 6000 DS®, and Cinnamon oil.
Another embodiment comprises cyclosporin A, Marlowet 4702®, and Cinnamon oil.
Another embodiment comprises cyclosporin A, Monalube 305®, and Cinnamon oil.
Another embodiment comprises cyclosporin A, Monalube 310®, and Cinnamon oil.
Another embodiment comprises cyclosporin A, Monalube 315®, and Cinnamon oil.
Another embodiment comprises cyclosporin A, Monalube 320®, and Cinnamon oil.
Another embodiment comprises cyclosporin A, Monalube 325®, and Cinnamon oil.
Another embodiment comprises cyclosporin A, Monalube 330®, and Cinnamon oil.
Another embodiment comprises cyclosporin A, Naturechem PGHS®, and Cinnamon oil.
Another embodiment comprises cyclosporin A, Polycastorol PLO-840®, and Cinnamon oil.
Another embodiment comprises cyclosporin A, Polytex 10M®, and Cinnamon oil.
Another embodiment comprises cyclosporin A, Ritasynt IP®, and Cinnamon oil.
Another embodiment comprises cyclosporin A, Ross Chem PEG 600 DT®, and Cinnamon oil.
Another embodiment comprises cyclosporin A, Schercemol PGMS®, and Cinnamon oil.
Another embodiment comprises cyclosporin A, Sponto H-44C®, and Cinnamon oil.
Another embodiment comprises cyclosporin A, Tegin G®, and Cinnamon oil.
Another embodiment comprises cyclosporin A, Witbreak DGE-182®, and Cinnamon oil.
Another embodiment comprises cyclosporin A, Witbreak DGE-182®, and Cinnamon oil.

Another embodiment comprises cyclosporin A, Witbreak DRA-21®, and Cinnamon oil.

Another embodiment comprises cyclosporin A, Witbreak DRA-21®, and Cinnamon oil.

Another embodiment comprises cyclosporin A, Witbreak DRA-50®, and Cinnamon oil.

Another embodiment comprises cyclosporin A, Witbreak DRA-50®, and Cinnamon oil.

Another embodiment comprises cyclosporin A, Witconol F26-46®, and Cinnamon oil.

Another embodiment comprises cyclosporin A, Witconol H-32®, and Cinnamon oil.

Another embodiment comprises cyclosporin A, Witconol H-33®, and Cinnamon oil.

Another embodiment comprises cyclosporin A, Witconol H-35A®, and Cinnamon oil.

Another embodiment comprises cyclosporin A, Witconol RHP®, and Cinnamon oil.

Another embodiment comprises cyclosporin A, and Cinnamon oil.

Another embodiment comprises cyclosporin A, a Lanolin-based Derivative, and Cinnamon oil.

Another embodiment comprises cyclosporin A, Amerchol CAB®, and Cinnamon oil.

Another embodiment comprises cyclosporin A, Amerchol L-101®, and Cinnamon oil.

Another embodiment comprises cyclosporin A, Amerlate LFA-LO®, and Cinnamon oil.

Another embodiment comprises cyclosporin A, Amerlate P®, and Cinnamon oil.

Another embodiment comprises cyclosporin A, Barre Common Degras®, and Cinnamon oil.

Another embodiment comprises cyclosporin A, Cholesterol NF®, and Cinnamon oil.

Another embodiment comprises cyclosporin A, Crodalan AWS®, and Cinnamon oil.

Another embodiment comprises cyclosporin A, Crodalan LA®, and Cinnamon oil.

Another embodiment comprises cyclosporin A, Emery 1650®, and Cinnamon oil.

Another embodiment comprises cyclosporin A, Emery 1650®, and Cinnamon oil.

Another embodiment comprises cyclosporin A, Emery 1740®, and Cinnamon oil.

Another embodiment comprises cyclosporin A, Emery 1740®, and Cinnamon oil.

Another embodiment comprises cyclosporin A, Forlan 500®, and Cinnamon oil.

Another embodiment comprises cyclosporin A, Forlan L®, and Cinnamon oil.

Another embodiment comprises cyclosporin A, Laneto 50®, and Cinnamon oil.

Another embodiment comprises cyclosporin A, Laneto 100®, and Cinnamon oil.

Another embodiment comprises cyclosporin A, Laneto AWS®, and Cinnamon oil.

Another embodiment comprises cyclosporin A, Lanfrax 1776®, and Cinnamon oil.

Another embodiment comprises cyclosporin A, Lanfrax 1776®, and Cinnamon oil.

Another embodiment comprises cyclosporin A, Lanogel 21®, and Cinnamon oil.

Another embodiment comprises cyclosporin A, Lipolan®, and Cinnamon oil.

Another embodiment comprises cyclosporin A, Lipolan 31®, and Cinnamon oil.

Another embodiment comprises cyclosporin A, OHlan®, and Cinnamon oil.

Another embodiment comprises cyclosporin A, Polychol 5®, and Cinnamon oil.

Another embodiment comprises cyclosporin A, Polychol 15®, and Cinnamon oil.

Another embodiment comprises cyclosporin A, Ritacetyl®, and Cinnamon oil.

Another embodiment comprises cyclosporin A, Ritachol®, and Cinnamon oil.

Another embodiment comprises cyclosporin A, Ritahydrox®, and Cinnamon oil.

Another embodiment comprises cyclosporin A, Ritalafa®, and Cinnamon oil.

Another embodiment comprises cyclosporin A, Ritalan®, and Cinnamon oil.

Another embodiment comprises cyclosporin A, Ritalan AWS®, and Cinnamon oil.

Another embodiment comprises cyclosporin A, Ritalan C®, and Cinnamon oil.

Another embodiment comprises cyclosporin A, Ritawax®, and Cinnamon oil.

Another embodiment comprises cyclosporin A, Ritawax AEO®, and Cinnamon oil.

Another embodiment comprises cyclosporin A, Ritawax ALA®, and Cinnamon oil.

Another embodiment comprises cyclosporin A, Solan/Solan 50/Super Solan®, and Cinnamon oil.

Another embodiment comprises cyclosporin A, Super Hartolan/Hartolan®, and Cinnamon oil.

Another embodiment comprises cyclosporin A, Supersat AWS-4®, and Cinnamon oil.

Another embodiment comprises cyclosporin A, Supersat AWS-24®, and Cinnamon oil.

Another embodiment comprises cyclosporin A, and Cinnamon oil.

Another embodiment comprises cyclosporin A, a Lecithin or Lecithin Derivative, and Cinnamon oil.

Another embodiment comprises cyclosporin A, Alcolec®, and Cinnamon oil.

Another embodiment comprises cyclosporin A, Lecithin®, and Cinnamon oil.

Another embodiment comprises cyclosporin A, Lexin K®, and Cinnamon oil.

Another embodiment comprises cyclosporin A, Natipide®, and Cinnamon oil.

Another embodiment comprises cyclosporin A, and Cinnamon oil.

Another embodiment comprises cyclosporin A, a Lignin or Lignin Derivative, and Cinnamon oil.

Another embodiment comprises cyclosporin A, Diwatex XP 9®, and Cinnamon oil.

Another embodiment comprises cyclosporin A, Dynasperse LCD®, and Cinnamon oil.

Another embodiment comprises cyclosporin A, Indulin SAL®, and Cinnamon oil.

Another embodiment comprises cyclosporin A, Indulin W-1®, and Cinnamon oil.

Another embodiment comprises cyclosporin A, Indulin W-5®, and Cinnamon oil.

Another embodiment comprises cyclosporin A, Lignosol FTA®, and Cinnamon oil.

Another embodiment comprises cyclosporin A, Lignosol SFX-65®, and Cinnamon oil.

Another embodiment comprises cyclosporin A, Marasperse 52 CF®, and Cinnamon oil.

Another embodiment comprises cyclosporin A, Marasperse AG®, and Cinnamon oil.

Another embodiment comprises cyclosporin A, Marasperse CBOS-4®, and Cinnamon oil.

Another embodiment comprises cyclosporin A, Ufoxane 2®, and Cinnamon oil.

Another embodiment comprises cyclosporin A, and Cinnamon oil.

Another embodiment comprises cyclosporin A, a Methyl Ester, and Cinnamon oil.

Another embodiment comprises cyclosporin A, E.B. Cleaner AK®, and Cinnamon oil.

Another embodiment comprises cyclosporin A, Oleocal ME-70®, and Cinnamon oil.

Another embodiment comprises cyclosporin A, Trade Name Company®, and Cinnamon oil.

Another embodiment comprises cyclosporin A, Methyl Esters (cont'd)®, and Cinnamon oil.

Another embodiment comprises cyclosporin A, Oleocal ME-92®, and Cinnamon oil.

Another embodiment comprises cyclosporin A, Oleocal ME-112®, and Cinnamon oil.

Another embodiment comprises cyclosporin A, Oleocal ME-130®, and Cinnamon oil.

Another embodiment comprises cyclosporin A, and Cinnamon oil.

Another embodiment comprises cyclosporin A, a Monoglyceride or a Derivative thereof, and Cinnamon oil.

Another embodiment comprises cyclosporin A, Dynacet 211®, and Cinnamon oil.

Another embodiment comprises cyclosporin A, Hetsorb S-20®, and Cinnamon oil.

Another embodiment comprises cyclosporin A, Imwitor 191®, and Cinnamon oil.

Another embodiment comprises cyclosporin A, Imwitor 370®, and Cinnamon oil.

Another embodiment comprises cyclosporin A, Imwitor 375®, and Cinnamon oil.

Another embodiment comprises cyclosporin A, Imwitor 900®, and Cinnamon oil.

Another embodiment comprises cyclosporin A, Imwitor 945®, and Cinnamon oil.

Another embodiment comprises cyclosporin A, Imwitor 2020®, and Cinnamon oil.

Another embodiment comprises cyclosporin A, Kemester 5500®, and Cinnamon oil.

Another embodiment comprises cyclosporin A, Kemester 6000®, and Cinnamon oil.

Another embodiment comprises cyclosporin A, Magrabar GMC®, and Cinnamon oil.

Another embodiment comprises cyclosporin A, Magrabar GMO-CK®, and Cinnamon oil.

Another embodiment comprises cyclosporin A, Magrabar GPC-10®, and Cinnamon oil.

Another embodiment comprises cyclosporin A, Magrabar MDG-5050®, and Cinnamon oil.

Another embodiment comprises cyclosporin A, Monalube 335®, and Cinnamon oil.

Another embodiment comprises cyclosporin A, Monoglycerides Glyceryl Monestearate Archer Daniels Midland Company®, and Cinnamon oil.

Another embodiment comprises cyclosporin A, Rita GMS®, and Cinnamon oil.

Another embodiment comprises cyclosporin A, Ritamulse SCG®, and Cinnamon oil.

Another embodiment comprises cyclosporin A, Softigen 701®, and Cinnamon oil.

Another embodiment comprises cyclosporin A, Tally 100 Plus®, and Cinnamon oil.

Another embodiment comprises cyclosporin A, and Cinnamon oil.

Another embodiment comprises cyclosporin A, a Polyethylene Glycol, and Cinnamon oil.

Another embodiment comprises cyclosporin A, Emulgade PL 68/50®, and Cinnamon oil.

Another embodiment comprises cyclosporin A, Lumulse PEG®, and Cinnamon oil.

Another embodiment comprises cyclosporin A, Rhodasurf PEG-400®, and Cinnamon oil.

Another embodiment comprises cyclosporin A, Rhodasurf PEG-600®, and Cinnamon oil.

Another embodiment comprises cyclosporin A, Witconol PEG-400®, and Cinnamon oil.

Another embodiment comprises cyclosporin A, and Cinnamon oil.

Another embodiment comprises cyclosporin A, a Polymeric Surfactant, and Cinnamon oil.

Another embodiment comprises cyclosporin A, Acritamer PNC-EG®, and Cinnamon oil.

Another embodiment comprises cyclosporin A, Ag-Rho DEP-775®, and Cinnamon oil.

Another embodiment comprises cyclosporin A, APG 325N Glycoside®, and Cinnamon oil.

Another embodiment comprises cyclosporin A, Aristoflex AVC®, and Cinnamon oil.

Another embodiment comprises cyclosporin A, Aristoflex HMB®, and Cinnamon oil.

Another embodiment comprises cyclosporin A, Burco NPS-225®, and Cinnamon oil.

Another embodiment comprises cyclosporin A, Burco NPS-816®, and Cinnamon oil.

Another embodiment comprises cyclosporin A, Chemocinate 5603®, and Cinnamon oil.

Another embodiment comprises cyclosporin A, Cosmedia Guar C-261N®, and Cinnamon oil.

Another embodiment comprises cyclosporin A, Gantrez S-95®, and Cinnamon oil.

Another embodiment comprises cyclosporin A, Glucopon 220 UP®, and Cinnamon oil.

Another embodiment comprises cyclosporin A, Glucopon 225 DK®, and Cinnamon oil.

Another embodiment comprises cyclosporin A, Glucopon 425 N®, and Cinnamon oil.

Another embodiment comprises cyclosporin A, Glucopon 600 UP®, and Cinnamon oil.

Another embodiment comprises cyclosporin A, Glucopon 625 UP®, and Cinnamon oil.

Another embodiment comprises cyclosporin A, Pemulen 1621®, and Cinnamon oil.

Another embodiment comprises cyclosporin A, Pemulen 1622®, and Cinnamon oil.

Another embodiment comprises cyclosporin A, Pemulen TR-1®, and Cinnamon oil.

Another embodiment comprises cyclosporin A, Pemulen TR-2®, and Cinnamon oil.

Another embodiment comprises cyclosporin A, Plantacare 818®, and Cinnamon oil.

Another embodiment comprises cyclosporin A, Plantapon LGC Sorb®, and Cinnamon oil.

Another embodiment comprises cyclosporin A, Plantaren 1200N®, and Cinnamon oil.

Another embodiment comprises cyclosporin A, Plantaren 2000N®, and Cinnamon oil.

Another embodiment comprises cyclosporin A, Viscolam AT 64®, and Cinnamon oil.

Another embodiment comprises cyclosporin A, Viscolam AT 64P®, and Cinnamon oil.

Another embodiment comprises cyclosporin A, Viscolam AT 100®, and Cinnamon oil.

Another embodiment comprises cyclosporin A, Viscolam MAC 7®, and Cinnamon oil.

Another embodiment comprises cyclosporin A, Viscolam SMC 20®, and Cinnamon oil.

Another embodiment comprises cyclosporin A, Witbreak RTC-323®, and Cinnamon oil.

Another embodiment comprises cyclosporin A, WSI 3700®, and Cinnamon oil.

Another embodiment comprises cyclosporin A, and Cinnamon oil.

Another embodiment comprises cyclosporin A, a Propoxylated or Ethoxylated Fatty Acid, Alcohol, or Alkyl Phenol, and Cinnamon oil.

Another embodiment comprises cyclosporin A, Antarox AA-60®, and Cinnamon oil.

Another embodiment comprises cyclosporin A, Antarox LF-224®, and Cinnamon oil.

Another embodiment comprises cyclosporin A, Burcomul DFE-45®, and Cinnamon oil.

Another embodiment comprises cyclosporin A, Burcoterge LFE-1000®, and Cinnamon oil.

Another embodiment comprises cyclosporin A, Chemal LF-25B®, and Cinnamon oil.

Another embodiment comprises cyclosporin A, Chemal LF-40B®, and Cinnamon oil.

Another embodiment comprises cyclosporin A, Dehypon LS-36®, and Cinnamon oil.

Another embodiment comprises cyclosporin A, Dehypon LS-36®, and Cinnamon oil.

Another embodiment comprises cyclosporin A, Dehypon LS-54®, and Cinnamon oil.

Another embodiment comprises cyclosporin A, Dehypon LS-54®, and Cinnamon oil.

Another embodiment comprises cyclosporin A, Delonic 100 VLF®, and Cinnamon oil.

Another embodiment comprises cyclosporin A, Delonic LF-60 MOD®, and Cinnamon oil.

Another embodiment comprises cyclosporin A, Empiderm B®, and Cinnamon oil.

Another embodiment comprises cyclosporin A, Ethylan 1206®, and Cinnamon oil.

Another embodiment comprises cyclosporin A, Ethylan NS-500K®, and Cinnamon oil.

Another embodiment comprises cyclosporin A, Ethylan NS-500LQ®, and Cinnamon oil.

Another embodiment comprises cyclosporin A, Genapol 1392®, and Cinnamon oil.

Another embodiment comprises cyclosporin A, Genapol 2317®, and Cinnamon oil.

Another embodiment comprises cyclosporin A, Genapol 26EP710®, and Cinnamon oil.

Another embodiment comprises cyclosporin A, Genapol EP 1022®, and Cinnamon oil.

Another embodiment comprises cyclosporin A, Genapol EP 1024®, and Cinnamon oil.

Another embodiment comprises cyclosporin A, Genapol EP 6068®, and Cinnamon oil.

Another embodiment comprises cyclosporin A, Genapol NP915®, and Cinnamon oil.

Another embodiment comprises cyclosporin A, Kieralon MFB®, and Cinnamon oil.

Another embodiment comprises cyclosporin A, Lumisolve CSA-80 V®, and Cinnamon oil.

Another embodiment comprises cyclosporin A, Marlowet 5001®, and Cinnamon oil.

Another embodiment comprises cyclosporin A, Marlox FK 64®, and Cinnamon oil.

Another embodiment comprises cyclosporin A, Marlox MO 124®, and Cinnamon oil.

Another embodiment comprises cyclosporin A, Marlox S 58®, and Cinnamon oil.

Another embodiment comprises cyclosporin A, Nonatell 1003®, and Cinnamon oil.

Another embodiment comprises cyclosporin A, Nonatell 1038®, and Cinnamon oil.

Another embodiment comprises cyclosporin A, Nonatell 1052®, and Cinnamon oil.

Another embodiment comprises cyclosporin A, Nonatell 1061®, and Cinnamon oil.

Another embodiment comprises cyclosporin A, Nonatell 1075®, and Cinnamon oil.

Another embodiment comprises cyclosporin A, Nonatell 1088®, and Cinnamon oil.

Another embodiment comprises cyclosporin A, Nonatell 1123®, and Cinnamon oil.

Another embodiment comprises cyclosporin A, Nonatell 1153®, and Cinnamon oil.

Another embodiment comprises cyclosporin A, Nonatell 1161®, and Cinnamon oil.

Another embodiment comprises cyclosporin A, Nonatell 1172®, and Cinnamon oil.

Another embodiment comprises cyclosporin A, Nonatell 1181®, and Cinnamon oil.

Another embodiment comprises cyclosporin A, Norfox 36®, and Cinnamon oil.

Another embodiment comprises cyclosporin A, Procetyl AWS®, and Cinnamon oil.

Another embodiment comprises cyclosporin A, Sandoxylate SX 412®, and Cinnamon oil.

Another embodiment comprises cyclosporin A, Sandoxylate SX 418®, and Cinnamon oil.

Another embodiment comprises cyclosporin A, Surfonic JL-80X®, and Cinnamon oil.

Another embodiment comprises cyclosporin A, Surfonic JL-80X-B1®, and Cinnamon oil.

Another embodiment comprises cyclosporin A, Surfonic L4-29X®, and Cinnamon oil.

Another embodiment comprises cyclosporin A, Surfonic LF®, and Cinnamon oil.

Another embodiment comprises cyclosporin A, T-Det A826®, and Cinnamon oil.

Another embodiment comprises cyclosporin A, T-Det LF-416®, and Cinnamon oil.

Another embodiment comprises cyclosporin A, Tergitol Min-Foam 1X®, and Cinnamon oil.

Another embodiment comprises cyclosporin A, Tergitol Min-Foam 2X®, and Cinnamon oil.

Another embodiment comprises cyclosporin A, Triton CF-21®, and Cinnamon oil.

Another embodiment comprises cyclosporin A, Triton CF-76®, and Cinnamon oil.

Another embodiment comprises cyclosporin A, Triton XL-80N®, and Cinnamon oil.

Another embodiment comprises cyclosporin A, Witconol NS-98®, and Cinnamon oil.

Another embodiment comprises cyclosporin A, Witconol NS-108LQ®, and Cinnamon oil.

Another embodiment comprises cyclosporin A, Witconol NS-145®, and Cinnamon oil.

Another embodiment comprises cyclosporin A, Witconol NS-179®, and Cinnamon oil.

Another embodiment comprises cyclosporin A, and Cinnamon oil.

Another embodiment comprises cyclosporin A, a Protein-based Surfactant, and Cinnamon oil.

Another embodiment comprises cyclosporin A, Amino-Foam W®, and Cinnamon oil.

Another embodiment comprises cyclosporin A, Amiter LGOD-2®, and Cinnamon oil.

Another embodiment comprises cyclosporin A, Amiter LGS-2®, and Cinnamon oil.

Another embodiment comprises cyclosporin A, Amiter LGS-5®, and Cinnamon oil.

Another embodiment comprises cyclosporin A, Lamepon S®, and Cinnamon oil.

Another embodiment comprises cyclosporin A, Lamepon S®, and Cinnamon oil.

Another embodiment comprises cyclosporin A, Maypon 4C®, and Cinnamon oil.

Another embodiment comprises cyclosporin A, May-Tein C®, and Cinnamon oil.

Another embodiment comprises cyclosporin A, May-Tein CT®, and Cinnamon oil.

Another embodiment comprises cyclosporin A, May-Tein KTS®, and Cinnamon oil.

Another embodiment comprises cyclosporin A, May-Tein SY®, and Cinnamon oil.

Another embodiment comprises cyclosporin A, Plantapon S®, and Cinnamon oil.

Another embodiment comprises cyclosporin A, Proteol APL®, and Cinnamon oil.

Another embodiment comprises cyclosporin A, Proteol OAT®, and Cinnamon oil.

Another embodiment comprises cyclosporin A, Pyroter CPI-40®, and Cinnamon oil.

Another embodiment comprises cyclosporin A, Pyroter GPI-25®, and Cinnamon oil.

Another embodiment comprises cyclosporin A, Supro-Tein S®, and Cinnamon oil.

Another embodiment comprises cyclosporin A, Supro-Tein V®, and Cinnamon oil.

Another embodiment comprises cyclosporin A, ®, and Cinnamon oil.

Another embodiment comprises cyclosporin A, a Sarcosine Derivative®, and Cinnamon oil.

Another embodiment comprises cyclosporin A, Crodasinic LS-30®, and Cinnamon oil.

Another embodiment comprises cyclosporin A, Vanseal CS®, and Cinnamon oil.

Another embodiment comprises cyclosporin A, Vanseal LS®, and Cinnamon oil.

Another embodiment comprises cyclosporin A, Vanseal MS®, and Cinnamon oil.

Another embodiment comprises cyclosporin A, Vanseal NACS-30®, and Cinnamon oil.

Another embodiment comprises cyclosporin A, Vanseal NALS-95®, and Cinnamon oil.

Another embodiment comprises cyclosporin A, Vanseal OS®, and Cinnamon oil.

Another embodiment comprises cyclosporin A, ®, and Cinnamon oil.

Another embodiment comprises cyclosporin A, a Silicone-based Surfactant®, and Cinnamon oil.

Another embodiment comprises cyclosporin A, Abil-B-9950®, and Cinnamon oil.

Another embodiment comprises cyclosporin A, Abil Care 85®, and Cinnamon oil.

Another embodiment comprises cyclosporin A, Abil EM 90®, and Cinnamon oil.

Another embodiment comprises cyclosporin A, Abil EM 97®, and Cinnamon oil.

Another embodiment comprises cyclosporin A, Abil WE-09®, and Cinnamon oil.

Another embodiment comprises cyclosporin A, Dow Corning 1248 Fluid®, and Cinnamon oil.

Another embodiment comprises cyclosporin A, Dow Corning 3225C®, and Cinnamon oil.

Another embodiment comprises cyclosporin A, Dow Corning 5200®, and Cinnamon oil.

Another embodiment comprises cyclosporin A, Dow Corning Q4-3667®, and Cinnamon oil.

Another embodiment comprises cyclosporin A, Monasil PCA®, and Cinnamon oil.

Another embodiment comprises cyclosporin A, Monasil PDM®, and Cinnamon oil.

Another embodiment comprises cyclosporin A, Monasil PLN®, and Cinnamon oil.

Another embodiment comprises cyclosporin A, Polyderm PPI-SI-WS®, and Cinnamon oil.

Another embodiment comprises cyclosporin A, Troysol 380W®, and Cinnamon oil.

Another embodiment comprises cyclosporin A, Troysol S366®, and Cinnamon oil.

Another embodiment comprises cyclosporin A, and Cinnamon oil.

Another embodiment comprises cyclosporin A, a Sorbitan Derivative, and Cinnamon oil.

Another embodiment comprises cyclosporin A, Alkamuls SML®, and Cinnamon oil.

Another embodiment comprises cyclosporin A, Alkamuls SMO®, and Cinnamon oil.

Another embodiment comprises cyclosporin A, Alkamuls STO®, and Cinnamon oil.

Another embodiment comprises cyclosporin A, Arlacel 20®, and Cinnamon oil.

Another embodiment comprises cyclosporin A, Arlacel 40®, and Cinnamon oil.

Another embodiment comprises cyclosporin A, Arlacel 60®, and Cinnamon oil.

Another embodiment comprises cyclosporin A, Arlacel 80®, and Cinnamon oil.

Another embodiment comprises cyclosporin A, Arlacel C®, and Cinnamon oil.

Another embodiment comprises cyclosporin A, Armul 21®, and Cinnamon oil.

Another embodiment comprises cyclosporin A, Atlox 80®, and Cinnamon oil.

Another embodiment comprises cyclosporin A, Atlox 847®, and Cinnamon oil.

Another embodiment comprises cyclosporin A, Atlox 1045A®, and Cinnamon oil.

Another embodiment comprises cyclosporin A, Canarcel 20®, and Cinnamon oil.

Another embodiment comprises cyclosporin A, Canarcel 60®, and Cinnamon oil.

Another embodiment comprises cyclosporin A, Canarcel 80®, and Cinnamon oil.

Another embodiment comprises cyclosporin A, Canarcel TW 20®, and Cinnamon oil.

Another embodiment comprises cyclosporin A, Canarcel TW 60®, and Cinnamon oil.

Another embodiment comprises cyclosporin A, Canarcel TW 80®, and Cinnamon oil.

Another embodiment comprises cyclosporin A, Coladet BSB-P®, and Cinnamon oil.

Another embodiment comprises cyclosporin A, Customulse O-20®, and Cinnamon oil.

Another embodiment comprises cyclosporin A, Dehymuls E®, and Cinnamon oil.

Another embodiment comprises cyclosporin A, DeSotan SMO®, and Cinnamon oil.

Another embodiment comprises cyclosporin A, DeSotan SMO-20®, and Cinnamon oil.

Another embodiment comprises cyclosporin A, DeSotan SMT®, and Cinnamon oil.

Another embodiment comprises cyclosporin A, DeSotan SMT-20®, and Cinnamon oil.

Another embodiment comprises cyclosporin A, Durfax 60®, and Cinnamon oil.

Another embodiment comprises cyclosporin A, Durfax 65®, and Cinnamon oil.

Another embodiment comprises cyclosporin A, Durfax 80®, and Cinnamon oil.

Another embodiment comprises cyclosporin A, Durtan 60®, and Cinnamon oil.

Another embodiment comprises cyclosporin A, Durtan 65®, and Cinnamon oil.

Another embodiment comprises cyclosporin A, Liposorb L®, and Cinnamon oil.
Another embodiment comprises cyclosporin A, Liposorb L-10®, and Cinnamon oil.
Another embodiment comprises cyclosporin A, Liposorb L-20®, and Cinnamon oil.
Another embodiment comprises cyclosporin A, Liposorb O®, and Cinnamon oil.
Another embodiment comprises cyclosporin A, Liposorb O-20®, and Cinnamon oil.
Another embodiment comprises cyclosporin A, Liposorb P®, and Cinnamon oil.
Another embodiment comprises cyclosporin A, Liposorb P-20®, and Cinnamon oil.
Another embodiment comprises cyclosporin A, Liposorb S®, and Cinnamon oil.
Another embodiment comprises cyclosporin A, Liposorb S-20®, and Cinnamon oil.
Another embodiment comprises cyclosporin A, Liposorb SQO®, and Cinnamon oil.
Another embodiment comprises cyclosporin A, Liposorb TO®, and Cinnamon oil.
Another embodiment comprises cyclosporin A, Liposorb TS®, and Cinnamon oil.
Another embodiment comprises cyclosporin A, Liposorb TS-20®, and Cinnamon oil.
Another embodiment comprises cyclosporin A, Lumisorb PS®, and Cinnamon oil.
Another embodiment comprises cyclosporin A, Lumisorb SMO (T)®, and Cinnamon oil.
Another embodiment comprises cyclosporin A, Lumisorb SMS K®, and Cinnamon oil.
Another embodiment comprises cyclosporin A, Lumisorb SSO®, and Cinnamon oil.
Another embodiment comprises cyclosporin A, Lumisorb STS K®, and Cinnamon oil.
Another embodiment comprises cyclosporin A, Lumisorb STT®, and Cinnamon oil.
Another embodiment comprises cyclosporin A, Magrabar SMO®, and Cinnamon oil.
Another embodiment comprises cyclosporin A, Magrabar SMO-VEG®, and Cinnamon oil.
Another embodiment comprises cyclosporin A, Magrabar SMT®, and Cinnamon oil.
Another embodiment comprises cyclosporin A, Magrabar STO®, and Cinnamon oil.
Another embodiment comprises cyclosporin A, Miracare BC-27®, and Cinnamon oil.
Another embodiment comprises cyclosporin A, Ritabate 20®, and Cinnamon oil.
Another embodiment comprises cyclosporin A, Ritabate 40®, and Cinnamon oil.
Another embodiment comprises cyclosporin A, Ritabate 60®, and Cinnamon oil.
Another embodiment comprises cyclosporin A, Ritabate 80®, and Cinnamon oil.
Another embodiment comprises cyclosporin A, T-Maz®, and Cinnamon oil.
Another embodiment comprises cyclosporin A, Tego SML®, and Cinnamon oil.
Another embodiment comprises cyclosporin A, Tego SML 20®, and Cinnamon oil.
Another embodiment comprises cyclosporin A, Tego SMO 80 V®, and Cinnamon oil.
Another embodiment comprises cyclosporin A, Tego SMO V®, and Cinnamon oil.
Another embodiment comprises cyclosporin A, Tego SMS®, and Cinnamon oil.
Another embodiment comprises cyclosporin A, Tego STO V®, and Cinnamon oil.
Another embodiment comprises cyclosporin A, Tween 21®, and Cinnamon oil.
Another embodiment comprises cyclosporin A, Tween 40®, and Cinnamon oil.
Another embodiment comprises cyclosporin A, Tween 60®, and Cinnamon oil.
Another embodiment comprises cyclosporin A, Tween 60 K®, and Cinnamon oil.
Another embodiment comprises cyclosporin A, Tween 61®, and Cinnamon oil.
Another embodiment comprises cyclosporin A, Tween 65®, and Cinnamon oil.
Another embodiment comprises cyclosporin A, Tween 80®, and Cinnamon oil.
Another embodiment comprises cyclosporin A, Tween 80 K®, and Cinnamon oil.
Another embodiment comprises cyclosporin A, Tween 81®, and Cinnamon oil.
Another embodiment comprises cyclosporin A, Tween 85®, and Cinnamon oil.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

In accordance with the present invention, the emulsions can be further stabilized using a polyelectrolyte, or polyelectrolytes if more than one, from the family of cross-linked polyacrylates, such as carbomers and Pemulen®.

Pemulen® is a registered trademark of B. F. Goodrich for polymeric emulsifiers and commercially available from B. F. Goodrich Company, Specialty Polymers & Chemicals Division, Cleveland, Ohio. Pemulens are Acrylates/C10-30 Alkyl Acrylate Cross-Polymers. They are high molecular weight co-polymers of acrylic acid and a long chain alkyl methacrylate cross-linked with allyl ether of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

Examples of useful formulations are shown in the table below.

| Ingredients | 1 | 2 | 3 | 4 | 5 | 6 | 7 | 8 | 9 | 10 | 11 |
| --- | --- | --- | --- | --- | --- | --- | --- | --- | --- | --- | --- |
| Cyclosporine A | 0.1 | 0.1 | 0.05 | 0.02 | 0.05 | 0.03 | 0.01 | 0.08 | 0.1 | 0.04 | 0.05 |
| Castor oil | 1.00 | 1.2 | | | | | | 0.50 | | | |

-continued

| Ingredients | 1 | 2 | 3 | 4 | 5 | 6 | 7 | 8 | 9 | 10 | 11 |
|---|---|---|---|---|---|---|---|---|---|---|---|
| Clove oil | 0.70 | | | | 0.50 | 0.40 | 0.20 | | | 0.50 | 0.80 |
| Cassia oil | | 0.4 | 0.20 | 0.70 | | | | 0.55 | 0.75 | | |
| Cottonseed oil | | | 0.60 | | | | | | | | |
| Soybean oil | | | | | | | 0.30 | | | | |
| Lavender oil | | | | | 0.30 | | | | 0.90 | | |
| Juniper oil | | | | | | 0.20 | | | | | |
| Corn oil | | | | 0.70 | | | | | | 0.40 | |
| Oliver oil | | | | | | | | 0.35 | | | |
| Mineral Oil | | | | | | | | | | | |
| Polysorbate-80 | 1.00 | 0.80 | | 1.50 | | | 0.30 | | 0.30 | 0.10 | 0.30 |
| Diglycerol | 0.70 | | | | | | | 0.20 | | | |
| Polyglycerol-3 | | | 1.00 | | | 0.10 | | | | 0.80 | |
| Simulsol OX 1005 L | | 0.60 | | | | | | | | | |
| Chemonic 435 | | | | | | | | | | | |
| Marlowet 4530 | | | | | | | | | | | |
| Brij52 | | | 0.50 | | 0.70 | 0.60 | | | | | |
| Brij78 | | | | | | | | | 1.20 | | |
| Bio Soft TD-630 | | | | | | | | | 1.3 | | |
| Canasol BJ 78 | | | | | 0.50 | | | | | | |
| Canasol BJ 52 | | | | 0.30 | | | | | | 0.80 | |
| Rhodasurf BEH 25 | | | | | | | | | | | |
| Desonic 9D | | | | | | | | | | | 0.60 |
| Glycerin | 2.00 | 1.70 | 1.50 | 2.00 | 1.00 | 2.00 | 2.00 | 2.00 | 2.00 | 1.50 | 2.00 |
| CMC | 0.50 | | | | 0.50 | | | 0.50 | | | |
| Pemulen TR-2 | | 0.05 | 0.03 | 0.05 | | | | | | | 0.02 |
| Purified Water | QS | QS | QS | QS | QS | QS | QS | QS | QS | QS | QS |
| Sodium Hydroxide | pH adj | pH adj | pH adj | pH adj | pH adj | pH adj | pH adj | pH adj | pH adj | pH adj | pH adj |
| pH | 7.2 | 7.5 | 6.3 | 7.3 | 7.4 | 7.8 | 6.8 | 7.1 | 7 | 7.2 | 7.2 |

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A composition comprising from 0.001% to about 0.4% cyclosporin A, a surfactant, and an oil selected from the group consisting of anise oil, clove oil, cinnamon oil, and combinations thereof, wherein said composition is an ophthalmically acceptable emulsion.

2. The composition of claim 1 wherein the oil is anise oil.

3. The composition of claim 2 wherein the cyclosporin A is from 0.005% to about 0.05%.

4. The composition of claim 3 wherein the cyclosporin A is 0.05%.

5. The composition of claim 1 wherein the oil is clove oil.

6. The composition of claim 5 wherein the cyclosporin A is from 0.005% to about 0.05%.

7. The composition of claim 6 wherein the cyclosporin A is 0.05%.

8. The composition of claim 1 wherein the oil is cinnamon oil.

9. The composition of claim 8 wherein the cyclosporin A is from 0.005% to about 0.05%.

10. The composition of claim 9 wherein the cyclosporin A is 0.05%.

* * * * *